US012790607B2

(12) United States Patent
Liu et al.

(10) Patent No.: US 12,790,607 B2
(45) Date of Patent: Nov. 10, 2026

(54) HIGHLY ERROR-PRONE ORTHOGONAL DNA REPLICATION SYSTEM FOR TARGETED CONTINUOUS EVOLUTION IN VIVO

(71) Applicant: The Regents of the University of California, Oakland, CA (US)

(72) Inventors: Chang C. Liu, Irvine, CA (US); Arjun Ravikumar, Washington, DC (US); Garri A. Arzumanyan, Irvine, CA (US); Alex A Javanpour, San Ramon, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1546 days.

(21) Appl. No.: 16/756,813

(22) PCT Filed: Oct. 19, 2018

(86) PCT No.: PCT/US2018/056794

§ 371 (c)(1),
(2) Date: Apr. 16, 2020

(87) PCT Pub. No.: WO2019/079775

PCT Pub. Date: Apr. 25, 2019

(65) Prior Publication Data

US 2023/0242902 A1 Aug. 3, 2023

Related U.S. Application Data

(60) Provisional application No. 62/679,059, filed on Jun. 1, 2018, provisional application No. 62/574,850, filed on Oct. 20, 2017.

(51) Int. Cl.
*C12N 15/10* (2006.01)
*C12N 9/12* (2006.01)

(52) U.S. Cl.
CPC ....... *C12N 15/1058* (2013.01); *C12N 9/1252* (2013.01); *C12N 15/1024* (2013.01)

(58) Field of Classification Search
CPC .............. C12N 15/1058; C12N 9/1252; C12N 15/1024
USPC ............................................................ 506/10
See application file for complete search history.

(56) References Cited

PUBLICATIONS

P05468-DPO2_KLULA. UniProt [online]. Last Updated 1988 [retrieved Dec. 20, 2023]. Retrieved from the Internet. <URL: https://www.uniprot.org/uniprotkb/P05468/entry> (Year: 1988).*

(Continued)

*Primary Examiner* — Heather Calamita
*Assistant Examiner* — Randi Lynn Beil
(74) *Attorney, Agent, or Firm* — Karen S. Canady; canady+lortz LLP

(57) ABSTRACT

The invention provides compositions comprising highly error-prone polymerases and methods of using the polymerases for rapid evolution of a nucleic acid sequence within host cells. The invention further provides a versatile synthetic biology platform for manipulating DNA replication inside a cell. The invention also provides a mutually orthogonal replication system for manipulating and tuning DNA replication of multiple nucleic acid molecules using the error-prone polymerases.

22 Claims, 9 Drawing Sheets

Specification includes a Sequence Listing.

(56) References Cited

PUBLICATIONS

P09804-DPO1_KLULA. UniProt [online]. Last Updated 1996 [retrieved Dec. 20, 2023]. Retrieved from the Internet. <URL: https://www.uniprot.org/uniprotkb/P09804/entry> (Year: 1996).*
Camps et al. Targeted gene evolution in *Escherichia coli* using a highly error-prone DNA polymerase I. PNAS. 100(17), 2003, 9727-9732. (Year: 2003).*
Ravikumar et al. An orthogonal DNA replication system in yeast. Nat Chem Biol, Mar. 2014, vol. 10, No. 3.
Herr et al. Mutator suppression and escape from replication error-induced extinction in yeast. PLoS Genet, Oct. 2011, vol. 7, No. 10.
GenBank Accession X01095.1. Yeast DNA killer plasmid pGKL 1, Jul. 25, 2016 (online). Retrieved from internet URL https://www.ncbi.nlm.nih.gov/nuccore/X10196.1.

* cited by examiner

| Variant | Mutations |
|---|---|
| A | I777K |
| B | F871Y |
| C | N423D |
| D | I777K, L900S |
| E | L474W, L640Y, I777K, W814N |
| F | Y431H, L640Y I777K, W814N |
| 4-1 | V574F, I777K, L900S |
| 4-2 | L477V, L640Y I777K, W814N |

HIGHLY ERROR-PRONE ORTHOGONAL DNA REPLICATION SYSTEM FOR TARGETED CONTINUOUS EVOLUTION IN VIVO

This patent application claims priority to U.S. Provisional Patent Application No. 62/574,850 filed on Oct. 20, 2017 and Application No. 62/679,059 filed on Jun. 1, 2018, which are incorporated by reference herein, in their entirety.

STATEMENT REGARDING FEDERALLY SPONSORED RESEARCH OR DEVELOPMENT

This invention was made with government support under Grant No. 1DP2GM119163-01 awarded by the National Institutes of Health (NIH); Grant No. MCB1545158 awarded by the National Science Foundation (NSF); and Grant No. HR0011-15-2-0031 and Grant No. DARPA-14-49-AS-BRICS-FP-017 issued by the Defense Advanced Research Projects Agency (DARPA). The government has certain rights in the invention.

SEQUENCE LISTING

The content of the ASCII text file of the sequence listing named "UCI022_ST25", which is 372 kb in size, was created on Dec. 1, 2025, and electronically submitted to Patent Center herewith the application. The sequence listing is incorporated herein by reference in its entirety.

BACKGROUND OF THE SYSTEM

The subject matter described herein relates generally to orthogonal nucleic acid replication systems utilizing mutant polymerases to continuously mutate user-defined nucleic acids in vivo.

Living organisms are continuously evolving systems amenable to massive parallelization. But their laboratory application to the generation of new function from specific genes suffers two constraints. First, organismal evolution is slow, as there is an inverse relationship between genome size and mutation rate. Second, natural evolution is untargeted, because mutations occur randomly across an organism's entire genome.

Historically, the field of laboratory evolution has sidestepped these constraints by implementing mutagenesis ex vivo, where mutation rate and the gene(s) subject to mutation can be controlled in a PCR. However, in this paradigm, evolution is neither continuous nor capable of massive parallelization, since ex vivo diversification requires labor-intensive DNA extraction, mutation, and transformation steps for each round of evolution.

There is thus a need in the art for novel orthogonal nucleic acid replication systems having altered capacity for generating mutations in vivo. The present invention addresses this unmet need in the art.

SUMMARY

Provided herein are embodiments of systems, apparatuses and methods for creating and using orthogonal nucleic acid replication systems utilizing mutant polymerases to continuously mutate user-defined genes in vivo. These orthogonal nucleic acid replication systems are separate from genomic nucleic acid replication systems and the mutant polymerases do not contribute to the generation of mutations in genomic nucleic acids. Rather these mutant polymerases generate mutations in plasmids during replication of said plasmids. Multiple, independent plasmids can each be replicated by their own dedicated mutant polymerase to create multiple, mutually orthogonal replication systems that operate together in vivo.

In one embodiment, the invention relates to a mutant polymerase, wherein said mutant polymerase comprises an altered mutation rate compared to a naturally occurring polymerase.

In one embodiment the mutation rate is at least $4.2\times10^{-6}$ mutations per nucleotide, which is the extinction threshold of the host cell (*Saccharomyces cerevisiae*), and which would result in the death of the host cell if used to generate mutations in genomic nucleic acids.

In one embodiment, the mutation rate is at least $1.64\times10^{-7}$ mutations per nucleotide, which would result in an unstable host cell (*Saccharomyces cerevisiae*) population if used to generate mutations in genomic nucleic acids.

In one embodiment, the mutation rate is at least $1\times10^{-5}$ mutations per nucleotide.

In one embodiment, the mutation rate is at least $1\times10^{-8}$ mutations per nucleotide.

In one embodiment, the mutation rate is increased by at least 25-fold, at least 100-fold, at least 1000-fold or at least 10,000-fold compared to a naturally occurring polymerase.

In one embodiment, the method replicates and introduces mutations into a target nucleic acid molecule using a mutant polymerase with an altered mutation rate which is sustained for at least 90 generations of cell replication. In one embodiment, the polymerase is a DNA polymerase.

In one embodiment, the mutant polymerase comprises at least one amino acid mutation relative to the parental polypeptide sequence.

In one embodiment, the polymerase comprises at least two amino acid mutations relative to the parental polypeptide sequence.

In one embodiment, the polymerase has at least three amino acid mutations relative to the parental polypeptide sequence.

In one embodiment, the polymerase has at least four amino acid mutations relative to the parental polypeptide sequence.

In one embodiment, the polymerase has at least one mutation in a region selected from the group consisting of Exo I (a.a. 352-362 in TP-DNAP1, a.a. 366-376 in TP-DNAP2), Exo II (a.a. 422-450 in TP-DNAP1, a.a. 416-430 in TP-DNAP2), Exo III (a.a. 550-563 in TP-DNAP1), pre-(S/T)Lx2h (a.a. 463-483 in TP-DNAP1, a.a. 464-481 in TP-DNAP2), (S/T)Lx2h (a.a. 488-493 in TP-DNAP1), Motif A (a.a. 640-650 in TP-DNAP1), Motif B (a.a. 776-787 in TP-DNAP1), Motif C (a.a 862-871 in TP-DNAP1, a.a. 874-883 in TP-DNAP2), pre-Motif B (a.a. 748-759 in TP-DNAP1), Tx2G/AR (a.a. 840-846 in TP-DNAP1) and KxY (a.a. 914-917 in TP-DNAP1).

In one embodiment, the mutant polymerase comprises the polypeptide sequence of TP-DNAP1 as set forth in SEQ ID NO:1 further comprising at least one mutation selected from the group consisting of: I287M, S289K, N291K, N291M, N291W, L295Q, Y296K, E298R, E298G, S305F, E298H, E298I, E298F, E298P, E298S, E298Y, E298V, I301A, I301C, I301E, I301L, I301K, I301M, I301S, I301Y, I301V, K302A, K302G, T303H, T303L, T303M, T303W, F304A, F304R, F304Y, S305N, S305G, I307L, D308Q, N309C, N309K, I311G, T310N, T310D, T310E, T310H, T310F, T310W, I311A, I311N, I311D, I311G, I311M, T312E, T312Q, Y313H, Y313M, Y313F, Y313W, Y313V, Y316R, I327Q, S330R, D333A, D333N, D333M, D333T, D333V, K344R, T352E, C354F, F355M, Y360F, K365N, N371A, N371C, N371M, I372C, C376I, Y382A, Y382V, K384D, V385W, G387H, R395P, V405I, V406C, V406Q, D407V, D407Q, D407A, D407C, D407G, D407H, D407M, D407F, D407T, G410H, G410Y, G410R, G410E, G410Q, G410I, G410L, G410K, G410M, G410F, G410S, G410T, G410W, E411A, E411R, E411N, E411D, E411G, E411L, E411K, E411S, E411T, L412V, N413E, N413H, N413T, N413I, I414H, I414F, S415T, S415V, I420Y, A421N, A421S, N423R, N423D, N423Q, N423E, N423W, N423Y, G425S, G426C, G426A, G426K, G426P, G426T, Y427A, Y427N, Y427D, Y427G, Y427H, Y427K, H430Q, Y431H, P439A, N450P, D460G, G461K, L473Y, L474F, L474W, L477I, L477T, L477V, N479P, S481F, K492T, K492V, T493P, H497N, K511H, S514R, S5331, 1549L, E550D, C556G, C556T, R557A, R557C, N558S, L561I, S564A, E569A, E569K, E569P, A573T, V574F, V574L, E575L, F578I, L592M, A599S, N611Q, N611P, K612A, K612Q, K612S, K612V, E613D, D614L, F616E, M618V, E620D, E620R, A621K, A621S, L622I, C627V, V630K, V630Y, N631A, C639T, C639I, C639V, C639Y, L640A, L640N, L640D, L640G, L640K, L640F, L640W, L640Y, K643N, K643S, K643V, L645N, L645M, Y646A, Y646F, A648S, S649A, F652G, F652L, Y653R, Y653H, Y653L, Q655H, P656A, R662T, R662A, R662C, S664H, D669G, E670M, I673V, Y675H, Y675L, R677Q, R677L, R677M, R677S, T679A, T679R, T679E, T679Q, N681Q, N681F, R682D, R682P, N683A, N683H, N683T, N684D, N687G, R692C, R692K, R692F, R692I, R692W, R692V, S693R, S693Q, S693G, H694I, H694T, N695E, N695Q, N695H, N695F, N695S, K696C, K696G, K696M, K696S, K696T, K696Y, T698M, T698A, T698L, E703D, E703R, E703H, E703W, E704N, E704D, E704G, E704I, E704M, E704V, E704K, S705R, S705L, S705F, T706E, T706R, T706Q, T706G, T706P, T706W, I708A, I708E, I708L, I708M, I708T, I708V, I708Q, A709N, N725R, I729F, I729W, I729V, S733R, S733N, S733E, S733Q, K769G, N773Q, V774A, V7741, 1775A, I777A, I777K, I777V, I778A, M779L, M779S, S781G, L782G, W783Y, K785R, K785S, A787V, W790L, W790P, V791H, D804M, W814N, I824V, I824E, Y829I, Y829F, S831T, P833C, M848N, M848D, M848H, M848P, K849H, I851L, K857S, E858H, E861R, C862I, S865G, D866N, S869T, F871I, F871Y, V872I, V872L, H873R, H873T, K874P, V897V, L900S, L909F, K934F, K934W, S955W, D958A, K959A, K959M, K962Q K967C, F968C and F968T.

In one embodiment, the mutant polymerase comprises the polypeptide sequence of TP-DNAP1 as set forth in SEQ ID NO:1 further comprising at least two mutations selected from the group consisting of: 1287M, S289K, N291K, N291M, N291W, L295Q, Y296K, E298R, E298G, S305F, E298H, E298I, E298F, E298P, E298S, E298Y, E298V, I301A, I301C, I301E, I301L, I301K, I301M, I301S, I301Y, I301V, K302A, K302G, T303H, T303L, T303M, T303W, F304A, F304R, F304Y, S305N, S305G, I307L, D308Q, N309C, N309K, I311G, T310N, T310D, T310E, T310H, T310F, T310W, I311A, I311N, I311D, I311M, T312E, T312Q, Y313H, Y313M, Y313F, Y313W, Y313V, Y316R, I327Q, S330R, D333A, D333N, D333M, D333T, D333V, K344R, T352E, C354F, F355M, Y360F, K365N, N371A, N371C, N371M, I372C, C376I, Y382A, Y382V, K384D, V385W, G387H, R395P, V405I, V406C, V406Q, D407V, D407Q, D407A, D407C, D407G, D407H, D407M, D407F, D407T, G410H, G410Y, G410R, G410E, G410Q, G410I, G410L, G410K, G410M, G410F, G410S, G410T, G410W, E411A, E411R, E411N, E411D, E411G, E411L, E411K, E411S, E411T, L412V, N413E, N413H, N413T, N4131, 1414H, I414F, S415T, S415V, I420Y, A421N, A421S, N423R, N423D, N423Q, N423E, N423W, N423Y, G425S, G426C, G426A, G426K, G426P, G426T, Y427A, Y427N, Y427D, Y427G, Y427H, Y427K, H430Q, Y431H, P439A, N450P, D460G, G461K, L473Y, L474F, L474W, L477I, L477T, L477V, N479P, S481F, K492T, K492V, T493P, H497N, K511H, S514R, S5331, 1549L, E550D, C556G, C556T, R557A, R557C, N558S, L561I, S564A, E569A, E569K, E569P, A573T, V574F, V574L, E575L, F578I, L592M, A599S, N611Q, N611P, K612A, K612Q, K612S, K612V, E613D, D614L, F616E, M618V, E620D, E620R, A621K, A621S, L622I, C627V, V630K, V630Y, N631A, C639T, C639I, C639V, C639Y, L640A, L640N, L640D, L640G, L640K, L640F, L640W, L640Y, K643N, K643S, K643V, L645N, L645M, Y646A, Y646F, A648S, S649A, F652G, F652L, Y653R, Y653H, Y653L, Q655H, P656A, R662T, R662A, R662C, S664H, D669G, E670M, I673V, Y675H, Y675L, R677Q, R677L, R677M, R677S, T679A, T679R, T679E, T679Q, N681Q, N681F, R682D, R682P, N683A, N683H, N683T, N684D, N687G, R692C, R692K, R692F, R692I, R692W, R692V, S693R, S693Q, S693G, H694I, H694T, N695E, N695Q, N695H, N695F, N695S, K696C, K696G, K696M, K696S, K696T, K696Y, T698M, T698A, T698L, E703D, E703R, E703H, E703W, E704N, E704D, E704G, E704I, E704M, E704V, E704K, S705R, S705L, S705F, T706E, T706R, T706Q, T706G, T706P, T706W, I708A, I708E, I708L, I708M, I708T, I708V, I708Q, A709N, N725R, I729F, I729W, I729V, S733R, S733N, S733E, S733Q, K769G, N773Q, V774A, V774I, I775A, I777A, I777K, I777V, I778A, M779L, M779S, S781G, L782G, W783Y, K785R, K785S, A787V, W790L, W790P, V791H, D804M, W814N, I824V, I824E, Y829I, Y829F, S831T, P833C, M848N, M848D, M848H, M848P, K849H, I851L, K857S, E858H, E861R, C862I, S865G, D866N, S869T, F871I, F871Y, V872I, V872L, H873R, H873T, K874P, V897V, L900S, L909F, K934F, K934W, S955W, D958A, K959A, K959M, K962Q K967C, F968C and F968T.

In one embodiment, the polymerase comprises the polypeptide sequence as set forth in SEQ ID NO:1 further comprising at least one combination of mutations selected from the group consisting of a combination of G410H and N423Q; a combination of E411T and G426C; a combination of A599S and C639T; a combination of L622I and C639I; a combination of I777K and W814N; a combination of S781G, L782G and W783Y; a combination of K849H and K857S; a combination of S955W and K967C; a combination of L622I, C639I and I775A; a combination of L622I, C639I and I777A; a combination of L622I, C639I and I777K; a combination of L622I, C639I, I777K and W814N; a combination of L622I, C639I, S781G, L782G and W783Y; a combination of C639Y, L640A and I777A; a combination of L640A and I775A; a combination of L640A and I777A; a combination of L640A and I777K; a combination of L640A, I777K and W814N; a combination of L640A and M779L; a combination of L640N and I777A; a combination of L640G and I775A; a combination of L640G and I777A; a combination of L640G, I777K and W814N; a combination of L640Y and I777A; a combination of L640Y, I777K and W814N; a combination of L645M and I777K; a combination of L645M and M779L; a combination of F652L and I775A; a combination of Y653L and I775A; a combination of Y653L and I777A; a combination of Y653L and I777K; a combination of I775A and F871Y; a combination of I775A and L900S; a combination of I775A and L909F; a combination of I775A and K934W; a combination of I775A and F968T; a combination of I777A and F871Y; a combination of I777A and V872I; a combination of I777A and L900S; a combination of I777A and L909F; a combination of I777A and K934W; a combination of I777K, W790L and K934W; a combination of I777K and F871Y; a combination of I777K and V872I; a combination of I777K and L900S; a combination of I777K and L909F; a combination of I777K and K934W; a combination of I777K and F968C; a combination of I777K and F968T; a combination of M779L and K934W; a combination of M779L and F968C; a combination of V7741 and F871Y; a combination of V7741 and L900S; a combination of V7741 and F968C; a combination of Y431H, L640Y, I777K and W814N; a combination of L474W, L640Y, I777K and W814N; a combination of V574F, I777K and L900S; a combination of L477V, L640Y, I777K and W814N.

In one embodiment, the nucleic acid molecule comprises a nucleotide sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11, or sequences having at least 90% identity thereto and encoding the same amino acid sequence.

In one embodiment, the invention relates to a cell comprising a mutant TP-DNAP1 polymerase, wherein said mutant polymerase comprises an altered mutation rate as compared to a naturally occurring TP-DNAP1 polymerase. In one embodiment, the cell is a yeast cell. In one embodiment, the cell further comprises a template molecule for replication by the mutant polymerase. In one embodiment, the template molecule is a p1 plasmid.

In one embodiment, the invention relates to a cell comprising a nucleic acid molecule encoding a mutant TP-DNAP1 polymerase, wherein said mutant polymerase comprises an altered mutation rate as compared to a naturally occurring TP-DNAP1 polymerase. In one embodiment, the cell is a yeast cell. In one embodiment, the cell further comprises a template molecule for replication by the mutant polymerase. In one embodiment, the template molecule is a p1 plasmid.

In one embodiment, the mutant polymerase comprises at least one amino acid mutation relative to the parental polypeptide sequence. In one embodiment, the polymerase comprises the TP-DNAP2 polypeptide sequence as set forth in SEQ ID NO:13 further comprising at least one mutation at amino acid residue S370, Y424, F882 or L474.

In one embodiment, the polymerase comprises the polypeptide sequence as set forth in SEQ ID NO:13 further comprising at least one of a S370Q, S370P, S370R, S370E, S370K, S370L, Y424Q, Y424E, Y424K, Y424G, Y424R, L474D, L474A, L474V, F882A, F882V or F882R mutation.

In one embodiment, the invention relates to a nucleic acid molecule encoding a mutant TP-DNAP2 polymerase, wherein said mutant polymerase comprises an altered mutation rate as compared to a naturally occurring TP-DNAP2 polymerase. In one embodiment, the nucleic acid molecule comprises a nucleotide sequence of SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46. In one embodiment, the nucleic acid molecule comprises a nucleotide sequence having at least 90% identity to a nucleotide sequence of SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46.

In one embodiment, the invention relates to a cell comprising a mutant TP-DNAP2 polymerase, wherein said mutant polymerase comprises an altered mutation rate as compared to a naturally occurring TP-DNAP2 polymerase. In one embodiment, the cell is a yeast cell. In one embodiment, the cell further comprises a template molecule for replication by the mutant polymerase. In one embodiment, the template molecule is a p2 plasmid.

In one embodiment, the invention relates to a cell comprising a nucleic acid molecule encoding a mutant TP-DNAP2 polymerase, wherein said mutant polymerase comprises an altered mutation rate as compared to a naturally occurring TP-DNAP2 polymerase. In one embodiment, the cell is a yeast cell. In one embodiment, the cell further comprises a template molecule for replication by the mutant polymerase. In one embodiment, the template molecule is a p2 plasmid.

In one embodiment, the invention relates to a nucleic acid molecule encoding a mutant polymerase, wherein said mutant polymerase comprises an altered mutation rate compared to a naturally occurring polymerase.

In one embodiment, the invention relates to a cell comprising a mutant polymerase, wherein said mutant polymerase comprises an altered mutation rate compared to a naturally occurring polymerase, or a nucleic acid molecule encoding a mutant polymerase.

In one embodiment, the cell is a yeast cell.

In one embodiment, the cell further comprises a template molecule for replication by the mutant polymerase.

In one embodiment, the template molecule is a non-genomic nucleic acid molecule.

In one embodiment, the template molecule is a plasmid.

In one embodiment, the mutant polymerase is a mutant p1 polymerase and the template molecule is a p1 plasmid.

In one embodiment, the mutant polymerase is a mutant p2 polymerase and the template molecule is a p2 plasmid.

In one embodiment, the invention relates to a method of generating a nucleic acid molecule comprising at least one mutation relative to a parental nucleic acid sequence, the method comprising replicating a template nucleic acid molecule with a mutant polymerase, wherein said mutant polymerase comprises an altered mutation rate compared to a naturally occurring polymerase, wherein the template nucleic acid molecule is replicated by the mutant polymerase.

In one embodiment, the mutant polymerase replicates the template nucleic acid molecule, but is orthogonal to genomic nucleic acid molecules, such that the polymerase does not replicate the genomic nucleic acid molecules and does not contribute to the generation of mutations in the genomic nucleic acid molecules.

In one embodiment, the invention relates to a method of specifically replicating at least one target nucleic acid molecule in the presence of one or more additional nucleic acid molecule, the method comprising replicating a target nucleic acid molecule with a polymerase specific for the replication of the target nucleic acid molecule, wherein the polymerase is orthogonal to the one or more additional nucleic acid molecule, such that the target nucleic acid molecule is replicated, but not the one or more additional nucleic acid molecule.

In one embodiment, the method comprises specifically replicating at least two different target nucleic acid molecules in the presence of host genomic nucleic acid molecules.

In one embodiment, the method comprises the steps of a) replicating a first target nucleic acid molecule with a first polymerase specific for the replication of the first target nucleic acid molecule, wherein the first polymerase is orthogonal to the second target nucleic acid molecule and also to host genomic nucleic acid molecules, and b) replicating a second target nucleic acid molecule with a second polymerase specific for the replication of the second target nucleic acid molecule, wherein the second polymerase is orthogonal to the first target nucleic acid molecule and also to host genomic nucleic acid molecules, such that the first target nucleic acid molecule is replicated by the first polymerase, but not the second polymerase, and the second target nucleic acid molecule is replicated by the second polymerase, but not the first polymerase, further wherein neither the first nor the second polymerase replicate host genomic nucleic acid molecules.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION OF THE SYSTEM

Figure 1:
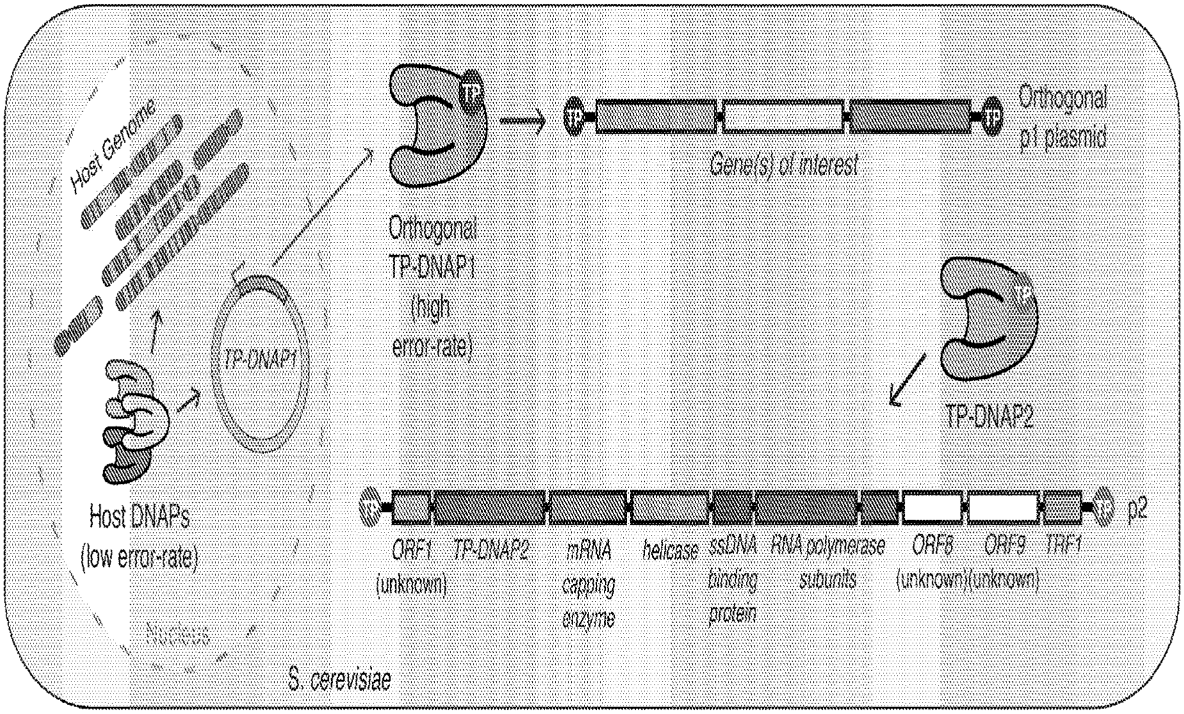
FIG. 1 depicts a schematic diagram of the architecture of the orthogonal DNA replication system containing TP-DNAP1, TP-DNAP2, the p1 plasmid and the p2 plasmid.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

The present invention relates generally to modified polymerases having an altered error-rate with respect to a parental polymerase and uses of the polymerases to synthesize nucleic acid molecules with an increased number of mutations. In one embodiment, the modified polymerase has an increased error-rate with respect to the parental polymerase.

In one embodiment the modified polymerases of the invention function in vivo to increase the mutation rate during nucleic acid synthesis.

In one embodiment the modified polymerases of the invention have a mutation rate that is at least $4.2\times10^{-6}$ mutations per nucleotide, which is the extinction threshold of the host cell (*Saccharomyces cerevisiae*), and which would result in the death of the host cell if used to generate errors in genomic nucleic acids. In one embodiment the modified polymerases of the invention have a mutation rate that is at least $1.64\times10^{-7}$ mutations per nucleotide, which would result in an unstable host cell population if used to generate errors in genomic nucleic acids.

In one embodiment, the modified polymerase of the invention may be a DNA polymerase, an RNA polymerase, or a reverse transcriptase. In one embodiment, the polymerase is a DNA polymerase. In one embodiment, the parental polymerase may be from any organism, including, but not limited to, a mammal, a bacterium, and a yeast. In one embodiment, the parental polymerase is a *Kluyveromyces lactis* polymerase TP-DNAP1. In another embodiment, the parental polymerase is a *Kluyveromyces lactis* polymerase TP-DNAP2.

The mutant polymerases of this invention contain at least one mutation that affects the fidelity, or error-rate, of the polymerase. In one embodiment, the mutant polymerase of the invention comprises an amino acid sequence as set forth in SEQ ID NO:1 further comprising at least one mutation selected from the mutations listed in Tables 2 and 3. In one embodiment, the mutant polymerase of the invention comprises an amino acid sequence as set forth in SEQ ID NO:1 further comprising at least two, three, four or more than four mutations selected from the mutations listed in Tables 2 and 3. In one embodiment, the mutant polymerase of the invention comprises an amino acid sequence as set forth in SEQ ID NO:13 further comprising at least one mutation selected from the mutations listed in Table 7. In one embodiment, the mutant polymerase of the invention comprises an amino acid sequence as set forth in SEQ ID NO:13 further comprising at least two, three, four or more than four mutations selected from the mutations listed in Table 7.

In one embodiment, the invention relates to a mutant polymerase of the invention. In one embodiment, the invention relates to compositions comprising a mutant polymerase of the invention. In one embodiment, the invention relates to nucleic acid molecules encoding a mutant polymerase of the invention. In one embodiment, the invention relates to cells modified with a nucleic acid molecule encoding a mutant polymerase of the invention.

In one embodiment, a cell modified with a nucleic acid molecule encoding a mutant polymerase of the invention may be from any organism, including, but not limited to, a mammal, a bacterium, and a yeast. In one embodiment, the cell is a yeast cell.

In one embodiment, the invention relates to methods of using a mutant polymerase for synthesizing a nucleic acid molecule. In one embodiment, the methods comprise replicating a template nucleic acid molecule with a mutant polymerase of the invention. In one embodiment, the template nucleic acid molecule is a p1 plasmid. In one embodiment, the p1 plasmid comprises a target nucleic acid sequence that encodes a protein, peptide or RNA molecule. In one embodiment, the template nucleic acid molecule is a p2 plasmid. In one embodiment, the p2 plasmid comprises a target nucleic acid sequence that encodes a protein, peptide or RNA molecule. In one embodiment, methods comprise replicating and introducing mutations into a target nucleic acid molecule using a mutant polymerase with an altered mutation rate which is sustained for at least 90 generations of cell replication.

In one embodiment, the mutant polymerase of the invention replicates the template nucleic acid molecule, but is orthogonal to genomic nucleic acid molecules, such that the polymerase does not replicate the genomic nucleic acid molecules and does not contribute to the generation of mutations in the genomic nucleic acid molecules.

In one embodiment, the invention relates to methods of using two mutant polymerases to synthesize nucleic acid molecules in an orthogonal system. In one embodiment the methods comprise the steps of a) contacting a p1 plasmid with TP-DNAP1 for the replication of the p1 plasmid, wherein TP-DNAP1 is orthogonal to the p2 plasmid and also to host genomic nucleic acid molecules, and b) contacting a p2 plasmid with a TP-DNAP2, wherein TP-DNAP2 is orthogonal to the p1 plasmid and also to host genomic nucleic acid molecules, such that the p1 plasmid is replicated by TP-DNAP1, but not TP-DNAP2, and the p2 plasmid is replicated by TP-DNAP2, but not TP-DNAP1, further wherein neither the TP-DNAP1 nor TP-DNAP2 replicate host genomic nucleic acid molecules.

DEFINITIONS

The articles "a" and "an" are used herein to refer to one or to more than one (i.e., to at least one) of the grammatical object of the article. By way of example, "an element" means one element or more than one element. "About" as used herein when referring to a measurable value such as an amount, a temporal duration, and the like, is meant to encompass variations of ±20% or +10%, more preferably ±5%, even more preferably +1%, and still more preferably ±0.1% from the specified value, as such variations are appropriate to perform the disclosed methods.

As used herein the terms "alteration," "defect," "variation," or "mutation," refers to a mutation in a gene in a cell that affects the function, activity, expression (transcription or translation) or conformation of the polypeptide that it encodes.

Mutations encompassed by the present invention can be any mutation of a gene in a cell that results in the enhancement or disruption of the function, activity, expression or conformation of the encoded polypeptide, including the complete absence of expression of the encoded protein and can include, for example, missense and nonsense mutations, insertions, deletions, frameshifts and premature terminations. Mutations may also be synonymous to the specific mutations in disclosed embodiments of the present invention, including amino acids that possess similar chemical characteristics to the disclosed mutations or their equivalents as known in the art.

The term "amino acid change" as used herein, refers to any mutation where the amino acid residue at a particular position in a sequence is different from that found at the corresponding location in the naturally occurring sequence. Such mutations can be nonsynonymous changes, conservative changes or non-conservative changes.

"Coding sequence" or "encoding nucleic acid" as used herein may refer to the nucleic acid (RNA or DNA molecule) that comprise a nucleotide sequence which encodes a sequence of amino acids. The coding sequence may further include initiation and termination signals operably linked to regulatory elements including a promoter and polyadenylation signal capable of directing expression in the one or more cells of a yeast cell or other eukaryotic cell wherein the nucleic acid is administered. The coding sequence may further include sequences that encode signal peptides.

The term "control" or "reference standard" describes a material comprising none, or a normal, low, or high level of one of more of the marker (or biomarker) expression products of one or more the markers (or biomarkers) of the invention, such that the control or reference standard may serve as a comparator against which a sample can be compared.

"Increased mutation rate" refers to polymerases with mutational levels which are at least 10% or more, for example, 20%, 30%, 40%, or 50%, 60%, 70%, 80%, 90% higher or more, and/or at least 1.05 fold, 1.06 fold, 1.07 fold, 1.08 fold, 1.09 fold, 1.1 fold, 1.11 fold, 1.12 fold, 1.13 fold, 1.14 fold, 1.15 fold, 1.16 fold, 1.17 fold, 1.18 fold, 1.19 fold, 1.2 fold, 1.25 fold, 1.3 fold, 1.35 fold, 1.4 fold, 1.45 fold, 1.5 fold, 1.55 fold, 1.6 fold, 1.65 fold, 1.7 fold, 1.75 fold, 1.8 fold, 1.85 fold, 1.9 fold, 1.95 fold, 2 fold, 2.1 fold, 2.2 fold, 2.3 fold, 2.4 fold, 2.5 fold, 2.6 fold, 2.7 fold, 2.8 fold, 2.9 fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 55 fold, 60 fold, 65 fold, 70 fold, 75 fold, 80 fold, 85 fold, 90 fold, 95 fold, 100 fold, 150 fold, 200 fold, 250 fold, 300 fold, 350 fold, 400 fold, 450 fold, 500 fold, 550 fold, 600 fold, 650 fold, 700 fold, 750 fold, 800 fold, 850 fold, 900 fold, 950 fold, 1000 fold, 1500 fold, 2000 fold, 2500 fold, 3000 fold, 3500 fold, 4000 fold, 5000 fold, 6000 fold, 7000 fold, 8000 fold, 9000 fold, or at least 10,000 fold higher or more, and any and all whole or partial increments there between than a control or naturally occurring polymerase.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "expression cassette" is a nucleic acid construct, generated recombinantly or synthetically, with a series of specified nucleic acid elements that permit transcription of a particular polynucleotide sequence in a host cell. An expression cassette may be part of a plasmid, cellular genome, viral genome, or nucleic acid fragment. Typically, an expression cassette includes a polynucleotide to be transcribed, operably linked to a promoter.

The term "gene" refers to a nucleic acid (e.g., DNA) sequence that includes coding sequences necessary for the production of a polypeptide, precursor, or RNA (e.g., mRNA). The polypeptide may be encoded by a full length coding sequence or by any portion of the coding sequence so long as the desired activity or functional property (e.g., enzymatic activity, ligand binding, signal transduction, immunogenicity, etc.) of the full-length or fragment is retained. The term also encompasses the coding region of a structural gene and the sequences located adjacent to the coding region on both the 5' and 3' ends for a distance of about 2 kb or more on either end such that the gene corresponds to the length of the full-length mRNA and 5' regulatory sequences which influence the transcriptional properties of the gene. Sequences located 5' of the coding region and present on the mRNA are referred to as 5-untranslated sequences. The 5'-untranslated sequences usually contain the regulatory sequences. Sequences located 3' or downstream of the coding region and present on the mRNA are referred to as 3'-untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. "Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10 of the positions in two sequences are matched or homologous then the two sequences are 60% homologous. By way of example, the DNA sequencesATTGCC and TATGGC share 50% homology. Generally, a comparison is made when two sequences are aligned to give maximum homology.

"Isolated" means altered or removed from the natural state. For example, a nucleic acid or a polypeptide naturally present in a living animal is not "isolated," but the same nucleic acid or polypeptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

By the term "modulating," as used herein, is meant mediating a detectable increase or decrease in the activity and/or level of a mRNA, polypeptide, or a response in a subject compared with the activity and/or level of a mRNA, polypeptide or a response in the subject in the absence of a treatment or compound, and/or compared with the activity and/or level of a mRNA, polypeptide, or a response in an otherwise identical but untreated subject.

The term "non-conservative mutation" or "non-conservative change" as used herein applies to both amino acid and nucleic acid sequences. With respect to particular nucleic acid sequences, "non-conservative mutations" refers to those nucleic acid changes which do not encode identical or essentially identical amino acid sequences, or where the nucleic acid does not encode an amino acid sequence, to sequences which have different nucleotide sequences.

As to amino acid sequences, one of skill will recognize that individual substitutions, deletions or additions to a nucleic acid, peptide, polypeptide, or protein sequence which alter, add or delete a single amino acid or a small percentage of amino acids in the encoded sequence where the alteration results in the substitution of an amino acid with a chemically dissimilar amino acid is a "non-conservative mutation".

In contrast, individual substitutions, deletions or additions to a nucleic acid, peptide, polypeptide, or protein sequence which alter a single amino acid or a small percentage of amino acids in the encoded sequence where the alteration results in the substitution of an amino acid with a chemically similar amino acid is a "conservative mutation".

Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "synonymous" or "silent" variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. The term also encompasses cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Unless otherwise indicated, a particular nucleic acid sequence also implicitly encompasses synonymously modified variants thereof (e.g., degenerate codon substitutions), alleles, orthologs, SNPs, and complementary sequences as well as the sequence explicitly indicated. For example, degenerate codon substitutions may be achieved by generating sequences in which one or more selected nucleotides that make up a codon is substituted without affecting the encoded amino acid residue (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). The term nucleic acid is used interchangeably with gene, cDNA, and mRNA encoded by a gene. An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this disclosure. It will be understood that when a nucleotide sequence is represented herein by a DNA sequence (e.g., A, T, G, and C), this also includes the corresponding RNA sequence (e.g., A, U, G, C) in which "U" replaces "T".

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

As used herein, the term "polymerase chain reaction" ("PCR") refers to the method of K. B. Mullis (U.S. Pat. Nos. 4,683,195 4,683,202, and 4,965,188, hereby incorporated by reference) for increasing the concentration of a segment of a target sequence in a mixture of DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". As used herein, the terms "PCR product," "PCR fragment," "amplification product" or "amplicon" refer to the resultant mixture of compounds after two or more cycles of the PCR steps of denaturation, annealing and extension are complete. These terms encompass the case where there has been amplification of one or more segments of one or more target sequences.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viruses, bacteria, fungi, plants, insects, and animals. A promoter may regulate the expression of a gene component constitutively, or differentially with respect to the cell, tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "regulating" as used herein can mean any method of altering the level or activity of a substrate. Non-limiting examples of regulating with regard to a protein include affecting expression (including transcription and/or translation), affecting folding, affecting degradation or protein turnover, and affecting localization of a protein. Non-limiting examples of regulating with regard to an enzyme further include affecting the enzymatic activity. "Regulator" refers to a molecule whose activity includes affecting the level or activity of a substrate. A regulator can be direct or indirect. A regulator can function to activate or inhibit or otherwise modulate its substrate.

A "reporter gene" encodes proteins that are readily detectable due to their biochemical characteristics, such as enzymatic activity or chemifluorescent features. One specific example of such a reporter is green fluorescent protein. Fluorescence generated from this protein can be detected with various commercially-available fluorescent detection systems. Other reporters can be detected by staining. The reporter can also be an enzyme that generates a detectable signal when contacted with an appropriate substrate. The reporter can be an enzyme that catalyzes the formation of a detectable product. Suitable enzymes include, but are not limited to, proteases, nucleases, lipases, phosphatases and hydrolases. The reporter can encode an enzyme whose substrates are substantially impermeable to eukaryotic plasma membranes, thus making it possible to tightly control signal formation. Specific examples of suitable reporter genes that encode enzymes include, but are not limited to, CAT (chloramphenicol acetyl transferase; Alton and Vapnek (1979) Nature 282: 864-869); luciferase (lux); β-galactosidase; LacZ; β.-glucuronidase; and alkaline phosphatase (Toh, et al. (1980) Eur. J. Biochem. 182: 231-238; and Hall et al. (1983) J. Mol. Appl. Gen. 2: 101), each of which are incorporated by reference herein in its entirety. Other suitable reporters include those that encode for a particular epitope that can be detected with a labelled antibody that specifically recognizes the epitope.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

"Vector" as used herein may mean a nucleic acid sequence containing an origin of replication. A vector may be a plasmid, virus, bacterial artificial chromosome or yeast artificial chromosome. A vector may be a DNA or RNA vector. A vector may be either a self-replicating extrachromosomal vector or a vector which integrates into a host genome.

As used herein, the term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to methods and compositions for modulating the mutation rate at a sequence of interest. The methods and compositions are based on the generation of a library of polymerases that are designed to have altered mutational rates. In one embodiment, a polymerase with an increased mutation rate generates mutations in a replicated DNA molecule at a higher frequency than a naturally occurring polymerase. Consequently, described herein are compositions and methods for generating low-fidelity or error-prone polymerases, wherein the polymerase has a mutation rate that is higher than the mutation rate of a naturally occurring polymerase.

Compositions

This invention relates, in part, to mutant polymerases having at least one mutation that results in an altered mutation rate of the polymerase relative to an endogenous, wild-type polymerase. In one embodiment, the endogenous or wild-type polymerase is encoded by a parent polynucleotide.

Polymerases Used as Parent Polymerases for Mutations

In certain embodiments, the parent polynucleotide encodes a DNA polymerase. The parent polynucleotide can also encode other polymerases including, but not limited to, an RNA polymerase, or a reverse transcriptase. In one embodiment, the parent polynucleotide used in the method for generating an improved polymerase encodes a naturally occurring polymerase. In one embodiment, the parent polynucleotide used in the method for generating an improved polymerase encodes a synthetic or non-naturally occurring polymerase.

Parent polymerases that may be modified to contain mutations that increase the mutation rate of the polymerase include, but are not limited to, polymerases from organisms such as humans, yeast, bacteria, and viruses, including phage.

In certain embodiments, the parent polymerase can also be a T7 polymerase. In certain embodiments, the parent polymerase can be an endogenous low fidelity polymerase. Exemplary endogenous low fidelity polymerases include, but are not limited to, terminal deoxynucleotidyl transferase (TdT) and DNA polymerases β, ζ, κ, η, ι, λ, μ, and Rev1. In other embodiments, the parent polymerases can also be HIV RT and DNA Polymerase I.

Numerous genes encoding endogenous polymerases have been isolated and sequenced. This sequence information is available on publicly accessible sequence databases such as GENBANK. A large compilation of the amino acid sequences of polymerases from a wide range of organisms can also be found in publicly accessible sequence databases. This information may be used in designing various embodiments of mutant polymerases of the invention and polynucleotides encoding these enzymes.

Genes encoding parent polymerase may be isolated using conventional cloning techniques in conjunction with publicly-available sequence information. Alternatively, many cloned polynucleotide sequences encoding polymerases have been deposited with publicly-accessible collection sites, e.g., the American type culture collection deposit accession number ATCC 40336 is a phage clone of Taq DNA polymerase.

The parent polynucleotide can encode any polymerase known to those of skill in the art. In one embodiment, the parent polynucleotide encodes a DNA polymerase from *K. lactis*. In one embodiment, the parental polymerase has the amino acid sequence for TP-DNAP1 as set forth in SEQ ID NO:1. In one embodiment, the parental polymerase is encoded by a nucleotide sequence for TP-DNAP1 as set forth in SEQ ID NO:2. In one embodiment, the parental polymerase has an amino acid sequence for TP-DNAP2 as set forth in SEQ ID NO:13. In one embodiment, the parental polymerase is encoded by a nucleotide sequence for TP-DNAP2 as set forth in SEQ ID NO:12.

Mutations to Alter Mutation Rate

The mutant polymerases of this invention contain at least one mutation that affects the fidelity, or mutation rate, of the polymerase.

In various embodiments, the mutant polymerases of this invention have mutation rates that are at least $4.2\times10^{-6}$ mutations per nucleotide, which is the extinction threshold of the host cell (*Saccharomyces cerevisiae*), and which would result in the death of the host cell if used to generate mutations in genomic nucleic acids.

In various embodiments, the mutant polymerases of this invention have mutation rates that are at least 1.64×10−7 mutations per nucleotide, which would result in an unstable host cell (*Saccharomyces cerevisiae*) population if used to generate mutations in genomic nucleic acids.

In various embodiments the mutant polymerases of this invention have an altered mutation rate which is sustained for at least 90 generations of cell replication.

In various embodiments, the mutant polymerase has a nucleotide sequence comprising at least one mutation relative to the nucleotide sequence of a parental polynucleotide. In one embodiment the mutant polymerase has at least 2, at least 3, at least 4, at least 5, at least 6, at least 7, at least 8, at least 9, at least 10 or more than 10 mutations relative to a parental polynucleotide.

In various embodiments, the mutant polymerase has at least one amino acid mutation relative to the amino acid sequence of a parental polypeptide. In one embodiment the mutant polymerase has at least 2, at least 3, at least 4, at least 5, at least 6, at least 7, at least 8, at least 9, at least 10 or more than 10 mutations relative to a parental polypeptide.

In one embodiment, the mutant polymerases of the invention, having at least one mutation that results in an increase in the mutation rate of the polymerase relative to an endogenous or wild-type polymerase, may further comprise at least one additional mutation. In one embodiment, an additional mutation does not result in an increase in the mutation rate of the polymerase relative to an endogenous or wild-type polymerase. In one embodiment, at least one additional mutation results in an additive or synergistic increase in the mutation rate of the polymerase relative to an endogenous or wild-type polymerase. In one embodiment the mutant polymerase has at least 2, at least 3, at least 4, at least 5, at least 6, at least 7, at least 8, at least 9, at least 10 or more than 10 mutations that result in an additive or synergistic increase in the mutation rate of the polymerase relative to an endogenous or wild-type polymerase.

Exemplary mutations that can be included in a mutant polymerase of the invention include, but are not limited to, the mutations set forth in Tables 2 and 3. Therefore, in various embodiments, the mutant polymerases of the invention have at least 1, at least 2, at least 3, at least 4, at least 5, at least 6, at least 7, at least 8, at least 9, at least 10, or more than 10 mutations selected from the mutations set forth in Tables 2 and 3.

In one embodiment, at least one mutation is in a region selected from: Exo I (a.a. 352-362 in TP-DNAP1), Exo II (a.a. 422-450 in TP-DNAP1), Exo III (a.a. 550-563 in TP-DNAP1), pre-(S/T)Lx2h (a.a. 463-483 in TP-DNAP1), (S/T)Lx2h (a.a. 488-493 in TP-DNAP1), Motif A (a.a. 640-650 in TP-DNAP1), Motif B (a.a. 776-787 in TP-DNAP1), Motif C (a.a 862-871 in TP-DNAP1), pre-Motif B (a.a. 748-759 in TP-DNAP1), Tx2G/AR (a.a. 840-846 in TP-DNAP1) and KxY (a.a. 914-917 in TP-DNAP1). These regions can be seen in FIG. 6. In one embodiment, at least one mutation is outside of the Exo I, Exo II, Exo III, pre-(S/T)Lx2h, (S/T)Lx2h, Motif A, Motif B, Motif C, pre-Motif B, Tx2G/AR and K×Y regions. In one embodiment, the mutant polymerases of the invention have at least 2 mutations. The at least two mutations can be in the same region, in different regions, a combination of inside a region and outside any region, or only outside of any region. The amino acids residues that comprise a specific region may vary depending on the parental polymerase, therefore the following amino acid residue designations, and amino acid designations throughout should be understood as exemplary for a given parental polypeptide sequence. Analogous regions or residues in alternative parental polypeptides may be identified by methods known in the art, including through structural models, by homology to polymerases with known structures, or by experimental characterization.

Exemplary mutations that can be included in a polymerase of the invention include, but are not limited to, the mutations set forth in Tables 2 and 3. Therefore, in various embodiments, the mutant polymerases of the invention have at least 1, at least 2, at least 3, at least 4, at least 5, at least 6, at least 7, at least 8, at least 9, at least 10 or more than 10 mutations selected from the mutations set forth in Tables 2 and 3. In one embodiment a DNA polymerase of the invention comprises at least one of N282Y, T303H, G410H, E411T, N423D, N423Q, N423R, G426A, G426C, Y427A, Y427S, Y431H, L474W, L477V, V574F, A599S, L622I, C639I, C639T, L640A, L640G, L640N, L640Y, K643V, L645M, F652L, Y653L, D669Q, E704K, V7741, 1775A, I777A, I777K, M779L, M779S, W814N, K849H, K857S, F871Y, V872I, L900S, L909F, K934W, S955W, K967C, F968C and F968T relative to the parent polypeptide sequence set forth in SEQ ID NO:1. In one embodiment a DNA polymerase of the invention comprises at least two of N282Y, T303H, G410H, E411T, N423D, N423Q, N423R, G426A, G426C, Y427A, Y427S, Y431H, L474W, L477V, V574F, A599S, L622I, C639I, C639T, L640A, L640G, L640N, L640Y, K643V, L645M, F652L, Y653L, D669Q, E704K, V7741, 1775A, I777A, I777K, M779L, M779S, W814N, K849H, K857S, F871Y, V872I, L900S, L909F, K934W, S955W, K967C, F968C and F968T relative to the parent polypeptide sequence set forth in SEQ ID NO:1. In one embodiment a DNA polymerase of the invention comprises at least three of N282Y, T303H, G410H, E411T, N423D, N423Q, N423R, G426A, G426C, Y427A, Y427S, Y431H, L474W, L477V, V574F, A599S, L622I, C639I, C639T, L640A, L640G, L640N, L640Y, K643V, L645M, F652L, Y653L, D669Q, E704K, V7741, 1775A, I777A, I777K, M779L, M779S, W814N, K849H, K857S, F871Y, V872I, L900S, L909F, K934W, S955W, K967C, F968C and F968T relative to the parent polypeptide sequence set forth in SEQ ID NO:1. Exemplary combinations of mutations that can be included in a mutant polymerase of the invention include, but are not limited to, a combination of L640Y, I777K, and W814N, a combination of L640Y, I777K, W814N and L477V, a combination of L640Y, I777K, W814N and Y431H, a combination of L640Y, I777K, W814N and L474W, and a combination of I777K, V574F and L900S, relative to the parent polypeptide sequence set forth in SEQ ID NO:1.

In one embodiment, the mutant error-prone polymerase is encoded by a nucleotide sequence set forth in SEQ ID NO:3 (encoding a mutant polymerase comprising a I777K mutation), SEQ ID NO:4 (encoding a mutant polymerase comprising a F871Y mutation), SEQ ID NO:5 (encoding a mutant polymerase comprising a N423D mutation), SEQ ID NO:6 (encoding a mutant polymerase comprising L640Y, I777K and W814N mutations), SEQ ID NO:7 (encoding a mutant polymerase comprising I777K and L900S mutations), SEQ ID NO:8 (encoding a mutant polymerase comprising Y431H, L640Y, I777K and W814N mutations), SEQ ID NO:9 (encoding a mutant polymerase comprising L474W, L640Y, I777K and W814N mutations), SEQ ID NO:10 (encoding a mutant polymerase comprising V574F, I777K, and L900S mutations) or SEQ ID NO: 11 (encoding a mutant polymerase comprising L477V, L640Y, I777K and W814N mutations). In one embodiment, the mutant error-prone polymerase is encoded by a nucleotide sequence having at least 90%, 91%, 92%, 93%, 94%, 95%, 96%, 97%, 98%, or at least 99% identity to a nucleotide sequence set forth in SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In one embodiment, a nucleotide sequence having at least 90%, 91%, 92%, 93%, 94%, 95%, 96%, 97%, 98%, or at least 99% identity to a nucleotide sequence set forth in SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11 encodes the same amino acid sequence as encoded by SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

In one embodiment, the mutant polymerase of the invention having an increased mutation rate has a mutation rate greater than $2.3\times10^{-9}$, $2.4\times10^{-9}$, $2.5\times10^{-9}$, $2.6\times10^{-9}$, $2.7\times10^{-9}$, $2.8\times10^{-9}$, $2.9\times10^{-9}$, $3\times10^{-9}$, $4\times10^{-9}$, $5\times10^{-9}$, $6\times10^{-9}$, $7\times10^{-9}$, $8\times10^{-9}$, $9\times10^{-9}$, $1\times10^{-8}$, $2\times10^{-8}$, $3\times10^{-8}$, $4\times10^{-8}$, $5\times10^{-8}$, $6\times10^{-8}$, $7\times10^{-8}$, $8\times10^{-8}$, $9\times10^{-8}$, $1\times10^{-7}$, $2\times10^{-7}$, $3\times10^{-7}$, $4\times10^{-7}$, $5\times10^{-7}$, $6\times10^{-7}$, $7\times10^{-7}$, $8\times10^{-7}$, $9\times10^{-7}$, $1\times10^{-6}$, $2\times10^{-6}$, $3\times10^{-6}$, $4\times10^{-6}$, $5\times10^{-6}$, $6\times10^{-6}$, $7\times10^{-6}$, $8\times10^{-6}$, $9\times10^{-6}$, $1\times10^{-5}$, $2\times10^{-5}$, $3\times10^{-5}$, $4\times10^{-5}$, $5\times10^{-5}$, $6\times10^{-5}$, $7\times10^{-5}$, $8\times10^{-5}$, $9\times10^{-5}$, or greater than $1\times10^{-4}$ mutations per nucleotide.

In one embodiment, the mutant polymerase of the invention has a mutation rate of at least 1.05 fold, 1.06 fold, 1.07 fold, 1.08 fold, 1.09 fold, 1.1 fold, 1.11 fold, 1.12 fold, 1.13 fold, 1.14 fold, 1.15 fold, 1.16 fold, 1.17 fold, 1.18 fold, 1.19 fold, 1.2 fold, 1.25 fold, 1.3 fold, 1.35 fold, 1.4 fold, 1.45 fold, 1.5 fold, 1.55 fold, 1.6 fold, 1.65 fold, 1.7 fold, 1.75 fold, 1.8 fold, 1.85 fold, 1.9 fold, 1.95 fold, 2 fold, 2.1 fold, 2.2 fold, 2.3 fold, 2.4 fold, 2.5 fold, 2.6 fold, 2.7 fold, 2.8 fold, 2.9 fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 55 fold, 60 fold, 65 fold, 70 fold, 75 fold, 80 fold, 85 fold, 90 fold, 95 fold, 100 fold, 150 fold, 200 fold, 250 fold, 300 fold, 350 fold, 400 fold, 450 fold, 500 fold, 550 fold, 600 fold, 650 fold, 700 fold, 750 fold, 800 fold, 850 fold, 900 fold, 950 fold, 1000 fold, 1500 fold, 2000 fold, 2500 fold, 3000 fold, 3500 fold, 4000 fold, 5000 fold, 6000 fold, 7000 fold, 8000 fold, 9000 fold, or at least 10,000 fold greater than the mutation rate of an endogenous or wild-type polymerase.

Additional Mutations

The mutant DNA polymerases of the invention can comprise numerous mutations in addition to those for increasing the mutation rate. These secondary mutations may be either inside or outside the Exo I, Exo II, Exo III, pre-(S/T)Lx2h, (S/T)Lx2h, Motif A, Motif B, Motif C, pre-Motif B, Tx2G/AR and KxY regions. In one embodiment, the secondary mutations may be those indicated in Table 2 and 3, with respect to SEQ ID NO:1. Secondary mutations can be selected so as to confer some useful property on the mutant polymerase. For example, additional mutations may be introduced to increase thermostability, decrease thermostability, increase processivity, decrease processivity, decrease 3'-5' exonuclease activity, increase 3'-5' exonuclease activity, decrease 5'-3' exonuclease activity, increase 5'-3' exonuclease activity, or increase expression or stability of the polymerase.

In some embodiments, the mutant polymerases comprise one or more secondary mutations that reduce or eliminate 3'-5' exonuclease activity. Exonuclease activity allows newly-added bases to be removed from the primer strand and then added back by polymerase.

In some embodiments, the mutant polymerases comprise one or more secondary mutations that do not affect the activity of the polymerase. Such mutations may be synonymous or conservative mutations.

Peptides

In one embodiment, the present invention comprises a peptide comprising a mutant polymerase with an altered mutation rate.

The peptide of the present invention may be made using chemical methods. For example, peptides can be synthesized by solid phase techniques (Roberge J Y et al. (1995) Science 269: 202-204), cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer.

The peptide may alternatively be made by recombinant means or by cleavage from a longer polypeptide. The composition of a peptide may be confirmed by amino acid analysis or sequencing.

The variants of the polypeptides according to the present invention may be one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, and/or (iii) fragments of the polypeptides and/or (iv) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two polypeptides is determined by comparing the amino acid sequence and its conserved amino acid substitutes of one polypeptide to a sequence of a second polypeptide. Variants are defined to include polypeptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to bind to ubiquitin or to a ubiquitylated protein. The present invention includes amino acid sequences that are at least 60%, 65%, 70%, 72%, 74%, 76%, 78%, 80%, 90%, or 95% similar or identical to the original amino acid sequence. The degree of identity between two polypeptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

The polypeptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction.

The polypeptides of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the aminoacylated tRNA. These reactions are referred to as post-aminoacylation modifications. For example, the epsilon-amino group of the lysine linked to its cognate tRNA ($tRNA_{LYS}$), could be modified with an amine specific photoaffinity label.

The term "functionally equivalent" as used herein refers to a polypeptide according to the invention that retains at least an altered mutation rate relative to a parental polymerase.

Nucleic Acids

In one embodiment, the invention includes an isolated nucleic acid comprising a nucleotide sequence encoding a mutant polymerase of the invention.

The nucleotide sequences encoding a mutant polymerase can alternatively comprise sequence variations with respect to the original nucleotide sequences, for example, substitutions, insertions and/or deletions of one or more nucleotides, with the condition that the resulting polynucleotide encodes a polypeptide according to the invention. Therefore, the scope of the present invention includes nucleotide sequences that are substantially homologous to the nucleotide sequences recited herein and encodes a mutant polymerase of the invention.

In the sense used in this description, a nucleotide sequence is "substantially homologous" to any of the nucleotide sequences describe herein when its nucleotide sequence has a degree of identity with respect to the nucleotide sequence of at least 60%, advantageously of at least 70%, preferably of at least 85%, and more preferably of at least 95%. A nucleotide sequence that is substantially homologous to a nucleotide sequence encoding a mutant polymerase can typically be isolated from a producer organism of the polypeptide of the invention based on the information contained in the nucleotide sequence by means of introducing synonymous, conservative or non-conservative substitutions, for example. Other examples of possible modifications include the insertion of one or more nucleotides in the sequence, the addition of one or more nucleotides in any of the ends of the sequence, or the deletion of one or more nucleotides in any end or inside the sequence. The degree of identity between two polynucleotides is determined using computer algorithms and methods that are widely known for the persons skilled in the art. The identity between two amino acid sequences is preferably determined by using the BLASTN algorithm [BLAST Manual, Altschul, S., et al., NCBI NLM NIH Bethesda, Md. 20894, Altschul, S., et al., J. Mol. Biol. 215: 403-410 (1990)].

In another aspect, the invention relates to a construct, comprising a nucleotide sequence encoding a mutant polymerase, or derivative thereof. In a particular embodiment, the construct is operatively bound to transcription, and optionally translation, control elements. The construct can incorporate an operatively bound regulatory sequence of the expression of the nucleotide sequence of the invention, thus forming an expression cassette.

A mutant polymerase may be prepared using recombinant DNA methods. Accordingly, nucleic acid molecules which encode a mutant polymerase may be incorporated in a known manner into an appropriate expression vector which ensures good expression of the mutant polymerase.

Therefore, in another aspect, the invention relates to a vector, comprising the nucleotide sequence of the invention or the construct of the invention. The choice of the vector will depend on the host cell in which it is to be subsequently introduced. In a particular embodiment, the vector of the invention is an expression vector. Suitable host cells include a wide variety of prokaryotic and eukaryotic host cells. In specific embodiments, the expression vector is selected from the group consisting of a viral vector, a bacterial vector, a yeast vector and a mammalian cell vector. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses.

In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.) Vectors suitable for the insertion of the polynucleotides are vectors derived from expression vectors in prokaryotes such as pUC18, pUC19, Bluescript and the derivatives thereof, mp18, mp19, pBR322, pMB9, ColE1, pCR1, RP4, phages and "shuttle" vectors such as pSA3 and pAT28, expression vectors in yeasts such as vectors of the type of 2 micron plasmids, integration plasmids, YEP vectors, centromeric plasmids with autonomously replicating sequences and the like, expression vectors in insect cells such as vectors of the pAC series and of the pVL, expression vectors in plants such as plBI, pEarleyGate, pAVA, pCAMBIA, pGSA, pGWB, pMDC, pMY, pORE series and the like, and expression vectors in eukaryotic cells based on viral vectors (adenoviruses, viruses associated to adenoviruses such as retroviruses and, particularly, lentiviruses) as well as non-viral vectors such as pSilencer 4.1-CMV (Ambion), pcDNA3, pcDNA3.1/hyg, pHMCV/Zeo, pCR3.1, pEFI/His, pIND/GS, pRc/HCMV2, pSV40/Zeo2, pTRACER-HCMV, pUB6/V5-His, pVAX1, pZeoSV2, pCI, pSVL and PKSV-10, pBPV-1, pML2d and pTDT1.

By way of illustration, the vector in which the nucleic acid sequence is introduced can be a plasmid which is or is not integrated in the genome of a host cell when it is introduced in the cell. Illustrative, non-limiting examples of vectors in which the nucleotide sequence of the invention or the gene construct of the invention can be inserted include a tet-on inducible vector for expression in eukaryotic cells.

The vector may be obtained by conventional methods known by persons skilled in the art (Sambrook et al., "Molecular cloning, a Laboratory Manual", 2nd ed., Cold Spring Harbor Laboratory Press, N.Y., 1989 Vol 1-3). In a particular embodiment, the vector is a vector useful for transforming yeast cells.

The recombinant expression vectors may also contain nucleic acid molecules which encode a portion which provides increased expression of the recombinant mutant polymerase; increased solubility of the recombinant mutant polymerase; and/or aid in the purification of the recombinant mutant polymerase by acting as a ligand in affinity purification. For example, a proteolytic cleavage site may be inserted in the recombinant peptide to allow separation of the recombinant mutant polymerase from the fusion portion after purification of the fusion protein. Examples of fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryote, virus, or eukaryote, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. Nos. 4,683,202, 5,928, 906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2001). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous. A promoter sequence exemplified in the experimental examples presented herein is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

In a particular embodiment, the expression of the nucleic acid is externally controlled. In a more particular embodiment, the expression is externally controlled using the methionine repressible MET3 promoter.

The recombinant expression vectors may also contain a selectable marker gene which facilitates the selection of transformed or transfected host cells. Suitable selectable marker genes are genes encoding proteins such as the neo gene from Tn5, HIS3, LEU2, URA3, TRP1, MET15, HIS4, β-galactosidase, β-lactamase, chloramphenicol acetyltransferase, firefly luciferase, or an immunoglobulin or portion thereof such as the Fc portion of an immunoglobulin preferably IgG. The selectable markers may be introduced on a separate vector from the nucleic acid of interest.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, β-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Recombinant expression vectors may be introduced into host cells to produce a recombinant cell. The cells can be prokaryotic or eukaryotic. The vector of the invention can be used to transform eukaryotic cells such as yeast cells (e.g. *Saccharomyces cerevisiae* cells), or mammal cells (e.g. epithelial kidney 293 cells or U2OS cells), or prokaryotic cells (e.g. *Escherichia coli* or *Bacillus subtilis*). Nucleic acid can be introduced into a cell using conventional techniques such as lithium acetate transformation, cytoduction techniques, cell mating, calcium phosphate or calcium chloride co-precipitation, DEAE-dextran-mediated transfection, lipofectin, electroporation or microinjection. Suitable methods for transforming and transfecting host cells may be found in Sambrook et al. (Molecular Cloning: A Laboratory Manual, 2nd Edition, Cold Spring Harbor Laboratory press (1989)), and other laboratory textbooks.

For example, a mutant polymerase of the invention may be expressed in bacterial cells, insect cells (using baculovirus), yeast cells or mammalian cells. Other suitable host cells can be found in Goeddel, Gene Expression Technology: Methods in Enzymology 185, Academic Press, San Diego, Calif. (1991).

Methods of Generating Mutant DNA Polymerases of the Invention

In one embodiment, the invention comprises methods for generating a polymerase having an altered mutation rate. In one embodiment, the method comprises the steps of: (a) providing a parent polynucleotide; (b) mutating the polynucleotide to generate a library of mutated polynucleotides; and (c) selecting from the library a mutated polynucleotide encoding a polymerase having an altered error-rate.

In one embodiment, the method comprises the steps of: (a) providing a parent polynucleotide; (b) mutating the parent polynucleotide at a residue predicted to affect the error-rate; and (c) selecting from the library a mutated polynucleotide encoding a polymerase having an altered error-rate.

Such polymerases can be generated by introducing mutations in specific residues which are identified as being in the appropriate region through structural models, by homology to polymerases with known structures, or by experimental characterization (e.g., site-directed mutagenesis). In some cases, the mutant polymerase has additional mutations, including but not limited to mutations that increase the mutation rate of the polymerase and mutations that decrease exonuclease activity.

The residues that affect the error-rate will vary depending on the particular polymerase and in some degree, will vary depending on the particular modified nucleotide. It will be appreciated by those of skill in the art that the mutations which confer the greatest mutation rates will vary depending on the particular modifications to the nucleotides, e.g., whether the modification alters the charge or interaction of a base, etc. Such mutations are usually, although not necessarily, substitution mutations. Several different amino acid residues may be substituted at a given position of a parent enzyme so as to give rise to mutations that increase the mutation rate of the polymerase.

The amino acid residues at a given residue position may be systematically varied so as to determine which amino acid substitutions are effective. In one embodiment, the mutations are non-conservative mutations.

A residue predicted to affect the error-rate can be a residue corresponding to a residue listed in Tables 2, 3, and 7. Corresponding residues between analogous proteins can be identified by any method known to those of skill in the art, including through structural models, by homology to polymerases with known structures, or by experimental characterization. In instances where large regions of homology can be found between polymerases, the determination of corresponding amino acid residues between different polymerases can be determined based on sequence homology. A large compilation of the amino acid sequences of polymerases from a wide range of organism and homology alignments between the sequences can be found in Braithwaite and Ito, Nucl. Acids Res. 21(4):787-802 (1993) and is useful for such purposes.

The mutations described above can be generated using any method typically used by those of skill in the art to introduce mutations at specific residues. Such methods are well described in Sambrook et al., Molecular Cloning: A Laboratory Manual, Cold Spring Harbor Laboratory Publications, Cold Spring Harbor, N.Y. (1982).

In one embodiment, the mutant polymerase of the invention has decreased exonuclease activity or completely lacks exonuclease activity. In one embodiment, the mutant polymerase retains strand displacement activity and processivity. In one embodiment, the mutant polymerase is capable of synthesizing nucleic acid molecules at a rate of at least 1 nt/sec; at least 10 nts/sec; at least 100 nts/sec or greater than at least 100 nts/sec.

Methods of Generating a Library of Mutants

Methods of generating a library of mutants are well known to those of skill in the art. In preferred embodiments, the polynucleotide is mutated via in vitro or in vivo recombination, site-directed mutagenesis, error-prone PCR, site-saturation mutagenesis, or gene shuffling recombination. In one embodiment, the parental polynucleotide is systematically mutated at specific amino acids. In one embodiment, the specific amino acids are in at least one region selected from Exo I, Exo II, Exo Ill, pre-(S/T)Lx2h, (S/T)Lx2h, Motif A, Motif B, Motif C, pre-Motif B, Tx2G/AR and K×Y regions.

In other preferred embodiments, the polynucleotides are first mutated using a method which randomly introduces mutations, such as error-prone PCR; screened for desired activity; mutated using a method which introduces all possible mutations at the mutant amino acids which confer the desired activity, such as site-saturation mutagenesis; and then recombined or further mutated by methods such as the StEP (staggered extension process) method or other single-site or multi-site mutagenesis methods. Site-directed mutagenesis techniques are well known in the art as exemplified by U.S. Pat. Nos. 4,711,848; 4,873,192; 5,071,743; 5,284,760; 5,354,670; 5,556,747; Zoller and Smith, Nucleic Acids Res. 10:6487-6500 (1982), and Edelman et al. DNA 2:183 (1983). Detailed protocols for site-directed mutagenesis are also given in many general molecular biology textbooks such as Sambrook et al. Molecular Cloning a Laboratory Manual 2nd Ed. Cold Spring Harbor Press, Cold Spring Harbor (1989), Ausubel et al. Current Protocols in Molecular Biology, (current edition). Additionally, many textbooks on PCR (the polymerase chain reaction), such as Diefenbach and Dveksler, PCR Primer: A Laboratory Manual, Cold Spring Harbor Press, Cold Spring Harbor, N.Y. (1995), describe methods of using PCR to introduce mutations.

In other embodiments, shuffling methods such as those described in U.S. Pat. No. 6,117,679, issued to Stemmer et al. are used to generate additional mutants from mutant polynucleotides with altered error-rates. In some cases, two polynucleotides encoding mutant versions of the same polymerase are shuffled. In other cases, a polynucleotide encoding one type of polymerase and a polynucleotide encoding a different polymerase with sufficient nucleotide homology to permit shuffling and are shuffled. Gene shuffling utilizes naturally occurring nucleotide substitutions among family genes as the driving force for evolution. (see, Chang, C.-C., Chen, T. T., Cox, B. W., Dawes, G. N., Stemmer, W. P. C., Punnonen, J., and Patten, P. A. Evolution of a cytokine using DNA family shuffling. Nat. Biotechnol., 17, 793-797. (1999); Hansson, L. O., B-Grob, R., Massoud, T., and Mannervik, B. Evolution of differential substrate specificities in Mu class glutathione transferases probed by DNA shuffling. J. Mol. Biol., 287, 265-276. (1999); and Kikuchi, M., Ohnishi, K., and Harayama, S. An effective family shuffling method using single-stranded DNA. Gene, 243, 133-137. (2000)).

In certain embodiments, the present invention also relates to a method of repeated cycles of nucleic acid mutation, transformation and selection, which allow for the creation of mutant proteins having enhanced charge-switch nucleotide polymerase activity.

Selection of Mutants with Desired Activity

Polynucleotides with desired activity can easily be selected using standard methods. The error-rate of a polymerase can be detected using an orthogonal replication system as described below, PCR-based assays, or any other methods known to those of skill in the art. Other properties of polymerases including, but not limited to replication activity, exonuclease activity, strand displacement activity and processivity can measured using assays well known in the art.

Methods of Using Mutant Polymerases

In one embodiment, the invention comprises methods of using the error-prone polymerases of this invention in any assay, test, or method where it would be useful to have sequences containing one or more mutations. Due to their high error-rate, the polymerases of this invention have utility in any molecular biology applications where it would either be advantageous or necessary to generate one or more random mutations in a newly synthesized nucleic acid molecule. In particular, these polymerases would be useful in methods where generation of multiple nucleic acid molecules having random mutations is advantageous or necessary. Exemplary embodiments include, but are not limited to methods investigating the effect of mutations on the level or activity of a protein or peptide.

More generally, the mutant polymerases of this invention can be substituted for the corresponding parent polymerase in most procedures that employ polymerases, particularly those where it would either be advantageous or necessary to generate one or more random mutations in a newly synthesized nucleic acid molecule. In one exemplary embodiment, the mutant polymerase of the invention is substituted for the wild type TP-DNAP1 in an orthogonal replication system as described in Ravikumar et al., Nat Chem Biol. 2014, 10(3): 175-177; Arzumanyan et al., ACS Synth. Biol. 2018, 7, 1722-1729; and Ravikumar et al., 2018, bioRxiv, 313338, which are incorporated herein by reference.

In one embodiment, the invention comprises in vivo methods of using the error-prone polymerases of this invention to generate nucleic acid sequences comprising at least one mutation relative to a parental nucleic acid sequence. In one embodiment, the in vivo methods include contacting a mutant polymerase of the invention with a template nucleic acid molecule, wherein the contacting is performed in a cell. In one embodiment, the mutant DNA polymerase of the invention is capable of replicating the template nucleic acid molecule, but does not replicate cellular genomic nucleic acid molecules, including, but not limited to cellular DNA. Therefore, in one embodiment, the mutant polymerase of the invention and the template nucleic acid molecule for use in the methods of the invention comprise an orthogonal replication system for specific replication of the template DNA molecule by the mutant DNA polymerase of the invention. In one embodiment, the method comprises modifying a cell with a construct for expressing a mutant polymerase of the invention. In various embodiments, the cell is a bacterial cell, insect cell, yeast cell or mammalian cell. In one exemplary embodiment, the cell is a yeast cell.

In one embodiment, the cell further comprises a template nucleic acid molecule. A template nucleic acid molecule for use in the method of the invention can be specific for replication by the mutant polymerase. In one embodiment, a template nucleic molecule is an exogenous nucleic acid molecule for the cell expressing the mutant polymerase of the invention. In one embodiment, the template nucleic acid molecule is a plasmid. Plasmids for use in the methods of the invention include, but are not limited to a p1 plasmid and a p2 plasmid.

Nucleic acid can be introduced into a cell using conventional techniques such as lithium acetate transformation, cytoduction techniques, cell mating, calcium phosphate or calcium chloride co-precipitation, DEAE-dextran-mediated transfection, lipofectin, electroporation or microinjection. Suitable methods for transforming and transfecting host cells may be found in Sambrook et al. (Molecular Cloning: A Laboratory Manual, 2nd Edition, Cold Spring Harbor Laboratory press (1989)), and other laboratory textbooks.

In one embodiment, method comprises incubating a mutant polymerase of the invention with a template nucleic acid molecule and one or more priming nucleic acid molecules under suitable polymerization conditions. In one embodiment, these conditions are provided by a reaction mixture containing ribonucleotide triphosphates (NTPs), deoxyribonucleotide triphosphates (dNTPs), dideoxyribonucleotide triphosphates (ddNTPs), or a combination thereof and a buffer containing a buffering agent, and optionally a divalent cation, and a monovalent cation.

Priming nucleic acid molecules, or "primers" generally refers to an oligonucleotide capable of acting as a point of initiation of nucleic acid synthesis when annealed to a nucleic acid template under conditions in which synthesis of a primer extension product is initiated, i.e., in the presence of nucleoside triphosphates and a polymerase in an appropriate buffer ("buffer" includes pH, ionic strength, cofactors, etc.) and at a suitable temperature. The primer typically contains 10-35 nucleotides, although the exact number is not critical to the successful application of the method. Short primer molecules generally require lower temperatures to form sufficiently stable hybrid complexes with the template.

DNA polymerases require a divalent cation for catalytic activity. Exemplary divalent cations that can be included in a reaction mixture include, but are not limited to, $Mn^{+2}$, $Mg^{+2}$, or $Co^{+2}$. The divalent cation can be supplied in the form of a salt such $MgCl_2$, $Mg(OAc)_2$, $MgSO_4$, $MnCl_2$, $Mn(OAc)_2$, or $MnSO_4$. Usable cation concentrations in a Tris-HCl buffer are for $MnCl_2$ from 0.5 to 7 mM, for example, between 0.5 and 2 mM, and for $MgCl_2$ from 0.5 to 10 mM. Usable cation concentrations in a Bicine/KOAc buffer are from 1 to 20 mM for $Mn(OAc)_2$, preferably between 2 and 5 mM. In one embodiment, the monovalent cation is supplied by the potassium, sodium, ammonium, or lithium salts of either chloride or acetate. For KCl, the concentration is between 1 and 200 mM, preferably the concentration is between 40 and 100 mM, although the optimum concentration may vary depending on the polymerase used in the reaction.

In one embodiment, deoxyribonucleotide triphosphates are added as solutions of the salts of dATP, dCTP, dGTP, dUTP, and dTTP, such as disodium or lithium salts. In one embodiment, a final concentration in the range of 1 μM to 2 mM each is suitable, and 100-600 μM is used, although the optimal concentration of the nucleotides may vary in the reverse transcription reaction depending on the total dNTP and divalent metal ion concentration, and on the buffer, salts, particular primers, and template. For longer products, i.e., greater than 1500 bp, 500 μM each dNTP and 2 mM $MnCl_2$ may be preferred when using a Tris-HCl buffer.

In one embodiment, a suitable buffering agent is Tris-HCl, preferably pH 8.3, although the pH may be in the range 8.0-8.8. The Tris-HCl concentration is from 5-250 mM. In one embodiment, the Tris-HCl concentration is from 10-100 mM. In one embodiment, a buffering agent is Bicine-KOH, MOPS-KOH, or HEPES-KOH, with a pH in the range 7.8-8.7.

In one embodiment, EDTA less than 0.5 mM may be present in a reverse transcription reaction mix. Detergents such as Tween-20™ and Nonidet™ P-40 are present in the enzyme dilution buffers. In one embodiment, a final concentration of non-ionic detergent approximately 0.1% or less is appropriate, and will not interfere with polymerase activity. Similarly, glycerol is often present in enzyme preparations and is generally diluted to a concentration of 1-20% in the reaction mix. In one embodiment, a mineral oil overlay may be added to prevent evaporation but is not necessary.

Mutually Orthogonal Replication Systems

Figure 7:
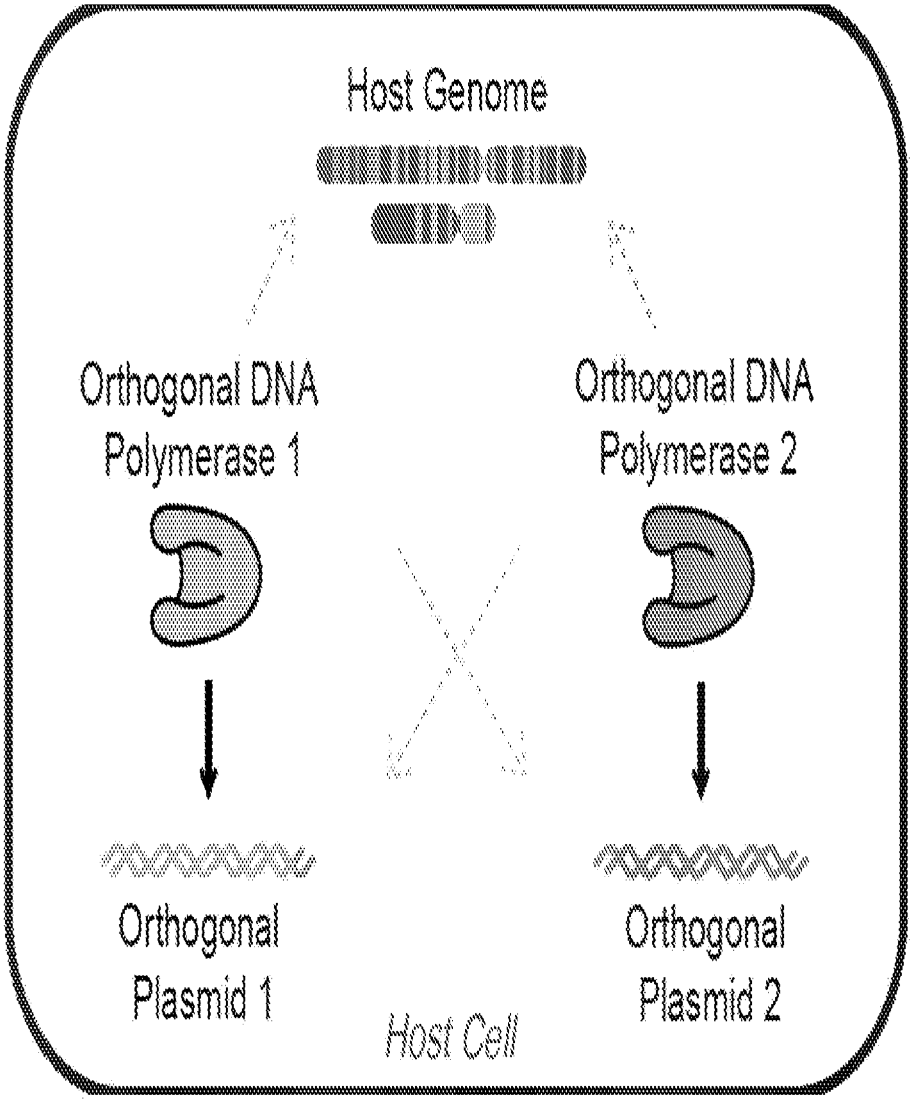
FIG. 7 depicts a schematic diagram of the architecture of the mutually orthogonal DNA replication system.

In one embodiment, the invention comprises a system comprising the orthogonal polymerases of this invention for use in any assay, test, or method where it would be useful to replicate a specific template nucleic acid molecule without altering or replicating other nucleic acid molecules which are present in the system. In one embodiment, the orthogonal replication system includes one or more orthogonal polymerases in a system for replicating one or more specific target nucleic acid molecules. In one embodiment, the orthogonal replication system includes two orthogonal polymerases in a system for replicating two specific target nucleic acid molecules (e.g., a dual orthogonal replication system.) This is illustrated in FIG. 7, which illustrates a dual orthogonal replication system which uses an orthogonal polymerase of this invention with an orthogonal plasmid.

In one embodiment, the method of the invention allows replication of a first template nucleic acid molecule with a first orthogonal polymerase having specificity for the first template and also replication of a second template nucleic acid molecule with a second orthogonal polymerase having specificity for the second template, wherein the first orthogonal polymerase does not replicate the second template, and the second orthogonal polymerase does not replicate the first template. Further, in one embodiment, the system includes genomic nucleic acid molecules and at least one polymerase specific for replication of genomic nucleic acid molecules (e.g., an endogenous polymerase), wherein the one or more orthogonal polymerases do not replicate the genomic nucleic acid molecule.

Use of the Orthogonal Replication Systems to Generate Mutations

In one embodiment, the method of the invention allows replication of a first template nucleic acid molecule with a first orthogonal polymerase having specificity for the first template and also replication of a second template nucleic acid molecule with a second orthogonal polymerase having specificity for the second template, wherein the first orthogonal polymerase does not replicate the second template, and the second orthogonal polymerase does not replicate the first template. Further, in one embodiment, the system includes genomic nucleic acid molecules and at least one polymerase specific for replication of genomic nucleic acid molecules (e.g., an endogenous polymerase), wherein the one or more orthogonal polymerase do not replicate the genomic nucleic acid molecules.

In various embodiments, the methods of the invention allow replication of a specific template nucleic acid with a polymerase having an altered (i.e., higher or lower) fidelity or error-rate without altering the fidelity of replication of another nucleic acid molecule that is present in the system. In one embodiment, the method of the invention allows replication of a first template nucleic acid molecule with a first mutant polymerase having altered fidelity and also replication of a second template nucleic acid molecule with a second mutant polymerase having altered fidelity, wherein the first mutant polymerase does not replicate the second template, and the second mutant polymerase does not replicate the first template. Further, in one embodiment, the system includes genomic nucleic acid molecules and at least one endogenous polymerase, wherein the one or more mutant polymerase do not replicate the genomic nucleic acid molecules. Due to their altered fidelity, the mutant polymerases of this invention have utility in any molecular biology applications where it would either be advantageous or necessary to generate one or more random mutations in a newly synthesized nucleic acid molecule. In particular, these polymerases would be useful in methods where generation of multiple nucleic acid molecules having random mutations is advantageous or necessary. Exemplary embodiments include, but are not limited to methods investigating the effect of mutations on the level or activity of a protein or peptide.

In one embodiment, the invention comprises in vivo methods of using the error-prone polymerases of this invention to generate nucleic acid sequences comprising at least one mutation relative to a parental nucleic acid sequence. In one embodiment, the in vivo methods include contacting a mutant polymerase of the invention with a template nucleic acid molecule, wherein the contacting is performed in a cell. In one embodiment, the mutant DNA polymerase of the invention is capable of replicating the template nucleic acid molecule, but does not replicate cellular genomic nucleic acid molecules, including, but not limited to cellular DNA. Therefore, in one embodiment, the mutant polymerase of the invention and the template nucleic acid molecule for use in the methods of the invention comprise an orthogonal replication system for specific replication of the template DNA molecule by the mutant DNA polymerase of the invention.

In one embodiment, method comprises modifying a cell with a construct for expressing a mutant polymerase of the invention. In various embodiments, the cell is a bacterial cell, insect cell, yeast cell or mammalian cell. In one exemplary embodiment, the cell is a yeast cell.

In one embodiment, the cell further comprises a template nucleic acid molecule. A template nucleic acid molecule for use in the method of the invention can be specific for replication by the mutant polymerase. In one embodiment, a template nucleic molecule is an exogenous nucleic acid molecule for the cell expressing the mutant polymerase of the invention.

Nucleic acid can be introduced into a cell using conventional techniques such as lithium acetate transformation, cytoduction techniques, cell mating, calcium phosphate or calcium chloride co-precipitation, DEAE-dextran-mediated transfection, lipofectin, electroporation or microinjection. Suitable methods for transforming and transfecting host cells may be found in Sambrook et al. (Molecular Cloning: A Laboratory Manual, 2nd Edition, Cold Spring Harbor Laboratory press (1989)), and other laboratory textbooks.

In one embodiment, method comprises incubating a mutant polymerase of the invention a template nucleic acid molecule and one or more priming nucleic acid molecules under suitable polymerization conditions. In one embodiment, these conditions are provided by a reaction mixture containing ribonucleotide triphosphates (NTPs), deoxyribonucleotide triphosphates (dNTPs), dideoxyribonucleotide triphosphates (ddNTPs), or a combination thereof and a buffer containing a buffering agent, and optionally a divalent cation, and a monovalent cation.

Priming nucleic acid molecules, or "primers" generally refers to an oligonucleotide capable of acting as a point of initiation of nucleic acid synthesis when annealed to a nucleic acid template under conditions in which synthesis of a primer extension product is initiated, i.e., in the presence of nucleoside triphosphates and a polymerase in an appropriate buffer ("buffer" includes pH, ionic strength, cofactors, etc.) and at a suitable temperature. The primer typically contains 10-35 nucleotides, although the exact number is not critical to the successful application of the method. Short primer molecules generally require lower temperatures to form sufficiently stable hybrid complexes with the template.

DNA polymerases require a divalent cation for catalytic activity. Exemplary divalent cations that can be included in a reaction mixture include, but are not limited to, $Mn^{+2}$, $Mg^{+2}$, or $Co^{+2}$. The divalent cation can be supplied in the form of a salt such $MgCl_2$, $Mg(OAc)_2$, $MgSO_4$, $MnCl_2$, $Mn(OAc)_2$, or $MnSO_4$. Usable cation concentrations in a Tris-HCl buffer are for $MnCl_2$ from 0.5 to 7 mM, for example, between 0.5 and 2 mM, and for $MgCl_2$ from 0.5 to 10 mM. Usable cation concentrations in a Bicine/KOAc buffer are from 1 to 20 mM for $Mn(OAc)_2$, preferably between 2 and 5 mM.

In one embodiment, the monovalent cation is supplied by the potassium, sodium, ammonium, or lithium salts of either chloride or acetate. For KCl, the concentration is between 1 and 200 mM, preferably the concentration is between 40 and 100 mM, although the optimum concentration may vary depending on the polymerase used in the reaction.

In one embodiment, deoxyribonucleotide triphosphates are added as solutions of the salts of dATP, dCTP, dGTP, dUTP, and dTTP, such as disodium or lithium salts. In one embodiment, a final concentration in the range of 1 μM to 2 mM each is suitable, and 100-600 μM is used, although the optimal concentration of the nucleotides may vary in the reverse transcription reaction depending on the total dNTP and divalent metal ion concentration, and on the buffer, salts, particular primers, and template. For longer products, i.e., greater than 1500 bp, 500 μM each dNTP and 2 mM $MnCl_2$ may be preferred when using a Tris-HCl buffer.

In one embodiment, a suitable buffering agent is Tris-HCl, preferably pH 8.3, although the pH may be in the range 8.0-8.8. The Tris-HCl concentration is from 5-250 mM. In one embodiment, the Tris-HCl concentration is from 10-100 mM. In one embodiment, a buffering agent is Bicine-KOH, MOPS-KOH, or HEPES-KOH, with a pH in the range 7.8-8.7.

In one embodiment, EDTA less than 0.5 mM may be present in a reverse transcription reaction mix. Detergents such as Tween-20™ and Nonidet™ P-40 are present in the enzyme dilution buffers. In one embodiment, a final concentration of non-ionic detergent approximately 0.1% or less is appropriate, and will not interfere with polymerase activity. Similarly, glycerol is often present in enzyme preparations and is generally diluted to a concentration of 1-20% in the reaction mix. In one embodiment, a mineral oil overlay may be added to prevent evaporation but is not necessary.

Kits

As described above, mutant polymerases with altered error-rates have numerous molecular biology applications. Thus, the invention also provides kits comprising mutant polymerases. Such kits can comprise compositions comprising a mutant polymerase described herein together with readily available materials and reagents. In one embodiment, the kit of the invention comprises a cell modified to express a mutant polymerase of the invention. Kits preferably contain detailed instructions for how to perform the procedures for which the kits are adapted. A wide variety of kits can be prepared, depending on the intended user of the kit and the particular need of the user.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: a Highly Error-Prone Orthogonal Replication System for Rapid Evolution of Proteins and Enzymes in Yeast The key focus of these experiments was to generate an orthogonal replication system with a polymerase having an increased mutation rate. Without being bound by a particular theory, it was hypothesized that the key determinant of mutation rate is the DNA polymerase (TP-DNAP1) that replicates the p1 plasmid (FIG. 1). Therefore, the goal of these experiments was to find new TP-DNAP1 variants that have high mutation rates. Initial efforts yielded error-prone TP-DNAP1 mutants by transplanting known fidelity-reducing mutations from related family B DNA polymerases into TP-DNAP1. However, few transplanted mutations produced error-prone TP-DNAP1s that still retained activity. Therefore, current microarray DNA synthesis technologies were used to create an exhaustive scanning saturation mutagenesis library of TP-DNAP1 and screen for variants that have elevated mutation rates. Fidelity-reducing mutations identified from this screen were then grouped and select groups were cloned together to generate combinatorial libraries of TP-DNAP1. An additional screen was performed using this library, to identify TP-DNAP1 variants with further elevated mutation rates. Fidelity-reducing mutations identified from this screen were then combined with select fidelity-reducing mutations identified from the first, exhaustive screen, to generate another combinatorial library of TP-DNAP1. An additional screen was performed using this library, to identify TP-DNAP1 variants with even further elevated mutation rates.

The materials and methods employed in these experiments are now described.

Materials and Methods

Development of an Orthogonal Replication System

An extrachromosomal orthogonal error-prone replication system was developed in yeast. At its core, this system consists of a heterologous DNA polymerase/plasmid pair that is orthogonal to host replication such that the orthogonal DNA polymerase (DNAP) replicates only the orthogonal plasmid and not the host genome. By engineering the orthogonal DNAP to be error-prone, a cell that rapidly mutates only the orthogonal plasmid, encoding only genes of interest was obtained. This constitutes a general genetic system for the continuous, parallelizable, targeted, rapid evolution of user-defined genes in vivo, and a versatile synthetic biology platform for manipulating DNA replication inside a cell. The orthogonal replication system is described in detail in Ravikumar et al., Nat Chem Biol. 2014, 10(3):175-177 and Arzumanyan et al., ACS Synth. Biol. 2018, 7, 1722-1729.

Mutational Screen

To clone the scanning saturation mutagenesis library of TP-DNAP1, a pool of ~19,000 oligonucleotides (130-200-mers) was obtained from Agilent Technologies and subcloned into an expression vector for TP-DNAP1. The oligo pool was designed as 29 sub-libraries, each covering a 25-50 variable amino acid region of the TP-DNAP1 open-reading frame and flanked by ~25 bp constant regions. The variable region consisted of a replacement of each amino acid in the w.t. sequence with 19 codons representing the 19 other amino acids. The mutagenic codons were chosen from a 20-codon genetic code with a maximal codon adaptation index for the *S. cerevisiae* genome. Constant regions were chosen for efficient PCR amplification. Each sub-library was PCR amplified and assembled into corresponding PCR-amplified plasmid 2 backbones by the Gibson method (Gibson et al., 2009). Assembled sub-libraries were transformed into *E. coli* at >30-fold coverage of theoretical diversity and plated on selective LB plates. After overnight growth at 37 °C, transformants were scraped from plates and resuspended in 0.9% NaCl for plasmid extraction. Control transformations containing only the plasmid 2 backbones were similarly treated, to verify a low frequency (<5%) of carry over of the template plasmid. Plasmids were extracted from individual clones of two sub-libraries and subject to analysis via agarose gel electrophoresis and Sanger sequencing.

Figure 6:
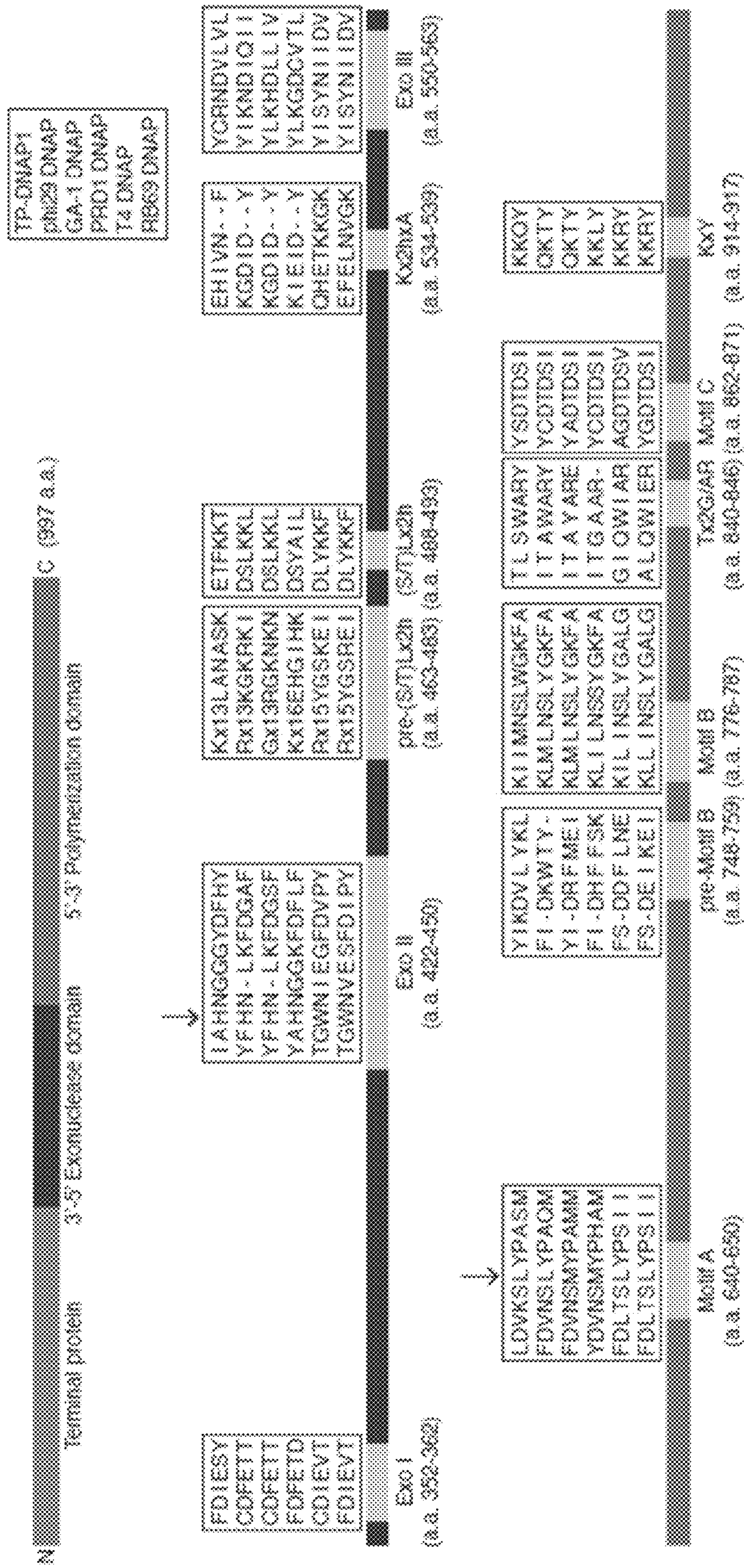
FIG. 6 depicts the architecture of TP-DNAP1, which consists of a fusion between the terminal protein, a 3'-5' proofreading exonuclease domain, and a DNA polymerization domain. Motifs responsible for fidelity in the exonuclease and proofreading domains are highlighted. A multiple sequence alignment between TP-DNAP1 and five closely related family B DNAPs, phi29 DNAP (SEQ ID NO: 53), GA-1 DNAP (SEQ ID NO: 54), PRD1 DNAP (SEQ ID NO: 55), T4 DNAP (SEQ ID NO: 56), RB69 DNAP (SEQ ID NO: 57), is shown. Noted are portions that align with corresponding portions of TP-DNAP1 of SEQ ID NO: 1: Exo I (a.a. 352-362; SEQ ID NO: 64-68, respectively), Exo II (a.a. 422-450; SEQ ID NO: 69-74, respectively), pre-(S/T)Lx2h (a.a. 463-483; SEQ ID NOs: 75-80, respectively), (S/T)Lx2h (a.a. 488-493; SEQ ID NOs: 81-84, respectively), Kx2hxA (a.a. 534-539; SEQ ID NOs: 85-89, respectively), Exo Ill (a.a. 550-563; SEQ ID NOs: 90-94, respectively), Motif A (a.a. 640-650; SEQ ID NOs: 95-99, respectively), pre-Motif B (a.a. 748-759; SEQ ID NOs: 100-105, respectively), Motif B (a.a. 776-787; SEQ ID NOs: 106-110, respectively), Tx2G/AR (a.a. 840-846; SEQ ID NOs: 111-116, respectively), Motif C (a.a 862-871; SEQ ID NOs: 117-121, respectively), and KxY (a.a. 914-917; SEQ ID NOs: 122-125, respectively).

To clone mutant TP-DNAP1 shuffling libraries, plasmids of 65 error-prone basis set mutants identified from a fidelity screen of the scanning saturation mutagenesis library were pooled and crossed by the Gibson method (Gibson et al., 2009). Since many basis set mutations encode mutations outside of strictly conserved motifs, the TP-DNAP1 open-reading frame was segmented into four regions to define broader boundaries for shuffling: the exonuclease domain (amino acids 1-596), motif A (amino acids 597-684), motif B (amino acids 685-819) and motif C (amino acids 820-987) (FIG. 6). To cross the 7 motif B basis set mutants with the 10 motif A and 8 motif C basis set mutants, the corresponding regions were PCR amplified from individual mutant TP-DNAP1 plasmids, and PCR amplicons from each region were pooled in equimolar ratios. Pooled fragments were assembled with a PCR-amplified backbone of the TP-DNAP1 expression vector, using the Gibson method (Gibson et al., 2009). Assembled libraries were transformed and extracted as described above. Shuffling libraries contained a large fraction of misassembled plasmids, as determined by agarose gel electrophoresis. The desired plasmid population was purified by gel extraction and re-transformation. Both transformation steps retained >100-fold coverage of theoretical library size. Plasmids were extracted from individual clones of the purified libraries and subject to analysis via gel electrophoresis and Sanger sequencing. To cross mutants identified from a fidelity screen of the motif A, B, and C double mutant libraries with exonuclease basis set mutants, a new region was defined to cover the double mutants (amino acids 597-987), and a similar cloning procedure was followed.

All yeast transformations (including p1 integrations) were performed as described previously (Ravikumar et al., 2014). Genomic modifications were made using a CRISPR-Cas9 system for *S. cerevisiae* (Ryan et al., 2016).

We note the following protocol modifications for library transformations: (i) 10 μg of plasmid DNA was added for each library transformation; (ii) cells were incubated at 30 °C for 45 min with rotation at ~10 r.p.m prior to heat shock; (iii) cells were resuspended in 0.9% NaCl after heat shock and a small portion was plated on selective synthetic complete (SC) medium to determine library size; (iv) the remaining resuspension was inoculated directly into 50 mL (per transformation) of selective SC media and grown to saturation at 30 °C.

Whole-cell DNA extractions followed the yeast DNA miniprep procedure described previously (Ravikumar et al., 2014). Cytoplasmic plasmid extraction followed the standard whole-cell yeast DNA extraction protocol with a few modifications: (1) cells were washing in 0.9% NaCl prior to treatment with Zymolyase (US Biological); (2) 200 μg/mL proteinase K (Fisher Scientific) was supplemented during SDS treatment for degradation of TP; (3) rotation at ~10 r.p.m was used during Zymolyase treatment.

A list of 99 homologs to TP-DNAP1 (EMBL accession number: CAA25568.1) was generated via protein BLAST (Altschul et al., 1990) with default settings. A multiple sequence alignment of TP-DNAP1 to these homologs was performed using Clustal Omega (Sievers et al., 2014) and the resulting alignment was analyzed using Jalview (Waterhouse et al., 2009).

Amino acid mutations were selected based on three criteria. First, candidate positions should be flanked on both sides by residues with sequence alignment to >75% of homologs. Second, the TP-DNAP1 amino acid at a candidate position should be represented across >25% of homologs. Third, amino acids not present in TP-DNAP1 at a candidate position should be conserved across >25% of homologs. If these criteria were met, then amino acids identified from the third criterion were introduced at the candidate position in TP-DNAP1.

All three TP-DNAP1 libraries were screened through small scale p1 fluctuation tests in a metastable *S. cerevisiae* strain, OR-Y24. OR-Y24 contains w.t. p1 and recombinant p1 that lacks w.t. TP-DNAP1, and instead, encodes a standardized fluorescence reporter of p1 copy number (Table 1), and a disabled version of the LEU2 selection marker (leu2 (Q180*)). As described previously (Ravikumar et al., 2014), leu2 (Q180*) contains a C→T mutation at base 538 in LEU2 at a site permissive to all single point mutants that generate missense mutations. Reversion to functional LEU2 can be detected on medium lacking leucine.

TABLE 1

Calibration curve of qPCR-determined p1 copy number to p1-encoded mKate2 fluorescence.

| TP-DNAP1 | mKate2 fluorescence (a.u.) | Average leu2 (Q180*) copy number per cell | Ratio |
|---|---|---|---|
| w.t. | 1455.5 | 68.9 | 0.047 |
| | 1650.14 | 88.1 | 0.053 |
| I777K | 1192.83 | 54.1 | 0.045 |
| | 1064.79 | 45.8 | 0.043 |
| I777K, L900S | 601.91 | 22.5 | 0.037 |
| | 617.55 | 38.6 | 0.063 |
| L474W, L640Y, | 298.97 | 8.63 | 0.029 |
| I777K | 180.05 | 11.1 | 0.062 |
| L477V, L640Y, | 288.24 | 16.9 | 0.058 |
| I777K, W614N | 233.35 | 15.6 | 0.067 |

Generally, to screen TP-DNAP1 mutants, OR-Y24 strains were transformed with TP-DNAP1 plasmids and the resulting yeast strains were passaged 3-4 times at 1:100 dilutions in SC-UH to fully cure w.t. p1. Cured strains were diluted 1:10,000 into selective SC media for fluctuation tests. Selective SC media used for p1 fluctuation tests lacked uracil, histidine and tryptophan, and was adjusted to pH 5.8 with NaOH (SC-UHW, pH 5.8). Absence of tryptophan and pH adjustment inhibited growth on reversion medium resulting from nonsense suppression of leu2 (Q180*). Dilutions were split into three 100 μL cultures and one 200 μL culture in 96-well trays, and cultures were grown to saturation for 2-2.5 days. Saturated 200 μL cultures were subject to a copy number measurement, as described below. The remaining three replicates were washed and resuspended in 35 μL 0.9% NaCl. 10 μL was spot plated onto solid SC medium selective for LEU2 revertants. Solid SC medium used for p1 fluctuation tests lacked uracil, histidine, tryptophan and leucine and was adjusted to pH 5.8 with NaOH (SC-UHLW, pH 5.8). Plates were incubated at 30 °C for 5-6 days, and afterwards, colony-count was determined for each spot.

Small-scale fluctuation data were analyzed by the MSS maximum-likelihood estimator method (Foster et al., 2006). Measuring cell titers was infeasible due to the large number of strains, so the average number of cells per culture was assumed to remain constant. Relative phenotypic mutation rates were calculated by normalization to p1 copy number.

Prior to screening the TP-DNAP1 scanning saturation mutagenesis library, a functional purification was imposed in OR-Y24 to eliminate frame-shifted TP-DNAP1 variants, which were common due to errors in oligonucleotide synthesis. The pilot study shown confirmed that sub-libraries transformed into OR-Y24 are enriched for full-length TP- DNAP1 variants after two passages in SC media lacking uracil and histidine (SC-UH). To purify the entire scanning saturation mutagenesis library, the remaining 27 TP-DNAP1 plasmid sub-libraries were individually transformed into OR-Y24, and the resulting yeast sub-libraries were passaged twice at 1:100 dilutions in SC-UH. Passaged yeast sub-libraries were individually plated on solid SC medium lacking histidine. For each sub-library, 24 colonies were propagated in small cultures of SC-UH, in order to verify that >90% of clones robustly grow under selection for p1 replication. Afterwards, purified yeast sub-libraries were plated on solid media and colonies from each were individually inoculated into small cultures of SC-UH at ~1-fold coverage of theoretical sub-library diversity. This resulted in a total of 13,625 clones. (This does not include sub-libraries 10-10, which correspond to the putative N-terminal TP of TP-DNAP1, which should not influence fidelity. These sub-libraries were cloned and purified, but omitted from the screen.) The arrayed clones were then cured of w.t. p1 and subject to small-scale p1 fluctuation tests, as described above. Then, 376 clones with the highest relative phenotypic mutation rates were subject to an additional small-scale p1 fluctuation test with six replicates. TP-DNAP1 expression vectors were isolated from 95 yeast clones with the highest relative phenotypic mutation rates and subject to Sanger sequencing. These TP-DNAP1s were characterized with large-scale p1 fluctuation tests, as described below.

Large-scale fluctuation tests of p1-encoded leu2 (Q180*) were performed to precisely determine per-base substitution rates for individually cloned or isolated TP-DNAP1 variants. Large-scale p1 fluctuation tests are performed similarly to small-scale p1 fluctuation tests, with several modifications. First, large-scale p1 fluctuation tests were typically performed with 36-48 replicates. For highly error-prone TP-DNAP1s obtained from later rounds of screening, fewer replicates (3-16) were used, which is sufficient for similar precision (Foster et al., 2006). Second, p1 copy number was determined by the flow cytometry method, described below. Third, cell titers were measured for each fluctuation test to estimate the average number of cells per culture. Cell resuspensions were diluted and plated on solid SC-UH medium, and colony counts were determined after incubation at 30 °C for 2-3 days. Alternatively, cell resuspensions were diluted and subject to an event-count measurement via flow cytometry. Fourth, inoculums of highly error-prone TP-DNAP1s occasionally contained pre-existing mutants, despite the 1:10,000 dilution, so mutant frequencies were estimated by plating pre-cultures on solid SC-UHLW, pH 5.8 medium. Plates were incubated for 2-3 days, in parallel with cultures grown for fluctuation tests. Pre-culture mutant titers were counted to estimate the number of replicates in the fluctuation test expected to contain pre-existing mutants (n). Revertants were counted from all replicates of the fluctuation tests, counts were sorted, and n replicates with the highest counts were omitted from calculations.

To calculate per-base substitution rates, fluctuation data were analyzed by the maximum likelihood method, implemented using newton.LD.plating in rSalvador 1.7 (Zheng, 2017). Phenotypic mutation rates were calculated by normalizing to the average number of cells per culture. Phenotypic mutation rates were divided by the measured p1 copy number and by the number of ways leu2 (Q180*) can revert to LEU2 (2.33 for the ochre codon) to yield per-base substitution rates. 95% confidence intervals were similarly scaled by these factors. All data related to large-scale p1 fluctuation tests are fully described in Table 2.

TABLE 2

Mutation-prone TP-DNAP1 Candidates

| TP-DNAP1 | p1 copy number (n) | Mutation rate (s.p.b.) | Lower 95% C.I. (s.p.b.) | Upper 95% C.I. (s.p.b.) | Number of replicates | Notes |
|---|---|---|---|---|---|---|
| K302G | 87.8 (1) | $2.27 \times 10^{-9}$ | $1.57 \times 10^{-9}$ | $3.15 \times 10^{-9}$ | 36 | From saturation mutagenesis library |
| T352E | 31.8 (1) | $4.58 \times 10^{-9}$ | $3.12 \times 10^{-9}$ | $3.12 \times 10^{-9}$ | 34 | From homology study |
| C354F | 25.1 (1) | $3.86 \times 10^{-9}$ | $2.46 \times 10^{-9}$ | $2.46 \times 10^{-9}$ | 36 | From homology study |
| F355M | 88.8 (1) | $4.63 \times 10^{-9}$ | $3.22 \times 10^{-9}$ | $6.35 \times 10^{-9}$ | 36 | From saturation mutagenesis library |
| Y360F | 47 (1) | $3.76 \times 10^{-9}$ | $2.65 \times 10^{-9}$ | $2.65 \times 10^{-9}$ | 36 | From homology study |
| N371A | 16.6 (1) | $6.03 \times 10^{-8}$ | $4.69 \times 10^{-8}$ | $7.54 \times 10^{-8}$ | 36 | From saturation mutagenesis library; Rd2 mutant |
| N371C | 26.9 (1) | $1.08 \times 10^{-8}$ | $7.85 \times 10^{-9}$ | $1.42 \times 10^{-8}$ | 36 | From saturation mutagenesis library; Rd2 mutant |
| N371M | 23.3 (1) | $1.56 \times 10^{-8}$ | $1.14 \times 10^{-8}$ | $2.06 \times 10^{-8}$ | 36 | From saturation mutagenesis library; Rd2 mutant |
| | 27 (1) | $1.10 \times 10^{-8}$ | $7.53 \times 10^{-9}$ | $1.53 \times 10^{-8}$ | 36 | |
| C376I | 58.1 (1) | $1.73 \times 10^{-9}$ | $1.13 \times 10^{-9}$ | $1.13 \times 10^{-9}$ | 33 | From homology study |
| K384D | 91.1 (1) | $2.84 \times 10^{-9}$ | $1.88 \times 10^{-9}$ | $4.06 \times 10^{-9}$ | 36 | From saturation mutagenesis library |
| V405I | 68.3 (1) | $2.34 \times 10^{-9}$ | $1.63 \times 10^{-9}$ | $1.63 \times 10^{-9}$ | 36 | From homology study |
| D407Q | 176 (1) | $1.50 \times 10^{-9}$ | $8.05 \times 10^{-10}$ | $2.50 \times 10^{-9}$ | 48 | From saturation mutagenesis library |
| | 160 (1) | $1.31 \times 10^{-9}$ | $6.33 \times 10^{-10}$ | $2.35 \times 10^{-9}$ | 48 | |
| G410H, N423Q | 55.4 (1) | $4.77 \times 10^{-8}$ | $3.94 \times 10^{-8}$ | $5.62 \times 10^{-8}$ | 24 | From saturation mutagenesis library; Rd2 mutant |
| | 60.3 (1) | $3.91 \times 10^{-8}$ | $3.21 \times 10^{-8}$ | $4.63 \times 10^{-8}$ | 24 | |
| | 61.7 (1) | $3.50 \times 10^{-8}$ | $2.97 \times 10^{-8}$ | $4.05 \times 10^{-8}$ | 36 | |
| G410Y | 138 (1) | $1.06 \times 10^{-9}$ | $6.42 \times 10^{-10}$ | $1.61 \times 10^{-9}$ | 24 | From saturation mutagenesis library |
| | 132 (1) | $3.08 \times 10^{-10}$ | $1.23 \times 10^{-10}$ | $6.20 \times 10^{-10}$ | 24 | |
| E411T, G426C | 31.7 (1) | $3.42 \times 10^{-9}$ | $2.05 \times 10^{-9}$ | $5.28 \times 10^{-9}$ | 24 | From saturation mutagenesis library |
| | 42.2 (1) | $3.10 \times 10^{-9}$ | $1.82 \times 10^{-9}$ | $4.81 \times 10^{-9}$ | 24 | |
| | 46 (1) | $1.84 \times 10^{-9}$ | $9.68 \times 10^{-10}$ | $3.10 \times 10^{-9}$ | 24 | |
| | 39.8 (1) | $1.58 \times 10^{-9}$ | $8.04 \times 10^{-10}$ | $2.72 \times 10^{-9}$ | 24 | |

TABLE 2-continued

Mutation-prone TP-DNAP1 Candidates

| TP-DNAP1 | p1 copy number (n) | Mutation rate (s.p.b.) | Lower 95% C.I. (s.p.b.) | Upper 95% C.I. (s.p.b.) | Number of replicates | Notes |
|---|---|---|---|---|---|---|
| N413I | 25.6 (1) | $7.89 \times 10^{-9}$ | $3.62 \times 10^{-9}$ | $1.46 \times 10^{-8}$ | 48 | From saturation |
| | 32.3 (1) | $4.47 \times 10^{-9}$ | $1.78 \times 10^{-9}$ | $9.04 \times 10^{-9}$ | 48 | mutagenesis library |
| | 41.4 (1) | $4.14 \times 10^{-9}$ | $1.78 \times 10^{-9}$ | $7.99 \times 10^{-9}$ | 48 | |
| | 33.4 (1) | $2.30 \times 10^{-9}$ | $5.73 \times 10^{-10}$ | $5.96 \times 10^{-9}$ | 45 | |
| I414H | 81.4 (1) | $1.87 \times 10^{-9}$ | $1.16 \times 10^{-9}$ | $2.79 \times 10^{-9}$ | 24 | From saturation |
| | 94 (1) | $8.43 \times 10^{-10}$ | $4.34 \times 10^{-10}$ | $1.44 \times 10^{-9}$ | 24 | mutagenesis library |
| I420Y | 3.52 (1) | $2.45 \times 10^{-9}$ | $4.08 \times 10^{-10}$ | $4.08 \times 10^{-10}$ | 35 | From homology study |
| A421N | 5.73 (1) | $9.76 \times 10^{-8}$ | $5.94 \times 10^{-8}$ | $1.49 \times 10^{-7}$ | 46 | From saturation |
| | 7.37 (1) | $7.80 \times 10^{-8}$ | $4.62 \times 10^{-8}$ | $1.21 \times 10^{-7}$ | 45 | mutagenesis library; Rd2 mutant |
| A421S | 33.6 (1) | $7.31 \times 10^{-9}$ | $5.34 \times 10^{-9}$ | $9.65 \times 10^{-9}$ | 36 | From saturation mutagenesis library; Rd2 mutant |
| N423R | 36.5 (1) | $3.67 \times 10^{-8}$ | $3.02 \times 10^{-8}$ | $4.36 \times 10^{-8}$ | 36 | From saturation |
| | 37.1 (1) | $3.27 \times 10^{-8}$ | $2.67 \times 10^{-8}$ | $3.92 \times 10^{-8}$ | 36 | mutagenesis library; Rd2 |
| | 37.6 (1) | $2.57 \times 10^{-8}$ | $1.99 \times 10^{-8}$ | $3.19 \times 10^{-8}$ | 24 | mutant |
| | 43.3 (1) | $2.07 \times 10^{-8}$ | $1.59 \times 10^{-8}$ | $2.60 \times 10^{-8}$ | 24 | |
| | 43.9 (1) | $1.97 \times 10^{-8}$ | $1.52 \times 10^{-8}$ | $2.47 \times 10^{-8}$ | 24 | |
| | 69.5 (1) | $1.55 \times 10^{-8}$ | $1.20 \times 10^{-8}$ | $1.93 \times 10^{-8}$ | 23 | |
| N423D | 4.61 (1) | $5.14 \times 10^{-7}$ | $3.89 \times 10^{-7}$ | $6.58 \times 10^{-7}$ | 48 | From Ravikumar et al., |
| | 4.84 (1) | $4.03 \times 10^{-7}$ | $2.99 \times 10^{-7}$ | $5.24 \times 10^{-7}$ | 48 | 2014; Rd1 mutant |
| | 10.6 (3) | $1.74 \times 10^{-7}$ | $1.49 \times 10^{-7}$ | $2.01 \times 10^{-7}$ | 48 | |
| | 9.48 (3) | $1.82 \times 10^{-7}$ | $1.52 \times 10^{-7}$ | $2.14 \times 10^{-7}$ | 44 | |
| | 7.46 (3) | $2.49 \times 10^{-7}$ | $2.07 \times 10^{-7}$ | $2.94 \times 10^{-7}$ | 45 | |
| N423E | 12.6 (1) | $2.67 \times 10^{-7}$ | $2.04 \times 10^{-7}$ | $3.39 \times 10^{-7}$ | 48 | From saturation |
| | 17.5 (1) | $1.81 \times 10^{-7}$ | $1.27 \times 10^{-7}$ | $2.48 \times 10^{-7}$ | 42 | mutagenesis library; Rd2 mutant |
| N423Q | 36.2 (1) | $6.43 \times 10^{-8}$ | $5.34 \times 10^{-8}$ | $7.59 \times 10^{-8}$ | 36 | From saturation |
| | 20.3 (1) | $6.19 \times 10^{-8}$ | $4.94 \times 10^{-8}$ | $7.52 \times 10^{-8}$ | 24 | mutagenesis library; Rd2 |
| | 25.8 (1) | $5.89 \times 10^{-8}$ | $4.78 \times 10^{-8}$ | $7.07 \times 10^{-8}$ | 36 | mutant |
| | 18.1 (1) | $5.26 \times 10^{-8}$ | $4.11 \times 10^{-8}$ | $6.52 \times 10^{-8}$ | 24 | |
| | 23.7 (1) | $4.86 \times 10^{-8}$ | $3.82 \times 10^{-8}$ | $5.98 \times 10^{-8}$ | 24 | |
| | 46.8 (1) | $3.10 \times 10^{-8}$ | $2.49 \times 10^{-8}$ | $3.74 \times 10^{-8}$ | 24 | |
| N423W | 22.5 (1) | $4.67 \times 10^{-9}$ | $2.96 \times 10^{-9}$ | $2.96 \times 10^{-9}$ | 35 | From homology study |
| N423Y | 4.65 (1) | $1.29 \times 10^{-9}$ | $7.36 \times 10^{-11}$ | $7.36 \times 10^{-11}$ | 34 | From homology study |
| G425S | 42.9 (1) | $3.04 \times 10^{-9}$ | $2.05 \times 10^{-9}$ | $2.05 \times 10^{-9}$ | 36 | From homology study |
| G426A | 52.2 (1) | $3.35 \times 10^{-9}$ | $2.35 \times 10^{-9}$ | $2.35 \times 10^{-9}$ | 36 | From homology study |
| G426K | 106 (1) | $1.31 \times 10^{-9}$ | $7.67 \times 10^{-10}$ | $2.04 \times 10^{-9}$ | 24 | From saturation |
| | 153 (1) | $1.25 \times 10^{-9}$ | $7.87 \times 10^{-10}$ | $1.85 \times 10^{-9}$ | 24 | mutagenesis library |
| G426P | 20.2 (1) | $1.52 \times 10^{-8}$ | $1.09 \times 10^{-8}$ | $2.02 \times 10^{-8}$ | 36 | From saturation mutagenesis library; Rd2 mutant |
| Y427A | 6.36 (3) | $2.14 \times 10^{-8}$ | $5.36 \times 10^{-9}$ | $5.51 \times 10^{-8}$ | 24 | From Ravikumar et al., 2014; Rd1 mutant |
| Y427N | 2.28 (1) | $1.65 \times 10^{-7}$ | $1.25 \times 10^{-7}$ | $1.25 \times 10^{-7}$ | 36 | From homology study; Rd1 mutant |
| Y427D | 1.49 (1) | $7.16 \times 10^{-8}$ | $4.41 \times 10^{-8}$ | $4.41 \times 10^{-8}$ | 36 | From homology study; Rd1 mutant |
| Y427G | 2.92 (1) | $7.31 \times 10^{-8}$ | $5.20 \times 10^{-8}$ | $5.20 \times 10^{-8}$ | 36 | From homology study; Rd1 mutant |
| Y427H | 15.4 (1) | $5.93 \times 10^{-8}$ | $4.14 \times 10^{-8}$ | $8.11 \times 10^{-8}$ | 36 | From saturation mutagenesis library; Rd2 mutant |
| Y427K | 7.09 (1) | $3.89 \times 10^{-8}$ | $2.88 \times 10^{-8}$ | $2.88 \times 10^{-8}$ | 36 | From homology study; Rd1 mutant |
| H430Q | 1.85 (1) | $3.84 \times 10^{-8}$ | $2.07 \times 10^{-8}$ | $2.07 \times 10^{-8}$ | 36 | From homology study; Rd1 mutant |
| Y431H | 31.7 (1) | $3.82 \times 10^{-8}$ | $3.10 \times 10^{-8}$ | $4.59 \times 10^{-8}$ | 36 | From saturation mutagenesis library; Rd2 mutant |
| P439A | 1.74 (1) | $2.14 \times 10^{-8}$ | $9.21 \times 10^{-9}$ | $9.21 \times 10^{-9}$ | 36 | From homology study; Rd1 mutant |
| N450P | 19.2 (1) | $4.19 \times 10^{-8}$ | $3.29 \times 10^{-8}$ | $5.17 \times 10^{-8}$ | 36 | From saturation mutagenesis library; Rd2 mutant |
| L473Y | 19.1 (1) | $1.90 \times 10^{-8}$ | $1.32 \times 10^{-8}$ | $2.61 \times 10^{-8}$ | 36 | From saturation mutagenesis library; Rd2 mutant |
| L474F | 17.2 (1) | $5.65 \times 10^{-8}$ | $4.42 \times 10^{-8}$ | $7.00 \times 10^{-8}$ | 36 | From saturation mutagenesis library; Rd2 mutant |
| L474W | 33.4 (1) | $1.02 \times 10^{-8}$ | $7.51 \times 10^{-9}$ | $1.34 \times 10^{-8}$ | 36 | From saturation |
| | 34.3 (1) | $9.92 \times 10^{-9}$ | $7.16 \times 10^{-9}$ | $1.32 \times 10^{-8}$ | 36 | mutagenesis library; Rd2 mutant |

TABLE 2-continued

Mutation-prone TP-DNAP1 Candidates

| TP-DNAP1 | p1 copy number (n) | Mutation rate (s.p.b.) | Lower 95% C.I. (s.p.b.) | Upper 95% C.I. (s.p.b.) | Number of replicates | Notes |
|---|---|---|---|---|---|---|
| L477I | 63.1 (1) | $4.33 \times 10^{-9}$ | $2.83 \times 10^{-9}$ | $6.24 \times 10^{-9}$ | 36 | From saturation mutagenesis library |
| L477T | 16 (1) | $1.08 \times 10^{-7}$ | $8.86 \times 10^{-8}$ | $1.29 \times 10^{-7}$ | 36 | From saturation mutagenesis library; Rd2 mutant |
| L477V | 36.4 (1) | $2.06 \times 10^{-8}$ | $1.62 \times 10^{-8}$ | $2.54 \times 10^{-8}$ | 36 | From saturation |
| | 46.2 (1) | $1.64 \times 10^{-8}$ | $1.22 \times 10^{-8}$ | $2.14 \times 10^{-8}$ | 36 | mutagenesis library; Rd2 mutant |
| N479P | 23.3 (1) | $8.02 \times 10^{-9}$ | $5.37 \times 10^{-9}$ | $1.13 \times 10^{-8}$ | 36 | From saturation mutagenesis library; Rd2 mutant |
| S481F | 25.5 (1) | $1.44 \times 10^{-8}$ | $1.04 \times 10^{-8}$ | $1.91 \times 10^{-8}$ | 36 | From saturation mutagenesis library; Rd2 mutant |
| K492T | 18.3 (1) | $4.94 \times 10^{-8}$ | $3.94 \times 10^{-8}$ | $6.04 \times 10^{-8}$ | 36 | From saturation |
| | 20 (1) | $4.40 \times 10^{-8}$ | $3.48 \times 10^{-8}$ | $5.41 \times 10^{-8}$ | 36 | mutagenesis library; Rd2 mutant |
| K492V | 21.2 (1) | $2.69 \times 10^{-8}$ | $2.05 \times 10^{-8}$ | $3.43 \times 10^{-8}$ | 36 | From saturation mutagenesis library; Rd2 |
| | 27.3 (1) | $2.03 \times 10^{-8}$ | $1.56 \times 10^{-8}$ | $2.57 \times 10^{-8}$ | 36 | mutant |
| T493P | 16.2 (1) | $4.95 \times 10^{-8}$ | $3.89 \times 10^{-8}$ | $6.13 \times 10^{-8}$ | 36 | From saturation |
| | 16.8 (1) | $3.75 \times 10^{-8}$ | $2.39 \times 10^{-8}$ | $5.50 \times 10^{-8}$ | 36 | mutagenesis library; Rd2 mutant |
| H497N | 15.7 (1) | $5.37 \times 10^{-8}$ | $4.03 \times 10^{-8}$ | $6.91 \times 10^{-8}$ | 36 | From saturation |
| | 15 (1) | $3.25 \times 10^{-8}$ | $2.43 \times 10^{-8}$ | $4.20 \times 10^{-8}$ | 36 | mutagenesis library; Rd2 mutant |
| K511H | 60.6 (1) | $1.49 \times 10^{-9}$ | $8.81 \times 10^{-10}$ | $2.32 \times 10^{-9}$ | 36 | From saturation mutagenesis library |
| S514R | 64.3 (1) | $3.57 \times 10^{-9}$ | $2.57 \times 10^{-9}$ | $4.77 \times 10^{-9}$ | 36 | From saturation mutagenesis library |
| S533I | 48.9 (1) | $1.86 \times 10^{-9}$ | $1.10 \times 10^{-9}$ | $2.89 \times 10^{-9}$ | 36 | From saturation mutagenesis library |
| I549L | 52.7 (1) | $3.75 \times 10^{-9}$ | $2.63 \times 10^{-9}$ | $2.63 \times 10^{-9}$ | 35 | From homology study |
| E550D | 56.3 (1) | $2.36 \times 10^{-9}$ | $1.60 \times 10^{-9}$ | $1.60 \times 10^{-9}$ | 36 | From homology study |
| C556G | 32.6 (1) | $1.36 \times 10^{-8}$ | $9.85 \times 10^{-9}$ | $1.81 \times 10^{-8}$ | 36 | From saturation |
| | 33.3 (1) | $9.37 \times 10^{-9}$ | $6.41 \times 10^{-9}$ | $1.30 \times 10^{-8}$ | 36 | mutagenesis library; Rd2 |
| | 35.4 (1) | $7.27 \times 10^{-9}$ | $5.21 \times 10^{-9}$ | $9.72 \times 10^{-9}$ | 36 | mutant |
| C556T | 16.9 (1) | $4.10 \times 10^{-8}$ | $3.04 \times 10^{-8}$ | $5.34 \times 10^{-8}$ | 36 | From saturation mutagenesis library; Rd2 mutant |
| R557A | 41.4 (1) | $1.90 \times 10^{-9}$ | $1.06 \times 10^{-9}$ | $3.06 \times 10^{-9}$ | 36 | From saturation mutagenesis library |
| R557C | 43.8 (1) | $2.65 \times 10^{-9}$ | $1.73 \times 10^{-9}$ | $1.73 \times 10^{-9}$ | 35 | From homology study |
| N558S | 14.1 (1) | $7.90 \times 10^{-9}$ | $4.39 \times 10^{-9}$ | $1.29 \times 10^{-8}$ | 36 | From saturation mutagenesis library; Rd2 mutant |
| L561I | 54.1 (1) | $2.84 \times 10^{-9}$ | $1.94 \times 10^{-9}$ | $1.94 \times 10^{-9}$ | 36 | From homology study |
| S564A | 53.7 (1) | $2.67 \times 10^{-9}$ | $1.84 \times 10^{-9}$ | $1.84 \times 10^{-9}$ | 36 | From homology study |
| E569A | 52 (1) | $2.51 \times 10^{-9}$ | $1.69 \times 10^{-9}$ | $1.69 \times 10^{-9}$ | 36 | From homology study |
| E569K | 48.7 (1) | $2.72 \times 10^{-9}$ | $1.82 \times 10^{-9}$ | $1.82 \times 10^{-9}$ | 36 | From homology study |
| E569P | 3.72 (1) | $3.20 \times 10^{-8}$ | $1.90 \times 10^{-8}$ | $1.90 \times 10^{-8}$ | 36 | From homology study; Rd1 mutant |
| A573T | 32.9 (1) | $5.24 \times 10^{-9}$ | $3.37 \times 10^{-9}$ | $7.65 \times 10^{-9}$ | 36 | From saturation |
| | 34.8 (1) | $4.82 \times 10^{-9}$ | $3.25 \times 10^{-9}$ | $6.77 \times 10^{-9}$ | 36 | mutagenesis library; Rd2 mutant |
| V574F | 20.9 (1) | $1.04 \times 10^{-8}$ | $7.17 \times 10^{-9}$ | $1.43 \times 10^{-8}$ | 36 | From saturation mutagenesis library; Rd2 mutant |
| V574L | 31.2 (1) | $9.34 \times 10^{-9}$ | $6.35 \times 10^{-9}$ | $1.30 \times 10^{-8}$ | 36 | From saturation mutagenesis library; Rd2 mutant |
| E575L | 35.5 (1) | $3.72 \times 10^{-9}$ | $2.45 \times 10^{-9}$ | $5.32 \times 10^{-9}$ | 36 | From saturation mutagenesis library |
| F578I | 22.8 (1) | $6.37 \times 10^{-9}$ | $4.12 \times 10^{-9}$ | $9.26 \times 10^{-9}$ | 36 | From saturation |
| | 22.7 (1) | $5.82 \times 10^{-9}$ | $3.54 \times 10^{-9}$ | $8.85 \times 10^{-9}$ | 36 | mutagenesis library; Rd2 |
| | 26.6 (1) | $4.38 \times 10^{-9}$ | $2.75 \times 10^{-9}$ | $6.51 \times 10^{-9}$ | 36 | mutant |
| L592M | 51.3 (1) | $1.28 \times 10^{-9}$ | $7.43 \times 10^{-10}$ | $7.43 \times 10^{-10}$ | 36 | From homology study |
| A599S, | 49.4 (3) | $3.33 \times 10^{-9}$ | $2.47 \times 10^{-9}$ | $4.35 \times 10^{-9}$ | 48 | From saturation |
| C639T | 54.7 (1) | $2.53 \times 10^{-9}$ | $1.61 \times 10^{-9}$ | $3.71 \times 10^{-9}$ | 36 | mutagenesis library |
| D614L | 50.5 (3) | $3.22 \times 10^{-9}$ | $1.48 \times 10^{-9}$ | $5.98 \times 10^{-9}$ | 45 | From homology study |
| M618V | 99.8 (1) | $2.20 \times 10^{-9}$ | $1.58 \times 10^{-9}$ | $1.58 \times 10^{-9}$ | 35 | From homology study |
| E620D | 20.8 (1) | $3.68 \times 10^{-9}$ | $2.11 \times 10^{-9}$ | $2.11 \times 10^{-9}$ | 36 | From homology study |
| A621K | 6.3 (1) | $2.35 \times 10^{-9}$ | $5.85 \times 10^{-10}$ | $5.85 \times 10^{-10}$ | 36 | From homology study |
| A621S | 63.5 (1) | $4.02 \times 10^{-9}$ | $2.94 \times 10^{-9}$ | $2.94 \times 10^{-9}$ | 35 | From homology study |

TABLE 2-continued

Mutation-prone TP-DNAP1 Candidates

| TP-DNAP1 | p1 copy number (n) | Mutation rate (s.p.b.) | Lower 95% C.I. (s.p.b.) | Upper 95% C.I. (s.p.b.) | Number of replicates | Notes |
|---|---|---|---|---|---|---|
| L622I, | 31.3 (3) | $4.78 \times 10^{-8}$ | $4.12 \times 10^{-8}$ | $5.46 \times 10^{-8}$ | 48 | From saturation |
| C639I | 42.9 (1) | $3.70 \times 10^{-8}$ | $3.06 \times 10^{-8}$ | $4.38 \times 10^{-8}$ | 36 | mutagenesis library; Rd2 mutant |
| C627V | 42.7 (1) | $4.73 \times 10^{-9}$ | $3.35 \times 10^{-9}$ | $3.35 \times 10^{-9}$ | 36 | From homology study |
| V630K | 57.3 (1) | $3.26 \times 10^{-9}$ | $2.28 \times 10^{-9}$ | $2.28 \times 10^{-9}$ | 36 | From homology study |
| V630Y | 50.7 (1) | $2.48 \times 10^{-9}$ | $1.59 \times 10^{-9}$ | $1.59 \times 10^{-9}$ | 35 | From homology study |
| N631A | 42.3 (1) | $1.87 \times 10^{-9}$ | $1.12 \times 10^{-9}$ | $2.90 \times 10^{-9}$ | 36 | From saturation mutagenesis library |
| C639V | 52.8 (1) | $2.54 \times 10^{-9}$ | $1.73 \times 10^{-9}$ | $1.73 \times 10^{-9}$ | 36 | From homology study |
| C639Y | 67.6 (3) | $2.90 \times 10^{-9}$ | $1.16 \times 10^{-9}$ | $5.88 \times 10^{-9}$ | 48 | From homology study |
| L640A | 4.26 (3) | $2.47 \times 10^{-7}$ | $1.54 \times 10^{-7}$ | $3.71 \times 10^{-7}$ | 45 | From homology study; Rd1 mutant |
| L640N | 5.62 (1) | $6.60 \times 10^{-9}$ | $2.84 \times 10^{-9}$ | $2.84 \times 10^{-9}$ | 36 | From homology study; Rd1 mutant |
| L640D | 4.51 (1) | $1.05 \times 10^{-9}$ | $6.00 \times 10^{-11}$ | $6.00 \times 10^{-11}$ | 36 | From homology study |
| L640G | 30 (1) | $7.47 \times 10^{-9}$ | $5.27 \times 10^{-9}$ | $5.27 \times 10^{-9}$ | 36 | From homology study; Rd1 mutant |
| | 38.8 (1) | $5.25 \times 10^{-9}$ | $3.67 \times 10^{-9}$ | $7.16 \times 10^{-9}$ | 36 | From saturation mutagenesis library; Rd1 mutant |
| L640K | 5.98 (1) | $1.75 \times 10^{-9}$ | $2.92 \times 10^{-10}$ | $2.92 \times 10^{-10}$ | 35 | From homology study |
| L640F | 19.7 (3) | $1.10 \times 10^{-8}$ | $5.52 \times 10^{-9}$ | $1.91 \times 10^{-8}$ | 47 | From homology study; Rd1 mutant |
| L640W | 51.6 (1) | $2.25 \times 10^{-9}$ | $1.51 \times 10^{-9}$ | $1.51 \times 10^{-9}$ | 36 | From homology study |
| L640Y | 59.3 (3) | $6.51 \times 10^{-9}$ | $3.85 \times 10^{-9}$ | $1.01 \times 10^{-8}$ | 46 | From homology study; Rd1 mutant |
| K643N | 37.4 (1) | $2.69 \times 10^{-9}$ | $1.68 \times 10^{-9}$ | $1.68 \times 10^{-9}$ | 36 | From homology study |
| K643S | 3.34 (1) | $2.42 \times 10^{-9}$ | $8.52 \times 10^{-10}$ | $8.52 \times 10^{-10}$ | 35 | From homology study |
| K643V | 7.31 (1) | $5.92 \times 10^{-10}$ | $1.47 \times 10^{-10}$ | $1.47 \times 10^{-10}$ | 36 | From homology study |
| L645N | 12.1 (3) | $6.21 \times 10^{-9}$ | $2.36 \times 10^{-9}$ | $1.13 \times 10^{-8}$ | 48 | From homology study |
| L645M | 69.1 (3) | $1.52 \times 10^{-8}$ | $8.75 \times 10^{-9}$ | $2.39 \times 10^{-8}$ | 21 | From homology study; Rd1 mutant |
| Y646A | 3.46 (1) | $2.25 \times 10^{-9}$ | $3.74 \times 10^{-10}$ | $3.74 \times 10^{-10}$ | 36 | From homology study |
| Y646F | 22.3 (1) | $4.42 \times 10^{-9}$ | $2.78 \times 10^{-9}$ | $2.78 \times 10^{-9}$ | 36 | From homology study |
| A648S | 30.2 (1) | $1.80 \times 10^{-9}$ | $9.99 \times 10^{-10}$ | $9.99 \times 10^{-10}$ | 35 | From homology study |
| S649A | 46.1 (1) | $3.88 \times 10^{-9}$ | $2.73 \times 10^{-9}$ | $2.73 \times 10^{-9}$ | 35 | From homology study |
| F652G | 58.5 (1) | $1.62 \times 10^{-9}$ | $9.06 \times 10^{-10}$ | $2.64 \times 10^{-9}$ | 24 | From saturation |
| | 56 (1) | $1.29 \times 10^{-9}$ | $6.33 \times 10^{-10}$ | $2.27 \times 10^{-9}$ | 23 | mutagenesis library |
| F652L | 2.45 (1) | $1.62 \times 10^{-8}$ | $7.00 \times 10^{-9}$ | $7.00 \times 10^{-9}$ | 36 | From homology study; Rd1 mutant |
| Y653R | 26.1 (1) | $3.08 \times 10^{-9}$ | $1.83 \times 10^{-9}$ | $1.83 \times 10^{-9}$ | 35 | From homology study |
| Y653H | 40.6 (1) | $2.79 \times 10^{-9}$ | $1.76 \times 10^{-9}$ | $1.76 \times 10^{-9}$ | 36 | From homology study |
| Y653L | 2.81 (1) | $1.42 \times 10^{-8}$ | $6.13 \times 10^{-9}$ | $6.13 \times 10^{-9}$ | 36 | From homology study; Rd1 mutant |
| Q655H | 37.9 (1) | $2.08 \times 10^{-9}$ | $1.26 \times 10^{-9}$ | $1.26 \times 10^{-9}$ | 36 | From homology study |
| P656A | 24.5 (1) | $6.17 \times 10^{-9}$ | $4.18 \times 10^{-9}$ | $4.18 \times 10^{-9}$ | 36 | From homology study; Rd1 mutant |
| R662T | 106 (1) | $1.83 \times 10^{-9}$ | $1.21 \times 10^{-9}$ | $2.61 \times 10^{-9}$ | 36 | From saturation |
| | 109 (1) | $1.26 \times 10^{-9}$ | $8.34 \times 10^{-10}$ | $1.81 \times 10^{-9}$ | 36 | mutagenesis library |
| S664H | 56 (1) | $1.57 \times 10^{-9}$ | $8.58 \times 10^{-10}$ | $2.58 \times 10^{-9}$ | 36 | From saturation |
| | 63.7 (1) | $1.27 \times 10^{-9}$ | $6.69 \times 10^{-10}$ | $2.12 \times 10^{-9}$ | 36 | mutagenesis library |
| I708Q | 122 (1) | $9.31 \times 10^{-10}$ | $6.05 \times 10^{-10}$ | $1.35 \times 10^{-9}$ | 36 | From saturation mutagenesis library |
| N725R | 54.6 (1) | $2.70 \times 10^{-9}$ | $1.80 \times 10^{-9}$ | $3.83 \times 10^{-9}$ | 36 | From saturation mutagenesis library |
| K769G | 49.9 (1) | $3.74 \times 10^{-9}$ | $2.57 \times 10^{-9}$ | $5.17 \times 10^{-9}$ | 36 | From saturation mutagenesis library |
| N773Q | 46 (1) | $4.80 \times 10^{-9}$ | $3.46 \times 10^{-9}$ | $3.46 \times 10^{-9}$ | 36 | From homology study |
| V774A | 52.8 (1) | $2.41 \times 10^{-9}$ | $1.59 \times 10^{-9}$ | $1.59 \times 10^{-9}$ | 36 | From homology study |
| V774I | 22.7 (1) | $9.02 \times 10^{-9}$ | $6.46 \times 10^{-9}$ | $6.46 \times 10^{-9}$ | 35 | From homology study; Rd1 mutant |
| I775A | 16.1 (3) | $8.66 \times 10^{-9}$ | $4.09 \times 10^{-9}$ | $1.44 \times 10^{-8}$ | 47 | From homology study; Rd1 |
| | 45.7 (1) | $3.05 \times 10^{-9}$ | $2.06 \times 10^{-9}$ | $2.06 \times 10^{-9}$ | 36 | mutant |
| I777A | 28.5 (1) | $8.63 \times 10^{-9}$ | $6.40 \times 10^{-9}$ | $6.40 \times 10^{-9}$ | 36 | From homology study; Rd1 mutant |
| I777K | 19.6 (3) | $2.39 \times 10^{-8}$ | $1.95 \times 10^{-8}$ | $2.88 \times 10^{-8}$ | 48 | From saturation |
| | 46.6 (1) | $8.06 \times 10^{-9}$ | $6.15 \times 10^{-9}$ | $1.02 \times 10^{-8}$ | 36 | mutagenesis library; Rd2 |
| | 49.8 (1) | $7.12 \times 10^{-9}$ | $5.21 \times 10^{-9}$ | $9.36 \times 10^{-9}$ | 36 | mutant |
| | 28.9 (3) | $1.68 \times 10^{-8}$ | $1.35 \times 10^{-8}$ | $2.05 \times 10^{-8}$ | 45 | |
| | 24.8 (3) | $2.05 \times 10^{-8}$ | $1.65 \times 10^{-8}$ | $2.49 \times 10^{-8}$ | 45 | |
| I777K, | 31.5 (3) | $1.86 \times 10^{-8}$ | $1.53 \times 10^{-8}$ | $2.23 \times 10^{-8}$ | 48 | From saturation |
| W814N | 39.6 (1) | $1.29 \times 10^{-8}$ | $9.96 \times 10^{-9}$ | $1.63 \times 10^{-8}$ | 36 | mutagenesis library; Rd2 mutant |
| I777V | 46.3 (1) | $4.71 \times 10^{-9}$ | $3.39 \times 10^{-9}$ | $3.39 \times 10^{-9}$ | 36 | From homology study |

TABLE 2-continued

| Mutation-prone TP-DNAP1 Candidates | | | | | | |
|---|---|---|---|---|---|---|
| TP-DNAP1 | p1 copy number (n) | Mutation rate (s.p.b.) | Lower 95% C.I. (s.p.b.) | Upper 95% C.I. (s.p.b.) | Number of replicates | Notes |
| I778A | 3.41 (3) | $5.13 \times 10^{-9}$ | $7.22 \times 10^{-10}$ | $1.22 \times 10^{-8}$ | 48 | From homology study |
| M779L | 43.2 (3) | $7.22 \times 10^{-9}$ | $4.34 \times 10^{-9}$ | $1.11 \times 10^{-8}$ | 46 | From homology study; Rd1 mutant |
| M779S | 3.58 (1) | $4.04 \times 10^{-9}$ | $1.01 \times 10^{-9}$ | $1.01 \times 10^{-9}$ | 36 | From homology study |
| S781G, L782G, W783Y | 23.7 (3) | $1.69 \times 10^{-8}$ | $8.83 \times 10^{-9}$ | $2.89 \times 10^{-8}$ | 48 | From homology study; Rd1 mutant |
| K785R | 5.93 (1) | $5.04 \times 10^{-9}$ | $2.17 \times 10^{-9}$ | $2.17 \times 10^{-9}$ | 36 | From homology study |
| K785S | 3.6 (1) | $2.23 \times 10^{-9}$ | $3.70 \times 10^{-10}$ | $3.70 \times 10^{-10}$ | 36 | From homology study |
| A787V | 49.9 (3) | $3.99 \times 10^{-9}$ | $1.72 \times 10^{-9}$ | $7.69 \times 10^{-9}$ | 48 | From homology study |
| W790P | 4.81 (3) | $1.03 \times 10^{-8}$ | $1.72 \times 10^{-9}$ | $3.19 \times 10^{-8}$ | 48 | From homology study |
| V791H | 50.9 (1) | $1.46 \times 10^{-9}$ | $8.37 \times 10^{-10}$ | $2.33 \times 10^{-9}$ | 36 | From saturation mutagenesis library |
| D804M | 86.1 (1) | $1.25 \times 10^{-9}$ | $7.69 \times 10^{-10}$ | $1.88 \times 10^{-9}$ | 36 | From saturation mutagenesis library |
| I824V | 75 (1) | $1.59 \times 10^{-9}$ | $1.02 \times 10^{-9}$ | $2.32 \times 10^{-9}$ | 36 | From saturation mutagenesis library |
| P833C | 22 (1) | $6.44 \times 10^{-9}$ | $4.11 \times 10^{-9}$ | $9.47 \times 10^{-9}$ | 36 | From saturation mutagenesis library; Rd2 mutant |
| M848N | 25.5 (1) | $3.31 \times 10^{-9}$ | $2.07 \times 10^{-9}$ | $2.07 \times 10^{-9}$ | 35 | From homology study |
| M848D | 6.65 (1) | $2.51 \times 10^{-10}$ | $3.38 \times 10^{-11}$ | $3.38 \times 10^{-11}$ | 36 | From homology study |
| M848H | 4.95 (1) | $3.48 \times 10^{-9}$ | $1.08 \times 10^{-9}$ | $1.08 \times 10^{-9}$ | 36 | From homology study |
| M848P | 7.73 (1) | $2.45 \times 10^{-9}$ | $7.62 \times 10^{-10}$ | $7.62 \times 10^{-10}$ | 35 | From homology study |
| K849H, | 25.9 (3) | $2.79 \times 10^{-9}$ | $1.80 \times 10^{-9}$ | $4.07 \times 10^{-9}$ | 48 | From saturation |
| K857S | 44 (1) | $2.12 \times 10^{-9}$ | $1.23 \times 10^{-9}$ | $3.35 \times 10^{-9}$ | 36 | mutagenesis library |
| I851L | 63.1 (1) | $4.68 \times 10^{-9}$ | $3.43 \times 10^{-9}$ | $6.14 \times 10^{-9}$ | 36 | From saturation mutagenesis library |
| E858H | 63.4 (1) | $1.90 \times 10^{-9}$ | $1.23 \times 10^{-9}$ | $2.75 \times 10^{-9}$ | 36 | From saturation mutagenesis library |
| E861R | 66 (1) | $1.69 \times 10^{-9}$ | $1.08 \times 10^{-9}$ | $1.08 \times 10^{-9}$ | 36 | From homology study |
| C862I | 4.18 (1) | $4.82 \times 10^{-10}$ | $6.23 \times 10^{-11}$ | $6.23 \times 10^{-11}$ | 35 | From homology study |
| S865G | 46.3 (1) | $2.03 \times 10^{-9}$ | $1.27 \times 10^{-9}$ | $1.27 \times 10^{-9}$ | 35 | From homology study |
| D866N | 3.46 (1) | $2.54 \times 10^{-9}$ | $4.23 \times 10^{-10}$ | $4.23 \times 10^{-10}$ | 36 | From homology study |
| S869T | 4.28 (1) | $1.74 \times 10^{-9}$ | $6.09 \times 10^{-10}$ | $6.09 \times 10^{-10}$ | 36 | From homology study |
| F871I | 48.3 (1) | $1.24 \times 10^{-9}$ | $7.03 \times 10^{-10}$ | $2.00 \times 10^{-9}$ | 36 | From saturation mutagenesis library |
| F871Y | 28 (3) | $3.92 \times 10^{-8}$ | $3.27 \times 10^{-8}$ | $4.61 \times 10^{-8}$ | 42 | From saturation |
| | 29.3 (3) | $4.29 \times 10^{-8}$ | $3.62 \times 10^{-8}$ | $5.00 \times 10^{-8}$ | 43 | mutagenesis library; Rd2 |
| | 35.5 (1) | $3.12 \times 10^{-8}$ | $2.50 \times 10^{-8}$ | $3.81 \times 10^{-8}$ | 36 | mutant |
| V872I | 5.18 (3) | $1.68 \times 10^{-8}$ | $5.21 \times 10^{-9}$ | $3.89 \times 10^{-8}$ | 48 | From homology study; Rd1 mutant |
| V872L | 60.4 (1) | $2.17 \times 10^{-9}$ | $1.46 \times 10^{-9}$ | $1.46 \times 10^{-9}$ | 36 | From homology study |
| H873R | 52.9 (1) | $2.75 \times 10^{-9}$ | $1.81 \times 10^{-9}$ | $1.81 \times 10^{-9}$ | 35 | From homology study |
| H873T | 49.5 (1) | $3.16 \times 10^{-9}$ | $2.16 \times 10^{-9}$ | $2.16 \times 10^{-9}$ | 36 | From homology study |
| K874P | 87.5 (1) | $3.01 \times 10^{-9}$ | $2.19 \times 10^{-9}$ | $3.98 \times 10^{-9}$ | 36 | From saturation mutagenesis library |
| L900S | 55.9 (1) | $5.24 \times 10^{-9}$ | $3.72 \times 10^{-9}$ | $7.05 \times 10^{-9}$ | 36 | From saturation |
| | 68.8 (1) | $4.77 \times 10^{-9}$ | $3.50 \times 10^{-9}$ | $6.26 \times 10^{-9}$ | 36 | mutagenesis library; Rd2 mutant |
| L909F | 58.2 (1) | $6.99 \times 10^{-9}$ | $5.34 \times 10^{-9}$ | $8.87 \times 10^{-9}$ | 36 | From saturation mutagenesis library; Rd2 mutant |
| K934F | 44.8 (1) | $2.23 \times 10^{-9}$ | $1.36 \times 10^{-9}$ | $3.41 \times 10^{-9}$ | 36 | From saturation mutagenesis library |
| K934W | 34 (1) | $1.20 \times 10^{-8}$ | $9.01 \times 10^{-9}$ | $1.55 \times 10^{-8}$ | 36 | From saturation mutagenesis library; Rd2 mutant |
| S955W, | 12.6 (3) | $5.69 \times 10^{-9}$ | $3.61 \times 10^{-9}$ | $8.41 \times 10^{-9}$ | 48 | From saturation |
| K967C | 21.9 (1) | $4.55 \times 10^{-9}$ | $2.46 \times 10^{-9}$ | $7.55 \times 10^{-9}$ | 36 | mutagenesis library |
| D958A | 88 (1) | $1.98 \times 10^{-9}$ | $1.34 \times 10^{-9}$ | $2.78 \times 10^{-9}$ | 36 | From saturation mutagenesis library |
| F968C | 14.4 (1) | $1.23 \times 10^{-8}$ | $7.42 \times 10^{-9}$ | $1.88 \times 10^{-8}$ | 36 | From saturation mutagenesis library; Rd2 mutant |
| F968T | 12.8 (1) | $1.98 \times 10^{-8}$ | $1.24 \times 10^{-8}$ | $2.96 \times 10^{-8}$ | 36 | From saturation mutagenesis library; Rd2 mutant |
| L622I, C639I, I775A | 16.1 (3) | $3.26 \times 10^{-8}$ | $2.56 \times 10^{-8}$ | $4.06 \times 10^{-8}$ | 48 | From shuffling library (A × B) |
| L622I, C639I, I777A | 7.74 (3) | $1.11 \times 10^{-7}$ | $9.04 \times 10^{-8}$ | $1.33 \times 10^{-7}$ | 48 | From shuffling library (A × B) |

TABLE 2-continued

Mutation-prone TP-DNAP1 Candidates

| TP-DNAP1 | p1 copy number (n) | Mutation rate (s.p.b.) | Lower 95% C.I. (s.p.b.) | Upper 95% C.I. (s.p.b.) | Number of replicates | Notes |
|---|---|---|---|---|---|---|
| L622I, C639I, I777K | 7.59 (3) | $3.06 \times 10^{-7}$ | $2.66 \times 10^{-7}$ | $3.47 \times 10^{-7}$ | 48 | From shuffling library (A × B) |
| L622I, C639I, I777K, W814N | 10.4 (3) | $1.44 \times 10^{-7}$ | $1.21 \times 10^{-7}$ | $1.69 \times 10^{-7}$ | 46 | From shuffling library (A × B) |
| L622I, C639I, S781G, L782G, W783Y | 11.4 (3) | $4.41 \times 10^{-10}$ | $2.52 \times 10^{-11}$ | $1.94 \times 10^{-9}$ | 48 | From shuffling library (A × B) |
| C639Y, L640A, I777A | 18.9 (3) | $7.16 \times 10^{-8}$ | $6.09 \times 10^{-8}$ | $8.29 \times 10^{-8}$ | 48 | From shuffling library (A × B) |
| L640A, I775A | 58.6 (3) | $1.68 \times 10^{-8}$ | $1.40 \times 10^{-8}$ | $1.98 \times 10^{-8}$ | 48 | From shuffling library (A × B) |
| L640A, I777A | 20.5 (3) | $9.06 \times 10^{-8}$ | $7.77 \times 10^{-8}$ | $1.04 \times 10^{-7}$ | 46 | From shuffling library (A × B) |
| L640A, I777K | 10.8 (3) | $1.83 \times 10^{-7}$ | $1.57 \times 10^{-7}$ | $2.09 \times 10^{-7}$ | 48 | From shuffling library (A × B) |
| L640A, I777K, W814N | 10.2 (3) | $5.41 \times 10^{-7}$ | $4.80 \times 10^{-7}$ | $6.02 \times 10^{-7}$ | 48 | From shuffling library (A × B) |
| L640A, M779L | 40.1 (3) | $2.79 \times 10^{-9}$ | $1.81 \times 10^{-9}$ | $4.07 \times 10^{-9}$ | 47 | From shuffling library (A × B) |
| L640N, I777A | 12.4 (3) | $3.04 \times 10^{-8}$ | $2.23 \times 10^{-8}$ | $3.98 \times 10^{-8}$ | 46 | From shuffling library (A × B) |
| L640G, I775A | 32.5 (3) | $1.81 \times 10^{-8}$ | $1.44 \times 10^{-8}$ | $2.21 \times 10^{-8}$ | 48 | From shuffling library (A × B) |
| L640G, I777A | 19.5 (3) | $9.28 \times 10^{-8}$ | $7.97 \times 10^{-8}$ | $1.06 \times 10^{-7}$ | 47 | From shuffling library (A × B) |
| L640G, I777K, W814N | 5.21 (3) | $2.63 \times 10^{-7}$ | $2.19 \times 10^{-7}$ | $3.09 \times 10^{-7}$ | 48 | From shuffling library (A × B) |
| L640Y, I777A | 43.1 (3) | $5.70 \times 10^{-8}$ | $4.96 \times 10^{-8}$ | $6.45 \times 10^{-8}$ | 45 | From shuffling library (A × B) |
| L640Y, | 13.8 (3) | $9.70 \times 10^{-7}$ | $7.97 \times 10^{-7}$ | $1.14 \times 10^{-6}$ | 16 | From shuffling library |
| I777K, | 2.56 (3) | $3.36 \times 10^{-6}$ | $2.23 \times 10^{-6}$ | $4.54 \times 10^{-6}$ | 6 | (A × B); Rd3 mutant |
| L645M, I777K | 13.1 (3) | $9.19 \times 10^{-9}$ | $5.72 \times 10^{-9}$ | $1.38 \times 10^{-8}$ | 46 | From shuffling library (A × B) |
| L645M, M779L | 8.71 (3) | $4.99 \times 10^{-9}$ | $2.15 \times 10^{-9}$ | $9.63 \times 10^{-9}$ | 47 | From shuffling library (A × B) |
| F652L, I775A | 14.4 (3) | $6.08 \times 10^{-9}$ | $3.60 \times 10^{-9}$ | $9.45 \times 10^{-9}$ | 45 | From shuffling library (A × B) |
| Y653L, I775A | 7.64 (3) | $9.70 \times 10^{-9}$ | $5.22 \times 10^{-9}$ | $1.62 \times 10^{-8}$ | 48 | From shuffling library (A × B) |
| Y653L, I777A | 8.52 (3) | $2.02 \times 10^{-8}$ | $1.31 \times 10^{-8}$ | $2.96 \times 10^{-8}$ | 45 | From shuffling library (A × B) |
| Y653L, I777K | 13.6 (3) | $9.59 \times 10^{-8}$ | $7.82 \times 10^{-8}$ | $1.15 \times 10^{-7}$ | 43 | From shuffling library (A × B) |
| I775A, F871Y | 39.4 (3) | $4.73 \times 10^{-8}$ | $4.09 \times 10^{-8}$ | $5.39 \times 10^{-8}$ | 48 | From shuffling library (B × C) |
| I775A, L900S | 39.1 (3) | $2.53 \times 10^{-8}$ | $2.12 \times 10^{-8}$ | $2.98 \times 10^{-8}$ | 48 | From shuffling library (B × C) |
| I775A, L909F | 31.8 (3) | $2.46 \times 10^{-8}$ | $2.03 \times 10^{-8}$ | $2.92 \times 10^{-8}$ | 48 | From shuffling library (B × C) |
| I775A, K934W | 28.8 (3) | $3.59 \times 10^{-8}$ | $3.00 \times 10^{-8}$ | $4.23 \times 10^{-8}$ | 48 | From shuffling library (B × C) |
| I775A, F968T | 6.62 (3) | $7.29 \times 10^{-8}$ | $5.52 \times 10^{-8}$ | $9.35 \times 10^{-8}$ | 45 | From shuffling library (B × C) |
| I777A, F871Y | 12.9 (3) | $2.57 \times 10^{-7}$ | $2.24 \times 10^{-7}$ | $2.91 \times 10^{-7}$ | 45 | From shuffling library (B × C) |
| I777A, V872I | 11.8 (3) | $1.34 \times 10^{-10}$ | $3.18 \times 10^{-10}$ | $1.89 \times 10^{-11}$ | 48 | From shuffling library (B × C) |
| I777A, L900S | 26.9 (3) | $1.36 \times 10^{-7}$ | $1.20 \times 10^{-7}$ | $1.51 \times 10^{-7}$ | 48 | From shuffling library (B × C) |
| I777A, L909F | 13 (3) | $1.07 \times 10^{-7}$ | $9.02 \times 10^{-8}$ | $1.24 \times 10^{-7}$ | 46 | From shuffling library (B × C) |
| I777A, K934W | 6.04 (3) | $1.86 \times 10^{-7}$ | $1.55 \times 10^{-7}$ | $2.18 \times 10^{-7}$ | 48 | From shuffling library (B × C) |
| I777K, W790L, K934W | 8.23 (3) | $2.02 \times 10^{-7}$ | $1.73 \times 10^{-7}$ | $2.33 \times 10^{-7}$ | 47 | From shuffling library (B × C) |

TABLE 2-continued

Mutation-prone TP-DNAP1 Candidates

| TP-DNAP1 | p1 copy number (n) | Mutation rate (s.p.b.) | Lower 95% C.I. (s.p.b.) | Upper 95% C.I. (s.p.b.) | Number of replicates | Notes |
|---|---|---|---|---|---|---|
| I777K, F871Y | 11.2 (3) | $1.35 \times 10^{-6}$ | $1.14 \times 10^{-6}$ | $1.56 \times 10^{-6}$ | 16 | From shuffling library (B × C); Rd3 mutant |
| I777K, V872I | 33 (3) | $2.59 \times 10^{-8}$ | $2.15 \times 10^{-8}$ | $3.06 \times 10^{-8}$ | 47 | From shuffling library (B × C) |
| I777K, L900S | 20.6 (3) | $9.22 \times 10^{-7}$ | $7.82 \times 10^{-7}$ | $1.05 \times 10^{-6}$ | 16 | From shuffling library (B × C); Rd3 mutant |
| | 12.4 (3) | $2.87 \times 10^{-6}$ | $2.07 \times 10^{-6}$ | $3.55 \times 10^{-6}$ | 4 | |
| | 15 (3) | $2.18 \times 10^{-6}$ | $1.55 \times 10^{-6}$ | $2.72 \times 10^{-6}$ | 4 | |
| I777K, L909F | 9.15 (3) | $2.22 \times 10^{-7}$ | $1.91 \times 10^{-7}$ | $2.55 \times 10^{-7}$ | 46 | From shuffling library (B × C) |
| I777K, K934W | 8.27 (3) | $2.71 \times 10^{-7}$ | $2.33 \times 10^{-7}$ | $3.11 \times 10^{-7}$ | 48 | From shuffling library (B × C) |
| I777K, F968C | 6.72 (3) | $6.67 \times 10^{-7}$ | $5.30 \times 10^{-7}$ | $8.07 \times 10^{-7}$ | 16 | From shuffling library (B × C) |
| I777K, F968T | 7.11 (3) | $3.19 \times 10^{-7}$ | $2.69 \times 10^{-7}$ | $3.71 \times 10^{-7}$ | 45 | From shuffling library (B × C) |
| M779L, K934W | 23.1 (3) | $2.85 \times 10^{-9}$ | $1.62 \times 10^{-9}$ | $4.57 \times 10^{-9}$ | 48 | From shuffling library (B × C) |
| M779L, F968C | 6.57 (3) | $3.13 \times 10^{-10}$ | $7.42 \times 10^{-10}$ | $4.40 \times 10^{-11}$ | 48 | From shuffling library (B × C) |
| V774I, F871Y | 6.57 (3) | $1.64 \times 10^{-7}$ | $1.33 \times 10^{-7}$ | $1.97 \times 10^{-7}$ | 43 | From shuffling library (B × C) |
| V774I, L900S | 20.7 (3) | $1.10 \times 10^{-7}$ | $9.54 \times 10^{-8}$ | $1.24 \times 10^{-7}$ | 46 | From shuffling library (B × C) |
| V774I, F968C | 8.91 (3) | $1.14 \times 10^{-7}$ | $9.11 \times 10^{-8}$ | $1.39 \times 10^{-7}$ | 46 | From shuffling library (B × C) |
| Y431H, L640Y, I777K, W814N | 9.69 (3) | $3.65 \times 10^{-6}$ | $2.65 \times 10^{-6}$ | $4.71 \times 10^{-6}$ | 11 | Rd4 mutant; Entries 4-6 for this TP-DNAP1 variant are measurements taken after 90 generations. |
| | 17.3 (3) | $1.65 \times 10^{-6}$ | $1.30 \times 10^{-6}$ | $1.99 \times 10^{-6}$ | 11 | |
| | 7.97 (3) | $2.67 \times 10^{-6}$ | $1.48 \times 10^{-6}$ | $3.89 \times 10^{-6}$ | 3 | |
| | 12.3 (3) | $2.33 \times 10^{-6}$ | $1.70 \times 10^{-6}$ | $2.90 \times 10^{-6}$ | 5 | |
| | 7.65 (3) | $4.29 \times 10^{-6}$ | $2.93 \times 10^{-6}$ | $5.66 \times 10^{-6}$ | 6 | |
| | 4.83 (3) | $3.24 \times 10^{-6}$ | $2.25 \times 10^{-6}$ | $4.17 \times 10^{-6}$ | 5 | |
| L474W, L640Y, I777K, W814N | 9.56 (3) | $4.03 \times 10^{-6}$ | $2.85 \times 10^{-6}$ | $5.13 \times 10^{-6}$ | 5 | Rd4 mutant; Entries 3-4 for this TP-DNAP1 variant are measurements taken after 90 generations. |
| | 3.55 (3) | $2.74 \times 10^{-6}$ | $1.84 \times 10^{-6}$ | $3.64 \times 10^{-6}$ | 5 | |
| | 3.82 (3) | $2.20 \times 10^{-6}$ | $1.49 \times 10^{-6}$ | $2.89 \times 10^{-6}$ | 5 | |
| | 2.38 (3) | $1.04 \times 10^{-6}$ | $6.08 \times 10^{-7}$ | $1.54 \times 10^{-6}$ | 6 | |
| V574F, I777K, L900S | 7.8 (3) | $4.86 \times 10^{-6}$ | $3.77 \times 10^{-6}$ | $5.94 \times 10^{-6}$ | 11 | Rd4 mutant; TP-DNAP1-4-1 Entries 4-6 for this TP-DNAP1 variant are measurements taken after 90 generations. |
| | 5.95 (3) | $8.53 \times 10^{-6}$ | $6.26 \times 10^{-6}$ | $1.09 \times 10^{-5}$ | 10 | |
| | 5.09 (3) | $3.78 \times 10^{-6}$ | $2.58 \times 10^{-6}$ | $4.86 \times 10^{-6}$ | 4 | |
| | 6.02 (3) | $7.58 \times 10^{-6}$ | $5.50 \times 10^{-6}$ | $9.47 \times 10^{-6}$ | 5 | |
| | 4.08 (3) | $6.87 \times 10^{-6}$ | $4.76 \times 10^{-6}$ | $8.89 \times 10^{-6}$ | 5 | |
| | 3.39 (3) | $7.71 \times 10^{-6}$ | $5.20 \times 10^{-6}$ | $1.00 \times 10^{-5}$ | 4 | |
| L477V, L640Y, I777K, W814N | 11.8 (3) | $7.19 \times 10^{-6}$ | $5.45 \times 10^{-6}$ | $8.68 \times 10^{-6}$ | 5 | Rd4 mutant; TP-DNAP1-4-2; Entries 4-6 for this TP-DNAP1 variant are measurements taken after 90 generations. |
| | 6.09 (3) | $1.88 \times 10^{-5}$ | $1.40 \times 10^{-5}$ | $2.30 \times 10^{-5}$ | 5 | |
| | 9.67 (3) | $9.41 \times 10^{-6}$ | $6.53 \times 10^{-6}$ | $1.17 \times 10^{-5}$ | 3 | |
| | 5.05 (3) | $1.15 \times 10^{-5}$ | $8.14 \times 10^{-6}$ | $1.45 \times 10^{-5}$ | 4 | |
| | 7.45 (3) | $1.19 \times 10^{-5}$ | $8.70 \times 10^{-6}$ | $1.48 \times 10^{-5}$ | 5 | |
| | 7.82 (3) | $9.22 \times 10^{-6}$ | $6.48 \times 10^{-6}$ | $1.16 \times 10^{-5}$ | 4 | |
| w.t. | 59.8 (1) | $2.49 \times 10^{-9}$ | $1.77 \times 10^{-9}$ | $3.37 \times 10^{-9}$ | 48 | Entries 24-27 for this TP-DNAP1 variant are measurements taken after 90 generations. |
| | 47.8 (3) | $4.21 \times 10^{-9}$ | $1.51 \times 10^{-9}$ | $9.03 \times 10^{-9}$ | 23 | |
| | 59.8 (1) | $2.63 \times 10^{-9}$ | $1.89 \times 10^{-9}$ | $1.89 \times 10^{-9}$ | 36 | |
| | 72.6 (1) | $4.37 \times 10^{-9}$ | $2.42 \times 10^{-9}$ | $7.16 \times 10^{-9}$ | 48 | |
| | 46.9 (1) | $3.83 \times 10^{-9}$ | $1.65 \times 10^{-9}$ | $7.39 \times 10^{-9}$ | 48 | |
| | 53.9 (1) | $2.69 \times 10^{-9}$ | $1.79 \times 10^{-9}$ | $3.83 \times 10^{-9}$ | 36 | |
| | 55.8 (1) | $2.38 \times 10^{-9}$ | $1.39 \times 10^{-9}$ | $3.73 \times 10^{-9}$ | 24 | |
| | 57.3 (1) | $2.36 \times 10^{-9}$ | $1.46 \times 10^{-9}$ | $3.55 \times 10^{-9}$ | 36 | |
| | 78.6 (1) | $2.26 \times 10^{-9}$ | $1.44 \times 10^{-9}$ | $3.30 \times 10^{-9}$ | 24 | |
| | 55.3 (1) | $2.23 \times 10^{-9}$ | $1.41 \times 10^{-9}$ | $3.28 \times 10^{-9}$ | 36 | |
| | 58.9 (1) | $2.06 \times 10^{-9}$ | $1.36 \times 10^{-9}$ | $2.95 \times 10^{-9}$ | 36 | |
| | 54.3 (1) | $1.96 \times 10^{-9}$ | $1.14 \times 10^{-9}$ | $3.09 \times 10^{-9}$ | 36 | |
| | 52.7 (1) | $1.95 \times 10^{-9}$ | $1.10 \times 10^{-9}$ | $3.14 \times 10^{-9}$ | 36 | |
| | 59.8 (1) | $1.84 \times 10^{-9}$ | $9.75 \times 10^{-10}$ | $3.07 \times 10^{-9}$ | 19 | |
| | 68.3 (1) | $1.73 \times 10^{-9}$ | $1.11 \times 10^{-9}$ | $2.52 \times 10^{-9}$ | 36 | |
| | 71.5 (1) | $1.65 \times 10^{-9}$ | $1.08 \times 10^{-9}$ | $2.39 \times 10^{-9}$ | 36 | |
| | 59.5 (1) | $1.62 \times 10^{-9}$ | $1.02 \times 10^{-9}$ | $2.39 \times 10^{-9}$ | 36 | |
| | 71.8 (1) | $1.37 \times 10^{-9}$ | $8.77 \times 10^{-10}$ | $2.01 \times 10^{-9}$ | 36 | |
| | 65.9 (1) | $1.22 \times 10^{-9}$ | $7.30 \times 10^{-10}$ | $1.89 \times 10^{-9}$ | 36 | |
| | 58.8 (1) | $1.16 \times 10^{-9}$ | $6.05 \times 10^{-10}$ | $1.96 \times 10^{-9}$ | 24 | |
| | 53.1 (3) | $3.10 \times 10^{-9}$ | $2.18 \times 10^{-9}$ | $4.24 \times 10^{-9}$ | 48 | |
| | 51.8 (3) | $2.23 \times 10^{-9}$ | $1.50 \times 10^{-9}$ | $3.15 \times 10^{-9}$ | 45 | |
| | 47.7 (3) | $2.49 \times 10^{-9}$ | $1.74 \times 10^{-9}$ | $3.42 \times 10^{-9}$ | 45 | |
| | 54.2 (3) | $1.85 \times 10^{-9}$ | $1.22 \times 10^{-9}$ | $2.65 \times 10^{-9}$ | 45 | |

TABLE 2-continued

| Mutation-prone TP-DNAP1 Candidates | | | | | | |
|---|---|---|---|---|---|---|
| TP-DNAP1 | p1 copy number (n) | Mutation rate (s.p.b.) | Lower 95% C.I. (s.p.b.) | Upper 95% C.I. (s.p.b.) | Number of replicates | Notes |
| | 46.9 (3) | $2.95 \times 10^{-9}$ | $2.05 \times 10^{-9}$ | $4.06 \times 10^{-9}$ | 45 | |
| | 45.2 (3) | $1.84 \times 10^{-9}$ | $1.15 \times 10^{-9}$ | $2.74 \times 10^{-9}$ | 45 | |
| | 51.4 (3) | $4.28 \times 10^{-9}$ | $3.05 \times 10^{-9}$ | $5.77 \times 10^{-9}$ | 45 | |

A calibration curve was established to correlate p1 copy number, determined via quantitative PCR (qPCR), with fluorescence of p1-encoded mKate2 (Table 1). Five TP-DNAP1 variants representing a wide range of copy numbers were transformed into ORY24 and passaged until w.t. p1 was displaced. The five OR-Y24 strains were grown to saturation, diluted 1:10,000 to mimic p1 fluctuation tests, and grown in triplicate 100 μL cultures and duplicate 40 mL cultures. 100 μL saturated cultures were subject to fluorescence measurement of mKate2 (ex/em=561 nm/620 nm, bandwidth=15 nm) on a flow cytometer (Invitrogen Attune NxT). Whole-cell DNA extracts were prepared from 40 mL cultures and used as templates for qPCR measurement of p1-encoded leu2 (Q180*), as described previously (Ravikumar et al., 2014). p1-encoded LEU2 was PCR amplified with qPCR-Leu2F and qPCR Leu2R; and genomic LEU3 was PCR amplified with qPCR-Leu3F and qPCR-Leu3R using SyBR Green (Fisher Scientific) master mix. The correlation of mKate2 fluorescence and qPCR-determined p1 copy number had a strong linear fit across p1 copy numbers ranging from 9-90, and had low background (y=0.048x+0.206, r2=0.954).

To assay p1 copy number for large-scale p1 fluctuation tests, additional replicates of OR-Y24 strains were grown from the 1:10,000 dilution in triplicate and saturated cultures were subject to fluorescence measurement via flow cytometry. Fluorescence measurements were converted to copy number with the linear calibration curve.

To assay relative p1 copy number for small-scale p1 fluctuation tests, an additional 200 μL culture of OR-Y24 strains were grown from the 1:10,000 dilution. 200 μL saturated cultures were subject to an OD600 measurement and fluorescence measurement of mKate2 (ex/em=588 nm/633 nm), using a microplate reader (TECAN Infinite M200 PRO). A linear relationship was assumed between p1 copy number and OD600-normalized mKate2 fluorescence. Copy numbers were calculated from normalization to a w.t. TP-DNAP1 control.

For a few large-scale p1 fluctuation tests, p1 copy number was assayed by the method of small scale p1 fluctuation tests (i.e. microplate reader measurement). For these experiments, mutant TP-DNAP1 p1 copy numbers were calculated by normalization to a w.t. TP-DNAP1 control. The copy number of this control was assumed to be the average w.t. TP-DNAP1 copy number from all large-scale p1 fluctuation tests that used flow cytometry measurements.

From mKate2 measurements of the 13,625 clones screened with small-scale p1 fluctuation tests, 283 clones exhibiting high fluorescence were chosen for additional characterization. TP-DNAP1 plasmids were isolated from these strains and subject to Sanger sequencing. 210 unique variants were identified and the corresponding plasmids were re-transformed into OR-Y24. Transformed strains were passaged in SC-UH until w.t. p1 was displaced, and subject to p1 copy number measurement in triplicate. Four high copy variants were directly subject to qPCR measurements for validation. To test the suppressor activity of the G410H mutation, which yields increased p1 copy number, this amino acid change was added to several low-activity TP-DNAP1 variants. p1 copy number was similarly assayed for these strains.

Figure 2:
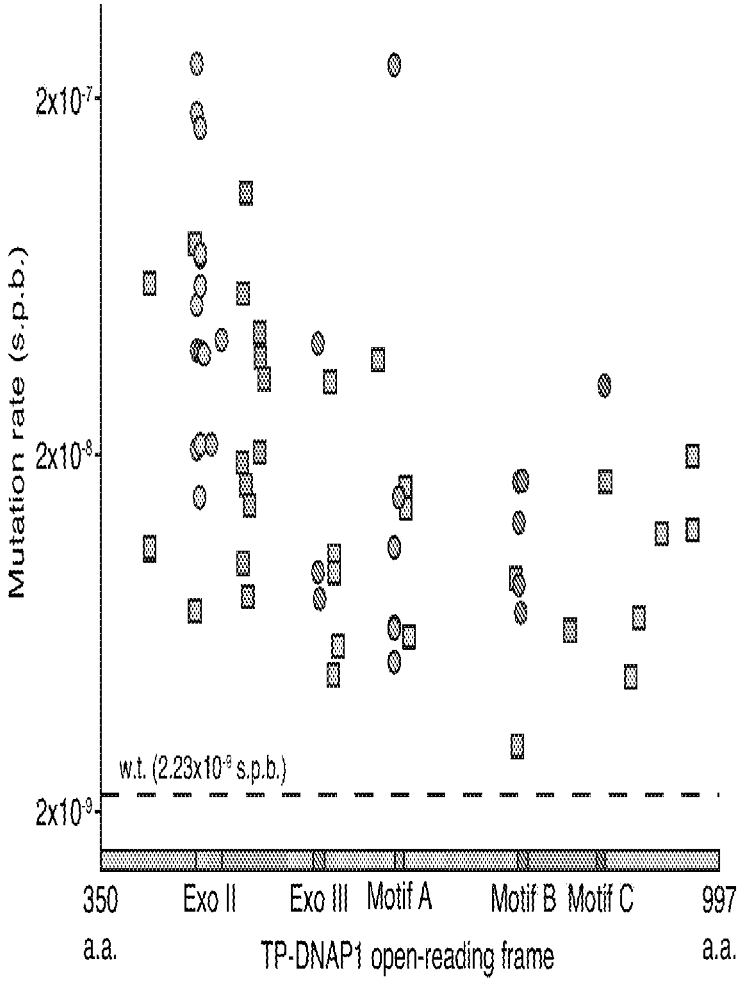
FIG. 2 depicts mutation rates of 65 TP-DNAP1 variants found from a homology study and a TP-DNAP1 library screen. Variants are ordered by amino acid position in the TP-DNAP1 open-reading frame. TP-DNAP1 substitution rates were measured with fluctuation tests using p1-encoded leu2 (Q180*).

From this screen, we found 95 promising error-prone TP-DNAP1 candidates (Table 2). After measuring their mutation rates more accurately through large-scale fluctuation tests, we identified 41 unique variants (Rd2 mutants) with error rates up to ~$2\times10^{-7}$ s.p.b. (Table 2). Unlike Rd1 mutants, Rd2 mutants retained high activity, and on average replicated p1 at only a 2-fold lower copy number than did wild type (w.t.) TP-DNAP1. Only 9 of the Rd2 hits contained mutations at positions considered in the homology-based library design that generated Rd1 hits, indicating that fidelity determinants of TP-DNAP1 can lie outside of the most-conserved regions of DNAPs. Incidentally, we also discovered 210 TP-DNAP1 variants that replicated p1 at a higher copy number than did w.t. TP-DNAP1 (Table 3), and added the mutation from one of these variants to several low-activity mutator TP-DNAP1s to confirm the generality of the activity-boosting phenotype (Table 4). (These variants were not included in subsequent experiments here, but should prove useful in future TP-DNAP1 engineering efforts.) Rd2 hits were combined with Rd1 hits to form a 65-member basis set of mutations that moderately increase the error rate of TP-DNAP1 (FIG. 2).

TABLE 3

| TP-DNAP1 Variants that Replicate p1 at a Higher Copy Number than w.t. TP-DNAP1 | | |
|---|---|---|
| Mutation | Mean fold-increase over w.t. | Standard deviation |
| I287M | 2.39 | 0.482 |
| S289K | 2.02 | 0.306 |
| N291K | 1.66 | 0.341 |
| N291M | 2.28 | 0.263 |
| N291W | 2.26 | 0.456 |
| L295Q | 2.48 | 0.285 |
| Y296K | 2.28 | 0.408 |
| E298R | 2.6 | 0.66 |
| E298G | 2.64 | 0.365 |
| E298G, S305F | 2.06 | 0.411 |
| E298H | 2.57 | 0.284 |
| E298I | 2.34 | 0.413 |
| E298F | 1.74 | 0.305 |
| E298P | 2.57 | 0.286 |
| E298S | 2.43 | 0.385 |
| E298Y | 2.17 | 0.357 |
| E298V | 2.64 | 0.387 |
| I301A | 2.41 | 0.251 |
| I301C | 2.46 | 0.457 |
| I301E | 2.57 | 0.32 |
| I301L | 2.94 | 0.981 |
| I301K | 2.71 | 0.34 |

TABLE 3-continued

TP-DNAP1 Variants that Replicate p1 at a Higher Copy Number than w.t. TP-DNAP1

| Mutation | Mean fold-increase over w.t. | Standard deviation |
|---|---|---|
| I301M | 2.76 | 0.326 |
| I301S | 2.29 | 0.408 |
| I301Y | 3.28 | 1.39 |
| I301V | 2.53 | 0.317 |
| K302A | 1.88 | 0.436 |
| T303H | 2.3 | 0.317 |
| T303L | 2.41 | 0.332 |
| T303M | 2.5 | 0.298 |
| T303W | 2.96 | 1.74 |
| F304A | 2.14 | 0.234 |
| F304R | 3.49 | 1.85 |
| F304Y | 2.41 | 0.451 |
| S305N | 2.3 | 0.278 |
| S305G | 2.53 | 0.369 |
| I307L | 2.76 | 0.391 |
| D308Q | 2.15 | 0.264 |
| N309C | 2.25 | 0.282 |
| N309K, I311G | 2.2 | 0.256 |
| T310N | 2.83 | 0.353 |
| T310D | 2.64 | 0.325 |
| T310E | 2.37 | 0.466 |
| T310H | 2.57 | 0.361 |
| T310F | 2.66 | 0.35 |
| T310W | 2.48 | 0.255 |
| I311A | 2.19 | 0.324 |
| I311N | 2.55 | 0.572 |
| I311D | 1.86 | 0.595 |
| I311G | 2.05 | 0.484 |
| I311M | 2.26 | 0.232 |
| T312E | 2.29 | 0.279 |
| T312Q | 2.85 | 0.486 |
| Y313H | 3.08 | 1.45 |
| Y313M | 1.94 | 0.373 |
| Y313F | 2.11 | 0.429 |
| Y313W | 2.15 | 0.563 |
| Y313V | 2.48 | 0.977 |
| Y316R | 2.46 | 0.778 |
| I327Q | 2.15 | 0.546 |
| S330R | 2.21 | 0.592 |
| D333A | 1.57 | 0.242 |
| D333N | 2.07 | 0.455 |
| D333N, K344R | 2.07 | 0.398 |
| D333M | 2.6 | 0.342 |
| D333T | 2.41 | 0.279 |
| D333V | 2.18 | 0.26 |
| K365N | 1.89 | 0.198 |
| I372C | 1.73 | 0.316 |
| Y382A | 1.6 | 0.18 |
| Y382V | 1.62 | 0.238 |
| V385W | 1.41 | 0.234 |
| G387H | 1.57 | 0.173 |
| R395P | 1.91 | 0.263 |
| V406C | 2.34 | 0.36 |
| V406Q | 2.16 | 0.231 |
| D407V, S415T | 1.95 | 0.216 |
| D407A | 2.25 | 0.305 |
| D407C | 2.26 | 0.408 |
| D407G | 2.53 | 0.281 |
| D407H | 2.57 | 0.314 |
| D407M | 2.71 | 0.283 |
| D407F | 2.28 | 0.286 |
| D407T | 3.95 | 1.87 |
| G410R | 2.87 | 0.46 |
| G410E | 2.37 | 0.284 |
| G410Q | 2.2 | 0.229 |
| G410H | 2.19 | 0.334 |
| G410I | 2.57 | 0.321 |
| G410L | 2.57 | 0.31 |
| G410K | 2.53 | 0.729 |
| G410M | 2.55 | 0.516 |
| G410F | 2.66 | 0.291 |
| G410S | 2.27 | 0.323 |
| G410T | 2.57 | 0.304 |

TABLE 3-continued

TP-DNAP1 Variants that Replicate p1 at a Higher Copy Number than w.t. TP-DNAP1

| Mutation | Mean fold-increase over w.t. | Standard deviation |
|---|---|---|
| G410W | 2.5 | 0.363 |
| G410Y | 2.73 | 1.36 |
| E411A | 2.08 | 0.407 |
| E411R | 2.07 | 0.278 |
| E411N | 1.9 | 0.309 |
| E411D | 2.32 | 0.28 |
| E411G | 1.54 | 0.357 |
| E411L | 2.22 | 0.335 |
| E411K | 2.39 | 0.307 |
| E411S | 1.52 | 0.162 |
| L412V | 2.21 | 0.365 |
| N413E | 2.62 | 0.366 |
| N413H | 2.2 | 0.327 |
| N413T | 1.76 | 0.228 |
| I414F | 1.29 | 0.186 |
| S415V | 1.44 | 0.223 |
| G426T | 1.22 | 0.141 |
| D460G | 1.63 | 0.221 |
| G461K | 2.15 | 1 |
| N611Q | 1.92 | 0.249 |
| N611P, V897V | 2.04 | 0.259 |
| K612A | 1.94 | 0.347 |
| K612Q | 2.04 | 0.249 |
| K612S | 1.75 | 0.531 |
| K612V | 1.85 | 0.355 |
| E613D | 1.82 | 0.196 |
| F616E | 2.2 | 0.249 |
| E620R | 2.29 | 0.744 |
| R662A | 1.75 | 0.196 |
| R662C | 1.7 | 0.227 |
| D669G, T698M | 1.65 | 0.274 |
| E670M, S693G | 1.55 | 0.368 |
| I673V, E703D | 1.88 | 0.229 |
| Y675H | 2.14 | 0.259 |
| Y675L | 1.96 | 0.244 |
| R677Q | 1.84 | 0.189 |
| R677L | 1.68 | 0.386 |
| R677M | 1.97 | 0.211 |
| R677S | 1.87 | 0.268 |
| T679A | 1.82 | 0.256 |
| T679R | 1.73 | 0.346 |
| T679E | 1.7 | 0.176 |
| T679Q | 1.71 | 0.369 |
| N681Q, R692I | 1.74 | 0.225 |
| N681F | 1.75 | 0.263 |
| R682D | 1.74 | 0.214 |
| R682P | 1.75 | 0.246 |
| N683A | 1.93 | 0.703 |
| N683H | 1.68 | 0.242 |
| N683T | 1.57 | 0.199 |
| N684D | 1.54 | 0.173 |
| N687G | 1.65 | 0.233 |
| R692C | 1.69 | 0.34 |
| R692I | 1.99 | 0.409 |
| R692K | 1.88 | 0.24 |
| R692F | 2.6 | 1.29 |
| R692F, T706E | 1.89 | 0.257 |
| R692W | 1.97 | 0.237 |
| R692V | 2.29 | 0.487 |
| S693R | 2.09 | 0.23 |
| S693Q | 2.22 | 0.382 |
| H694I | 1.78 | 0.264 |
| H694T | 1.92 | 0.311 |
| N695E | 2.34 | 0.328 |
| N695Q | 1.68 | 0.622 |
| N695H | 1.76 | 0.183 |
| N695F | 1.44 | 0.265 |
| N695S | 1.82 | 0.365 |
| K696C | 1.87 | 0.228 |
| K696G | 2.11 | 0.231 |
| K696M | 1.71 | 0.248 |
| K696S, E704V | 1.86 | 0.253 |
| K696T | 2.12 | 0.257 |

TABLE 3-continued

| TP-DNAP1 Variants that Replicate p1 at a Higher Copy Number than w.t. TP-DNAP1 | | |
|---|---|---|
| Mutation | Mean fold-increase over w.t. | Standard deviation |
| K696Y | 1.49 | 0.159 |
| T698A | 2.02 | 0.228 |
| T698L | 2 | 0.266 |
| T698M | 1.75 | 0.239 |
| E703R | 1.84 | 0.274 |
| E703H | 1.53 | 0.164 |
| E703W | 1.72 | 0.213 |
| E704N | 1.85 | 0.376 |
| E704D | 1.89 | 0.366 |
| E704G | 1.75 | 0.215 |
| E704I | 1.35 | 0.202 |
| E704K | 1.8 | 0.422 |
| E704M | 2.02 | 0.228 |
| S705R | 1.84 | 0.277 |
| S705L | 1.98 | 0.308 |
| S705F | 1.76 | 0.204 |
| T706R | 2 | 0.332 |
| T706Q | 2.92 | 1.5 |
| T706G | 1.72 | 0.226 |
| T706P | 1.73 | 0.235 |
| T706W | 1.73 | 0.297 |
| I708A | 2.55 | 0.276 |
| I708E | 2.41 | 0.264 |
| I708L | 2.16 | 0.284 |
| I708M | 2.32 | 0.35 |
| I708T | 2.41 | 0.57 |
| I708V | 2.01 | 0.6 |
| A709N | 2.01 | 0.522 |
| I729F | 1.7 | 0.285 |
| I729W | 1.97 | 0.406 |
| I729V | 1.87 | 0.254 |
| S733R | 1.98 | 0.207 |
| S733N | 1.86 | 0.266 |
| S733E | 2.06 | 0.354 |
| S733Q | 1.86 | 0.191 |
| I824E | 2.12 | 0.327 |
| Y829I | 1.86 | 0.202 |
| Y829F | 2.46 | 0.787 |
| S831T | 1.71 | 0.182 |
| K959A | 1.55 | 0.166 |
| K959M | 2.02 | 0.288 |
| K962Q | 1.56 | 0.171 |

TABLE 4

| Mutation G410H broadly increases activity of TP-DNAP1 variants Fold-change of p1 copy number over w.t. | | |
|---|---|---|
| | G410 (w.t.) | G410H |
| w.t. | 1.0 ± 0.27 | 1.53 ± 0.33 |
| N423R | 0.59 ± 0.11 | 1.03 ± 0.21 |
| N423Q | 0.44 ± 0.22 | 0.93 ± 0.18 |
| L640A | 0.069 ± 0.015 | 1.19 ± 0.22 |
| N423R, L640A | 0.092 ± 0.056 | 0.24 ± 0.082 |

Figure 3:
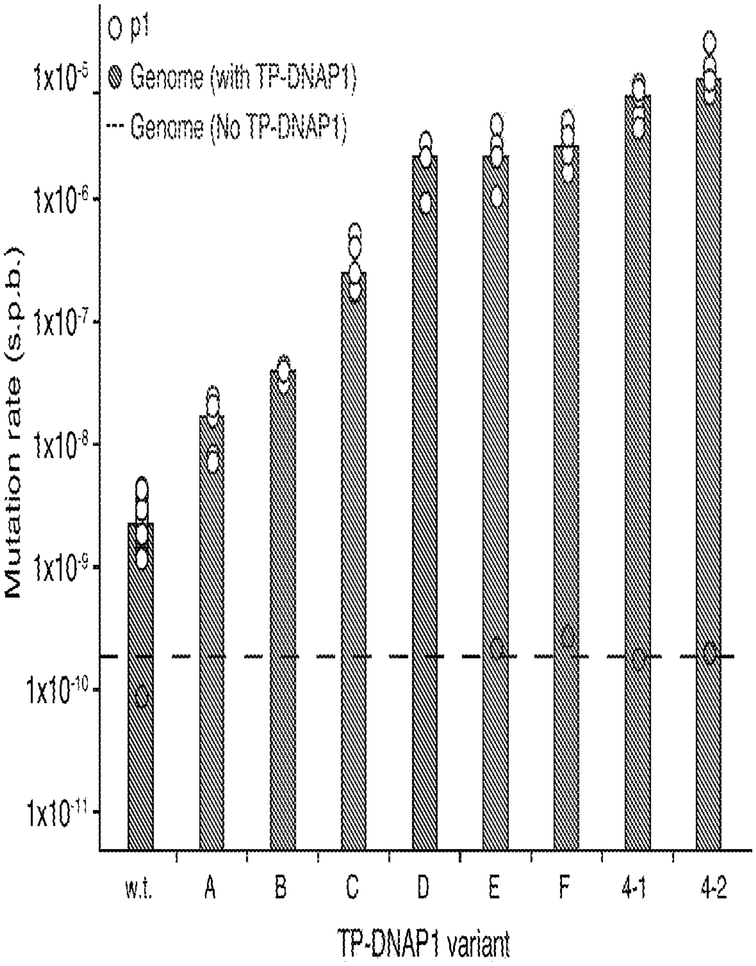
FIG. 3 depicts mutation rates of a representative panel of TP-DNAP1 variants and genomic substitution rates in the presence of highly error-prone variants. TP-DNAP1 substitution rates were measured with fluctuation tests using p1-encoded leu2 (Q180*). Open circles represent measurements from independent fluctuation tests, and bars denote median measurements. Genomic substitution rates were determined for strains harboring p1 and each TP-DNAP1 variant as well as for the TP-DNAP1 parent strain, AH22, which lacks p1 and TP-DNAP1. Genomic substitution rates were measured at the URA3 locus in large-scale fluctuation tests and are shown as individual measurements.

Using this basis set, we designed, cloned, and screened combinatorial libraries in order to find highly error-prone TP-DNAP1s. To limit combinatorial diversity in our designs, we grouped basis set mutations according to their proximity to DNAP motifs known to affect fidelity (i.e. the A and C motifs in the palm domain, the B motif in the fingers domain, and the Exo I, II, and III motifs in the exonuclease domain (Joyce and Steitz, 1994)) and cloned only inter-motif combinations. We expected that synergy between inter-motif mutations from different domains (e.g. motif A mutations with motif B mutations) would yield super-additive or super-multiplicative reductions in fidelity, as observed with RB69 DNAP and *E. coli* Pol I, respectively (Bebenek et al., 2001; Camps et al., 2003). We screened a library of motif B mutants crossed with motif A and C mutants and found 46 mutators (Table 2). The most error-prone of these 46 include three TP-DNAP1 variants (Rd3 mutants) with mutation rates of ~$1\times10^{-6}$ s.p.b., representing a ~400-fold increase over the w.t. TP-DNAP1 mutation rate and a ~10,000-fold increase over the yeast genomic mutation rate. We then crossed these Rd3 mutants with all of the exonuclease domain mutants from our basis set. After screening the resulting library, we obtained four hits (Rd4 mutants), including two highly error-prone variants, TP-DNAP1-4-1 (V574F, I777K, L900S) and TP-DNAP1-4-2 (L477V, L640Y, I777K, W814N), that replicate p1 at mutation rates of ~$7\times10^{-6}$ s.p.b. and ~$1\times10^{-5}$ s.p.b., respectively, and that both sustain a p1 copy number of ~5 (FIG. 3; Table 2). Additional rounds of library design and screening should reach even higher error rates, but these two Rd4 mutants are already exceptionally error prone, so we ended our polymerase engineering effort at this point. As a practical guide, for facile generation of DNA libraries in vivo with TP-DNAP1-4-2, a 1 μL saturated yeast culture is theoretically sufficient for 1-fold coverage of all single mutants of a 1 kb gene and a 200 mL culture is sufficient for all double mutants. With mutational accumulation, highly diverse libraries can be generated in even smaller volumes: 1-fold coverage of all double mutants of a 1 kb gene can be achieved in a 650 μL culture with just 50 generations of propagation.

Fluctuation tests of the genomic URA3 gene were performed to determine genomic per-base substitution rates, as previously described (Ravikumar et al., 2014). Fluctuation data were analyzed by the maximum likelihood method, as described for large-scale p1 fluctuation tests. Phenotypic mutation rates were divided by the target size for loss of function of URA3 via base pair substitution (Lang et al., 2008), to yield per-base substitution rates. 95% confidence intervals were similarly scaled by these factors. All data related to genomic URA3 fluctuation tests are fully described in Table 5.

TABLE 5

| Yeast genomic substitution mutation rates in the presence of error-prone TP-DNAP1 variants | | | | |
|---|---|---|---|---|
| TP-DNAP1 | Mutation rate (s.p.b.) | Lower 95% C.I. (s.p.b.) | Upper 95% C.I. (s.p.b.) | Number of replicates |
| None (AH22) | $1.86\times10^{-10}$ | $1.34\times10^{-10}$ | $2.50\times10^{-10}$ | 187 |
| w.t. | $8.73\times10^{-11}$ | $3.47\times10^{-11}$ | $1.77\times10^{-10}$ | 90 |
| L474W, L640Y, I777K, W814N | $2.17\times10^{-10}$ | $7.80\times10^{-11}$ | $4.67\times10^{-10}$ | 90 |
| Y431H, L640Y, I777K, W814N | $2.68\times10^{-10}$ | $1.53\times10^{-11}$ | $1.18\times10^{-9}$ | 90 |

TABLE 5-continued

Yeast genomic substitution mutation rates in the presence of error-prone TP-DNAP1 variants

| TP-DNAP1 | Mutation rate (s.p.b.) | Lower 95% C.I. (s.p.b.) | Upper 95% C.I. (s.p.b.) | Number of replicates |
|---|---|---|---|---|
| V574F, I777K, L900S | $1.76 \times 10^{-10}$ | $4.37 \times 10^{-11}$ | $4.55 \times 10^{-10}$ | 90 |
| L477V, L640Y, I777K, W814N | $1.98 \times 10^{-10}$ | $1.40 \times 10^{-10}$ | $2.71 \times 10^{-10}$ | 186 |

We found that the high p1 mutation rates driven by error-prone TP-DNAP1s remained completely stable for the longest duration tested (90 generations; Table 2), and genomic mutation rates remain unchanged in the presence of p1 replication by the most error-prone TP-DNAP1, TP-DNAP1-4-2 (FIG. 3; Table 5). Therefore, the mutant TP-DNAP1 of the invention can durably sustain in vivo mutagenesis with complete orthogonality (i.e. at least ~100,000-fold mutational targeting) to enable continuous evolution experiments.

Comparison of Error-Prone TP-DNAP1 Variants to Elevated Genomic Mutation Rates

The mutant TP-DNAP1 of the invention can access and sustain mutation rates that untargeted genome mutagenesis cannot. There is a theoretically predicted and empirically observed inverse relationship between the length of an information-encoding polymer, such as a gene or genome, and the tolerable error rate of replication (Biebricher et al., 2006; Bull et al., 2007; Drake 1991; Nowak and Schuster, 1989). At sufficiently high mutation rates, essential genetic information is destroyed every generation, guaranteeing extinction, and even moderately elevated mutation rates can erode fitness (Herr et al., 2011; Wilke et al., 2001). Continuous directed evolution systems fundamentally work by targeting mutagenesis to desired genes in order to bypass the low error thresholds of large cellular genomes, but existing systems still elevate genome-wide mutation rates of cells or phages, falling short of a complete bypass (Badran and Liu, 2015; Camps et al., 2003; Crook et al., 2016; Esvelt et al., 2011; Fabret et al., 2000; Finney-Manchester and Maheshri, 2013; Halperin et al., 2018; Moore et al., 2018). Since the mutant TP-DNAP1 is fully orthogonal to genomic replication, it achieves the complete bypass of genomic error thresholds for genes of interest, which should result in the ability to run in vivo continuous evolution for indefinitely large numbers of generation at mutation rates that are exclusively limited by the thresholds of user-selected genes.

Figure 4:
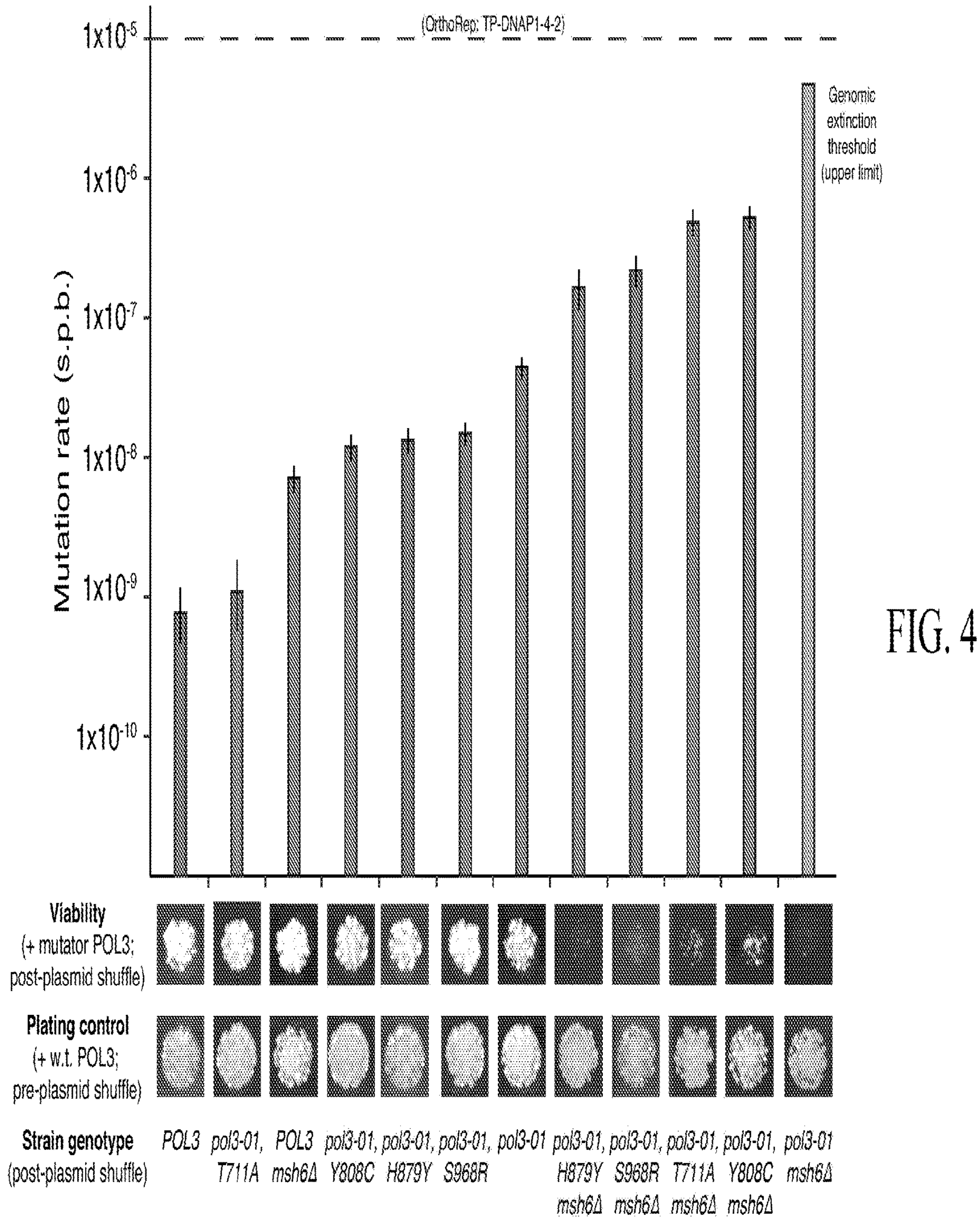
FIG. 4 depicts a series of yeast genomic mutator strains spanning mutation rates from the w.t. rate to the extinction threshold (upper limit). TP-DNAP1's parent strain, AH22, was modified to express its genomic w.t. POL3 from a plasmid, and POL3 variants were introduced into w.t. or mismatch repair-deficient (Δmsh6) versions of this strain via plasmid shuffle. W.t. POL3 is retained in pre-plasmid shuffle plating controls. Genomic mutation rates were measured ~15 generations after plasmid shuffle. The projected mutation rate of the inviable pol3-01, Δmsh6 strain was calculated as the product of the mutational increases due to pol3-01 (58-fold) and Δmsh6 mutations (106-fold, averaged across genotypes). The proofreading deficient pol3-01 allele encodes POL3 (D321A, E323A). T711A, Y808C, H879Y, and S968R are suppressor mutations that reduce the error rate of pol3-01.

In order to demonstrate the limitations of genomic error thresholds on continuous evolution, we experimentally applied high mutation rates to the host genome. This was done by transplanting previously discovered mutations that increase the substitution mutation rate of POL3 (Herr et al., 2011), the primary yeast lagging strand DNAP, into w.t. or mismatch repair deficient (Δmsh6) versions of AH22, the parent of TP-DNAP1-containing strains. Mutator phenotypes, verified by fluctuation tests at a genomic locus, were accompanied by severe growth defects and led to immediate extinction in the case of pol3-01, Δmsh6 AH22 (FIG. 4). In agreement with a previous estimate (Herr et al., 2011), the projected mutation rate imposed in this nonviable AH22 strain was $4.72\times10^{-6}$ s.p.b., calculated from the individual contribution of pol3-01 and the average effect of MSH6 loss. This mutation rate is presumed to exceed the haploid yeast error induced extinction threshold thereby killing the host cell (Herr et al., 2011). Since replication of p1 by TP-DNAP1-4-2 occurs at a higher mutation rate than $4.72\times10^{-6}$ s.p.b., we conclude that the mutant TP-DNAP1 can stably exceed categorical mutation rate limits on replicating cellular genomes.

Figure 5:
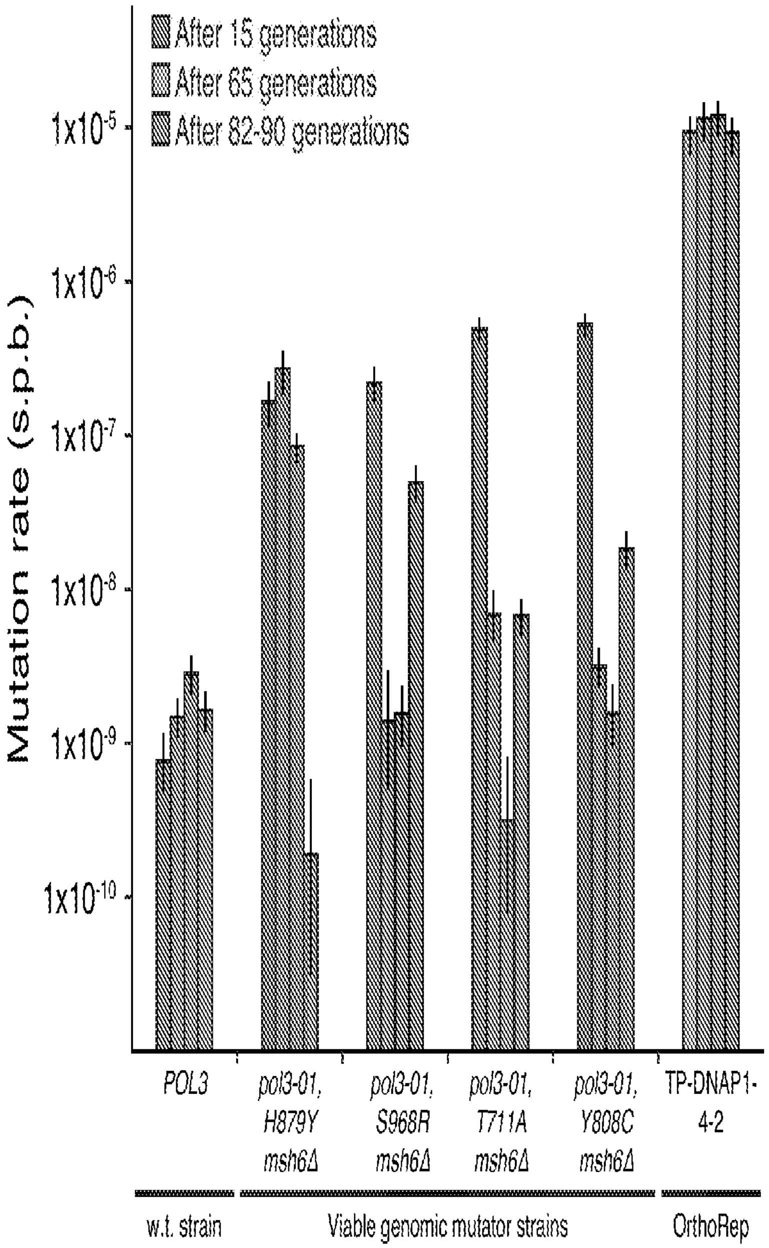
FIG. 5 depicts the mutational stability of viable genomic mutator strains versus TP-DNAP1. Strains harboring POL3 variants or TP-DNAP1-4-2 were passaged in triplicate for 82 or 90 generations, respectively. Afterwards, genomic or TP-DNAP1 substitution mutation rates were measured at the genomic CAN1 locus or with p1-encoded leu2 (Q180*), respectively.

We also asked whether viable genomic mutator strains could sustain mutagenesis. Four AH22 strains with mutation rates of $1.64\times10^{-7}$-$5.24\times10^{-7}$ s.p.b. were propagated for 82 generations in triplicate, and afterwards, a clone from each was subject to genomic mutation rate measurements via fluctuation tests (FIG. 5). Across replicates, the mutation rate drops an average of 284-fold (FIG. 5), likely due to suppressor mutants that alleviate deleterious genome mutagenesis and overtake the population (Herr et al., 2011). In contrast, mutagenesis on p1 remains constant (FIG. 5). This indicates that in durations relevant to directed evolution experiments, even moderate genome mutagenesis is unsustainable whereas continuous mutagenesis in the invention is sustainable.

To construct POL3 mutator strains, plasmids were transformed into AH22 encoding wild-type POL3 on a URA3 plasmid or Δmsh6 AH22 encoding wild-type POL3 on a URA3 plasmid. Transformants were expanded in selective SC medium and spot plated on selective SC medium or selective SC medium supplemented with 5-FOA (1 g/L) for plasmid shuffle of the plasmid encoding wild-type POL3 via URA3 counter-selection (Boeke et al., 1984).

Fluctuation tests of the genomic CAN1 gene were performed to determine genomic per-base substitution rates. To minimize propagation of POL3 mutator strains, fluctuation tests were performed directly on colonies from plasmid shuffle plates. For each strain, 48 colonies from plasmid shuffle plates were individually scraped and resuspended in 120 μL 0.9% NaCl. 10 μL from each resuspension was diluted and subject to an event counts measurement via flow cytometry. This was done to identify colonies of similar cell count, because fluctuation tests are only appropriate when final population sizes for all replicates are similar. 24 resuspensions with similar event counts were used for fluctuation tests. 90 μL from the 24 resuspensions were mixed and plated onto SC medium lacking arginine and supplemented with 10× canavanine (0.6 g/L). 10 μL from four of the 24 resuspensions was pooled, diluted and titered on solid SC medium. Plates were incubated at 30 °C. Colonies were counted from titer plates after 2-4 days and from spot plates after 3-6 days. Based on titer counts, the average number of generations that occurred during colony formation was ~15.

To test the stability of mutator phenotypes, three colonies from each plasmid shuffle plate were passaged ten times at 1:100 dilutions (67 generations). A single clone from each final population was isolated and subject to CAN1 fluctuation tests. This was performed using a protocol similar to that described previously for URA3 fluctuation tests (Ravikumar et al., 2014), except cultures from CAN1 fluctuation tests were plated onto solid SC medium lacking arginine and supplemented with 10× canavanine (0.6 g/L).

Fluctuation data were analyzed as described above for URA3 fluctuation data, but with mutation frequency parameters for CAN1 (Lang et al., 2008). The Fenton approximation (Fenton, 1960) was used to calculate the predicted rate of the extinct mutator strain. All data related to genomic CAN1 fluctuation tests are fully described in FIG. 4 and FIG. 5.

Use of Error-Prone TP-DNAP1 for High-Throughput Evolution of Drug Resistance

Sustainable, continuous, and targeted mutagenesis with the mutant polymerases of the invention can be used to understand and predict drug resistance in high-throughput evolution experiments that abundantly sample adaptive trajectories and outcomes. PfDHFR resistance to the antimalarial drug, pyrimethamine, occurs in the wild primarily through four active site mutations (N51I, C59R, S108N, and I164L), but the broader resistance landscape remains largely unknown. Laboratory evolution and landscape-mapping studies have mostly been limited to the quadruple mutant fitness peak (qm-wild) and suggest that resistance reproducibly arises from the crucial S108N mutation, followed by step-wise paths to qm-wild (Chusacultanachai et al., 2002; Hankins et al., 2001; Japrung et al., 2007; Lozovsky et al., 2009; Sirawaraporn et al., 1997; Wooden et al., 1997). We asked whether high-throughput directed evolution of PfDHFR resistance to pyrimethamine would reveal a more complex landscape with additional fitness peaks, including ones that forgo S108N.

We used mutant TP-DNAP1 to evolve PfDHFR resistance to pyrimethamine in 90 independent 0.5 mL cultures. Based on a well-established yeast model of PfDHFR, we constructed transgenic yeast strains that lack endogenous DHFR and depend on p1-encoded PfDHFR. These strains acquired sensitivity to pyrimethamine and in pilot studies, evolved resistance by accumulating mutations in PfDHFR. We found that resistance arose more commonly and successfully as the mutation rate of p1 was increased, suggesting that the mutant polymerases of the invention could indeed be used to drive rapid PfDHFR evolution. To perform a large-scale resistance evolution experiment, strain OR-Y8, which uses the most mutagenic TP-DNAP1 (TP-DNAP1-4-2) to replicate p1-encoded PfDHFR, was seeded into 90 independent 0.5 mL cultures containing pyrimethamine. Cultures were grown to saturation and uniformly passaged at 1:100 dilutions into media containing gradually increasing pyrimethamine concentrations chosen to maintain strong selection as populations adapted. After just 13 passages (i.e. 87 generations), 78 surviving populations adapted to media containing the maximum soluble concentration of pyrimethamine (3 mM). (Revival experiments showed that extinction of the 12 replicates was stochastic and that they could also adapt given repeated chances (Table 6).) From Sanger sequencing analysis of bulk adapted populations, we identified 37 unique protein-coding mutations across all replicates and as many as six amino acid changes in a single population. A large fraction of these mutations are predicted to be adaptive. For example, ten of the 37 mutations have been previously reported to yield pyrimethamine resistance (Chusacultanachai et al., 2002; Hankins et al., 2001; Japrung et al., 2007; Tanaka et al., 1990). In addition to these 37 mutations, several mutations identified in the promoter region increased gene expression; and we hypothesize that some of the observed synonymous mutations in PfDHFR reduce translational suppression mediated by binding of PfDHFR to its own mRNA sequence (Zhang and Rathod, 2002).

TABLE 6

| Stochastic extinction in revival experiments of PfDHFR evolution Index of extinct population in 96-well tray | | |
|---|---|---|
| Original experiment | Revival experiment 1 | Revival experiment 2 |
| 1 | 51 | 39 |
| 9 | 63 | 51 |
| 32 | 66 | 63 |
| 33 | 84 | 88 |
| 34 | | 90 |
| 40 | | 92 |
| 42 | | |
| 49 | | |
| 50 | | |
| 55 | | |
| 57 | | |
| 90 | | |

Adapted populations primarily converged on a region of the PfDHFR resistance landscape that contains previously unidentified S108N-based genotypes as fit as qm-wild. Across all replicates, we observed seven pervasive coding changes, including 737_738insA, which creates an adaptive C-terminal truncation. The two most common mutations, C59R and S108N, occur together in 62/78 adapted populations. Although these mutations are present in qm-wild, only one population accumulated a third mutation from the qm-wild peak. Instead, most populations diverged from qm-wild and acquired combinations of C50R, D54N, or Y57H in addition to C59R and S108N, indicating a new region in the PfDHFR resistance landscape with high fitness. To validate this, we fully mapped the resistance landscape of this region defined by C50R (10000), D54N (01000), Y57H (00100), C59R (00010), and S108N (00001) by constructing and measuring the MIC of all combinations of these five mutations. We found that this region is indeed highly fit and contains four alleles that have similar or higher pyrimethamine MICs than qm-wild (11110, 10111, 01111 and 11111). Since these alleles are close in genotype, differing by only one or two mutations, they approximate a fitness plateau. In two replicate lines of our evolution experiment, this plateau is reached via 01111. Although most replicates in our experiment do not reach this particular plateau, the 00111 intermediate was frequently accessed. In these instances, additional adaptive mutations were often acquired outside of the five-mutation landscape. For example, one of the replicates contains the previously reported C6Y resistance mutation, alongside Y57H, C59R, and S108N. Since 00111 by itself is almost as resistant as genotypes on the plateau, these populations likely achieved comparable fitness atop neighboring peaks in the wider landscape. Taken together, we conclude that our evolution experiments were able to rapidly identify previously unknown solutions to PfDHFR resistance.

Epistasis among mutations in S108N-based trajectories directs adaptation to 01111 and leads to the observed convergence of 00111 across replicate lines. Because S108N is a highly adaptive single mutant, 00001 rapidly and repeatedly fixed first in evolving populations, and blocked access to the 96/120 possible trajectories in this landscape that start with other first-step mutations. From 00001, access to the fitness plateau is constrained by negative epistasis between S108N and D54N, which is relieved and changes sign only when Y57H and C59R are both present. (We note that adapted populations in our evolution experiment containing high frequencies of D54N, C59R and S108N without Y57H, typically carry other, potentially compensatory, promoter and coding mutations that take the place of Y57H.) As a result, just eight of the 24 possible paths from 00001 to the plateau avoid inactive PfDHFR intermediates. Adapting populations limited to these paths likely follow the greediest one. This explains why our experiment finds that evolution, particularly of 00111 and 01111, is largely repeatable.

Notably, 11110 lies on the fitness plateau without requiring S108N. Three populations in our experiment avoid mutation at S108 and can access this unique quadruple mutant. We attribute this to a rare clonal interference event where the 01100 double mutant arises and displaces a population that has nearly fixed 00001. One of these replicates additionally fixed C59R to reach 01110, the triple mutant with the highest MIC. Stronger selection for pyrimethamine resistance, if feasible, should also fix C50R and lead to 11110.

Since 11110 is suppressed by rapid fixation of S108N, weaker early selection or greater population structure (Salverda et al., 2017; Szendro et al., 2013), should allow alternative first-step mutations (e.g. Y57H, C59R) to fix and increase the chance of reaching 11110. Alternatively, random initial mutations created by neutral drift have been shown to direct drug resistance evolution along new trajectories (Salverda et al., 2011). We examined this latter possibility by repeating evolution from a variant of w.t. PfDHFR with a synonymous codon change at S108 (AGC→TCA) that prevents mutation to N through a single substitution. Twelve populations starting from this allele were evolved under the same pyrimethamine regimen described for the large-scale experiment. In this experiment, the ten surviving populations dramatically shifted towards a new, convergent outcome that avoids S108N and fixes D54N instead. Seven of these ten populations reached the 01100 double mutant that can subsequently access 11110. Since different pyrimethamine-resistant mutants should respond differently to other DHFR inhibitors, the existence of S108N-independent outcomes and the ability to steer the population towards these through weaker selection or neutral drift may have implications for drugs schedule design. In the future, we aim to leverage the scalability of the mutant polymerases of the invention, by starting evolution from hundreds of neutral variants of PfDHFR, to capture the scope of trajectories that may be available from standing variation in natural *P. falciparum* populations and predict selection conditions that may prefer one trajectory over another. Here, we conclude that our large-scale evolution experiment is able to identify a rare path to pyrimethamine resistance that avoids the commonly observed S108N mutation that is crucial in natural PfDHFR resistance.

Several adaptive populations in our experiment access the broader landscape beyond 11111. As described above, in some replicates, 00111 serves as a stepping-stone to neighboring fitness peaks through additional mutations like C6Y. In other replicates, we find a suboptimal peak containing C59Y (10121) at which populations are occasionally trapped. In one replicate, D54N fixes with S108T and avoids negative epistasis with S108N. Future analysis will include less frequent candidate adaptive mutations that occur in multiple replicates (e.g. Y35H, 1150T, D222N, L251S, T268A) or fix independently in time (e.g. M2491). However, our analysis of only the most common adaptive mutations and mutational paths has already uncovered new peaks in the landscape of PfDHFR-mediated drug resistance and provides examples of how epistasis results in evolutionary repeatability, and how the existence of greedy mutations such as S108N can render a highly adaptive outcome (11110) rare through early fixation. In other words, high-throughput directed evolution with the mutant polymerases of the invention enables the discovery of new fit regions of adaptive landscapes and thorough studies of molecular evolution at the level of a single protein.

Example 2: Mutually Orthogonal DNA Replication Systems In Vivo

The experiments presented herein demonstrate the development of an additional DNAP/plasmid pair which is orthogonal to genomic replication in *S. cerevisiae* and is also orthogonal to a previously developed DNAP/plasmid pair, such that the two DNAP/plasmid pairs are mutually orthogonal to each other. This solidifies two platforms for independently expanding the properties of DNA replication in vivo.

The two orthogonal replication systems are based on the cytoplasmically-localized pGKL1/pGKL2 (p1/p2) plasmids originating from *Kluyveromyces lactis* (Strak et al., 1990, Yeast 6:1-29; Klassen et al., 2007, Microbial Linear Plasmids pp. 187-226). Both p1 and p2 encode their own DNAPs, TP-DNAP1 and TP-DNAP2, respectively. It was previously demonstrated that engineered error-prone variants of TP-DNAP1 increase the mutation rate of p1 to ~$10^{-5}$ substitutions per base (s.p.b.) without affecting the genomic mutation rate of ~$10^{-10}$ s.p.b. in *S. cerevisiae* (Ravikumar et al., 2018, bioRxiv, 313338). It was also found that p1 replication strictly requires TP-DNAP1 (Ravikumar et al., 2014, Nature Chemical Biology, 10:175-177). This allowed the development of TP-DNAP1 and p1 as an orthogonal DNAP/plasmid pair such that engineered changes to TP-DNAP1 only act on p1 but not on the genome. However, it was not known whether orthogonality to genomic replication holds true for TP-DNAP2 and p2 nor whether the TP-DNAP1/p1 and TP-DNAP2/p2 pairs are mutually orthogonal. Here, error-prone TP-DNAP2s are developed, and the associated genetic techniques necessary to engineer the p2 plasmid and TP-DNAP2 are reported. Finally, the experiments provided demonstrate that the TP-DNAP2/p2 pair is both orthogonal to genomic replication and to p1 replication.

The existence of mutually orthogonal genetically tractable replication systems is significant for three main reasons. First, the finding of two mutually orthogonal DNA replication systems should lay the foundation for novel applications in synthetic biology. For example, in vivo accelerated evolution (Ravikumar et al., 2018, bioRxiv, 313338) of different genes or sets of genes can now be carried out at two distinct custom mutation rates, which could be useful for evolving components in hierarchically organized signaling pathways. Another possibility includes using inducible error-prone orthogonal DNAPs to record multiple cellular events or external stimuli, where the number of mutational events in p1 and p2 would be independent readouts of the amount of exposure to two signals experienced by cells. In addition, the freedom to engineer two orthogonal DNAPs in vivo may enable propagation of different XNA's in living cells, whereas current efforts are limited to either using novel base-pairs recognized by host DNAPs or engineering DNAPs to synthesize XNA with novel backbones in vitro (Taylor et al., 2015, Nature, 518: 427-430; Pinheiro et al., 2012, Science, 336:341-344; Malyshev et al., 2014, Nature, 509:385-388). Second is a practical consideration. A primary motivation for developing an orthogonal replication (OrthoRep) system was to achieve continuous rapid evolution of target genes in vivo at extreme mutation rates that the genome cannot withstand (Ravikumar et al., 2018, bioRxiv, 313338). This was achieved by making TP-DNAP1 highly error-prone so that it rapidly mutates the p1 plasmid but spares the genome. The mutual orthogonality demonstrated here ensures that any essential accessory genes encoded on p2 are also spared by error-prone TP-DNAP1s during directed evolution experiments of genes on p1 in OrthoRep. Third, the result provides in vivo evidence that DNA initiation of p1 and p2 use independent components. p1 and p2 both contain terminal proteins (TPs) linked to their 5' termini, which act as origins of replication, akin to other protein-primed DNA replication systems like those found in bacteriophage €>29 and adenovirus (Rodriguez et al., J. Mol. Biol, 337:829-841; Mysiak et al., 2004, Nucleic Acids Res, 32:3913-3920). The lack of homology between the TPs of p1 and p2 suggested that TP-DNAP1 and TP-DNAP2 may use distinct molecular interactions for plasmid initiation. In addition, in vitro biochemical data shows that TP-DNAP1 can initiate replication from p1's inverted terminal repeat (ITR), hypothesized to act in concert with p1's TP to form an origin of replication, but cannot initiate replication from p2's ITR. The identification of mutual orthogonality between p1 and p2 replication demonstrates that highly specific TP-DNAP interactions with cognate TPs and ITRs govern plasmid initiation, encouraging future studies on the mechanisms of protein-primed DNA replication and suggesting a potential approach for engineering additional orthogonal replication systems that operate concurrently in the same cell (FIG. 7).

The materials and methods employed in these experiments are now described.

Materials and Methods

All oligonucleotide primers and synthesized gene fragments (gBlocks®) were purchased from IDT. Enzymes for PCR and cloning were obtained from NEB. All plasmids, including TP-DNAP2 libraries were cloned using Gibson assembly with overlap regions of 20-30 bp. Vectors harboring homologous recombination cassettes for p2 integrations were cloned as previously described for p1 integration cassettes (Ravikumar et al., 2018, bioRxiv, 313338; Ravikumar et al., 2014, Nature Chemical Biology, 10:175-177).

Plasmid pGA55 was cloned as follows: three gene fragments constituting recoded TP-DNAP2 were assembled with the vector backbone of a yeast shuttle vector containing CEN6/ARS4 and HIS3 for propagation in yeast, and ColE1 and KanR for propagation in *E. coli*. The resulting vector was used for TP-DNAP2 complementation and generation of TP-DNAP2 libraries.

*S. cerevisiae* strain AR-Y292 served as the parent for all strains used in this study and contains the wild type pGKL1 and pGKL2 (or p1 and p2) linear plasmids. GA-Y021 and GA-Y069 were created from AR-Y292 by p2 integration methods described below. AR-Y436 is a derivative of AR-Y292 encoding a functional copy of URA3 at the endogenous genomic locus, for 5-FOA-based fluctuation tests of genomic mutation rates in presence of mutagenic TP-DNAP2 variants.

Strains for testing mutual orthogonality were generated by transforming a panel of CEN6/ARS4 vectors encoding TP-DNAP1 or TP-DNAP2 variants into two base strains, AR-Y304 and GA-Y021. AR-Y304 (Ravikumar et al., 2014, Nature Chemical Biology, 10:175-177) contains recombinant p1 encoding mKate2, URA3 and leu2* without disturbing the native TP-DNAP1 ORF. Similarly, GA-Y021 encodes recombinant p2 that replaces ORF1 with mKate2, URA3 and leu2* without disturbing the native TP-DNAP2 ORF.

All yeast transformations were performed using the high-efficiency LiAc/SS carrier DNA/PEG method (Gietz and Schiestl, 2007, Nat Protoc, 2:31-34). For integrations into p2, 2-5 μg of plasmid containing the appropriate integration cassette was digested with ScaI, yielding a linearized cassette with blunt ends containing the genes of interest flanked by regions of homology to p2. The products of the digestion reaction were directly transformed into appropriate AR-Y292-derived strains harboring wild type p1 and p2, and plated on selective solid SC medium. Colonies appeared after 4-5 days of growth at 30 °C. CEN6/ARS4 plasmids were also transformed with the LiAc/SS carrier DNA/PEG method, but with only 500-3000 ng of DNA for individual vectors and with at least 10 μg of plasmid DNA for TP-DNAP2 library transformations, to maintain 6-fold coverage.

p1, p2, and all derived linear plasmids were extracted using a modified version of the yeast DNA extraction protocol detailed in (Amberg et al., 2005, Methods in yeast genetics: a Cold Spring Harbor Laboratory course manual, Cold Spring Harbor Laboratory Press, Cold Spring Harbor, N.Y.). The modifications were as follows: (i) cells spun down from 40 mL of saturated culture were washed in 0.9% NaCl before treatment with Zymolyase (US Biological) to break up flocculated cells; (ii) 200 μg/mL proteinase K (Sigma) was supplemented during SDS treatment for degradation of TP; (iii) Rotation at ~10 r.p.m. was used during Zymolyase and proteinase K treatments. This large-scale extraction protocol was used for preparing DNA for absolute quantification by qPCR. For qualitative analysis by agarose gel electrophoresis, this extraction protocol was scaled down to extract DNA from only 1.5 mL of saturated yeast culture.

To achieve active curing of the cytoplasmic p2 plasmid, the yeast Cas9 genomic modification system developed by Cate and coworkers was repurposed for cytoplasmic targeting (Ryan et al., 2014, Elife 3). The SV-40 nuclear localization signal and 8×HIS tag were removed from the pCAS plasmid (Addgene plasmid #60847) to localize Cas9 to the cytoplasm where p2 (and p1) plasmids propagate. Appropriate 20 nt spacers were cloned into this vector to target different sites in p2. These modified pCAS vectors were transformed into the strains harboring p2 plasmids to be cut, and plated on solid selective SC medium containing 1 g/L monosodium glutamate (MSG) as the nitrogen source and supplemented with G418 (400 μg/mL). Colonies that appeared after incubation at 30 °C for 2 days were inoculated into liquid selective SC medium with 1 g/L MSG and G418 (200 μg/mL) and passaged once at a 1:1000 dilution to cure the targeted p2 plasmid. The resulting cultures were then subjected to DNA extraction and analysis by gel electrophoresis to verify loss of the targeted p2 plasmid. To minimize potential toxicity due to Cas9 expression, final strains lacking the pCAS vector were isolated by passaging without G418 selection, and replica plating clones on solid medium with and without G418 to screen for loss of the pCAS vector.

TP-DNAP1 and TP-DNAP2 peptide sequences were aligned using protein BLAST and four candidates residues for library generation were chosen by two criteria (Altschul et al., 1997, Nucleic Acids Res, 25:3389-3402). First, candidate TP-DNAP2 residues must match a residue in TP-DNAP1 known to affect fidelity, based on prior studies (Ravikumar et al., 2018, bioRxiv, 313338; Ravikumar et al., 2014, Nature Chemical Biology, 10:175-177). Second, at least 25% of the 20 neighboring residues must align. This analysis yielded positions S370, Y424, L474 and F882.

To clone the expression vector for wild type TP-DNAP2 (pGA55), TP-DNAP2 was codon optimized for expression in *S. cerevisiae* with GenScript's OptimumGene™ tool, and the recoded ORF was synthesized as three gene fragments, which were assembled downstream of the REV1 promoter in a CEN6/ARS4 vector containing selection markers HIS3 and KanR. The four TP-DNAP2 NNK libraries were cloned from pGA55 via Gibson assembly. First, a two-step PCR was performed to limit bias in the NNK incorporation that may result from annealing between the degenerate codon and the plasmid template. Linear PCR fragments of pGA55 were generated with 5' ends that terminate immediately 3' of the library codons and 3' ends in the plasmid backbone. These linear amplicons were purified, diluted to 40 ng/μL, and re-amplified in PCR reactions with a forward primer containing Gibson overlap regions and NNK overhangs at the corresponding library site in TP-DNAP2, and the same reverse primer used in the initial PCR. These PCR products were then purified and treated with DpnI for 6 hours at 37 °C to digest any pGA55 plasmid carry-through. The second Gibson fragment was PCR amplified from pGA55 to include the vector backbone starting 5' in KanR and 3' leading up to, but not including the library codon. For each library, 100 ng of corresponding PCR amplicons were combined in a 20 μL Gibson assembly reaction, and incubated at 50 °C for 1 hour. The assemblies were purified and concentrated in 12 μL of $ddH_2O$. 5 μL of the purified assembly products were then transformed into electrocompetent Top 10 cells and recovered at 37 °C for 1 hour. Each transformation was plated at 1×, 10× and 100× dilutions on solid LB medium supplemented with kanamycin (50 μg/mL). After overnight incubation at 37 °C, colony counts on the 10× and 100× plates were used to calculate the transformation efficiency. All transformations yielded more than 3200 transformants, corresponding to >100-fold coverage of each library in *E. coli* (each NNK library has a theoretical diversity of 32). The transformants from the 1× plates were then harvested by resuspension in 5 mL of sterile ddH2O. Library plasmid DNA was extracted from *E. coli* using the Zyppy™ Plasmid Miniprep Kit. Library quality was determined by verifying plasmid library sizes by agarose gel and Sanger sequencing of bulk library populations as well as 8 individual clones from each library.

For fluctuation tests used to measure p2 mutation rates, leu2* served as a marker for detecting mutational events. leu2* is a disabled version of LEU2, where Q180 is replaced with a TAA stop codon. Q180 is a permissive site where mutation to any other codon other than TAG and TGA results in functional reversion to LEU2. These mutational events can be detected by plating scores of parallel cultures on medium lacking leucine and counting the number distribution of functional LEU2 mutants.

For TP-DNAP2 library screening, each library member was subjected to small-scale leu2* fluctuation tests with six replicates. 190 library members from each yeast library transformation were arrayed and inoculated into liquid SC medium lacking uracil and histidine, and passaged three times at 1:10,000 dilutions. mKate2 fluorescence was measured at every passage on a microplate reader (TECAN Infinite® 200 PRO, settings: λex=588, λem=633) to track p2 copy number stabilization. To perform fluctuation tests, each library member was diluted 1:10,000 into liquid SC medium buffered to pH 5.8 and lacking uracil, histidine, tryptophan, and dilutions were split into six 100 μL replicates. Cultures were grown for 48 hours at 30 °C to reach saturation. Saturated cultures were washed with 200 μL 0.9% NaCl to remove residual leucine and resuspended in 35 μL of 0.9% NaCl. 10 μL of this resuspension was spot plated onto solid SC medium buffered to pH 5.8 and lacking uracil, histidine, tryptophan and leucine. Spot plates were allowed to dry and incubated at 30 °C. Colonies were counted after 5 days. Colony counts were used to calculate the expected number of LEU2 functional mutants (m), using the p0 method (Foster, 2006, Methods Enzymol, 409:195-213).

To precisely measure p1 and p2 per-base substitution mutation rates, several modifications were made to the small-scale protocol. First, 36 replicates were performed for reconfirmation of candidate TP-DNAP2 mutators, and 48 replicates for genomic and mutual orthogonality experiments. Titers were also determined for each strain after spot plating by pooling the residual volume from 4 replicates and plating dilutions on YPD. The expected number of LEU2 functional mutants (m) was determined by the Ma-Sandri-Sarkar maximum likelihood estimator (as calculated by the FALCOR tool and corrected for partial plating (Foster, 2006, Methods Enzymol, 409:195-213; Sarkar et al., 1992, Genetica, 85:173-179; Hall et al., 2009, Bioinformatics, 25:1564-1565). The mean mKate2 fluorescence was determined from 50,000 event counts on Attune™ NxT Flow Cytometer and converted to p2 copy number by using a calibration curve. To determine per-base substitution rates, the corrected m was normalized to the average cell titer, the p2 copy number, and the target size for functional leu2* reversion (2.33 bp). 95% confidence intervals were similarly scaled.

```
Primers used for LEU2 qPCR:
forward
(5'-GCTAATGTTTTGGCCTCTTC-3'; SEQ ID NO: 60)

reverse
(5'-ATTTAGGTGGGTTGGGTTCT-3'; SEQ ID NO: 61)
```

```
Primers used for LEU3 qPCR:
forward
(5'-CAGCAACTAAGGACAAGG-3'; SEQ ID NO: 62)

reverse
(5'-GGTCGTTAATGAGCTTCC-3'; SEQ ID NO: 63)
```

Fluctuation tests using genomically encoded URA3 were performed in the presence of TP-DNAP2 variants to determine the genomic per-base substitution rates, similarly to previously described protocols (Lang and Murray, 2008, Genetics, 178:67-82). AR-Y292 derived strains harboring the appropriate TP-DNAP2 variant encoded on a CEN6/ARS4 vector (with a HIS3 marker) were grown in liquid SC medium lacking uracil and histidine until saturation. Each strain was diluted 1:5,000 into SC medium lacking histidine and aliquoted into 48 replicates of 200 μL each. Cultures were grown for 48 hours at 30 °C to reach saturation. Saturated cultures were washed with 400 μL 0.9% NaCl and resuspended in 420 μL 0.9% NaCl. 400 μL from each replicate was spot plated on pre-dried solid SC medium lacking histidine and supplemented with 5-FOA (1 g/L). The residual 20 μL from six replicates were pooled, diluted, and plated on solid YPD medium to determine cell titers. Plates were allowed to dry before incubation at 30 °C. Colonies were counted on titer plates after 2 days, and on spot plates after 5 days of growth. The expected number of mutants (m) was calculated using the MSS maximum likelihood estimator method via the FALCOR tool, and corrected for partial plating, as described above. To determine per-base substitution rates, the corrected m was normalized to the average cell titer, the URA3 copy number (1 in haploid yeast), and the target size for 5-FOA resistance via substitutions in URA3 (104 bp). 95% confidence intervals were similarly scaled.

A standard curve relating p2 copy number to mKate2 fluorescence was prepared by combining quantitative PCR with flow cytometry. During the 1:10,000 back dilution step of the leu2* fluctuation tests for the mutual orthogonality experiment, six strains with mKate2 encoded on p2 were diluted into liquid SC medium buffered to pH 5.8 and lacking uracil, histidine and tryptophan to yield 50 mL of saturated culture. After 48 hours of growth at 30 °C, a small portion of each culture was diluted 1:100 in 0.9% NaCl and analyzed on a flow cytometer (Attune™ NxT Flow Cytometer, settings: λex=561, λem=620; gain=550) to determine the mean red fluorescence from 50,000 counts. Genomic DNA and linear plasmids were extracted from the remaining 40 mL of each culture using the large-scale DNA extraction protocol detailed above to ensure complete and unbiased extraction of linear plasmids relative to genomic DNA. All extracts were diluted 4000-fold for use in two distinct qPCR reactions, one to quantify p2-encoded leu2* and the other to quantify the genomic copy of LEU3. Each 20 μL qPCR reaction consisted of 5 μL of template DNA, 2 μL forward primer (5 μM), 2 μL reverse primer (5 μM), 1 μL ddH2O, and 10 μL of Thermo Scientific™ Maxima SYBR Green/Fluorescein qPCR Master Mix (2×).

A standard curve for each primer set was prepared by performing qPCR on a dilution series of DNA extracted from F102-2 (25×, 125×, 625×, 3125×). Non-template controls with only $ddH_2O$ were included for each primer set to detect contamination. All qPCR's were performed in triplicate on the Roche LightCycler® 480 System using the following protocol:

qPCR:

1) 95 °C for 10 minutes
2) 40×:
   95 °C for 15 seconds
   60 °C for 1 minute
   measurement
3) 95 °C for 1 minute
4) 55 °C for 1 minute Primer melting curve: Ramp up to 95 °C at 0.11 °C/s, with 5 measurements per °C.

Cycle threshold (Ct) values were determined by the LightCycler® 480 software (fit-points method, threshold=1.75). Ct values from both standard curves were plotted against log ([DNA]). The slope and y-intercept were calculated using linear regression. Each sample's average Ct values were converted into copy number values by using the following equation: copy number=10((sample Ct−yintercept)/slope). The calculated leu2* copy number was divided by the LEU3 copy number to normalize to genomes extracted and account for variance in DNA extraction efficiency across samples.

The results of the experiments are now described.

The strategy used for probing orthogonality of the TP-DNAP2/p2 DNAP/plasmid pair is based on engineering and using error-prone TP-DNAP1 and TP-DNAP2 variants to measure whether they increase mutation rates of genes on p1, p2, and/or the host genome. Without being bound by theory, it was hypothesized that if error-prone TP-DNAP1s only increase the mutation rate of p1 (but not of p2 and the host genome) and error-prone TP-DNAP2s only increase the mutation rate of p2 (but not of p1 and the host genome), then the results would indicate that TP-DNAP1/p1 and TP-DNAP2/p2 are mutually orthogonal DNA replication systems that are both orthogonal to genomic replication.

First, a reliable method for encoding and expressing user-defined genes on p2 was developed. To measure mutation rates of p2 replication, mKate2, URA3, and leu2* (mUL*) were encoded on p2. mKate2 would serve as a fluorescent reporter for copy number, URA3 as a selection marker, and leu2*, which contains a stop codon at a permissive site in LEU2 (Q180*), would serve as a reporter for substitution mutation rates in fluctuation tests that measure reversion to functional LEU2. Without being bound by theory, it was hypothesized that mUL* could be integrated onto p2 via in vivo homologous recombination, following similar procedures to those used for manipulating p1 (Ravikumar et al., 2018, bioRxiv, 313338; Ravikumar et al., 2014, Nature Chemical Biology, 10:175-177). A DNA cassette was constructed encoding mUL* flanked by regions homologous to p2 such that successful recombination would result in the replacement of the non-essential ORF1 found on wildtype (wt) p2 (Schaffrath et al., 1992, Curr Genet 21:357-363). After transformation of this cassette into *S. cerevisiae* strain AR-Y292 containing wt p1 and p2, several clones exhibiting uracil prototrophy and detectable fluorescence from mKate2 were isolated. Extraction of cytoplasmic plasmids from these clones confirmed presence of the recombinant p2-delORF1-mUL*, but only at low copy as confirmed by DNA gel electrophoresis and PCR with primers specific to p2-delORF1-mUL*. In contrast to similar cassette integrations into p1, passaging under selection for URA3 expression failed to cure the parental wt p2 plasmid and increase the copy number of p2-delORF1-mUL* to levels easily detectable by gel electrophoresis. Although p2-delORF1-mUL* encodes all the necessary genes for its own replication and was selected for through URA3, it is likely that the shorter size of wt p2 provided it with enough of a replicative advantage to be maintained.

Therefore, more active methods were employed to cure the parental wt p2 plasmid. A yeast CRISPR/Cas9 vector (Ryan et al., 2014, Elife 3) and three candidate sgRNAs to target ORF1, which is present in wt p2 but not in p2-delORF1-mUL, were used. One of the three sgRNA's expressed in conjunction with a cytoplasmically-localized Cas9 achieved complete curing of p2 and a concomitant increase in the copy number of p2-delORF1-mUL*. This was evidenced by an increase in mKate2 fluorescent signal and a brighter p2-delORF1-mUL* DNA gel electrophoresis band. Curing of parental p2 to undetectable levels was confirmed by lack of PCR amplification with primers specific to p2, yielding strain GA-Y021.

Using GA-Y021, the mutation rate of p2 replication by wt TP-DNAP2, still encoded on p2-delORF1-mUL*, was measured with a previously described fluctuation test where the number distribution of functional LEU2 mutants is used to calculate mutation rate by the MSS method (Foster, 2006, Methods Enzymol, 409:195-213; Sarkar et al., 1992, Genetica, 85:173-179; Hall et al., 2009, Bioinformatics, 25:1564-1565). The mutation rate of p2-delORF1-mUL* replication was $5.96\times10^{-10}$ s.p.b. (95% C.I.: $3.57\times10^{-10}$-$8.77\times10^{-10}$) with a copy number of 128 per cell (Table 7, Entry 1). This is similar to the wild type p1 mutation rate and copy number, which are $1.39\times10^{-9}$ and 124, respectively (Ravikumar et al., Nat Chem Biol. 2014, 10(3):175-177).

TABLE 7

| Mutation-prone TP-DNAP2 Candidates | | | |
|---|---|---|---|
| Entry | TP-DNAP2 variant in trans | Per-base substitution rate pf p2($\times10^{-10}$) | Fold increase |
| 1 | None | 5.96 (3.57-8.77) | — |
| 2 | S370Q | 83.0 (62.8-105) | 13.9 |
| 3 | Y424Q | 77.5 (56.9-100) | 13.0 |
| 4 | Y424E | 73.3 (55.2-93.3) | 12.3 |
| 5 | S370P | 50.1 (32.4-70.4) | 8.4 |
| 6 | Y424K | 44.4 (32.2-58.0) | 7.5 |
| 7 | S370R | 31.9 (22.4-42.5) | 5.3 |
| 8 | Y424G | 28.8 (20.0-38.7) | 4.8 |
| 9 | S370E | 27.9 (19.7-37.2) | 4.7 |
| 10 | S370K | 26.2 (18.0-35.4) | 4.4 |
| 11 | Y424R | 19.6 (13.0-27.1) | 3.3 |
| 12 | S370L | 14.8 (9.32-21.1) | 2.5 |
| 13 | L474D | 12.2 (7.33-17.9) | 2.0 |
| 14 | F882A | 11.7 (4.92-20.4) | 2.0 |
| 15 | F882V | 10.8 (6.30-16.2) | 1.8 |
| 16 | L474A | 8.37 (4.80-12.6) | 1.4 |
| 17 | F882R | 7.32 (3.92-11.5) | 1.2 |
| 18 | L474V | 5.76 (2.88-9.33) | 1.0 |

To facilitate the straightforward testing of error-prone TP-DNAP2s, it was demonstrated that p2 replication could be fully sustained by TP-DNAP2 encoded in trans, on a standard yeast nuclear plasmid, rather than in cis, on p2. First, TP-DNAP2, which is ORF2 of p2, was deleted by homologous recombination of a synthetic cassette encoding URA3. Since p2 is a multi-copy plasmid, the resulting strain (GA-Y069) harbored a mixture of the parental wt p2 and the recombinant p2 with ORF2 deleted (p2-delORF2-URA3), along with unaltered p1. In this strain, both the wt p2 and recombinant p2-delORF2-URA3 plasmids rely on TP-DNAP2 encoded on the parental wt p2 plasmid for replication. Thus, loss of wt p2 should disable replication of p2-delORF2-URA3. Indeed, when the parental p2 plasmid was cured by targeting ORF2 of wt p2 with Cas9, it was found that all p2-delORF2-URA3 was also lost and that the strain could no longer grow in the absence of uracil. Next, the same experiment was repeated in the presence of a codon-optimized TP-DNAP2 expressed in trans from a standard yeast CEN6/ARS4 nuclear plasmid (pGA55-reTP-DNAP2). After p2 was fully cured by Cas9, it was found that p2 was not present, p2-delORF2-URA3 remained, and this strain could grow in the absence of uracil. In addition, p1 was also maintained, indicating that the accessory genes encoded on p2-delORF2-URA3 necessary for replication of both p1 and p2 and transcription of TP-DNAP1 on p1 were still functional. Therefore, p2-derived plasmids can be replicated by TP-DNAP2 encoded on a standard nuclear plasmid, simplifying the characterization of p2 replication by error-prone TP-DNAP2 variants.

To identify error-prone TP-DNAP2s, a small library of TP-DNAP2s diversified at locations hypothesized to be responsible for DNAP fidelity was screened. An alignment between TP-DNAP1 and TP-DNAP2 revealed that S370, Y424, L474, and F882 in TP-DNAP2 were homologous to residues in TP-DNAP1 that were previously found could be mutated to yield error-prone TP-DNAP1s (Ravikumar et al., 2018, bioRxiv, 313338; Ravikumar et al., 2014, Nature Chemical Biology, 10:175-177). Four distinct site-saturation mutagenesis libraries were generated, each diversifying S370, Y424, L474, or F882 in TP-DNAP2 encoded on pGA55-reTP-DNAP2. Due to unsuccessful attempts to generate a strain with a full deletion of p2-encoded TP-DNAP2 and simultaneous integration of mKate, URA3, and leu2*, each library was transformed into GA-Y021 for convenient screening. However, since GA-Y021 still encodes wt TP-DNAP2 on p2-delORF1-mUL*, p2 mutation rates measured in this format are the result of in tandem replication of p2 by wt TP-DNAP2 and each TP-DNAP2 variant encoded in trans. 6-fold coverage of each library was maintained by picking 190 yeast colonies and passaging under selection for URA3 to stabilize the copy number of p2-delORF1-mUL* in the presence of the newly introduced TP-DNAP2 variants. To screen for TP-DNAP2 variants with increased p2 mutation rate, each library member was subjected to a preliminary, small scale leu2*fluctuation test with six replicates. Seventeen candidate mutators with the highest expected number of mutants m calculated by the p0 method were then chosen for reconfirmation. Reconfirmation consisted of extracting the CEN6/ARS4 plasmids encoding TP-DNAP2 variants, retransforming into a fresh GA-Y021 background and repeating leu2*fluctuation tests with 36 replicates to determine p2 mutation rate with higher precision. Two error-prone TP-DNAP2 variants, S370Q and Y424Q, increased p2's substitution mutation rate by ~14- and ~13-fold, respectively (Table 7, Entries 2 and 3). These variants were not active enough to fully complement a deletion of the native TP-DNAP2 and sustain p2-delORF2-URA3 replication on their own, making the measured mutation rates an underestimate of their true per-base substitution rate. Despite this, these two error-prone TP-DNAP2 variants elevate p2 mutation rate to high enough levels for measuring orthogonality.

To show that p2 replication is orthogonal to genomic replication, the mutation rate of the host genome was measured in the presence of error-prone TP-DNAP2 variants. Like p1 replication by TP-DNAP1, p2 replication by TP-DNAP2 occurs in the cytoplasm via a protein-primed mechanism, making it likely that p2 replication is orthogonal to host genome replication. To test this, CEN6/ARS4 vectors lacking TP-DNAP2, or encoding codon optimized versions of TP-DNAP2$^{WT}$, TP-DNAP2$^{S370Q}$, or TP-DNAP2$^{Y424Q}$ were transformed into AR-Y436. AR-Y436 contains wt p1 and p2, as well as an intact URA3 locus in the host genome. Genomic per-base substitution rates were determined via fluctuation tests based on the frequency of 5-FOA resistant clones arising from mutations in the genomic URA3 locus, as previously described (Ravikumar et al., 2014, Nature Chemical Biology, 10:175-177; Lang and Murray, 2008, Genetics, 178:67-82). The substitution rich spectrum of URA3-disabling mutations makes this assay ideal for detecting whether the elevated substitution rate of TP-DNAP2$^{S370Q}$ or TP-DNAP2$^{Y424Q}$ contributes to genomic mutation. No increase in the host genomic mutation rate was observed when error-prone variants of TP-DNAP2$^{S370Q}$ and TP-DNAP2$^{Y424Q}$ were present (Table 8).

TABLE 8

| Genomic Mutation Rate Is Unaltered by Error-Prone TP-DNAP2 Variants | | |
|---|---|---|
| Entry | TP-DNAP2 in trans | per-base substitution rate at genomic URA3 locus ($\times10^{-10}$) |
| 1 | none | 1.6 (0.8-2.4) |
| 2 | WT | 2.2 (1.2-3.4) |
| 3 | Y424Q | 1.8 (1.0-2.9) |
| 4 | S370Q | 1.8 (1.0-2.8) |

Figure 8:
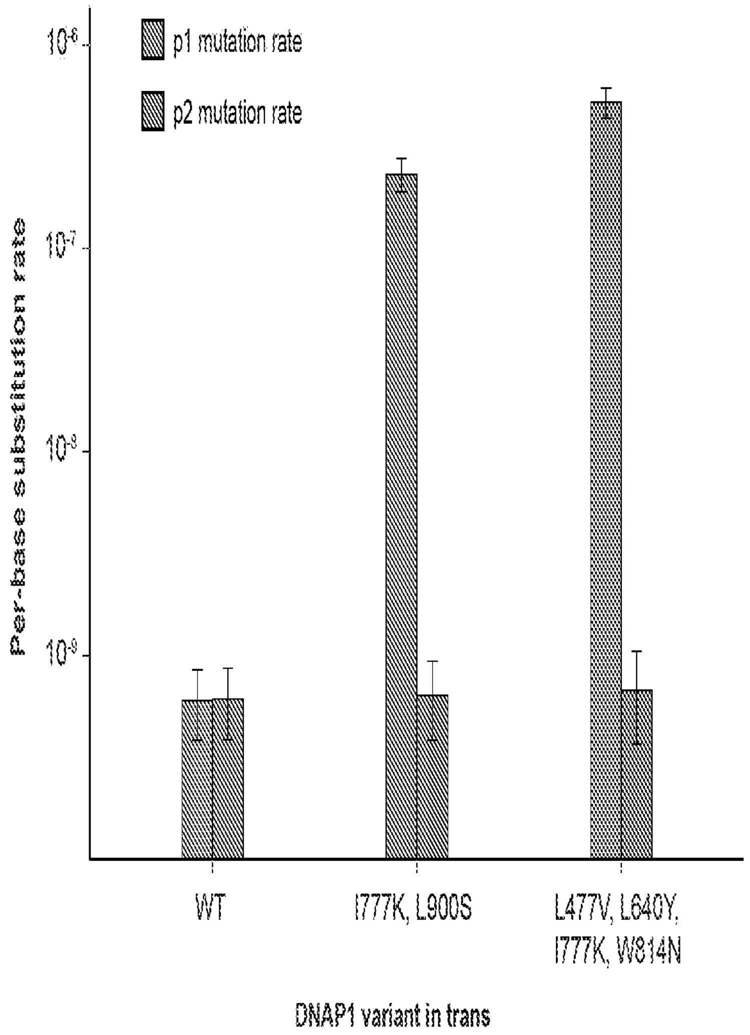
FIG. 8 depicts a chart showing that mutagenic TP-DNAP1 variants increase p1 mutation rate (left) by 380- and 870-fold, without any increase in p2 mutation rate (right).
Figure 9:
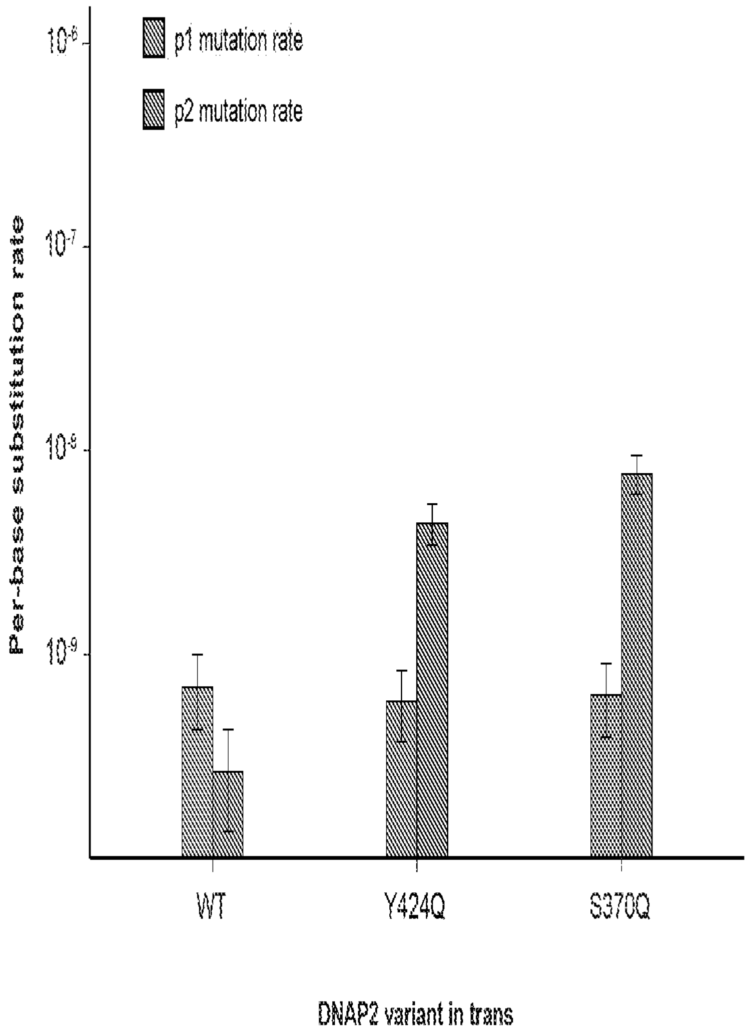
FIG. 9 depicts a chart showing that mutagenic TP-DNAP2 variants increase p2 mutation rate (right) by 16- and 29-fold, without a similar increase in p1 mutation rate (left).

To test whether the replication mechanisms of p1 and p2 are mutually orthogonal in vivo, p1 and p2 mutation rates were measured in the presence of a panel of TP-DNAP1 and TP-DNAP2 variants with varying mutation rates. Changes in p1 or p2 mutation rate induced by TP-DNAP variants would therefore signal a degree of cross-replication between TP-DNAP1/p1 and TP-DNAP2/p2, if any. A panel of six polymerases was introduced on CEN6/ARS4 vectors into two separate base strains, AR-Y304 (p1 mutation rate reporter strain) and GA-Y021 (p2 mutation rate reporter strain), encoding mKate2, URA3, and leu2* on either p1 or p2, respectively. Included in this panel were TP-DNAP1$^{WT}$ and two error-prone TP-DNAP1 variants found in previous screens: TP-DNAP1$^{I777K, L900S}$ and TP-DNAP1$^{L477V, L640Y, I777K, W814N}$. Also included were TP-DNAP2$^{WT}$ and the error-prone TP-DNAP2$^{S370Q}$ and TP-DNAP2$^{Y424Q}$ variants found in this work. In AR-Y304 and GA-Y021, both p1 and p2 still encode their native wt TP-DNAP's. Any contribution to replication by a third TP-DNAP encoded in trans is monitored by detecting changes in linear plasmid mutation rate. Importantly, these experiments afford each DNAP an opportunity to replicate its native plasmid and lose its attached TP, becoming "spent" and perhaps more likely to replicate its noncognate linear plasmid through DNAP exchange (Klassen and Meinhardt, 2007, Linear Protein-Primed Replicating Plasmids in Eukaryotic Microbes, in Microbial Linear Plasmids, pp 1 87-226. Springer, Berlin, Heidelberg). The presence of TP-DNAP1$^{WT}$ or TP-DNAP2$^{WT}$ in trans had no effect on their noncognate linear plasmids' mutation rate. Mutagenic variants TP-DNAP1$^{I777K, L900S}$ and TP-DNAP1$^{L477V, L640Y, I777K, W814N}$ increased p1's mutation rate by 380- and 870-fold, respectively, but caused no statistically significant change in p2's mutation rate (FIG. 8). Likewise, p1 mutation rate was unaltered in the presence of mutagenic TP-DNAP2$^{S370Q}$ and TP-DNAP2$^{Y424Q}$, which increased p2 mutation rate by 29- and 16-fold, respectively (FIG. 9). Thus, TP-DNAP1 replicates p1 with at least 870-fold specificity over p2, while TP-DNAP2 targets p2 with at least 29-fold specificity over p1. The level of mutual orthogonality measured here is limited by the error-rates of DNAPs used, especially that of TP-DNAP2 variants. Future discovery of more mutagenic TP-DNAP1 or TP-DNAP2 variants may prove an even greater orthogonality between these two replication systems.

In summary, p1 replication by TP-DNAP1 and p2 replication by TP-DNAP2 are both orthogonal to genomic replication and to each other, resulting in two mutually orthogonal DNA replication systems in the same cell. This pair of orthogonal replication systems will enable the in vivo evolution of multiple genes at different elevated mutation rates, molecular recording of biological signals in two distinct DNA channels, and the establishment of additional mutually orthogonal DNAP/plasmid pairs by engineering new TPs.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

Thus, a system for creating and using orthogonal DNA replication systems utilizing mutant DNA polymerases to generate continuous mutations in vivo has been described.

What is claimed is:

1. A host cell comprising a mutant terminal protein DNA polymerase (TP-DNAP) and a non-genomic nucleic acid template molecule, wherein said mutant TP-DNAP is a variant having at least two amino acid mutations relative to the parental polypeptide sequence of SEQ ID NO: 1 or SEQ ID NO: 13, wherein said mutant TP-DNAP and said non-genomic nucleic acid template molecule are orthogonal to the host cell, and wherein said mutant TP-DNAP comprises a mutant TP-DNAP selected from:

(a) S370Q and/or Y424Q substitutions relative to SEQ ID NO: 13, (b) N423R, N423Q, and/or L640A substitutions relative to SEQ ID NO: 1, and (c) SEQ ID NO: 8, 9, 10, or 11.

2. The host cell of claim 1, wherein the non-genomic nucleic acid template molecule is a plasmid.

3. The host cell of claim 2, herein the mutation rate of plasmid replication does not decrease after culturing of said host cell.

4. The host cell of claim 1, wherein the genomic DNA of said host cell is not replicated by the mutant TP-DNAP.

5. The host cell of claim 2, wherein the mutant TP-DNAP replicates the plasmid at mutation rate at least 1.05-fold to 100,000-fold greater than the mutation rate of the genome of said host cell.

6. The host cell of claim 2, wherein the mutant TP-DNAP replicates the plasmid at a mutation rate of at least 2-fold to 10,000-fold greater than the mutation rate of the parental wild-type polymerase.

7. The host cell of claim 1, wherein the mutant TP-DNAP has a mutation rate range of $1\times10^{-9}$ substitution mutations per nucleotide to $1\times10^{-5}$ substitution mutations per nucleotide.

8. The host cell of claim 1, wherein the mutant TP-DNAP is encoded in a nucleic acid molecule.

9. The host cell of claim 1, wherein said host cell is a yeast cell.

10. The host cell of claim 1, wherein said mutant TP-DNAP further comprises at least one mutation at an amino acid residue selected from the group consisting of: I287, S289, N291, L295, Y296, E298, S305, I301, K302, T303, F304, 1307, D308, N309, T310, I311, T312, Y313, Y316, I327, S330, D333, K344, T352, C354, F355, Y360, K365, N371, I372, C376, Y382, K384, V385, G387, R395, V405, V406, D407, G410, E411, L412, N413, I414, S415, I420, A421, G425, G426, H430, Y431, P439, N450, D460, G461, L473, L474, L477, N479, S481, K492, T493, H497, K511, S514, S533, I549, E550, C556, R557, N558, L561, S564, E569, A573, V574, E575, F578, L592, A599, N611, K612, E613, D614, F616, M618, E620, A621, L622, C627, V630, N631, C639, L640, K643, L645, A648, S649, F652, Y653, Q655, P656, R662, S664, D669, E670, I673, Y675, R677, T679, N681, R682, N683, N684, N687, R692, S693, H694, N695, K696, T698, E703, E704, S705, T706, I708, A709, N725, I729, S733, K769, N773, V774, I775, I777, I778, M779, S781, L782, W783, K785, A787, W790, V791, D804, W814, I824, Y829, S831, P833, M848, K849, I851, K857, E858, E861, C862, S865, D866, S869, F871, V872, H873, K874, V897, L900, L909, K934, S955, D958, K959, K962, K967 and F968.

11. The host cell of claim 1, wherein the mutant TP-DNAP comprises a variant of the polypeptide sequence as set forth in SEQ ID NO:1.

12. The host cell of claim 11, wherein the mutant TP-DNAP is a variant of TP-DNAP1 and further wherein the non-genomic template molecule is a plasmid (p1 plasmid) that is replicated by TP-DNAP1 and not replicated by TP-DNAP2.

13. The host cell of claim 1, wherein the mutant TP-DNAP comprises a variant of the polypeptide sequence as set forth in SEQ ID NO:13.

14. The host cell of claim 13, wherein the mutant TP-DNAP is a variant of TP-DNAP2 and further wherein the non-genomic template molecule is a plasmid (p2 plasmid) that is replicated by TP-DNAP2 and not replicated by TP-DNAP1.

15. The host cell of claim 1, wherein said mutant TP-DNAP further comprises at least two mutations at an amino acid residue selected from the group consisting of: N282, I287, S289, N291, L295, Y296, E298, S305, I301, K302, T303, F304, I307, D308, N309, T310, I311, T312, Y313, Y316, I327, S330, D333, K344, T352, C354, F355, Y360, K365, N371, I372, C376, Y382, K384, V385, G387, R395, V405, V406, D407, G410, E411, L412, N413, I414, S415, I420, A421, G425, G426, H430, Y431, P439, N449, N450, D460, G461, L473, L474, L477, N479, S481, K492, T493, H497, K511, S514, S533, I549, E550, C556, R557, N558, L561, S564, E569, A573, V574, E575, F578, L592, A599, N611, K612, E613, D614, F616, M618, E620, A621, L622, C627, V630, N631, C639, L640, K643, L645, A648, S649, F652, Y653, Q655, P656, R662, S664, D669, E670, I673, Y675, R677, T679, N681, R682, N683, N684, N687, R692, S693, H694, N695, K696, T698, E703, E704, S705, T706, I708, A709, N725, I729, S733, K769, N773, V774, I775, I777, I778, M779, S781, L782, W783, K785, A787, W790, V791, D804, W814, I824, Y829, S831, P833, M848, K849, I851, K857, E858, E861, C862, S865, D866, S869, F871, V872, H873, K874, V897, L900, L909, K934, S955, D958, K959, K962, K967 and F968.

16. The host cell of claim 1, wherein the mutant TP-DNAP is a variant of TP-DNAP1 comprising the amino acid sequence as set forth in SEQ ID NO:1 and said mutant polymerase replicates a p1 plasmid at a mutation rate with an increase of a range of at least 25-fold to 10,000-fold compared to the parental TP-DNAP1.

17. The host cell of claim 16, wherein said mutant TP-DNAP has at least three amino acid mutations relative to the parental polypeptide sequence.

18. The host cell of claim 16, wherein said mutant TP-DNAP has at least four amino acid mutations relative to the parental polypeptide sequence.

19. The host cell of claim 16, wherein said mutant TP-DNAP has at least one mutation in a region selected from the group consisting of Exo I, Exo II, Exo III, pre-(S/T)Lx2h, (S/T)Lx2h, Motif A, Motif B, Motif C, pre-Motif B, Tx2G/AR and KxY.

20. The host cell of claim 11, wherein said mutant TP-DNAP comprises SEQ ID NO: 8, 9, 10, or 11.

21. The host cell of claim 13, wherein said mutant TP-DNAP comprises S370Q and/or Y424Q.

22. The host cell of claim 11, wherein said mutant TP-DNAP comprises a mutation selected from N423R, N423Q, and/or L640A.

* * * * *

SEQUENCE LISTING

```
<160> NUMBER OF SEQ ID NOS: 125

<210> SEQ ID NO 1
<211> LENGTH: 987
<212> TYPE: PRT
<213> ORGANISM: Kluyveromyces lactis

<400> SEQUENCE: 1

Met Asp Tyr Lys Asp Lys Ala Leu Asn Asp Leu Arg Asn Val Tyr Ala
1               5                   10                  15

Asp Phe Asp Ser Leu Pro Leu Asp Phe Arg Gln Ile Leu Ile Lys Asp
            20                  25                  30

Arg Ala Thr Leu Leu Gln Lys Glu Asp Val Glu Lys Lys Ile Leu Glu
        35                  40                  45

Arg Gln Glu Asp Ala Lys Lys Tyr Ala Glu Tyr Leu Lys Gln Ser Glu
    50                  55                  60

Ile Pro Glu Arg Ile Ser Leu Pro Asn Ile Lys Arg His Lys Gly Val
65                  70                  75                  80

Ser Ile Ser Phe Glu Glu Thr Ser Glu Asp Met Val Leu Glu Pro Arg
                85                  90                  95

Pro Phe Ile Phe Asp Gly Leu Asn Ile Arg Cys Phe Arg Arg Glu Thr
            100                 105                 110

Ile Phe Ser Leu Lys Asn Lys Ile Leu Asn Met Val Lys Glu Ser Ser
        115                 120                 125

Ser Phe Lys Asn Val Ser Arg Gln Ser Val Ser Phe Met Tyr Phe Lys
    130                 135                 140
```

```
Ile Phe Asn Lys Gly Lys Val Ile Ala Ser Thr Lys Ser Val Asn Ile
145                 150                 155                 160

Tyr Glu Asp Lys Ile Asp Glu Arg Leu Glu Asp Leu Cys Asn Asn Phe
                165                 170                 175

Asp Asp Val Leu Lys Lys Ile Ile Asp Val Thr Tyr Gly Tyr Glu Ser
            180                 185                 190

Leu Phe Val Ser Glu Thr Tyr Ser Tyr Val Ile Phe Tyr Ala Lys Ser
        195                 200                 205

Ile Tyr Phe Pro Gln Pro Arg Cys Val Asn Asn Trp Gly Asn Asn Ile
    210                 215                 220

Pro Asn Ile Leu Thr Phe Asp Ser Phe Lys Leu Phe Thr Ala Asn Lys
225                 230                 235                 240

Asn Asn Val Ser Cys Ile Lys Gln Cys Ser Arg Phe Leu Trp Gln Lys
                245                 250                 255

Asp Phe Asn Thr Leu Glu Glu Met Ile Glu Tyr Lys Asn Gly Asn Ile
            260                 265                 270

Cys Ile Val Thr Pro Gln Leu His Ile Asn Asp Val Arg Asp Ile Lys
        275                 280                 285

Ser Phe Asn Asp Ile Arg Leu Tyr Ser Glu Ser Pro Ile Lys Thr Phe
    290                 295                 300

Ser Val Ile Asp Asn Thr Ile Thr Tyr Leu Phe Tyr Phe Lys Glu His
305                 310                 315                 320

Leu Gly Val Ile Phe Asn Ile Thr Lys Ser Arg His Asp Arg Arg Val
                325                 330                 335

Thr Lys Phe Ser Pro Leu Ser Lys Phe Ser Asp Val Lys Asn Ile Thr
            340                 345                 350

Val Cys Phe Asp Ile Glu Ser Tyr Phe Asp Pro Glu Lys Glu Ser Asn
        355                 360                 365

Gln Val Asn Ile Pro Phe Ile Cys Cys Ala Ser Ile Ile Tyr Asn Lys
    370                 375                 380

Val Ile Gly Asn Ile Val Asp Phe Glu Gly Arg Asp Cys Val Ala Gln
385                 390                 395                 400

Met Ile Glu Tyr Val Val Asp Ile Cys Gly Glu Leu Asn Ile Ser Ser
                405                 410                 415

Val Glu Leu Ile Ala His Asn Gly Gly Gly Tyr Asp Phe His Tyr Ile
            420                 425                 430

Leu Ser Ser Met Tyr Asn Pro Ala Ala Ile Lys Asn Ile Leu Ile Arg
        435                 440                 445

Asn Asn Ser Phe Ile Ser Phe Asn Phe Ala His Asp Gly Val Lys Phe
    450                 455                 460

Ser Val Lys Asp Ser Tyr Ser Phe Leu Leu Cys Ser Leu Ala Asn Ala
465                 470                 475                 480

Ser Lys Ala Phe Leu Asn Glu Glu Thr Phe Lys Lys Thr Asp Phe Pro
                485                 490                 495

His His Asp Leu Lys Thr Ala Asp Asp Leu Tyr Lys Val Tyr Lys Glu
            500                 505                 510

Trp Ser Ser Val Asn Thr Glu Ile Asn His Val Val Glu Lys Glu Lys
        515                 520                 525

Leu Leu Ile Thr Ser Glu His Ile Val Asn Phe Thr Lys Asn Asp Lys
    530                 535                 540

Ser Lys Thr Leu Ile Glu Trp Ser Lys Asp Tyr Cys Arg Asn Asp Val
545                 550                 555                 560
```

```
Leu Val Leu Ser Lys Val Trp Leu Glu Phe Lys Asn Ala Val Glu Asp
                565                 570                 575

Ile Phe Asn Cys Glu Leu Val Asp Gln Thr Met Thr Leu Ala Gly Leu
            580                 585                 590

Ser Tyr Lys Leu Phe Gln Ala Asn Met Pro Phe Asp Val Glu Leu Arg
        595                 600                 605

His Pro Asn Lys Glu Asp Tyr Phe Asn Met Arg Glu Ala Leu Ile Gly
    610                 615                 620

Gly Arg Cys Ile Ser Val Asn Gly Ile Tyr Lys Asp Val Leu Cys Leu
625                 630                 635                 640

Asp Val Lys Ser Leu Tyr Pro Ala Ser Met Ala Phe Tyr Asp Gln Pro
                645                 650                 655

Tyr Gly Ser Phe Lys Arg Val Ser Ser Arg Pro Lys Asp Glu Leu Gly
            660                 665                 670

Ile Tyr Tyr Val Arg Val Thr Pro Asn Arg Asn Asn Lys Ser Asn Phe
        675                 680                 685

Phe Pro Ile Arg Ser His Asn Lys Ile Thr Tyr Asn Asn Phe Glu Glu
    690                 695                 700

Ser Thr Tyr Ile Ala Trp Tyr Thr Asn Val Asp Ile Asp Ile Gly Leu
705                 710                 715                 720

Ser Glu Gly His Asn Ile Glu Tyr Ile Pro Phe Asp Ser Tyr Gly Asn
                725                 730                 735

Ile Gly Tyr Ser Trp Ser Lys Lys Gly Lys Ile Phe Glu Lys Tyr Ile
            740                 745                 750

Lys Asp Val Leu Tyr Lys Leu Lys Ile Lys Tyr Glu Lys Gln Asn Asn
        755                 760                 765

Lys Val Lys Arg Asn Val Ile Lys Ile Ile Met Asn Ser Leu Trp Gly
    770                 775                 780

Lys Phe Ala Gln Lys Trp Val Asn Phe Glu Tyr Phe Ile Lys Ser Glu
785                 790                 795                 800

Asp Asp Ile Asp Phe Glu Ser Glu Glu Ala Tyr Lys Ile Trp Asp Thr
                805                 810                 815

Asp Phe Met Leu Ile Lys Lys Ile Lys Glu Ser Thr Tyr Ser Ser Lys
            820                 825                 830

Pro Ile Gln Asn Gly Val Phe Thr Leu Ser Trp Ala Arg Tyr His Met
        835                 840                 845

Lys Ser Ile Trp Asp Ala Gly Ala Lys Glu Gly Ala Glu Cys Ile Tyr
    850                 855                 860

Ser Asp Thr Asp Ser Ile Phe Val His Lys Glu His Phe Lys Lys Asn
865                 870                 875                 880

Ala Lys Phe Met Leu Asn Gly Leu Lys Val Pro Ile Ile Gly Ser Glu
                885                 890                 895

Val Gly Gln Leu Glu Leu Glu Cys Glu Phe Asp Lys Leu Leu Cys Ala
            900                 905                 910

Gly Lys Lys Gln Tyr Met Gly Phe Tyr Thr Tyr Phe Gln Asp Gly Lys
        915                 920                 925

Pro Cys Ile Lys Glu Lys Lys Arg Phe Lys Gly Ile Pro Ser Asn Tyr
    930                 935                 940

Ile Ile Pro Glu Leu Tyr Ala His Leu Leu Ser Gly Ala Asp Lys Glu
945                 950                 955                 960

Ala Lys Ile Gln Phe Leu Lys Phe Arg Arg Glu Trp Gly Ser Val Lys
                965                 970                 975
```

Gly Tyr Ile Glu Asn Lys Thr Val Lys Ala Thr
980 985

<210> SEQ ID NO 2
<211> LENGTH: 2964
<212> TYPE: DNA
<213> ORGANISM: Kluyveromyces lactis

<400> SEQUENCE: 2
atggactaca aagacaaagc attaaacgac ttgagaaacg tatacgcaga cttcgactcc 60
ttgccattgg acttcagaca aatcttaatt aaggatagag ctacattgtt gcaaaaggaa 120
gacgttgaaa agaaaatttt ggaaagacaa gaagatgcca aaaagtacgc tgaatacttg 180
aagcaatcag aaatcccaga aagaatctcc ttacctaaca tcaagagaca taagggtgta 240
tcaatctcct ttgaagaaac atctgaagat atggtcttgg aaccaagacc ttttatcttc 300
gacggtttga acatcagatg tttcagaaga gaaaccatat tcagtttgaa aaataagatt 360
ttgaacatgg ttaaggaatc ttcatccttt aaaaacgttt caagacaaag tgtatctttt 420
atgtacttca aaatttttaa taagggtaaa gttattgcaa gtacaaagtc tgttaacatc 480
tatgaagata agatcgacga aagattggaa gatttgtgta acaacttcga tgacgtattg 540
aaaaagatta tagacgtcac ctatggttac gaatccttat tcgttagtga aacttactct 600
tacgtaatat tctatgctaa atcaatctac tttccacaac ctagatgcgt taacaactgg 660
ggtaacaaca tcccaaacat cttgacattc gattccttta agcttttcac cgcaaacaaa 720
aacaacgtta gttgtatcaa gcaatgttca agatttttgt ggcaaaaaga tttcaacact 780
ttagaagaaa tgatagaata caagaacggt aatatttgta tcgtcacacc acaattgcat 840
atcaacgatg ttagagacat caagtcattc aacgatatca gattgtactc agaatcccct 900
attaaaacat tttccgttat tgataacact atcacatatt tgttttactt caaggaacat 960
ttgggtgtta tttttaacat cactaagtca agacatgata gaagagtaac aaaattttca 1020
ccattgtcca agttcagtga cgtcaaaaat atcactgttt gtttcgatat cgaaagttac 1080
ttcgacccag aaaaggaatc taaccaagtt aacatccctt tcatttgttg cgcttcaatc 1140
atctataata aggttattgg taacatcgtc gattttgaag gtagagactg tgtcgcacaa 1200
atgatcgaat acgttgtaga tatttgcggt gaattgaaca taagttctgt tgaattgatc 1260
gcccataacg gtggtggtta tgatttccac tacatcttgt catccatgta taatccagct 1320
gcaattaaaa acatattgat cagaaacaac tcttttattt cttttaattt cgcacatgat 1380
ggtgtcaagt tctctgttaa ggacagttac tcatttttgt tgtgtagttt ggccaacgct 1440
tctaaagcat tttaaacga agaaactttt aagaaaactg atttccctca tcacgacttg 1500
aaaactgccg atgacttata taaggtctac aaggaatgga gttctgttaa cacagaaatt 1560
aaccatgtcg ttgaaaagga aaagttgttg atcacctctg aacacatcgt taacttcacc 1620
aagaacgata agagtaagac tttgatcgaa tggtctaagg attactgtag aaacgacgta 1680
ttggtcttgt ctaaggtttg gttggagttt aaaaacgctg tagaagatat ttttaactgc 1740
gaattggtag accaaaccat gactttggct ggtttgtcat acaagttgtt ccaagcaaac 1800
atgccattcg atgtcgaatt gagacatcct aataaggaag actacttcaa catgagagaa 1860
gcattgattg gtggtagatg tatctctgtt aacggtatct acaaggatgt tttgtgctta 1920
gacgtaaaat cattatatcc agcttctatg gctttctatg atcaacctta cggttctttt 1980
aagagagttt catccagacc aaaagatgaa ttgggtatct attacgttag agtaacccca 2040
aacagaaaca acaagtcaaa ctttttccct atcagatccc ataataagat cacttacaac 2100
aacttcgaag aatcaactta tattgcttgg tacacaaacg ttgatatcga cattggtttg 2160
tcagaaggtc acaacatcga atacatccct ttcgattcct atggtaacat tggttactca 2220
tggtccaaaa agggtaaaat ttttgaaaag tacatcaagg atgttttgta caaattgaag 2280
ataaaatatg aaaagcaaaa taacaaggta aaaagaaatg tcatcaaaat catcatgaac 2340
tcattgtggg gtaaattcgc ccaaaagtgg gttaacttcg aatacttcat caagtcagaa 2400
gatgacattg atttcgaatc cgaagaagca tataaaattt gggatacaga cttcatgttg 2460
atcaaaaaga ttaaggaatc tacctacagt tctaagccaa tacaaaacgg tgtttttact 2520
ttaagttggg ccagatatca catgaagtct atttgggatg caggtgccaa agaaggtgct 2580
gaatgtatct attcagatac agactccata ttcgttcata aggaacactt caaaaagaat 2640
gcaaagttta tgttgaacgg tttgaaagta ccaatcatcg gttctgaagt cggtcaattg 2700
gaattagaat gtgaatttga taaattgttg tgcgccggta aaaagcaata catgggtttc 2760
tacacttact tccaagatgg taaaccttgc atcaaggaaa agaaaagatt caaaggtata 2820
ccaagtaact acatcatacc tgaattgtat gctcacttgt tatctggtgc agataaggaa 2880
gccaaaattc aatttttaaa attcagaaga gaatggggtt ccgtcaaggg ttacatagaa 2940
aataagactg tcaaagccac ctaa 2964

<210> SEQ ID NO 3
<211> LENGTH: 2964
<212> TYPE: DNA
<213> ORGANISM: Kluyveromyces lactis

<400> SEQUENCE: 3
atggactaca aagacaaagc attaaacgac ttgagaaacg tatacgcaga cttcgactcc 60
ttgccattgg acttcagaca aatcttaatt aaggatagag ctacattgtt gcaaaaggaa 120
gacgttgaaa agaaaatttt ggaaagacaa gaagatgcca aaaagtacgc tgaatacttg 180
aagcaatcag aaatcccaga aagaatctcc ttacctaaca tcaagagaca taagggtgta 240
tcaatctcct ttgaagaaac atctgaagat atggtcttgg aaccaagacc ttttatcttc 300
gacggtttga acatcagatg tttcagaaga gaaaccatat tcagtttgaa aaataagatt 360
ttgaacatgg ttaaggaatc ttcatccttt aaaaacgttt caagacaaag tgtatctttt 420
atgtacttca aaatttttaa taagggtaaa gttattgcaa gtacaaagtc tgttaacatc 480
tatgaagata agatcgacga aagattggaa gatttgtgta acaacttcga tgacgtattg 540
aaaaagatta tagacgtcac ctatggttac gaatccttat tcgttagtga aacttactct 600
tacgtaatat tctatgctaa atcaatctac tttccacaac ctagatgcgt taacaactgg 660
ggtaacaaca tcccaaacat cttgacattc gattccttta agcttttcac cgcaaacaaa 720
aacaacgtta gttgtatcaa gcaatgttca agatttttgt ggcaaaaaga tttcaacact 780
ttagaagaaa tgatagaata caagaacggt aatatttgta tcgtcacacc acaattgcat 840
atcaacgatg ttagagacat caagtcattc aacgatatca gattgtactc agaatcccct 900
attaaaacat tttccgttat tgataacact atcacatatt tgttttactt caaggaacat 960
ttgggtgtta tttttaacat cactaagtca agacatgata gaagagtaac aaaattttca 1020
ccattgtcca agttcagtga cgtcaaaaat atcactgttt gtttcgatat cgaaagttac 1080
ttcgacccag aaaaggaatc taaccaagtt aacatccctt tcatttgttg cgcttcaatc 1140

```
atctataata aggttattgg taacatcgtc gattttgaag gtagagactg tgtcgcacaa   1200
atgatcgaat acgttgtaga tatttgcggt gaattgaaca taagttctgt tgaattgatc   1260
gcccataacg gtggtggtta tgatttccac tacatcttgt catccatgta taatccagct   1320
gcaattaaaa acatattgat cagaaacaac tcttttattt cttttaattt cgcacatgat   1380
ggtgtcaagt tctctgttaa ggacagttac tcatttttgt tgtgtagttt ggccaacgct   1440
tctaaagcat tttaaacga agaaactttt aagaaaactg atttccctca tcacgacttg   1500
aaaactgccg atgacttata taaggtctac aaggaatgga gttctgttaa cacagaaatt   1560
aaccatgtcg ttgaaaagga aagttgttg atcacctctg aacacatcgt taacttcacc   1620
aagaacgata agagtaagac tttgatcgaa tggtctaagg attactgtag aaacgacgta   1680
ttggtcttgt ctaaggtttg gttggagttt aaaaacgctg tagaagatat ttttaactgc   1740
gaattggtag accaaaccat gactttggct ggtttgtcat acaagttgtt ccaagcaaac   1800
atgccattcg atgtcgaatt gagacatcct aataaggaag actacttcaa catgagagaa   1860
gcattgattg gtggtagatg tatctctgtt aacggtatct acaaggatgt tttgtgctta   1920
gacgtaaaat cattatatcc agcttctatg gctttctatg atcaacctta cggttctttt   1980
aagagagttt catccagacc aaaagatgaa ttgggtatct attacgttag agtaacccca   2040
aacagaaaca acaagtcaaa ctttttccct atcagatccc ataataagat cacttacaac   2100
aacttcgaag aatcaactta tattgcttgg tacacaaacg ttgatatcga cattggtttg   2160
tcagaaggtc acaacatcga atacatccct ttcgattcct atggtaacat tggttactca   2220
tggtccaaaa agggtaaaat ttttgaaaag tacatcaagg atgttttgta caaattgaag   2280
ataaaatatg aaaagcaaaa taacaaggta aaaagaaatg tcatcaaaaa gatcatgaac   2340
tcattgtggg gtaaattcgc ccaaaagtgg gttaacttcg aatacttcat caagtcagaa   2400
gatgacattg atttcgaatc cgaagaagca tataaaattt gggatacaga cttcatgttg   2460
atcaaaaaga ttaaggaatc tacctacagt tctaagccaa tacaaaacgg tgtttttact   2520
ttaagttggg ccagatatca catgaagtct atttgggatg caggtgccaa agaaggtgct   2580
gaatgtatct attcagatac agactccata ttcgttcata aggaacactt caaaaagaat   2640
gcaaagttta tgttgaacgg tttgaaagta ccaatcatcg gttctgaagt cggtcaattg   2700
gaattagaat gtgaatttga taaattgttg tgcgccggta aaaagcaata catgggtttc   2760
tacacttact tccaagatgg taaaccttgc atcaaggaaa agaaaagatt caaaggtata   2820
ccaagtaact acatcatacc tgaattgtat gctcacttgt tatctggtgc agataaggaa   2880
gccaaaattc aattttaaa attcagaaga gaatggggtt ccgtcaaggg ttacatagaa   2940
aataagactg tcaaagccac ctaa                                          2964
```

<210> SEQ ID NO 4
<211> LENGTH: 2964
<212> TYPE: DNA
<213> ORGANISM: Kluyveromyces lactis

<400> SEQUENCE: 4

```
atggactaca aagacaaagc attaaacgac ttgagaaacg tatacgcaga cttcgactcc     60
ttgccattgg acttcagaca aatcttaatt aaggatagag ctacattgtt gcaaaaggaa    120
gacgttgaaa agaaaatttt ggaaagacaa gaagatgcca aaaagtacgc tgaatacttg    180
aagcaatcag aaatcccaga aagaatctcc ttacctaaca tcaagagaca taagggtgta    240
tcaatctcct ttgaagaaac atctgaagat atggtcttgg aaccaagacc ttttatcttc    300
```

```
gacggtttga acatcagatg tttcagaaga gaaaccatat tcagtttgaa aaataagatt    360
ttgaacatgg ttaaggaatc ttcatccttt aaaaacgttt caagacaaag tgtatctttt    420
atgtacttca aaatttttaa taagggtaaa gttattgcaa gtacaaagtc tgttaacatc    480
tatgaagata agatcgacga aagattggaa gatttgtgta acaacttcga tgacgtattg    540
aaaaagatta tagacgtcac ctatggttac gaatccttat tcgttagtga aacttactct    600
tacgtaatat tctatgctaa atcaatctac tttccacaac ctagatgcgt taacaactgg    660
ggtaacaaca tcccaaacat cttgacattc gattccttta agcttttcac cgcaaacaaa    720
aacaacgtta gttgtatcaa gcaatgttca agatttttgt ggcaaaaaga tttcaacact    780
ttagaagaaa tgatagaata caagaacggt aatatttgta tcgtcacacc acaattgcat    840
atcaacgatg ttagagacat caagtcattc aacgatatca gattgtactc agaatcccct    900
attaaaacat tttccgttat tgataacact atcacatatt tgttttactt caaggaacat    960
ttgggtgtta tttttaacat cactaagtca agacatgata gaagagtaac aaaatttca   1020
ccattgtcca agttcagtga cgtcaaaaat atcactgttt gtttcgatat cgaaagttac   1080
ttcgacccag aaaaggaatc taaccaagtt aacatccctt tcatttgttg cgcttcaatc   1140
atctataata aggttattgg taacatcgtc gattttgaag gtagagactg tgtcgcacaa   1200
atgatcgaat acgttgtaga tatttgcggt gaattgaaca taagttctgt tgaattgatc   1260
gcccataacg gtggtggtta tgatttccac tacatcttgt catccatgta taatccagct   1320
gcaattaaaa acatattgat cagaaacaac tcttttattt cttttaattt cgcacatgat   1380
ggtgtcaagt tctctgttaa ggacagttac tcatttttgt tgtgtagttt ggccaacgct   1440
tctaaagcat ttttaaacga agaaactttt aagaaaactg atttccctca tcacgacttg   1500
aaaactgccg atgacttata taaggtctac aaggaatgga gttctgttaa cacagaaatt   1560
aaccatgtcg ttgaaaagga aaagttgttg atcacctctg aacacatcgt taacttcacc   1620
aagaacgata agagtaagac tttgatcgaa tggtctaagg attactgtag aaacgacgta   1680
ttggtcttgt ctaaggtttg gttggagttt aaaaacgctg tagaagatat ttttaactgc   1740
gaattggtag accaaaccat gactttggct ggtttgtcat acaagttgtt ccaagcaaac   1800
atgccattcg atgtcgaatt gagacatcct aataaggaag actacttcaa catgagagaa   1860
gcattgattg gtggtagatg tatctctgtt aacggtatct acaaggatgt tttgtgctta   1920
gacgtaaaat cattatatcc agcttctatg gctttctatg atcaacctta cggttctttt   1980
aagagagttt catccagacc aaaagatgaa ttgggtatct attacgttag agtaacccca   2040
aacagaaaca acaagtcaaa ctttttccct atcagatccc ataataagat cacttacaac   2100
aacttcgaag aatcaactta tattgcttgg tacacaaacg ttgatatcga cattggtttg   2160
tcagaaggtc acaacatcga atacatccct ttcgattcct atggtaacat tggttactca   2220
tggtccaaaa agggtaaaat ttttgaaaag tacatcaagg atgttttgta caaattgaag   2280
ataaaatatg aaaagcaaaa taacaaggta aaaagaaatg tcatcaaaat catcatgaac   2340
tcattgtggg gtaaattcgc ccaaaagtgg gttaacttcg aatacttcat caagtcagaa   2400
gatgacattg atttcgaatc cgaagaagca tataaaattt gggatacaga cttcatgttg   2460
atcaaaaaga ttaaggaatc tacctacagt tctaagccaa tacaaaacgg tgtttttact   2520
ttaagttggg ccagatatca catgaagtct atttgggatg caggtgccaa agaaggtgct   2580
gaatgtatct attcagatac agactccata tacgttcata aggaacactt caaaaagaat   2640
```

```
gcaaagttta tgttgaacgg tttgaaagta ccaatcatcg gttctgaagt cggtcaattg   2700

gaattagaat gtgaatttga taaattgttg tgcgccggta aaaagcaata catgggtttc   2760

tacacttact tccaagatgg taaaccttgc atcaaggaaa agaaaagatt caaaggtata   2820

ccaagtaact acatcatacc tgaattgtat gctcacttgt tatctggtgc agataaggaa   2880

gccaaaattc aatttttaaa attcagaaga gaatggggtt ccgtcaaggg ttacatagaa   2940

aataagactg tcaaagccac ctaa                                          2964
```

<210> SEQ ID NO 5
<211> LENGTH: 2964
<212> TYPE: DNA
<213> ORGANISM: Kluyveromyces lactis

<400> SEQUENCE: 5

```
atggactaca aagacaaagc attaaacgac ttgagaaacg tatacgcaga cttcgactcc     60

ttgccattgg acttcagaca aatcttaatt aaggatagag ctacattgtt gcaaaaggaa    120

gacgttgaaa agaaaatttt ggaaagacaa gaagatgcca aaaagtacgc tgaatacttg    180

aagcaatcag aaatcccaga aagaatctcc ttacctaaca tcaagagaca taagggtgta    240

tcaatctcct ttgaagaaac atctgaagat atggtcttgg aaccaagacc ttttatcttc    300

gacggtttga acatcagatg tttcagaaga gaaaccatat tcagtttgaa aaataagatt    360

ttgaacatgg ttaaggaatc ttcatccttt aaaaacgttt caagacaaag tgtatctttt    420

atgtacttca aaatttttaa taagggtaaa gttattgcaa gtacaaagtc tgttaacatc    480

tatgaagata agatcgacga aagattggaa gatttgtgta acaacttcga tgacgtattg    540

aaaaagatta tagacgtcac ctatggttac gaatccttat tcgttagtga aacttactct    600

tacgtaatat tctatgctaa atcaatctac tttccacaac ctagatgcgt taacaactgg    660

ggtaacaaca tcccaaacat cttgacattc gattccttta agcttttcac cgcaaacaaa    720

aacaacgtta gttgtatcaa gcaatgttca agatttttgt ggcaaaaaga tttcaacact    780

ttagaagaaa tgatagaata caagaacggt aatatttgta tcgtcacacc acaattgcat    840

atcaacgatg ttagagacat caagtcattc aacgatatca gattgtactc agaatcccct    900

attaaaacat tttccgttat tgataacact atcacatatt tgttttactt caaggaacat    960

ttgggtgtta tttttaacat cactaagtca agacatgata gaagagtaac aaaattttca   1020

ccattgtcca agttcagtga cgtcaaaaat atcactgttt gtttcgatat cgaaagttac   1080

ttcgacccag aaaaggaatc taaccaagtt aacatccctt tcatttgttg cgcttcaatc   1140

atctataata aggttattgg taacatcgtc gattttgaag gtagagactg tgtcgcacaa   1200

atgatcgaat acgttgtaga tatttgcggt gaattgaaca taagttctgt tgaattgatc   1260

gcccatgacg gtggtggtta tgatttccac tacatcttgt catccatgta taatccagct   1320

gcaattaaaa acatattgat cagaaacaac tcttttattt cttttaattt cgcacatgat   1380

ggtgtcaagt tctctgttaa ggacagttac tcatttttgt tgtgtagttt ggccaacgct   1440

tctaaagcat tttaaacga agaaactttt aagaaaactg atttccctca tcacgacttg   1500

aaaactgccg atgacttata taaggtctac aaggaatgga gttctgttaa cacagaaatt   1560

aaccatgtcg ttgaaaagga aaagttgttg atcacctctg aacacatcgt taacttcacc   1620

aagaacgata agagtaagac tttgatcgaa tggtctaagg attactgtag aaacgacgta   1680

ttggtcttgt ctaaggtttg gttggagttt aaaaacgctg tagaagatat ttttaactgc   1740

gaattggtag accaaaccat gactttggct ggtttgtcat acaagttgtt ccaagcaaac   1800
```

```
atgccattcg atgtcgaatt gagacatcct aataaggaag actacttcaa catgagagaa   1860
gcattgattg gtggtagatg tatctctgtt aacggtatct acaaggatgt tttgtgctta   1920
gacgtaaaat cattatatcc agcttctatg gctttctatg atcaacctta cggttctttt   1980
aagagagttt catccagacc aaaagatgaa ttgggtatct attacgttag agtaacccca   2040
aacagaaaca acaagtcaaa ctttttccct atcagatccc ataataagat cacttacaac   2100
aacttcgaag aatcaactta tattgcttgg tacacaaacg ttgatatcga cattggtttg   2160
tcagaaggtc acaacatcga atacatccct ttcgattcct atggtaacat tggttactca   2220
tggtccaaaa agggtaaaat ttttgaaaag tacatcaagg atgttttgta caaattgaag   2280
ataaaatatg aaaagcaaaa taacaaggta aaaagaaatg tcatcaaaat catcatgaac   2340
tcattgtggg gtaaattcgc ccaaaagtgg gttaacttcg aatacttcat caagtcagaa   2400
gatgacattg atttcgaatc cgaagaagca tataaaattt gggatacaga cttcatgttg   2460
atcaaaaaga ttaaggaatc tacctacagt tctaagccaa tacaaaacgg tgtttttact   2520
ttaagttggg ccagatatca catgaagtct atttgggatg caggtgccaa agaaggtgct   2580
gaatgtatct attcagatac agactccata ttcgttcata aggaacactt caaaaagaat   2640
gcaaagttta tgttgaacgg tttgaaagta ccaatcatcg gttctgaagt cggtcaattg   2700
gaattagaat gtgaatttga taaattgttg tgcgccggta aaaagcaata catgggtttc   2760
tacacttact tccaagatgg taaaccttgc atcaaggaaa agaaaagatt caaaggtata   2820
ccaagtaact acatcatacc tgaattgtat gctcacttgt tatctggtgc agataaggaa   2880
gccaaaattc aatttttaaa attcagaaga gaatggggtt ccgtcaaggg ttacatagaa   2940
aataagactg tcaaagccac ctaa                                          2964
```

<210> SEQ ID NO 6
<211> LENGTH: 2964
<212> TYPE: DNA
<213> ORGANISM: Kluyveromyces lactis

<400> SEQUENCE: 6

```
atggactaca aagacaaagc attaaacgac ttgagaaacg tatacgcaga cttcgactcc     60
ttgccattgg acttcagaca aatcttaatt aaggatagag ctacattgtt gcaaaaggaa    120
gacgttgaaa agaaaatttt ggaaagacaa gaagatgcca aaaagtacgc tgaatacttg    180
aagcaatcag aaatcccaga aagaatctcc ttacctaaca tcaagagaca taagggtgta    240
tcaatctcct ttgaagaaac atctgaagat atggtcttgg aaccaagacc ttttatcttc    300
gacggtttga acatcagatg tttcagaaga gaaaccatat tcagtttgaa aaataagatt    360
ttgaacatgg ttaaggaatc ttcatccttt aaaaacgttt caagacaaag tgtatctttt    420
atgtacttca aaatttttaa taagggtaaa gttattgcaa gtacaaagtc tgttaacatc    480
tatgaagata agatcgacga aagattggaa gatttgtgta acaacttcga tgacgtattg    540
aaaaagatta tagacgtcac ctatggttac gaatccttat tcgttagtga aacttactct    600
tacgtaatat tctatgctaa atcaatctac tttccacaac ctagatgcgt taacaactgg    660
ggtaacaaca tcccaaacat cttgacattc gattccttta agcttttcac cgcaaacaaa    720
aacaacgtta gttgtatcaa gcaatgttca agatttttgt ggcaaaaaga tttcaacact    780
ttagaagaaa tgatagaata caagaacggt aatatttgta tcgtcacacc acaattgcat    840
atcaacgatg ttagagacat caagtcattc aacgatatca gattgtactc agaatcccct    900
```

```
attaaaacat tttccgttat tgataacact atcacatatt tgttttactt caaggaacat    960
ttgggtgtta tttttaacat cactaagtca agacatgata gaagagtaac aaaattttca   1020
ccattgtcca agttcagtga cgtcaaaaat atcactgttt gtttcgatat cgaaagttac   1080
ttcgacccag aaaaggaatc taaccaagtt aacatccctt tcatttgttg cgcttcaatc   1140
atctataata aggttattgg taacatcgtc gattttgaag gtagagactg tgtcgcacaa   1200
atgatcgaat acgttgtaga tatttgcggt gaattgaaca taagttctgt tgaattgatc   1260
gcccataacg gtggtggtta tgatttccac tacatcttgt catccatgta taatccagct   1320
gcaattaaaa acatattgat cagaaacaac tcttttattt cttttaattt cgcacatgat   1380
ggtgtcaagt tctctgttaa ggacagttac tcatttttgt tgtgtagttt ggccaacgct   1440
tctaaagcat tttaaacga agaaactttt aagaaaactg atttccctca tcacgacttg   1500
aaaactgccg atgacttata taaggtctac aaggaatgga gttctgttaa cacagaaatt   1560
aaccatgtcg ttgaaaagga aaagttgttg atcacctctg aacacatcgt taacttcacc   1620
aagaacgata agagtaagac tttgatcgaa tggtctaagg attactgtag aaacgacgta   1680
ttggtcttgt ctaaggtttg gttggagttt aaaaacgctg tagaagatat ttttaactgc   1740
gaattggtag accaaaccat gactttggct ggtttgtcat acaagttgtt ccaagcaaac   1800
atgccattcg atgtcgaatt gagacatcct aataaggaag actacttcaa catgagagaa   1860
gcattgattg gtggtagatg tatctctgtt aacggtatct acaaggatgt tttgtgctat   1920
gacgtaaaat cattatatcc agcttctatg gctttctatg atcaacctta cggttctttt   1980
aagagagttt catccagacc aaaagatgaa ttgggtatct attacgttag agtaacccca   2040
aacagaaaca acaagtcaaa ctttttccct atcagatccc ataataagat cacttacaac   2100
aacttcgaag aatcaactta tattgcttgg tacacaaacg ttgatatcga cattggtttg   2160
tcagaaggtc acaacatcga atacatccct ttcgattcct atggtaacat tggttactca   2220
tggtccaaaa agggtaaaat ttttgaaaag tacatcaagg atgttttgta caaattgaag   2280
ataaaatatg aaaagcaaaa taacaaggta aaaagaaatg tcatcaaaaa gatcatgaac   2340
tcattgtggg gtaaattcgc ccaaaagtgg gttaacttcg aatacttcat caagtcagaa   2400
gatgacattg atttcgaatc cgaagaagca tataaaatta acgatacaga cttcatgttg   2460
atcaaaaaga ttaaggaatc tacctacagt tctaagccaa tacaaaacgg tgtttttact   2520
ttaagttggg ccagatatca catgaagtct atttgggatg caggtgccaa agaaggtgct   2580
gaatgtatct attcagatac agactccata ttcgttcata aggaacactt caaaaagaat   2640
gcaaagttta tgttgaacgg tttgaaagta ccaatcatcg gttctgaagt cggtcaattg   2700
gaattagaat gtgaatttga taaattgttg tgcgccggta aaaagcaata catgggtttc   2760
tacacttact tccaagatgg taaaccttgc atcaaggaaa agaaaagatt caaaggtata   2820
ccaagtaact acatcatacc tgaattgtat gctcacttgt tatctggtgc agataaggaa   2880
gccaaaattc aatttttaaa attcagaaga gaatggggtt ccgtcaaggg ttacatagaa   2940
aataagactg tcaaagccac ctaa                                          2964
```

<210> SEQ ID NO 7
<211> LENGTH: 2964
<212> TYPE: DNA
<213> ORGANISM: Kluyveromyces lactis

<400> SEQUENCE: 7
atggactaca aagacaaagc attaaacgac ttgagaaacg tatacgcaga cttcgactcc 60
ttgccattgg acttcagaca aatcttaatt aaggatagag ctacattgtt gcaaaaggaa 120
gacgttgaaa agaaaatttt ggaaagacaa gaagatgcca aaaagtacgc tgaatacttg 180
aagcaatcag aaatcccaga aagaatctcc ttacctaaca tcaagagaca taagggtgta 240
tcaatctcct ttgaagaaac atctgaagat atggtcttgg aaccaagacc ttttatcttc 300
gacggtttga acatcagatg tttcagaaga gaaaccatat tcagtttgaa aaataagatt 360
ttgaacatgg ttaaggaatc ttcatccttt aaaaacgttt caagacaaag tgtatctttt 420
atgtacttca aaatttttaa taagggtaaa gttattgcaa gtacaaagtc tgttaacatc 480
tatgaagata agatcgacga aagattggaa gatttgtgta acaacttcga tgacgtattg 540
aaaaagatta tagacgtcac ctatggttac gaatccttat tcgttagtga aacttactct 600
tacgtaatat tctatgctaa atcaatctac tttccacaac ctagatgcgt taacaactgg 660
ggtaacaaca tcccaaacat cttgacattc gattccttta agcttttcac cgcaaacaaa 720
aacaacgtta gttgtatcaa gcaatgttca agatttttgt ggcaaaaaga tttcaacact 780
ttagaagaaa tgatagaata caagaacggt aatatttgta tcgtcacacc acaattgcat 840
atcaacgatg ttagagacat caagtcattc aacgatatca gattgtactc agaatcccct 900
attaaaacat tttccgttat tgataacact atcacatatt tgttttactt caaggaacat 960
ttgggtgtta tttttaacat cactaagtca agacatgata gaagagtaac aaaattttca 1020
ccattgtcca agttcagtga cgtcaaaaat atcactgttt gtttcgatat cgaaagttac 1080
ttcgacccag aaaaggaatc taaccaagtt aacatccctt tcatttgttg cgcttcaatc 1140
atctataata aggttattgg taacatcgtc gattttgaag gtagagactg tgtcgcacaa 1200
atgatcgaat acgttgtaga tatttgcggt gaattgaaca taagttctgt tgaattgatc 1260
gcccataacg gtggtggtta tgatttccac tacatcttgt catccatgta taatccagct 1320
gcaattaaaa acatattgat cagaaacaac tcttttattt cttttaattt cgcacatgat 1380
ggtgtcaagt tctctgttaa ggacagttac tcatttttgt tgtgtagttt ggccaacgct 1440
tctaaagcat ttttaaacga agaaactttt aagaaaactg atttccctca tcacgacttg 1500
aaaactgccg atgacttata taaggtctac aaggaatgga gttctgttaa cacagaaatt 1560
aaccatgtcg ttgaaaagga aaagttgttg atcacctctg aacacatcgt taacttcacc 1620
aagaacgata agagtaagac tttgatcgaa tggtctaagg attactgtag aaacgacgta 1680
ttggtcttgt ctaaggtttg gttggagttt aaaaacgctg tagaagatat ttttaactgc 1740
gaattggtag accaaaccat gactttggct ggtttgtcat acaagttgtt ccaagcaaac 1800
atgccattcg atgtcgaatt gagacatcct aataaggaag actacttcaa catgagagaa 1860
gcattgattg gtggtagatg tatctctgtt aacggtatct acaaggatgt tttgtgctta 1920
gacgtaaaat cattatatcc agcttctatg gctttctatg atcaacctta cggttctttt 1980
aagagagttt catccagacc aaaagatgaa ttgggtatct attacgttag agtaacccca 2040
aacagaaaca acaagtcaaa ctttttccct atcagatccc ataataagat cacttacaac 2100
aacttcgaag aatcaactta tattgcttgg tacacaaacg ttgatatcga cattggtttg 2160
tcagaaggtc acaacatcga atacatccct ttcgattcct atggtaacat tggttactca 2220
tggtccaaaa agggtaaaat ttttgaaaag tacatcaagg atgttttgta caaattgaag 2280
ataaaatatg aaaagcaaaa taacaaggta aaaagaaatg tcatcaaaaa gatcatgaac 2340
tcattgtggg gtaaattcgc ccaaaagtgg gttaacttcg aatacttcat caagtcagaa 2400
gatgacattg atttcgaatc cgaagaagca tataaaattt gggatacaga cttcatgttg 2460
atcaaaaaga ttaaggaatc tacctacagt tctaagccaa tacaaaacgg tgtttttact 2520
ttaagttggg ccagatatca catgaagtct atttgggatg caggtgccaa agaaggtgct 2580
gaatgtatct attcagatac agactccata ttcgttcata aggaacactt caaaaagaat 2640
gcaaagttta tgttgaacgg tttgaaagta ccaatcatcg gttctgaagt cggtcaatct 2700
gaattagaat gtgaatttga taaattgttg tgcgccggta aaaagcaata catgggtttc 2760
tacacttact tccaagatgg taaaccttgc atcaaggaaa agaaaagatt caaaggtata 2820
ccaagtaact acatcatacc tgaattgtat gctcacttgt tatctggtgc agataaggaa 2880
gccaaaattc aatttttaaa attcagaaga gaatggggtt ccgtcaaggg ttacatagaa 2940
aataagactg tcaaagccac ctaa 2964

<210> SEQ ID NO 8
<211> LENGTH: 2964
<212> TYPE: DNA
<213> ORGANISM: Kluyveromyces lactis

<400> SEQUENCE: 8
atggactaca aagacaaagc attaaacgac ttgagaaacg tatacgcaga cttcgactcc 60
ttgccattgg acttcagaca aatcttaatt aaggatagag ctacattgtt gcaaaaggaa 120
gacgttgaaa agaaaatttt ggaaagacaa gaagatgcca aaaagtacgc tgaatacttg 180
aagcaatcag aaatcccaga aagaatctcc ttacctaaca tcaagagaca taagggtgta 240
tcaatctcct ttgaagaaac atctgaagat atggtcttgg aaccaagacc ttttatcttc 300
gacggtttga acatcagatg tttcagaaga gaaaccatat tcagtttgaa aaataagatt 360
ttgaacatgg ttaaggaatc ttcatccttt aaaaacgttt caagacaaag tgtatctttt 420
atgtacttca aaatttttaa taagggtaaa gttattgcaa gtacaaagtc tgttaacatc 480
tatgaagata agatcgacga aagattggaa gatttgtgta acaacttcga tgacgtattg 540
aaaaagatta tagacgtcac ctatggttac gaatccttat tcgttagtga aacttactct 600
tacgtaatat tctatgctaa atcaatctac tttccacaac ctagatgcgt taacaactgg 660
ggtaacaaca tcccaaacat cttgacattc gattccttta agcttttcac cgcaaacaaa 720
aacaacgtta gttgtatcaa gcaatgttca agatttttgt ggcaaaaaga tttcaacact 780
ttagaagaaa tgatagaata caagaacggt aatatttgta tcgtcacacc acaattgcat 840
atcaacgatg ttagagacat caagtcattc aacgatatca gattgtactc agaatcccct 900
attaaaacat tttccgttat tgataacact atcacatatt tgttttactt caaggaacat 960
ttgggtgtta tttttaacat cactaagtca agacatgata gaagagtaac aaaattttca 1020
ccattgtcca agttcagtga cgtcaaaaat atcactgttt gtttcgatat cgaaagttac 1080
ttcgacccag aaaaggaatc taaccaagtt aacatccctt tcatttgttg cgcttcaatc 1140
atctataata aggttattgg taacatcgtc gattttgaag gtagagactg tgtcgcacaa 1200
atgatcgaat acgttgtaga tatttgcggt gaattgaaca taagttctgt tgaattgatc 1260
gcccataacg gtggtggtta tgatttccac cacatcttgt catccatgta taatccagct 1320
gcaattaaaa acatattgat cagaaacaac tcttttattt cttttaattt cgcacatgat 1380
ggtgtcaagt tctctgttaa ggacagttac tcatttttgt tgtgtagttt ggccaacgct 1440

```
tctaaagcat ttttaaacga agaaactttt aagaaaactg atttccctca tcacgacttg   1500
aaaactgccg atgacttata taaggtctac aaggaatgga gttctgttaa cacagaaatt   1560
aaccatgtcg ttgaaaagga aaagttgttg atcacctctg aacacatcgt taacttcacc   1620
aagaacgata agagtaagac tttgatcgaa tggtctaagg attactgtag aaacgacgta   1680
ttggtcttgt ctaaggtttg gttggagttt aaaaacgctg tagaagatat ttttaactgc   1740
gaattggtag accaaaccat gactttggct ggtttgtcat acaagttgtt ccaagcaaac   1800
atgccattcg atgtcgaatt gagacatcct aataaggaag actacttcaa catgagagaa   1860
gcattgattg gtggtagatg tatctctgtt aacggtatct acaaggatgt tttgtgctat   1920
gacgtaaaat cattatatcc agcttctatg gctttctatg atcaacctta cggttctttt   1980
aagagagttt catccagacc aaaagatgaa ttgggtatct attacgttag agtaacccca   2040
aacagaaaca acaagtcaaa ctttttccct atcagatccc ataataagat cacttacaac   2100
aacttcgaag aatcaactta tattgcttgg tacacaaacg ttgatatcga cattggtttg   2160
tcagaaggtc acaacatcga atacatccct ttcgattcct atggtaacat tggttactca   2220
tggtccaaaa agggtaaaat ttttgaaaag tacatcaagg atgttttgta caaattgaag   2280
ataaaatatg aaaagcaaaa taacaaggta aaaagaaatg tcatcaaaaa gatcatgaac   2340
tcattgtggg gtaaattcgc ccaaaagtgg gttaacttcg aatacttcat caagtcagaa   2400
gatgacattg atttcgaatc cgaagaagca tataaaatta acgatacaga cttcatgttg   2460
atcaaaaaga ttaaggaatc tacctacagt tctaagccaa tacaaaacgg tgtttttact   2520
ttaagttggg ccagatatca catgaagtct atttgggatg caggtgccaa agaaggtgct   2580
gaatgtatct attcagatac agactccata ttcgttcata aggaacactt caaaaagaat   2640
gcaaagttta tgttgaacgg tttgaaagta ccaatcatcg gttctgaagt cggtcaattg   2700
gaattagaat gtgaatttga taaattgttg tgcgccggta aaaagcaata catgggtttc   2760
tacacttact tccaagatgg taaaccttgc atcaaggaaa agaaaagatt caaaggtata   2820
ccaagtaact acatcatacc tgaattgtat gctcacttgt tatctggtgc agataaggaa   2880
gccaaaattc aatttttaaa attcagaaga gaatggggtt ccgtcaaggg ttacatagaa   2940
aataagactg tcaaagccac ctaa                                          2964
```

<210> SEQ ID NO 9
<211> LENGTH: 2964
<212> TYPE: DNA
<213> ORGANISM: Kluyveromyces lactis

<400> SEQUENCE: 9

```
atggactaca aagacaaagc attaaacgac ttgagaaacg tatacgcaga cttcgactcc     60
ttgccattgg acttcagaca aatcttaatt aaggatagag ctacattgtt gcaaaaggaa    120
gacgttgaaa agaaaatttt ggaaagacaa gaagatgcca aaaagtacgc tgaatacttg    180
aagcaatcag aaatcccaga aagaatctcc ttacctaaca tcaagagaca taagggtgta    240
tcaatctcct ttgaagaaac atctgaagat atggtcttgg aaccaagacc ttttatcttc    300
gacggtttga acatcagatg tttcagaaga gaaaccatat tcagtttgaa aaataagatt    360
ttgaacatgg ttaaggaatc ttcatccttt aaaaacgttt caagacaaag tgtatctttt    420
atgtacttca aaatttttaa taagggtaaa gttattgcaa gtacaaagtc tgttaacatc    480
tatgaagata agatcgacga aagattggaa gatttgtgta acaacttcga tgacgtattg    540
```

-continued

```
aaaaagatta tagacgtcac ctatggttac gaatccttat tcgttagtga aacttactct    600
tacgtaatat tctatgctaa atcaatctac tttccacaac ctagatgcgt taacaactgg    660
ggtaacaaca tcccaaacat cttgacattc gattccttta agcttttcac cgcaaacaaa    720
aacaacgtta gttgtatcaa gcaatgttca agatttttgt ggcaaaaaga tttcaacact    780
ttagaagaaa tgatagaata caagaacggt aatatttgta tcgtcacacc acaattgcat    840
atcaacgatg ttagagacat caagtcattc aacgatatca gattgtactc agaatcccct    900
attaaaacat tttccgttat tgataacact atcacatatt tgttttactt caaggaacat    960
ttgggtgtta tttttaacat cactaagtca agacatgata gaagagtaac aaaattttca   1020
ccattgtcca agttcagtga cgtcaaaaat atcactgttt gtttcgatat cgaaagttac   1080
ttcgacccag aaaaggaatc taaccaagtt aacatccctt tcatttgttg cgcttcaatc   1140
atctataata aggttattgg taacatcgtc gattttgaag gtagagactg tgtcgcacaa   1200
atgatcgaat acgttgtaga tatttgcggt gaattgaaca taagttctgt tgaattgatc   1260
gcccataacg gtggtggtta tgatttccac tacatcttgt catccatgta taatccagct   1320
gcaattaaaa acatattgat cagaaacaac tcttttattt cttttaattt cgcacatgat   1380
ggtgtcaagt tctctgttaa ggacagttac tcatttttgt ggtgtagttt ggccaacgct   1440
tctaaagcat tttaaaacga agaaactttt aagaaaactg atttccctca tcacgacttg   1500
aaaactgccg atgacttata taaggtctac aaggaatgga gttctgttaa cacagaaatt   1560
aaccatgtcg ttgaaaagga aaagttgttg atcacctctg aacacatcgt taacttcacc   1620
aagaacgata agagtaagac tttgatcgaa tggtctaagg attactgtag aaacgacgta   1680
ttggtcttgt ctaaggtttg gttggagttt aaaaacgctg tagaagatat ttttaactgc   1740
gaattggtag accaaaccat gactttggct ggtttgtcat acaagttgtt ccaagcaaac   1800
atgccattcg atgtcgaatt gagacatcct aataaggaag actacttcaa catgagagaa   1860
gcattgattg gtggtagatg tatctctgtt aacggtatct acaaggatgt tttgtgctat   1920
gacgtaaaat cattatatcc agcttctatg gctttctatg atcaacctta cggttctttt   1980
aagagagttt catccagacc aaaagatgaa ttgggtatct attacgttag agtaacccca   2040
aacagaaaca acaagtcaaa ctttttccct atcagatccc ataataagat cacttacaac   2100
aacttcgaag aatcaactta tattgcttgg tacacaaacg ttgatatcga cattggtttg   2160
tcagaaggtc acaacatcga atacatccct ttcgattcct atggtaacat tggttactca   2220
tggtccaaaa agggtaaaat ttttgaaaag tacatcaagg atgttttgta caaattgaag   2280
ataaaatatg aaaagcaaaa taacaaggta aaaagaaatg tcatcaaaaa gatcatgaac   2340
tcattgtggg gtaaattcgc ccaaaagtgg gttaacttcg aatacttcat caagtcagaa   2400
gatgacattg atttcgaatc cgaagaagca tataaaatta acgatacaga cttcatgttg   2460
atcaaaaaga ttaaggaatc tacctacagt tctaagccaa tacaaaacgg tgtttttact   2520
ttaagttggg ccagatatca catgaagtct atttgggatg caggtgccaa agaaggtgct   2580
gaatgtatct attcagatac agactccata ttcgttcata aggaacactt caaaaagaat   2640
gcaaagttta tgttgaacgg tttgaaagta ccaatcatcg gttctgaagt cggtcaattg   2700
gaattagaat gtgaatttga taaattgttg tgcgccggta aaaagcaata catgggtttc   2760
tacacttact tccaagatgg taaaccttgc atcaaggaaa agaaaagatt caaaggtata   2820
```

```
ccaagtaact acatcatacc tgaattgtat gctcacttgt tatctggtgc agataaggaa   2880

gccaaaattc aatttttaaa attcagaaga gaatggggtt ccgtcaaggg ttacatagaa   2940

aataagactg tcaaagccac ctaa                                          2964
```

<210> SEQ ID NO 10
<211> LENGTH: 2964
<212> TYPE: DNA
<213> ORGANISM: Kluyveromyces lactis

<400> SEQUENCE: 10

```
atggactaca aagacaaagc attaaacgac ttgagaaacg tatacgcaga cttcgactcc     60

ttgccattgg acttcagaca aatcttaatt aaggatagag ctacattgtt gcaaaaggaa    120

gacgttgaaa agaaaatttt ggaaagacaa gaagatgcca aaaagtacgc tgaatacttg    180

aagcaatcag aaatcccaga aagaatctcc ttacctaaca tcaagagaca taagggtgta    240

tcaatctcct ttgaagaaac atctgaagat atggtcttgg aaccaagacc ttttatcttc    300

gacggtttga acatcagatg tttcagaaga gaaaccatat tcagtttgaa aaataagatt    360

ttgaacatgg ttaaggaatc ttcatccttt aaaaacgttt caagacaaag tgtatctttt    420

atgtacttca aaatttttaa taagggtaaa gttattgcaa gtacaaagtc tgttaacatc    480

tatgaagata agatcgacga aagattggaa gatttgtgta acaacttcga tgacgtattg    540

aaaaagatta tagacgtcac ctatggttac gaatccttat tcgttagtga aacttactct    600

tacgtaatat tctatgctaa atcaatctac tttccacaac ctagatgcgt taacaactgg    660

ggtaacaaca tcccaaacat cttgacattc gattccttta agcttttcac cgcaaacaaa    720

aacaacgtta gttgtatcaa gcaatgttca agatttttgt ggcaaaaaga tttcaacact    780

ttagaagaaa tgatagaata caagaacggt aatatttgta tcgtcacacc acaattgcat    840

atcaacgatg ttagagacat caagtcattc aacgatatca gattgtactc agaatcccct    900

attaaaacat tttccgttat tgataacact atcacatatt tgttttactt caaggaacat    960

ttgggtgtta tttttaacat cactaagtca agacatgata gaagagtaac aaaatttttca   1020

ccattgtcca agttcagtga cgtcaaaaat atcactgttt gtttcgatat cgaaagttac   1080

ttcgacccag aaaaggaatc taaccaagtt aacatccctt tcatttgttg cgcttcaatc   1140

atctataata aggttattgg taacatcgtc gattttgaag gtagagactg tgtcgcacaa   1200

atgatcgaat acgttgtaga tatttgcggt gaattgaaca taagttctgt tgaattgatc   1260

gcccataacg gtggtggtta tgatttccac tacatcttgt catccatgta taatccagct   1320

gcaattaaaa acatattgat cagaaacaac tcttttattt cttttaattt cgcacatgat   1380

ggtgtcaagt tctctgttaa ggacagttac tcatttttgt tgtgtagttt ggccaacgct   1440

tctaaagcat tttaaacga agaaactttt aagaaaactg atttccctca tcacgacttg   1500

aaaactgccg atgacttata taaggtctac aaggaatgga gttctgttaa cacagaaatt   1560

aaccatgtcg ttgaaaagga aaagttgttg atcacctctg aacacatcgt taacttcacc   1620

aagaacgata agagtaagac tttgatcgaa tggtctaagg attactgtag aaacgacgta   1680

ttggtcttgt ctaaggtttg gttggagttt aaaaacgctt tcgaagatat ttttaactgc   1740

gaattggtag accaaaccat gactttggct ggtttgtcat acaagttgtt ccaagcaaac   1800

atgccattcg atgtcgaatt gagacatcct aataaggaag actacttcaa catgagagaa   1860

gcattgattg gtggtagatg tatctctgtt aacggtatct acaaggatgt tttgtgctta   1920
```

```
gacgtaaaat cattatatcc agcttctatg gctttctatg atcaacctta cggttctttt   1980

aagagagttt catccagacc aaaagatgaa ttgggtatct attacgttag agtaacccca   2040

aacagaaaca acaagtcaaa ctttttccct atcagatccc ataataagat cacttacaac   2100

aacttcgaag aatcaactta tattgcttgg tacacaaacg ttgatatcga cattggtttg   2160

tcagaaggtc acaacatcga atacatccct ttcgattcct atggtaacat tggttactca   2220

tggtccaaaa agggtaaaat ttttgaaaag tacatcaagg atgtttttgta caaattgaag   2280

ataaaatatg aaaagcaaaa taacaaggta aaaagaaatg tcatcaaaaa gatcatgaac   2340

tcattgtggg gtaaattcgc ccaaaagtgg gttaacttcg aatacttcat caagtcagaa   2400

gatgacattg atttcgaatc cgaagaagca tataaaattt gggatacaga cttcatgttg   2460

atcaaaaaga ttaaggaatc tacctacagt tctaagccaa tacaaaacgg tgtttttact   2520

ttaagttggg ccagatatca catgaagtct atttgggatg caggtgccaa agaaggtgct   2580

gaatgtatct attcagatac agactccata ttcgttcata aggaacactt caaaaagaat   2640

gcaaagttta tgttgaacgg tttgaaagta ccaatcatcg gttctgaagt cggtcaatct   2700

gaattagaat gtgaatttga taaattgttg tgcgccggta aaaagcaata catgggtttc   2760

tacacttact tccaagatgg taaaccttgc atcaaggaaa agaaaagatt caaaggtata   2820

ccaagtaact acatcatacc tgaattgtat gctcacttgt tatctggtgc agataaggaa   2880

gccaaaattc aatttttaaa attcagaaga gaatggggtt ccgtcaaggg ttacatagaa   2940

aataagactg tcaaagccac ctaa                                           2964
```

<210> SEQ ID NO 11
<211> LENGTH: 2964
<212> TYPE: DNA
<213> ORGANISM: Kluyveromyces lactis

<400> SEQUENCE: 11

```
atggactaca aagacaaagc attaaacgac ttgagaaacg tatacgcaga cttcgactcc     60

ttgccattgg acttcagaca aatcttaatt aaggatagag ctacattgtt gcaaaaggaa    120

gacgttgaaa agaaaatttt ggaaagacaa gaagatgcca aaaagtacgc tgaatacttg    180

aagcaatcag aaatcccaga aagaatctcc ttacctaaca tcaagagaca taagggtgta    240

tcaatctcct ttgaagaaac atctgaagat atggtcttgg aaccaagacc ttttatcttc    300

gacggtttga acatcagatg tttcagaaga gaaaccatat tcagtttgaa aaataagatt    360

ttgaacatgg ttaaggaatc ttcatccttt aaaaacgttt caagacaaag tgtatctttt    420

atgtacttca aatttttaa taagggtaaa gttattgcaa gtacaaagtc tgttaacatc    480

tatgaagata agatcgacga aagattggaa gatttgtgta acaacttcga tgacgtattg    540

aaaaagatta tagacgtcac ctatggttac gaatccttat tcgttagtga aacttactct    600

tacgtaatat tctatgctaa atcaatctac tttccacaac ctagatgcgt taacaactgg    660

ggtaacaaca tcccaaacat cttgacattc gattccttta agcttttcac cgcaaacaaa    720

aacaacgtta gttgtatcaa gcaatgttca agatttttgt ggcaaaaaga tttcaacact    780

ttagaagaaa tgatagaata caagaacggt aatatttgta tcgtcacacc acaattgcat    840

atcaacgatg ttagagacat caagtcattc aacgatatca gattgtactc agaatcccct    900

attaaaacat tttccgttat tgataacact atcacatatt tgttttactt caaggaacat    960

ttgggtgtta tttttaacat cactaagtca agacatgata gaagagtaac aaaattttca   1020

ccattgtcca agttcagtga cgtcaaaaat atcactgttt gtttcgatat cgaaagttac   1080
```

ttcgacccag aaaaggaatc taaccaagtt aacatccctt tcatttgttg cgcttcaatc 1140
atctataata aggttattgg taacatcgtc gattttgaag gtagagactg tgtcgcacaa 1200
atgatcgaat acgttgtaga tatttgcggt gaattgaaca taagttctgt tgaattgatc 1260
gcccataacg gtggtggtta tgatttccac tacatcttgt catccatgta taatccagct 1320
gcaattaaaa acatattgat cagaaacaac tcttttattt cttttaattt cgcacatgat 1380
ggtgtcaagt tctctgttaa ggacagttac tcatttttgt tgtgtagtgt tgccaacgct 1440
tctaaagcat ttttaaacga agaaactttt aagaaaactg atttccctca tcacgacttg 1500
aaaactgccg atgacttata taaggtctac aaggaatgga gttctgttaa cacagaaatt 1560
aaccatgtcg ttgaaaagga aaagttgttg atcacctctg aacacatcgt taacttcacc 1620
aagaacgata agagtaagac tttgatcgaa tggtctaagg attactgtag aaacgacgta 1680
ttggtcttgt ctaaggtttg gttggagttt aaaaacgctg tagaagatat ttttaactgc 1740
gaattggtag accaaaccat gactttggct ggtttgtcat acaagttgtt ccaagcaaac 1800
atgccattcg atgtcgaatt gagacatcct aataaggaag actacttcaa catgagagaa 1860
gcattgattg gtggtagatg tatctctgtt aacggtatct acaaggatgt tttgtgctat 1920
gacgtaaaat cattatatcc agcttctatg gctttctatg atcaacctta cggttctttt 1980
aagagagttt catccagacc aaaagatgaa ttgggtatct attacgttag agtaacccca 2040
aacagaaaca acaagtcaaa ctttttccct atcagatccc ataataagat cacttacaac 2100
aacttcgaag aatcaactta tattgcttgg tacacaaacg ttgatatcga cattggtttg 2160
tcagaaggtc acaacatcga atacatccct ttcgattcct atggtaacat tggttactca 2220
tggtccaaaa agggtaaaat ttttgaaaag tacatcaagg atgttttgta caaattgaag 2280
ataaaatatg aaaagcaaaa taacaaggta aaaagaaatg tcatcaaaaa gatcatgaac 2340
tcattgtggg gtaaattcgc ccaaaagtgg gttaacttcg aatacttcat caagtcagaa 2400
gatgacattg atttcgaatc cgaagaagca tataaaatta acgatacaga cttcatgttg 2460
atcaaaaaga ttaaggaatc tacctacagt tctaagccaa tacaaaacgg tgtttttact 2520
ttaagttggg ccagatatca catgaagtct atttgggatg caggtgccaa agaaggtgct 2580
gaatgtatct attcagatac agactccata ttcgttcata aggaacactt caaaaagaat 2640
gcaaagttta tgttgaacgg tttgaaagta ccaatcatcg gttctgaagt cggtcaattg 2700
gaattagaat gtgaatttga taaattgttg tgcgccggta aaaagcaata catgggtttc 2760
tacacttact tccaagatgg taaaccttgc atcaaggaaa agaaaagatt caaaggtata 2820
ccaagtaact acatcatacc tgaattgtat gctcacttgt tatctggtgc agataaggaa 2880
gccaaaattc aatttttaaa attcagaaga gaatggggtt ccgtcaaggg ttacatagaa 2940
aataagactg tcaaagccac ctaa 2964

<210> SEQ ID NO 12
<211> LENGTH: 2985
<212> TYPE: DNA
<213> ORGANISM: Kluyveromyces lactis

<400> SEQUENCE: 12
atgaacgatg aattagcctt tttgaactcc caaatagatg attatagtga cgacattgaa 60
tttttgagaa ccgaagtctt tagaatcaat agatattcta aatcaatcta ttctttaatg 120
aagaattctt caaaggaagc tattaaagaa actattgagt ttaataagta tggtcaagaa 180

```
attcattcta agattaaaga aaaggaaatt tcattaattg aagcaattaa attgatggaa    240
aagaaatata aatatttgag atcattgaat aagactaaag ataaatctaa gaaaaagaaa    300
attcatacaa aagatattga aactttgaaa acaatctata aacaaaagc tgattttgat    360
attagaaatt ttaaaaatgc tgaaactttt acttatgaaa attactcttt gttaattcca    420
tcagaaaagg aattgattga tttgatccca gaaatcgaag aagattactc ttactacttc    480
tacgtttcat taactatcac aggtccaact atctttggtg gtgttacaag aaaagttcca    540
atcatcgata cttatggtga cattaataag gatttctaca ataagattaa agaaaacatc    600
acaaaagttt tggatagagt tccattctac gaagaaaagg aatcagaaat tatttgtaag    660
aaagttttga tcactttgac agttaataag tgggaatcta tcgataagtg gtacaagaac    720
gttaagtcta agtctaaaaa gtttaaagat tttactttgt ttttagcttc tgatacttct    780
aaaaattgtg ttcaacaatg tgttgaatat ttgggtggta aatggaacac taactactct    840
ttggaaaaga tgatcccaca acaaaagatt gttacataca tcccattgtt gatggatatc    900
caatacgttc aatctatgga agatttgatc tcagatttcg atgaaccaaa cactgattgt    960
aagaacatcg ctagattgtt aaagtggaat ggtcacatgg gtgtgatcac aaagatcgac   1020
aaggatgtta agattaatag aatacaaaga aagagaatca tcgatgttga aaataaggaa   1080
gttaaagaag ttttctttga tattgaatct ttttcagatg aaactaaaca tcaaatccca   1140
tatttgattt gttggtctta cttgggtgaa ttatattaca gaacaggtaa aaattgtatc   1200
aaagaatttg ttgaagaaat tttatcttac aacgttgata tcatcttgta tgcttggtac   1260
ggttcaggtt atgattacca acatgttttg ccatacatga agtctaaatg tattaaggat   1320
aagtacatta ttaagaataa tatgattact tacggtgaat tatactacga aaacgcaatc   1380
atatatttga aagatccata cttgtttatt ttaacatctt tggataaagc atctaaggct   1440
tttaatgtta ttaataaggg tgaatttcca cattctatca tccattcatg ggaagatttg   1500
aataagattt tgccaaactg ggttaagatc caaaagagaa tgattgaata taaagatgat   1560
aataagttga acatctatta caagaacatc gaaattttcg aaaatgatag aaattataat   1620
actatcttag aaaatgctat tgaatactgt aaagttgatg ttttggcaat ggaaaaggtt   1680
tggatcaagt ttaagaaatt gttggaaaag aatttgaaca ttactgtttc agttaagact   1740
tttacattat ctcaattgtc aatgaagatc atggaatcta aattgccaaa gtacgttaaa   1800
ttgtacgttc caacattgga agaatattca aagatcagaa atgctatcta tggtggtaga   1860
gttatttcta aaaatggtat ctatgaagaa aacatcgttt acgctgatgt tgtttcttta   1920
tacccatcag caatgaaatt gttgaagcat tcttatggta aaccaaaatt ggttgattac   1980
atcgatttcg aaaagcatgg tatctaccgt gttactttgt tgaataagca tgatcaagaa   2040
cctaaaaatt acttaaactt tgttccaaga agaattaata gaaaattgac ttgggaatgg   2100
ttcaagatac atgaaggttg gtatcataca tacgatttga tcatcgctaa gtctgaaggt   2160
ttcgatatct attgccatga aggtttcgaa tacccagaaa aggattacat tttcaatgat   2220
ttcattgata cattatactc tatgaaagaa actcatacag catgttcatg tgaagaacaa   2280
ccatgtccaa tcagaatggt tgctaagatc gcattgaatg gtggtggtta tggtaaattt   2340
gttcaaaaac caatcgataa ggaaatatat atcgttaaga gagatgttgt tgctggtgaa   2400
tgtgataaat tacaagaaaa cgaaaatggt gaaatttgta ttggtaaaag attggttaaa   2460
agaccattat tttataattt ggattcagaa aactacgata aaatgattat tgaaaaagaa   2520
gatgaaccaa tctattctac tcaatgtggt atctcaatct tgtctgcatc aagatataga   2580
```

```
ttatacaaat tgtgtaagca attcgaaaac atcgatatca tctattctga tacagattca   2640

atttttgtta aacaaaaatc agttgattgg gaattgttta aatctaagtg tggttcagaa   2700

ttaggtcaat tggattctac tatcgatgat actaagaacg ctatcatctc aaagatgtac   2760

attggtggtg ctaagatgta tgcttttgaa tacttaaaca ataagaataa gttgatcact   2820

aaattgcatt gtaaaggtgt tccaaactac atgttgtctt taaaccaatt caaatatttg   2880

atggaatcac cagataacac aattgcatat aaatttgaaa ttattagaag aaaattggta   2940

aatgtcataa ctaaggactt gatcaaagat atcaagcaga cttga                   2985
```

```
<210> SEQ ID NO 13
<211> LENGTH: 994
<212> TYPE: PRT
<213> ORGANISM: Kluyveromyces lactis

<400> SEQUENCE: 13

Met Asn Asp Glu Leu Ala Phe Leu Asn Ser Gln Ile Asp Asp Tyr Ser
1               5                   10                  15

Asp Asp Ile Glu Phe Leu Arg Thr Glu Val Phe Arg Ile Asn Arg Tyr
            20                  25                  30

Ser Lys Ser Ile Tyr Ser Leu Met Lys Asn Ser Ser Lys Glu Ala Ile
        35                  40                  45

Lys Glu Thr Ile Glu Phe Asn Lys Tyr Gly Gln Glu Ile His Ser Lys
    50                  55                  60

Ile Lys Glu Lys Glu Ile Ser Leu Ile Glu Ala Ile Lys Leu Met Glu
65                  70                  75                  80

Lys Lys Tyr Lys Tyr Leu Arg Ser Leu Asn Lys Thr Lys Asp Lys Ser
                85                  90                  95

Lys Lys Lys Lys Ile His Thr Lys Asp Ile Glu Thr Leu Lys Thr Ile
            100                 105                 110

Tyr Lys Thr Lys Ala Asp Phe Asp Ile Arg Asn Phe Lys Asn Ala Glu
        115                 120                 125

Thr Phe Thr Tyr Glu Asn Tyr Ser Leu Leu Ile Pro Ser Glu Lys Glu
    130                 135                 140

Leu Ile Asp Leu Ile Pro Glu Ile Glu Glu Asp Tyr Ser Tyr Tyr Phe
145                 150                 155                 160

Tyr Val Ser Leu Thr Ile Thr Gly Pro Thr Ile Phe Gly Gly Val Thr
                165                 170                 175

Arg Lys Val Pro Ile Ile Asp Thr Tyr Gly Asp Ile Asn Lys Asp Phe
            180                 185                 190

Tyr Asn Lys Ile Lys Glu Asn Ile Thr Lys Val Leu Asp Arg Val Pro
        195                 200                 205

Phe Tyr Glu Glu Lys Glu Ser Glu Ile Ile Cys Lys Lys Val Leu Ile
    210                 215                 220

Thr Leu Thr Val Asn Lys Trp Glu Ser Ile Asp Lys Trp Tyr Lys Asn
225                 230                 235                 240

Val Lys Ser Lys Ser Lys Lys Phe Lys Asp Phe Thr Leu Phe Leu Ala
                245                 250                 255

Ser Asp Thr Ser Lys Asn Cys Val Gln Gln Cys Val Glu Tyr Leu Gly
            260                 265                 270

Gly Lys Trp Asn Thr Asn Tyr Ser Leu Glu Lys Met Ile Pro Gln Gln
        275                 280                 285

Lys Ile Val Thr Tyr Ile Pro Leu Leu Met Asp Ile Gln Tyr Val Gln
    290                 295                 300
```

```
Ser Met Glu Asp Leu Ile Ser Asp Phe Asp Glu Pro Asn Thr Asp Cys
305                 310                 315                 320

Lys Asn Ile Ala Arg Leu Leu Lys Trp Asn Gly His Met Gly Val Ile
                325                 330                 335

Thr Lys Ile Asp Lys Asp Val Lys Ile Asn Arg Ile Gln Arg Lys Arg
            340                 345                 350

Ile Ile Asp Val Glu Asn Lys Glu Val Lys Glu Val Phe Phe Asp Ile
        355                 360                 365

Glu Ser Phe Ser Asp Glu Thr Lys His Gln Ile Pro Tyr Leu Ile Cys
    370                 375                 380

Trp Ser Tyr Leu Gly Glu Leu Tyr Tyr Arg Thr Gly Lys Asn Cys Ile
385                 390                 395                 400

Lys Glu Phe Val Glu Glu Ile Leu Ser Tyr Asn Val Asp Ile Ile Leu
                405                 410                 415

Tyr Ala Trp Tyr Gly Ser Gly Tyr Asp Tyr Gln His Val Leu Pro Tyr
            420                 425                 430

Met Lys Ser Lys Cys Ile Lys Asp Lys Tyr Ile Ile Lys Asn Asn Met
        435                 440                 445

Ile Thr Tyr Gly Glu Leu Tyr Tyr Glu Asn Ala Ile Ile Tyr Leu Lys
    450                 455                 460

Asp Pro Tyr Leu Phe Ile Leu Thr Ser Leu Asp Lys Ala Ser Lys Ala
465                 470                 475                 480

Phe Asn Val Ile Asn Lys Gly Glu Phe Pro His Ser Ile Ile His Ser
                485                 490                 495

Trp Glu Asp Leu Asn Lys Ile Leu Pro Asn Trp Val Lys Ile Gln Lys
            500                 505                 510

Arg Met Ile Glu Tyr Lys Asp Asp Asn Lys Leu Asn Ile Tyr Tyr Lys
        515                 520                 525

Asn Ile Glu Ile Phe Glu Asn Asp Arg Asn Tyr Asn Thr Ile Leu Glu
    530                 535                 540

Asn Ala Ile Glu Tyr Cys Lys Val Asp Val Leu Ala Met Glu Lys Val
545                 550                 555                 560

Trp Ile Lys Phe Lys Lys Leu Leu Glu Lys Asn Leu Asn Ile Thr Val
                565                 570                 575

Ser Val Lys Thr Phe Thr Leu Ser Gln Leu Ser Met Lys Ile Met Glu
            580                 585                 590

Ser Lys Leu Pro Lys Tyr Val Lys Leu Tyr Val Pro Thr Leu Glu Glu
        595                 600                 605

Tyr Ser Lys Ile Arg Asn Ala Ile Tyr Gly Gly Arg Val Ile Ser Lys
    610                 615                 620

Asn Gly Ile Tyr Glu Glu Asn Ile Val Tyr Ala Asp Val Val Ser Leu
625                 630                 635                 640

Tyr Pro Ser Ala Met Lys Leu Leu Lys His Ser Tyr Gly Lys Pro Lys
                645                 650                 655

Leu Val Asp Tyr Ile Asp Phe Glu Lys His Gly Ile Tyr Arg Val Thr
            660                 665                 670

Leu Leu Asn Lys His Asp Gln Glu Pro Lys Asn Tyr Leu Asn Phe Val
        675                 680                 685

Pro Arg Arg Ile Asn Arg Lys Leu Thr Trp Glu Trp Phe Lys Ile His
    690                 695                 700

Glu Gly Trp Tyr His Thr Tyr Asp Leu Ile Ile Ala Lys Ser Glu Gly
705                 710                 715                 720
```

Phe Asp Ile Tyr Cys His Glu Gly Phe Glu Tyr Pro Glu Lys Asp Tyr
725 730 735

Ile Phe Asn Asp Phe Ile Asp Thr Leu Tyr Ser Met Lys Glu Thr His
740 745 750

Thr Ala Cys Ser Cys Glu Glu Gln Pro Cys Pro Ile Arg Met Val Ala
755 760 765

Lys Ile Ala Leu Asn Gly Gly Gly Tyr Gly Lys Phe Val Gln Lys Pro
770 775 780

Ile Asp Lys Glu Ile Tyr Ile Val Lys Arg Asp Val Val Ala Gly Glu
785 790 795 800

Cys Asp Lys Leu Gln Glu Asn Glu Asn Gly Glu Ile Cys Ile Gly Lys
805 810 815

Arg Leu Val Lys Arg Pro Leu Phe Tyr Asn Leu Asp Ser Glu Asn Tyr
820 825 830

Asp Lys Met Ile Ile Glu Lys Glu Asp Glu Pro Ile Tyr Ser Thr Gln
835 840 845

Cys Gly Ile Ser Ile Leu Ser Ala Ser Arg Tyr Arg Leu Tyr Lys Leu
850 855 860

Cys Lys Gln Phe Glu Asn Ile Asp Ile Ile Tyr Ser Asp Thr Asp Ser
865 870 875 880

Ile Phe Val Lys Gln Lys Ser Val Asp Trp Glu Leu Phe Lys Ser Lys
885 890 895

Cys Gly Ser Glu Leu Gly Gln Leu Asp Ser Thr Ile Asp Asp Thr Lys
900 905 910

Asn Ala Ile Ile Ser Lys Met Tyr Ile Gly Gly Ala Lys Met Tyr Ala
915 920 925

Phe Glu Tyr Leu Asn Asn Lys Asn Lys Leu Ile Thr Lys Leu His Cys
930 935 940

Lys Gly Val Pro Asn Tyr Met Leu Ser Leu Asn Gln Phe Lys Tyr Leu
945 950 955 960

Met Glu Ser Pro Asp Asn Thr Ile Ala Tyr Lys Phe Glu Ile Ile Arg
965 970 975

Arg Lys Leu Val Asn Val Ile Thr Lys Asp Leu Ile Lys Asp Ile Lys
980 985 990

Gln Thr

<210> SEQ ID NO 14
<211> LENGTH: 2985
<212> TYPE: DNA
<213> ORGANISM: Kluyveromyces lactis

<400> SEQUENCE: 14
atgaacgatg aattagcctt tttgaactcc caaatagatg attatagtga cgacattgaa 60
tttttgagaa ccgaagtctt tagaatcaat agatattcta aatcaatcta ttctttaatg 120
aagaattctt caaaggaagc tattaaagaa actattgagt ttaataagta tggtcaagaa 180
attcattcta agattaaaga aaaggaaatt tcattaattg aagcaattaa attgatggaa 240
aagaaatata aatatttgag atcattgaat aagactaaag ataaatctaa gaaaaagaaa 300
attcatacaa aagatattga aactttgaaa acaatctata aaacaaaagc tgattttgat 360
attagaaatt ttaaaaatgc tgaaactttt acttatgaaa attactcttt gttaattcca 420
tcagaaaagg aattgattga tttgatccca gaaatcgaag aagattactc ttactacttc 480
tacgtttcat taactatcac aggtccaact atctttggtg gtgttacaag aaaagttcca 540
atcatcgata cttatggtga cattaataag gatttctaca ataagattaa agaaaacatc 600
acaaaagttt tggatagagt tccattctac gaagaaaagg aatcagaaat tatttgtaag 660
aaagttttga tcactttgac agttaataag tgggaatcta tcgataagtg gtacaagaac 720
gttaagtcta agtctaaaaa gtttaaagat tttactttgt ttttagcttc tgatacttct 780
aaaaattgtg ttcaacaatg tgttgaatat ttgggtggta aatggaacac taactactct 840
ttggaaaaga tgatcccaca acaaaagatt gttacataca tcccattgtt gatggatatc 900
caatacgttc aatctatgga agatttgatc tcagatttcg atgaaccaaa cactgattgt 960
aagaacatcg ctagattgtt aaagtggaat ggtcacatgg gtgtgatcac aaagatcgac 1020
aaggatgtta agattaatag aatacaaaga aagagaatca tcgatgttga aaataaggaa 1080
gttaaagaag ttttctttga tattgaacag ttttcagatg aaactaaaca tcaaatccca 1140
tatttgattt gttggtctta cttgggtgaa ttatattaca gaacaggtaa aaattgtatc 1200
aaagaatttg ttgaagaaat tttatcttac aacgttgata tcatcttgta tgcttggtac 1260
ggttcaggtt atgattacca acatgttttg ccatacatga agtctaaatg tattaaggat 1320
aagtacatta ttaagaataa tatgattact tacggtgaat tatactacga aaacgcaatc 1380
atatatttga aagatccata cttgtttatt ttaacatctt tggataaagc atctaaggct 1440
tttaatgtta ttaataaggg tgaatttcca cattctatca tccattcatg ggaagatttg 1500
aataagattt tgccaaactg ggttaagatc caaaagagaa tgattgaata taaagatgat 1560
aataagttga acatctatta caagaacatc gaaattttcg aaaatgatag aaattataat 1620
actatcttag aaaatgctat tgaatactgt aaagttgatg ttttggcaat ggaaaaggtt 1680
tggatcaagt ttaagaaatt gttggaaaag aatttgaaca ttactgtttc agttaagact 1740
tttacattat ctcaattgtc aatgaagatc atggaatcta aattgccaaa gtacgttaaa 1800
ttgtacgttc caacattgga agaatattca aagatcagaa atgctatcta tggtggtaga 1860
gttatttcta aaaatggtat ctatgaagaa aacatcgttt acgctgatgt tgtttcttta 1920
tacccatcag caatgaaatt gttgaagcat tcttatggta aaccaaaatt ggttgattac 1980
atcgatttcg aaaagcatgg tatctaccgt gttactttgt tgaataagca tgatcaagaa 2040
cctaaaaatt acttaaactt tgttccaaga agaattaata gaaaattgac ttgggaatgg 2100
ttcaagatac atgaaggttg gtatcataca tacgatttga tcatcgctaa gtctgaaggt 2160
ttcgatatct attgccatga aggtttcgaa tacccagaaa aggattacat tttcaatgat 2220
ttcattgata cattatactc tatgaaagaa actcatacag catgttcatg tgaagaacaa 2280
ccatgtccaa tcagaatggt tgctaagatc gcattgaatg gtggtggtta tggtaaattt 2340
gttcaaaaac caatcgataa ggaaatatat atcgttaaga gagatgttgt tgctggtgaa 2400
tgtgataaat tacaagaaaa cgaaaatggt gaaatttgta ttggtaaaag attggttaaa 2460
agaccattat tttataattt ggattcagaa aactacgata aaatgattat tgaaaaagaa 2520
gatgaaccaa tctattctac tcaatgtggt atctcaatct tgtctgcatc aagatataga 2580
ttatacaaat tgtgtaagca attcgaaaac atcgatatca tctattctga tacagattca 2640
atttttgtta aacaaaaatc agttgattgg gaattgttta aatctaagtg tggttcagaa 2700
ttaggtcaat tggattctac tatcgatgat actaagaacg ctatcatctc aaagatgtac 2760
attggtggtg ctaagatgta tgcttttgaa tacttaaaca ataagaataa gttgatcact 2820
aaattgcatt gtaaaggtgt tccaaactac atgttgtctt taaaccaatt caaatatttg 2880
atggaatcac cagataacac aattgcatat aaatttgaaa ttattagaag aaaattggta 2940
aatgtcataa ctaaggactt gatcaaagat atcaagcaga cttga 2985

<210> SEQ ID NO 15
<211> LENGTH: 994
<212> TYPE: PRT
<213> ORGANISM: Kluyveromyces lactis

<400> SEQUENCE: 15

Met Asn Asp Glu Leu Ala Phe Leu Asn Ser Gln Ile Asp Asp Tyr Ser
1 5 10 15

Asp Asp Ile Glu Phe Leu Arg Thr Glu Val Phe Arg Ile Asn Arg Tyr
20 25 30

Ser Lys Ser Ile Tyr Ser Leu Met Lys Asn Ser Ser Lys Glu Ala Ile
35 40 45

Lys Glu Thr Ile Glu Phe Asn Lys Tyr Gly Gln Glu Ile His Ser Lys
50 55 60

Ile Lys Glu Lys Glu Ile Ser Leu Ile Glu Ala Ile Lys Leu Met Glu
65 70 75 80

Lys Lys Tyr Lys Tyr Leu Arg Ser Leu Asn Lys Thr Lys Asp Lys Ser
85 90 95

Lys Lys Lys Lys Ile His Thr Lys Asp Ile Glu Thr Leu Lys Thr Ile
100 105 110

Tyr Lys Thr Lys Ala Asp Phe Asp Ile Arg Asn Phe Lys Asn Ala Glu
115 120 125

Thr Phe Thr Tyr Glu Asn Tyr Ser Leu Leu Ile Pro Ser Glu Lys Glu
130 135 140

Leu Ile Asp Leu Ile Pro Glu Ile Glu Glu Asp Tyr Ser Tyr Tyr Phe
145 150 155 160

Tyr Val Ser Leu Thr Ile Thr Gly Pro Thr Ile Phe Gly Gly Val Thr
165 170 175

Arg Lys Val Pro Ile Ile Asp Thr Tyr Gly Asp Ile Asn Lys Asp Phe
180 185 190

Tyr Asn Lys Ile Lys Glu Asn Ile Thr Lys Val Leu Asp Arg Val Pro
195 200 205

Phe Tyr Glu Glu Lys Glu Ser Glu Ile Ile Cys Lys Lys Val Leu Ile
210 215 220

Thr Leu Thr Val Asn Lys Trp Glu Ser Ile Asp Lys Trp Tyr Lys Asn
225 230 235 240

Val Lys Ser Lys Ser Lys Lys Phe Lys Asp Phe Thr Leu Phe Leu Ala
245 250 255

Ser Asp Thr Ser Lys Asn Cys Val Gln Gln Cys Val Glu Tyr Leu Gly
260 265 270

Gly Lys Trp Asn Thr Asn Tyr Ser Leu Glu Lys Met Ile Pro Gln Gln
275 280 285

Lys Ile Val Thr Tyr Ile Pro Leu Leu Met Asp Ile Gln Tyr Val Gln
290 295 300

Ser Met Glu Asp Leu Ile Ser Asp Phe Asp Glu Pro Asn Thr Asp Cys
305 310 315 320

Lys Asn Ile Ala Arg Leu Leu Lys Trp Asn Gly His Met Gly Val Ile
325 330 335

```
Thr Lys Ile Asp Lys Asp Val Lys Ile Asn Arg Ile Gln Arg Lys Arg
            340                 345                 350

Ile Ile Asp Val Glu Asn Lys Glu Val Lys Glu Val Phe Phe Asp Ile
        355                 360                 365

Glu Gln Phe Ser Asp Glu Thr Lys His Gln Ile Pro Tyr Leu Ile Cys
    370                 375                 380

Trp Ser Tyr Leu Gly Glu Leu Tyr Tyr Arg Thr Gly Lys Asn Cys Ile
385                 390                 395                 400

Lys Glu Phe Val Glu Glu Ile Leu Ser Tyr Asn Val Asp Ile Ile Leu
                405                 410                 415

Tyr Ala Trp Tyr Gly Ser Gly Tyr Asp Tyr Gln His Val Leu Pro Tyr
            420                 425                 430

Met Lys Ser Lys Cys Ile Lys Asp Lys Tyr Ile Ile Lys Asn Asn Met
        435                 440                 445

Ile Thr Tyr Gly Glu Leu Tyr Tyr Glu Asn Ala Ile Ile Tyr Leu Lys
    450                 455                 460

Asp Pro Tyr Leu Phe Ile Leu Thr Ser Leu Asp Lys Ala Ser Lys Ala
465                 470                 475                 480

Phe Asn Val Ile Asn Lys Gly Glu Phe Pro His Ser Ile Ile His Ser
                485                 490                 495

Trp Glu Asp Leu Asn Lys Ile Leu Pro Asn Trp Val Lys Ile Gln Lys
            500                 505                 510

Arg Met Ile Glu Tyr Lys Asp Asp Asn Lys Leu Asn Ile Tyr Tyr Lys
        515                 520                 525

Asn Ile Glu Ile Phe Glu Asn Asp Arg Asn Tyr Asn Thr Ile Leu Glu
    530                 535                 540

Asn Ala Ile Glu Tyr Cys Lys Val Asp Val Leu Ala Met Glu Lys Val
545                 550                 555                 560

Trp Ile Lys Phe Lys Lys Leu Leu Glu Lys Asn Leu Asn Ile Thr Val
                565                 570                 575

Ser Val Lys Thr Phe Thr Leu Ser Gln Leu Ser Met Lys Ile Met Glu
            580                 585                 590

Ser Lys Leu Pro Lys Tyr Val Lys Leu Tyr Val Pro Thr Leu Glu Glu
        595                 600                 605

Tyr Ser Lys Ile Arg Asn Ala Ile Tyr Gly Gly Arg Val Ile Ser Lys
    610                 615                 620

Asn Gly Ile Tyr Glu Glu Asn Ile Val Tyr Ala Asp Val Val Ser Leu
625                 630                 635                 640

Tyr Pro Ser Ala Met Lys Leu Leu Lys His Ser Tyr Gly Lys Pro Lys
                645                 650                 655

Leu Val Asp Tyr Ile Asp Phe Glu Lys His Gly Ile Tyr Arg Val Thr
            660                 665                 670

Leu Leu Asn Lys His Asp Gln Glu Pro Lys Asn Tyr Leu Asn Phe Val
        675                 680                 685

Pro Arg Arg Ile Asn Arg Lys Leu Thr Trp Glu Trp Phe Lys Ile His
    690                 695                 700

Glu Gly Trp Tyr His Thr Tyr Asp Leu Ile Ile Ala Lys Ser Glu Gly
705                 710                 715                 720

Phe Asp Ile Tyr Cys His Glu Gly Phe Glu Tyr Pro Glu Lys Asp Tyr
                725                 730                 735

Ile Phe Asn Asp Phe Ile Asp Thr Leu Tyr Ser Met Lys Glu Thr His
            740                 745                 750
```

Thr Ala Cys Ser Cys Glu Glu Gln Pro Cys Pro Ile Arg Met Val Ala
755 760 765

Lys Ile Ala Leu Asn Gly Gly Gly Tyr Gly Lys Phe Val Gln Lys Pro
770 775 780

Ile Asp Lys Glu Ile Tyr Ile Val Lys Arg Asp Val Val Ala Gly Glu
785 790 795 800

Cys Asp Lys Leu Gln Glu Asn Glu Asn Gly Glu Ile Cys Ile Gly Lys
805 810 815

Arg Leu Val Lys Arg Pro Leu Phe Tyr Asn Leu Asp Ser Glu Asn Tyr
820 825 830

Asp Lys Met Ile Ile Glu Lys Glu Asp Glu Pro Ile Tyr Ser Thr Gln
835 840 845

Cys Gly Ile Ser Ile Leu Ser Ala Ser Arg Tyr Arg Leu Tyr Lys Leu
850 855 860

Cys Lys Gln Phe Glu Asn Ile Asp Ile Ile Tyr Ser Asp Thr Asp Ser
865 870 875 880

Ile Phe Val Lys Gln Lys Ser Val Asp Trp Glu Leu Phe Lys Ser Lys
885 890 895

Cys Gly Ser Glu Leu Gly Gln Leu Asp Ser Thr Ile Asp Asp Thr Lys
900 905 910

Asn Ala Ile Ile Ser Lys Met Tyr Ile Gly Gly Ala Lys Met Tyr Ala
915 920 925

Phe Glu Tyr Leu Asn Asn Lys Asn Lys Leu Ile Thr Lys Leu His Cys
930 935 940

Lys Gly Val Pro Asn Tyr Met Leu Ser Leu Asn Gln Phe Lys Tyr Leu
945 950 955 960

Met Glu Ser Pro Asp Asn Thr Ile Ala Tyr Lys Phe Glu Ile Ile Arg
965 970 975

Arg Lys Leu Val Asn Val Ile Thr Lys Asp Leu Ile Lys Asp Ile Lys
980 985 990

Gln Thr

<210> SEQ ID NO 16
<211> LENGTH: 2985
<212> TYPE: DNA
<213> ORGANISM: Kluyveromyces lactis

<400> SEQUENCE: 16
atgaacgatg aattagcctt tttgaactcc caaatagatg attatagtga cgacattgaa 60
tttttgagaa ccgaagtctt tagaatcaat agatattcta aatcaatcta ttctttaatg 120
aagaattctt caaaggaagc tattaaagaa actattgagt ttaataagta tggtcaagaa 180
attcattcta agattaaaga aaaggaaatt tcattaattg aagcaattaa attgatggaa 240
aagaaatata aatatttgag atcattgaat aagactaaag ataaatctaa gaaaaagaaa 300
attcatacaa aagatattga aactttgaaa acaatctata aaacaaaagc tgattttgat 360
attagaaatt ttaaaaatgc tgaaactttt acttatgaaa attactcttt gttaattcca 420
tcagaaaagg aattgattga tttgatccca gaaatcgaag aagattactc ttactacttc 480
tacgtttcat taactatcac aggtccaact atctttggtg gtgttacaag aaaagttcca 540
atcatcgata cttatggtga cattaataag gatttctaca ataagattaa agaaaacatc 600
acaaaagttt tggatagagt tccattctac gaagaaaagg aatcagaaat tatttgtaag 660
aaagttttga tcactttgac agttaataag tgggaatcta tcgataagtg gtacaagaac 720

```
gttaagtcta agtctaaaaa gtttaaagat tttactttgt ttttagcttc tgatacttct    780
aaaaattgtg ttcaacaatg tgttgaatat ttgggtggta aatggaacac taactactct    840
ttggaaaaga tgatcccaca acaaaagatt gttacataca tcccattgtt gatggatatc    900
caatacgttc aatctatgga agatttgatc tcagatttcg atgaaccaaa cactgattgt    960
aagaacatcg ctagattgtt aaagtggaat ggtcacatgg gtgtgatcac aaagatcgac   1020
aaggatgtta agattaatag aatacaaaga aagagaatca tcgatgttga aaataaggaa   1080
gttaaagaag ttttctttga tattgaatct ttttcagatg aaactaaaca tcaaatccca   1140
tatttgattt gttggtctta cttgggtgaa ttatattaca gaacaggtaa aaattgtatc   1200
aaagaatttg ttgaagaaat tttatcttac aacgttgata tcatcttgta tgcttggtac   1260
ggttcaggtc aggattacca acatgttttg ccatacatga agtctaaatg tattaaggat   1320
aagtacatta ttaagaataa tatgattact tacggtgaat tatactacga aaacgcaatc   1380
atatatttga aagatccata cttgtttatt ttaacatctt tggataaagc atctaaggct   1440
tttaatgtta ttaataaggg tgaatttcca cattctatca tccattcatg ggaagatttg   1500
aataagattt tgccaaactg ggttaagatc caaaagagaa tgattgaata taaagatgat   1560
aataagttga acatctatta caagaacatc gaaattttcg aaaatgatag aaattataat   1620
actatcttag aaaatgctat tgaatactgt aaagttgatg ttttggcaat ggaaaaggtt   1680
tggatcaagt ttaagaaatt gttggaaaag aatttgaaca ttactgtttc agttaagact   1740
tttacattat ctcaattgtc aatgaagatc atggaatcta aattgccaaa gtacgttaaa   1800
ttgtacgttc caacattgga agaatattca aagatcagaa atgctatcta tggtggtaga   1860
gttatttcta aaaatggtat ctatgaagaa aacatcgttt acgctgatgt tgtttcttta   1920
tacccatcag caatgaaatt gttgaagcat tcttatggta aaccaaaatt ggttgattac   1980
atcgatttcg aaaagcatgg tatctaccgt gttactttgt tgaataagca tgatcaagaa   2040
cctaaaaatt acttaaactt tgttccaaga agaattaata gaaaattgac ttgggaatgg   2100
ttcaagatac atgaaggttg gtatcataca tacgatttga tcatcgctaa gtctgaaggt   2160
ttcgatatct attgccatga aggtttcgaa tacccagaaa aggattacat tttcaatgat   2220
ttcattgata cattatactc tatgaaagaa actcatacag catgttcatg tgaagaacaa   2280
ccatgtccaa tcagaatggt tgctaagatc gcattgaatg gtggtggtta tggtaaattt   2340
gttcaaaaac caatcgataa ggaaatatat atcgttaaga gagatgttgt tgctggtgaa   2400
tgtgataaat tacaagaaaa cgaaaatggt gaaatttgta ttggtaaaag attggttaaa   2460
agaccattat tttataattt ggattcagaa aactacgata aaatgattat tgaaaaagaa   2520
gatgaaccaa tctattctac tcaatgtggt atctcaatct tgtctgcatc aagatataga   2580
ttatacaaat tgtgtaagca attcgaaaac atcgatatca tctattctga tacagattca   2640
atttttgtta aacaaaaatc agttgattgg gaattgttta aatctaagtg tggttcagaa   2700
ttaggtcaat tggattctac tatcgatgat actaagaacg ctatcatctc aaagatgtac   2760
attggtggtg ctaagatgta tgcttttgaa tacttaaaca ataagaataa gttgatcact   2820
aaattgcatt gtaaaggtgt tccaaactac atgttgtctt taaaccaatt caaatatttg   2880
atggaatcac cagataacac aattgcatat aaatttgaaa ttattagaag aaaattggta   2940
aatgtcataa ctaaggactt gatcaaagat atcaagcaga cttga                   2985
```

<210> SEQ ID NO 17
<211> LENGTH: 994

<212> TYPE: PRT
<213> ORGANISM: Kluyveromyces lactis

<400> SEQUENCE: 17

```
Met Asn Asp Glu Leu Ala Phe Leu Asn Ser Gln Ile Asp Asp Tyr Ser
1               5                   10                  15

Asp Asp Ile Glu Phe Leu Arg Thr Glu Val Phe Arg Ile Asn Arg Tyr
            20                  25                  30

Ser Lys Ser Ile Tyr Ser Leu Met Lys Asn Ser Ser Lys Glu Ala Ile
        35                  40                  45

Lys Glu Thr Ile Glu Phe Asn Lys Tyr Gly Gln Glu Ile His Ser Lys
    50                  55                  60

Ile Lys Glu Lys Glu Ile Ser Leu Ile Glu Ala Ile Lys Leu Met Glu
65                  70                  75                  80

Lys Lys Tyr Lys Tyr Leu Arg Ser Leu Asn Lys Thr Lys Asp Lys Ser
                85                  90                  95

Lys Lys Lys Lys Ile His Thr Lys Asp Ile Glu Thr Leu Lys Thr Ile
            100                 105                 110

Tyr Lys Thr Lys Ala Asp Phe Asp Ile Arg Asn Phe Lys Asn Ala Glu
        115                 120                 125

Thr Phe Thr Tyr Glu Asn Tyr Ser Leu Leu Ile Pro Ser Glu Lys Glu
    130                 135                 140

Leu Ile Asp Leu Ile Pro Glu Ile Glu Glu Asp Tyr Ser Tyr Tyr Phe
145                 150                 155                 160

Tyr Val Ser Leu Thr Ile Thr Gly Pro Thr Ile Phe Gly Gly Val Thr
                165                 170                 175

Arg Lys Val Pro Ile Ile Asp Thr Tyr Gly Asp Ile Asn Lys Asp Phe
            180                 185                 190

Tyr Asn Lys Ile Lys Glu Asn Ile Thr Lys Val Leu Asp Arg Val Pro
        195                 200                 205

Phe Tyr Glu Glu Lys Glu Ser Glu Ile Ile Cys Lys Lys Val Leu Ile
    210                 215                 220

Thr Leu Thr Val Asn Lys Trp Glu Ser Ile Asp Lys Trp Tyr Lys Asn
225                 230                 235                 240

Val Lys Ser Lys Ser Lys Lys Phe Lys Asp Phe Thr Leu Phe Leu Ala
                245                 250                 255

Ser Asp Thr Ser Lys Asn Cys Val Gln Gln Cys Val Glu Tyr Leu Gly
            260                 265                 270

Gly Lys Trp Asn Thr Asn Tyr Ser Leu Glu Lys Met Ile Pro Gln Gln
        275                 280                 285

Lys Ile Val Thr Tyr Ile Pro Leu Leu Met Asp Ile Gln Tyr Val Gln
    290                 295                 300

Ser Met Glu Asp Leu Ile Ser Asp Phe Asp Glu Pro Asn Thr Asp Cys
305                 310                 315                 320

Lys Asn Ile Ala Arg Leu Leu Lys Trp Asn Gly His Met Gly Val Ile
                325                 330                 335

Thr Lys Ile Asp Lys Asp Val Lys Ile Asn Arg Ile Gln Arg Lys Arg
            340                 345                 350

Ile Ile Asp Val Glu Asn Lys Glu Val Lys Glu Val Phe Phe Asp Ile
        355                 360                 365

Glu Ser Phe Ser Asp Glu Thr Lys His Gln Ile Pro Tyr Leu Ile Cys
    370                 375                 380

Trp Ser Tyr Leu Gly Glu Leu Tyr Tyr Arg Thr Gly Lys Asn Cys Ile
385                 390                 395                 400
```

```
Lys Glu Phe Val Glu Glu Ile Leu Ser Tyr Asn Val Asp Ile Ile Leu
                405                 410                 415

Tyr Ala Trp Tyr Gly Ser Gly Gln Asp Tyr Gln His Val Leu Pro Tyr
            420                 425                 430

Met Lys Ser Lys Cys Ile Lys Asp Lys Tyr Ile Ile Lys Asn Asn Met
        435                 440                 445

Ile Thr Tyr Gly Glu Leu Tyr Tyr Glu Asn Ala Ile Ile Tyr Leu Lys
    450                 455                 460

Asp Pro Tyr Leu Phe Ile Leu Thr Ser Leu Asp Lys Ala Ser Lys Ala
465                 470                 475                 480

Phe Asn Val Ile Asn Lys Gly Glu Phe Pro His Ser Ile Ile His Ser
                485                 490                 495

Trp Glu Asp Leu Asn Lys Ile Leu Pro Asn Trp Val Lys Ile Gln Lys
            500                 505                 510

Arg Met Ile Glu Tyr Lys Asp Asp Asn Lys Leu Asn Ile Tyr Tyr Lys
        515                 520                 525

Asn Ile Glu Ile Phe Glu Asn Asp Arg Asn Tyr Asn Thr Ile Leu Glu
    530                 535                 540

Asn Ala Ile Glu Tyr Cys Lys Val Asp Val Leu Ala Met Glu Lys Val
545                 550                 555                 560

Trp Ile Lys Phe Lys Lys Leu Leu Glu Lys Asn Leu Asn Ile Thr Val
                565                 570                 575

Ser Val Lys Thr Phe Thr Leu Ser Gln Leu Ser Met Lys Ile Met Glu
            580                 585                 590

Ser Lys Leu Pro Lys Tyr Val Lys Leu Tyr Val Pro Thr Leu Glu Glu
        595                 600                 605

Tyr Ser Lys Ile Arg Asn Ala Ile Tyr Gly Gly Arg Val Ile Ser Lys
    610                 615                 620

Asn Gly Ile Tyr Glu Glu Asn Ile Val Tyr Ala Asp Val Val Ser Leu
625                 630                 635                 640

Tyr Pro Ser Ala Met Lys Leu Leu Lys His Ser Tyr Gly Lys Pro Lys
                645                 650                 655

Leu Val Asp Tyr Ile Asp Phe Glu Lys His Gly Ile Tyr Arg Val Thr
            660                 665                 670

Leu Leu Asn Lys His Asp Gln Glu Pro Lys Asn Tyr Leu Asn Phe Val
        675                 680                 685

Pro Arg Arg Ile Asn Arg Lys Leu Thr Trp Glu Trp Phe Lys Ile His
    690                 695                 700

Glu Gly Trp Tyr His Thr Tyr Asp Leu Ile Ile Ala Lys Ser Glu Gly
705                 710                 715                 720

Phe Asp Ile Tyr Cys His Glu Gly Phe Glu Tyr Pro Glu Lys Asp Tyr
                725                 730                 735

Ile Phe Asn Asp Phe Ile Asp Thr Leu Tyr Ser Met Lys Glu Thr His
            740                 745                 750

Thr Ala Cys Ser Cys Glu Glu Gln Pro Cys Pro Ile Arg Met Val Ala
        755                 760                 765

Lys Ile Ala Leu Asn Gly Gly Gly Tyr Gly Lys Phe Val Gln Lys Pro
    770                 775                 780

Ile Asp Lys Glu Ile Tyr Ile Val Lys Arg Asp Val Val Ala Gly Glu
785                 790                 795                 800

Cys Asp Lys Leu Gln Glu Asn Glu Asn Gly Glu Ile Cys Ile Gly Lys
                805                 810                 815
```

```
Arg Leu Val Lys Arg Pro Leu Phe Tyr Asn Leu Asp Ser Glu Asn Tyr
            820                 825                 830

Asp Lys Met Ile Ile Glu Lys Glu Asp Glu Pro Ile Tyr Ser Thr Gln
        835                 840                 845

Cys Gly Ile Ser Ile Leu Ser Ala Ser Arg Tyr Arg Leu Tyr Lys Leu
    850                 855                 860

Cys Lys Gln Phe Glu Asn Ile Asp Ile Ile Tyr Ser Asp Thr Asp Ser
865                 870                 875                 880

Ile Phe Val Lys Gln Lys Ser Val Asp Trp Glu Leu Phe Lys Ser Lys
                885                 890                 895

Cys Gly Ser Glu Leu Gly Gln Leu Asp Ser Thr Ile Asp Asp Thr Lys
            900                 905                 910

Asn Ala Ile Ile Ser Lys Met Tyr Ile Gly Gly Ala Lys Met Tyr Ala
        915                 920                 925

Phe Glu Tyr Leu Asn Asn Lys Asn Lys Leu Ile Thr Lys Leu His Cys
    930                 935                 940

Lys Gly Val Pro Asn Tyr Met Leu Ser Leu Asn Gln Phe Lys Tyr Leu
945                 950                 955                 960

Met Glu Ser Pro Asp Asn Thr Ile Ala Tyr Lys Phe Glu Ile Ile Arg
                965                 970                 975

Arg Lys Leu Val Asn Val Ile Thr Lys Asp Leu Ile Lys Asp Ile Lys
            980                 985                 990

Gln Thr


<210> SEQ ID NO 18
<211> LENGTH: 2985
<212> TYPE: DNA
<213> ORGANISM: Kluyveromyces lactis

<400> SEQUENCE: 18

atgaacgatg aattagcctt tttgaactcc caaatagatg attatagtga cgacattgaa     60

tttttgagaa ccgaagtctt tagaatcaat agatattcta aatcaatcta ttctttaatg    120

aagaattctt caaaggaagc tattaaagaa actattgagt ttaataagta tggtcaagaa    180

attcattcta agattaaaga aaaggaaatt tcattaattg aagcaattaa attgatggaa    240

aagaaatata aatatttgag atcattgaat aagactaaag ataaatctaa gaaaaagaaa    300

attcatacaa aagatattga aactttgaaa acaatctata aaacaaaagc tgattttgat    360

attagaaatt ttaaaaatgc tgaaactttt acttatgaaa attactcttt gttaattcca    420

tcagaaaagg aattgattga tttgatccca gaaatcgaag aagattactc ttactacttc    480

tacgtttcat taactatcac aggtccaact atctttggtg gtgttacaag aaaagttcca    540

atcatcgata cttatggtga cattaataag gatttctaca ataagattaa agaaaacatc    600

acaaaagttt tggatagagt tccattctac gaagaaaagg aatcagaaat tatttgtaag    660

aaagttttga tcactttgac agttaataag tgggaatcta tcgataagtg gtacaagaac    720

gttaagtcta agtctaaaaa gtttaaagat tttactttgt ttttagcttc tgatacttct    780

aaaaattgtg ttcaacaatg tgttgaatat ttgggtggta aatggaacac taactactct    840

ttggaaaaga tgatcccaca acaaaagatt gttacataca tcccattgtt gatggatatc    900

caatacgttc aatctatgga agatttgatc tcagatttcg atgaaccaaa cactgattgt    960

aagaacatcg ctagattgtt aaagtggaat ggtcacatgg gtgtgatcac aaagatcgac   1020

aaggatgtta agattaatag aatacaaaga aagagaatca tcgatgttga aaataaggaa   1080
```

gttaaagaag ttttctttga tattgaatct ttttcagatg aaactaaaca tcaaatccca 1140
tatttgattt gttggtctta cttgggtgaa ttatattaca gaacaggtaa aaattgtatc 1200
aaagaatttg ttgaagaaat tttatcttac aacgttgata tcatcttgta tgcttggtac 1260
ggttcaggtg aggattacca acatgttttg ccatacatga agtctaaatg tattaaggat 1320
aagtacatta ttaagaataa tatgattact tacggtgaat tatactacga aaacgcaatc 1380
atatatttga aagatccata cttgtttatt ttaacatctt tggataaagc atctaaggct 1440
tttaatgtta ttaataaggg tgaatttcca cattctatca tccattcatg ggaagatttg 1500
aataagattt tgccaaactg ggttaagatc caaaagagaa tgattgaata taaagatgat 1560
aataagttga acatctatta caagaacatc gaaattttcg aaaatgatag aaattataat 1620
actatcttag aaaatgctat tgaatactgt aaagttgatg ttttggcaat ggaaaaggtt 1680
tggatcaagt ttaagaaatt gttggaaaag aatttgaaca ttactgtttc agttaagact 1740
tttacattat ctcaattgtc aatgaagatc atggaatcta aattgccaaa gtacgttaaa 1800
ttgtacgttc caacattgga agaatattca aagatcagaa atgctatcta tggtggtaga 1860
gttatttcta aaaatggtat ctatgaagaa aacatcgttt acgctgatgt tgtttcttta 1920
tacccatcag caatgaaatt gttgaagcat tcttatggta aaccaaaatt ggttgattac 1980
atcgatttcg aaaagcatgg tatctaccgt gttactttgt tgaataagca tgatcaagaa 2040
cctaaaaatt acttaaactt tgttccaaga agaattaata gaaaattgac ttgggaatgg 2100
ttcaagatac atgaaggttg gtatcataca tacgatttga tcatcgctaa gtctgaaggt 2160
ttcgatatct attgccatga aggtttcgaa tacccagaaa aggattacat tttcaatgat 2220
ttcattgata cattatactc tatgaaagaa actcatacag catgttcatg tgaagaacaa 2280
ccatgtccaa tcagaatggt tgctaagatc gcattgaatg gtggtggtta tggtaaattt 2340
gttcaaaaac caatcgataa ggaaatatat atcgttaaga gagatgttgt tgctggtgaa 2400
tgtgataaat tacaagaaaa cgaaaatggt gaaatttgta ttggtaaaag attggttaaa 2460
agaccattat tttataattt ggattcagaa aactacgata aaatgattat tgaaaaagaa 2520
gatgaaccaa tctattctac tcaatgtggt atctcaatct tgtctgcatc aagatataga 2580
ttatacaaat tgtgtaagca attcgaaaac atcgatatca tctattctga tacagattca 2640
atttttgtta aacaaaaatc agttgattgg gaattgttta aatctaagtg tggttcagaa 2700
ttaggtcaat tggattctac tatcgatgat actaagaacg ctatcatctc aaagatgtac 2760
attggtggtg ctaagatgta tgcttttgaa tacttaaaca ataagaataa gttgatcact 2820
aaattgcatt gtaaaggtgt tccaaactac atgttgtctt taaaccaatt caaatatttg 2880
atggaatcac cagataacac aattgcatat aaatttgaaa ttattagaag aaaattggta 2940
aatgtcataa ctaaggactt gatcaaagat atcaagcaga cttga 2985

<210> SEQ ID NO 19
<211> LENGTH: 994
<212> TYPE: PRT
<213> ORGANISM: Kluyveromyces lactis

<400> SEQUENCE: 19

Met Asn Asp Glu Leu Ala Phe Leu Asn Ser Gln Ile Asp Asp Tyr Ser
1 5 10 15

Asp Asp Ile Glu Phe Leu Arg Thr Glu Val Phe Arg Ile Asn Arg Tyr
20 25 30

```
Ser Lys Ser Ile Tyr Ser Leu Met Lys Asn Ser Ser Lys Glu Ala Ile
        35                  40                  45

Lys Glu Thr Ile Glu Phe Asn Lys Tyr Gly Gln Glu Ile His Ser Lys
    50                  55                  60

Ile Lys Glu Lys Glu Ile Ser Leu Ile Glu Ala Ile Lys Leu Met Glu
65                  70                  75                  80

Lys Lys Tyr Lys Tyr Leu Arg Ser Leu Asn Lys Thr Lys Asp Lys Ser
                85                  90                  95

Lys Lys Lys Lys Ile His Thr Lys Asp Ile Glu Thr Leu Lys Thr Ile
            100                 105                 110

Tyr Lys Thr Lys Ala Asp Phe Asp Ile Arg Asn Phe Lys Asn Ala Glu
        115                 120                 125

Thr Phe Thr Tyr Glu Asn Tyr Ser Leu Leu Ile Pro Ser Glu Lys Glu
    130                 135                 140

Leu Ile Asp Leu Ile Pro Glu Ile Glu Glu Asp Tyr Ser Tyr Tyr Phe
145                 150                 155                 160

Tyr Val Ser Leu Thr Ile Thr Gly Pro Thr Ile Phe Gly Gly Val Thr
                165                 170                 175

Arg Lys Val Pro Ile Ile Asp Thr Tyr Gly Asp Ile Asn Lys Asp Phe
            180                 185                 190

Tyr Asn Lys Ile Lys Glu Asn Ile Thr Lys Val Leu Asp Arg Val Pro
        195                 200                 205

Phe Tyr Glu Glu Lys Glu Ser Glu Ile Ile Cys Lys Lys Val Leu Ile
    210                 215                 220

Thr Leu Thr Val Asn Lys Trp Glu Ser Ile Asp Lys Trp Tyr Lys Asn
225                 230                 235                 240

Val Lys Ser Lys Ser Lys Lys Phe Lys Asp Phe Thr Leu Phe Leu Ala
                245                 250                 255

Ser Asp Thr Ser Lys Asn Cys Val Gln Gln Cys Val Glu Tyr Leu Gly
            260                 265                 270

Gly Lys Trp Asn Thr Asn Tyr Ser Leu Glu Lys Met Ile Pro Gln Gln
        275                 280                 285

Lys Ile Val Thr Tyr Ile Pro Leu Leu Met Asp Ile Gln Tyr Val Gln
    290                 295                 300

Ser Met Glu Asp Leu Ile Ser Asp Phe Asp Glu Pro Asn Thr Asp Cys
305                 310                 315                 320

Lys Asn Ile Ala Arg Leu Leu Lys Trp Asn Gly His Met Gly Val Ile
                325                 330                 335

Thr Lys Ile Asp Lys Asp Val Lys Ile Asn Arg Ile Gln Arg Lys Arg
            340                 345                 350

Ile Ile Asp Val Glu Asn Lys Glu Val Lys Glu Val Phe Phe Asp Ile
        355                 360                 365

Glu Ser Phe Ser Asp Glu Thr Lys His Gln Ile Pro Tyr Leu Ile Cys
    370                 375                 380

Trp Ser Tyr Leu Gly Glu Leu Tyr Tyr Arg Thr Gly Lys Asn Cys Ile
385                 390                 395                 400

Lys Glu Phe Val Glu Glu Ile Leu Ser Tyr Asn Val Asp Ile Ile Leu
                405                 410                 415

Tyr Ala Trp Tyr Gly Ser Gly Glu Asp Tyr Gln His Val Leu Pro Tyr
            420                 425                 430

Met Lys Ser Lys Cys Ile Lys Asp Lys Tyr Ile Ile Lys Asn Asn Met
        435                 440                 445
```

-continued

```
Ile Thr Tyr Gly Glu Leu Tyr Tyr Glu Asn Ala Ile Ile Tyr Leu Lys
    450                 455                 460

Asp Pro Tyr Leu Phe Ile Leu Thr Ser Leu Asp Lys Ala Ser Lys Ala
465                 470                 475                 480

Phe Asn Val Ile Asn Lys Gly Glu Phe Pro His Ser Ile Ile His Ser
                485                 490                 495

Trp Glu Asp Leu Asn Lys Ile Leu Pro Asn Trp Val Lys Ile Gln Lys
            500                 505                 510

Arg Met Ile Glu Tyr Lys Asp Asp Asn Lys Leu Asn Ile Tyr Tyr Lys
        515                 520                 525

Asn Ile Glu Ile Phe Glu Asn Asp Arg Asn Tyr Asn Thr Ile Leu Glu
    530                 535                 540

Asn Ala Ile Glu Tyr Cys Lys Val Asp Val Leu Ala Met Glu Lys Val
545                 550                 555                 560

Trp Ile Lys Phe Lys Lys Leu Leu Glu Lys Asn Leu Asn Ile Thr Val
                565                 570                 575

Ser Val Lys Thr Phe Thr Leu Ser Gln Leu Ser Met Lys Ile Met Glu
            580                 585                 590

Ser Lys Leu Pro Lys Tyr Val Lys Leu Tyr Val Pro Thr Leu Glu Glu
        595                 600                 605

Tyr Ser Lys Ile Arg Asn Ala Ile Tyr Gly Gly Arg Val Ile Ser Lys
    610                 615                 620

Asn Gly Ile Tyr Glu Glu Asn Ile Val Tyr Ala Asp Val Val Ser Leu
625                 630                 635                 640

Tyr Pro Ser Ala Met Lys Leu Leu Lys His Ser Tyr Gly Lys Pro Lys
                645                 650                 655

Leu Val Asp Tyr Ile Asp Phe Glu Lys His Gly Ile Tyr Arg Val Thr
            660                 665                 670

Leu Leu Asn Lys His Asp Gln Glu Pro Lys Asn Tyr Leu Asn Phe Val
        675                 680                 685

Pro Arg Arg Ile Asn Arg Lys Leu Thr Trp Glu Trp Phe Lys Ile His
    690                 695                 700

Glu Gly Trp Tyr His Thr Tyr Asp Leu Ile Ile Ala Lys Ser Glu Gly
705                 710                 715                 720

Phe Asp Ile Tyr Cys His Glu Gly Phe Glu Tyr Pro Glu Lys Asp Tyr
                725                 730                 735

Ile Phe Asn Asp Phe Ile Asp Thr Leu Tyr Ser Met Lys Glu Thr His
            740                 745                 750

Thr Ala Cys Ser Cys Glu Glu Gln Pro Cys Pro Ile Arg Met Val Ala
        755                 760                 765

Lys Ile Ala Leu Asn Gly Gly Gly Tyr Gly Lys Phe Val Gln Lys Pro
    770                 775                 780

Ile Asp Lys Glu Ile Tyr Ile Val Lys Arg Asp Val Val Ala Gly Glu
785                 790                 795                 800

Cys Asp Lys Leu Gln Glu Asn Glu Asn Gly Glu Ile Cys Ile Gly Lys
                805                 810                 815

Arg Leu Val Lys Arg Pro Leu Phe Tyr Asn Leu Asp Ser Glu Asn Tyr
            820                 825                 830

Asp Lys Met Ile Ile Glu Lys Glu Asp Glu Pro Ile Tyr Ser Thr Gln
        835                 840                 845

Cys Gly Ile Ser Ile Leu Ser Ala Ser Arg Tyr Arg Leu Tyr Lys Leu
    850                 855                 860
```

Cys Lys Gln Phe Glu Asn Ile Asp Ile Ile Tyr Ser Asp Thr Asp Ser
865 870 875 880

Ile Phe Val Lys Gln Lys Ser Val Asp Trp Glu Leu Phe Lys Ser Lys
885 890 895

Cys Gly Ser Glu Leu Gly Gln Leu Asp Ser Thr Ile Asp Asp Thr Lys
900 905 910

Asn Ala Ile Ile Ser Lys Met Tyr Ile Gly Gly Ala Lys Met Tyr Ala
915 920 925

Phe Glu Tyr Leu Asn Asn Lys Asn Lys Leu Ile Thr Lys Leu His Cys
930 935 940

Lys Gly Val Pro Asn Tyr Met Leu Ser Leu Asn Gln Phe Lys Tyr Leu
945 950 955 960

Met Glu Ser Pro Asp Asn Thr Ile Ala Tyr Lys Phe Glu Ile Ile Arg
965 970 975

Arg Lys Leu Val Asn Val Ile Thr Lys Asp Leu Ile Lys Asp Ile Lys
980 985 990

Gln Thr

<210> SEQ ID NO 20
<211> LENGTH: 2985
<212> TYPE: DNA
<213> ORGANISM: Kluyveromyces lactis

<400> SEQUENCE: 20
atgaacgatg aattagcctt tttgaactcc caaatagatg attatagtga cgacattgaa 60
tttttgagaa ccgaagtctt tagaatcaat agatattcta aatcaatcta ttctttaatg 120
aagaattctt caaaggaagc tattaaagaa actattgagt ttaataagta tggtcaagaa 180
attcattcta agattaaaga aaaggaaatt tcattaattg aagcaattaa attgatggaa 240
aagaaatata aatatttgag atcattgaat aagactaaag ataaatctaa gaaaaagaaa 300
attcatacaa aagatattga aactttgaaa acaatctata aaacaaaagc tgattttgat 360
attagaaatt ttaaaaatgc tgaaactttt acttatgaaa attactcttt gttaattcca 420
tcagaaaagg aattgattga tttgatccca gaaatcgaag aagattactc ttactacttc 480
tacgtttcat taactatcac aggtccaact atctttggtg gtgttacaag aaaagttcca 540
atcatcgata cttatggtga cattaataag gatttctaca ataagattaa agaaaacatc 600
acaaaagttt tggatagagt tccattctac gaagaaaagg aatcagaaat tatttgtaag 660
aaagttttga tcactttgac agttaataag tgggaatcta tcgataagtg gtacaagaac 720
gttaagtcta agtctaaaaa gtttaaagat tttactttgt ttttagcttc tgatacttct 780
aaaaattgtg ttcaacaatg tgttgaatat ttgggtggta aatggaacac taactactct 840
ttggaaaaga tgatcccaca acaaaagatt gttacataca tcccattgtt gatggatatc 900
caatacgttc aatctatgga agatttgatc tcagatttcg atgaaccaaa cactgattgt 960
aagaacatcg ctagattgtt aaagtggaat ggtcacatgg gtgtgatcac aaagatcgac 1020
aaggatgtta agattaatag aatacaaaga aagagaatca tcgatgttga aaataaggaa 1080
gttaaagaag ttttctttga tattgaacct ttttcagatg aaactaaaca tcaaatccca 1140
tatttgattt gttggtctta cttgggtgaa ttatattaca gaacaggtaa aaattgtatc 1200
aaagaatttg ttgaagaaat tttatcttac aacgttgata tcatcttgta tgcttggtac 1260
ggttcaggtt atgattacca acatgttttg ccatacatga agtctaaatg tattaaggat 1320

```
aagtacatta ttaagaataa tatgattact tacggtgaat tatactacga aaacgcaatc   1380
atatatttga aagatccata cttgtttatt ttaacatctt tggataaagc atctaaggct   1440
tttaatgtta ttaataaggg tgaatttcca cattctatca tccattcatg ggaagatttg   1500
aataagattt tgccaaactg ggttaagatc caaaagagaa tgattgaata taaagatgat   1560
aataagttga acatctatta caagaacatc gaaattttcg aaaatgatag aaattataat   1620
actatcttag aaaatgctat tgaatactgt aaagttgatg ttttggcaat ggaaaaggtt   1680
tggatcaagt ttaagaaatt gttggaaaag aatttgaaca ttactgtttc agttaagact   1740
tttacattat ctcaattgtc aatgaagatc atggaatcta aattgccaaa gtacgttaaa   1800
ttgtacgttc caacattgga agaatattca aagatcagaa atgctatcta tggtggtaga   1860
gttatttcta aaaatggtat ctatgaagaa aacatcgttt acgctgatgt tgtttcttta   1920
tacccatcag caatgaaatt gttgaagcat tcttatggta aaccaaaatt ggttgattac   1980
atcgatttcg aaaagcatgg tatctaccgt gttactttgt tgaataagca tgatcaagaa   2040
cctaaaaatt acttaaactt tgttccaaga agaattaata gaaaattgac ttgggaatgg   2100
ttcaagatac atgaaggttg gtatcataca tacgatttga tcatcgctaa gtctgaaggt   2160
ttcgatatct attgccatga aggtttcgaa tacccagaaa aggattacat tttcaatgat   2220
ttcattgata cattatactc tatgaaagaa actcatacag catgttcatg tgaagaacaa   2280
ccatgtccaa tcagaatggt tgctaagatc gcattgaatg gtggtggtta tggtaaattt   2340
gttcaaaaac caatcgataa ggaaatatat atcgttaaga gagatgttgt tgctggtgaa   2400
tgtgataaat tacaagaaaa cgaaaatggt gaaatttgta ttggtaaaag attggttaaa   2460
agaccattat tttataattt ggattcagaa aactacgata aaatgattat tgaaaaagaa   2520
gatgaaccaa tctattctac tcaatgtggt atctcaatct tgtctgcatc aagatataga   2580
ttatacaaat tgtgtaagca attcgaaaac atcgatatca tctattctga tacagattca   2640
atttttgtta aacaaaaatc agttgattgg gaattgttta aatctaagtg tggttcagaa   2700
ttaggtcaat tggattctac tatcgatgat actaagaacg ctatcatctc aaagatgtac   2760
attggtggtg ctaagatgta tgcttttgaa tacttaaaca ataagaataa gttgatcact   2820
aaattgcatt gtaaaggtgt tccaaactac atgttgtctt taaaccaatt caaatatttg   2880
atggaatcac cagataacac aattgcatat aaatttgaaa ttattagaag aaaattggta   2940
aatgtcataa ctaaggactt gatcaaagat atcaagcaga cttga                  2985
```

<210> SEQ ID NO 21
<211> LENGTH: 994
<212> TYPE: PRT
<213> ORGANISM: Kluyveromyces lactis

<400> SEQUENCE: 21

```
Met Asn Asp Glu Leu Ala Phe Leu Asn Ser Gln Ile Asp Asp Tyr Ser
1               5                   10                  15

Asp Asp Ile Glu Phe Leu Arg Thr Glu Val Phe Arg Ile Asn Arg Tyr
            20                  25                  30

Ser Lys Ser Ile Tyr Ser Leu Met Lys Asn Ser Ser Lys Glu Ala Ile
        35                  40                  45

Lys Glu Thr Ile Glu Phe Asn Lys Tyr Gly Gln Glu Ile His Ser Lys
    50                  55                  60

Ile Lys Glu Lys Glu Ile Ser Leu Ile Glu Ala Ile Lys Leu Met Glu
65                  70                  75                  80
```

```
Lys Lys Tyr Lys Tyr Leu Arg Ser Leu Asn Lys Thr Lys Asp Lys Ser
                85                  90                  95

Lys Lys Lys Lys Ile His Thr Lys Asp Ile Glu Thr Leu Lys Thr Ile
            100                 105                 110

Tyr Lys Thr Lys Ala Asp Phe Asp Ile Arg Asn Phe Lys Asn Ala Glu
        115                 120                 125

Thr Phe Thr Tyr Glu Asn Tyr Ser Leu Leu Ile Pro Ser Glu Lys Glu
    130                 135                 140

Leu Ile Asp Leu Ile Pro Glu Ile Glu Glu Asp Tyr Ser Tyr Tyr Phe
145                 150                 155                 160

Tyr Val Ser Leu Thr Ile Thr Gly Pro Thr Ile Phe Gly Gly Val Thr
                165                 170                 175

Arg Lys Val Pro Ile Ile Asp Thr Tyr Gly Asp Ile Asn Lys Asp Phe
            180                 185                 190

Tyr Asn Lys Ile Lys Glu Asn Ile Thr Lys Val Leu Asp Arg Val Pro
        195                 200                 205

Phe Tyr Glu Glu Lys Glu Ser Glu Ile Ile Cys Lys Lys Val Leu Ile
    210                 215                 220

Thr Leu Thr Val Asn Lys Trp Glu Ser Ile Asp Lys Trp Tyr Lys Asn
225                 230                 235                 240

Val Lys Ser Lys Ser Lys Lys Phe Lys Asp Phe Thr Leu Phe Leu Ala
                245                 250                 255

Ser Asp Thr Ser Lys Asn Cys Val Gln Gln Cys Val Glu Tyr Leu Gly
            260                 265                 270

Gly Lys Trp Asn Thr Asn Tyr Ser Leu Glu Lys Met Ile Pro Gln Gln
        275                 280                 285

Lys Ile Val Thr Tyr Ile Pro Leu Leu Met Asp Ile Gln Tyr Val Gln
    290                 295                 300

Ser Met Glu Asp Leu Ile Ser Asp Phe Asp Glu Pro Asn Thr Asp Cys
305                 310                 315                 320

Lys Asn Ile Ala Arg Leu Leu Lys Trp Asn Gly His Met Gly Val Ile
                325                 330                 335

Thr Lys Ile Asp Lys Asp Val Lys Ile Asn Arg Ile Gln Arg Lys Arg
            340                 345                 350

Ile Ile Asp Val Glu Asn Lys Glu Val Lys Glu Val Phe Phe Asp Ile
        355                 360                 365

Glu Pro Phe Ser Asp Glu Thr Lys His Gln Ile Pro Tyr Leu Ile Cys
    370                 375                 380

Trp Ser Tyr Leu Gly Glu Leu Tyr Tyr Arg Thr Gly Lys Asn Cys Ile
385                 390                 395                 400

Lys Glu Phe Val Glu Glu Ile Leu Ser Tyr Asn Val Asp Ile Ile Leu
                405                 410                 415

Tyr Ala Trp Tyr Gly Ser Gly Tyr Asp Tyr Gln His Val Leu Pro Tyr
            420                 425                 430

Met Lys Ser Lys Cys Ile Lys Asp Lys Tyr Ile Ile Lys Asn Asn Met
        435                 440                 445

Ile Thr Tyr Gly Glu Leu Tyr Tyr Glu Asn Ala Ile Ile Tyr Leu Lys
    450                 455                 460

Asp Pro Tyr Leu Phe Ile Leu Thr Ser Leu Asp Lys Ala Ser Lys Ala
465                 470                 475                 480

Phe Asn Val Ile Asn Lys Gly Glu Phe Pro His Ser Ile Ile His Ser
                485                 490                 495
```

```
Trp Glu Asp Leu Asn Lys Ile Leu Pro Asn Trp Val Lys Ile Gln Lys
            500                 505                 510

Arg Met Ile Glu Tyr Lys Asp Asp Asn Lys Leu Asn Ile Tyr Tyr Lys
        515                 520                 525

Asn Ile Glu Ile Phe Glu Asn Asp Arg Asn Tyr Asn Thr Ile Leu Glu
    530                 535                 540

Asn Ala Ile Glu Tyr Cys Lys Val Asp Val Leu Ala Met Glu Lys Val
545                 550                 555                 560

Trp Ile Lys Phe Lys Lys Leu Leu Glu Lys Asn Leu Asn Ile Thr Val
                565                 570                 575

Ser Val Lys Thr Phe Thr Leu Ser Gln Leu Ser Met Lys Ile Met Glu
            580                 585                 590

Ser Lys Leu Pro Lys Tyr Val Lys Leu Tyr Val Pro Thr Leu Glu Glu
        595                 600                 605

Tyr Ser Lys Ile Arg Asn Ala Ile Tyr Gly Gly Arg Val Ile Ser Lys
    610                 615                 620

Asn Gly Ile Tyr Glu Glu Asn Ile Val Tyr Ala Asp Val Val Ser Leu
625                 630                 635                 640

Tyr Pro Ser Ala Met Lys Leu Leu Lys His Ser Tyr Gly Lys Pro Lys
                645                 650                 655

Leu Val Asp Tyr Ile Asp Phe Glu Lys His Gly Ile Tyr Arg Val Thr
            660                 665                 670

Leu Leu Asn Lys His Asp Gln Glu Pro Lys Asn Tyr Leu Asn Phe Val
        675                 680                 685

Pro Arg Arg Ile Asn Arg Lys Leu Thr Trp Glu Trp Phe Lys Ile His
    690                 695                 700

Glu Gly Trp Tyr His Thr Tyr Asp Leu Ile Ile Ala Lys Ser Glu Gly
705                 710                 715                 720

Phe Asp Ile Tyr Cys His Glu Gly Phe Glu Tyr Pro Glu Lys Asp Tyr
                725                 730                 735

Ile Phe Asn Asp Phe Ile Asp Thr Leu Tyr Ser Met Lys Glu Thr His
            740                 745                 750

Thr Ala Cys Ser Cys Glu Glu Gln Pro Cys Pro Ile Arg Met Val Ala
        755                 760                 765

Lys Ile Ala Leu Asn Gly Gly Gly Tyr Gly Lys Phe Val Gln Lys Pro
    770                 775                 780

Ile Asp Lys Glu Ile Tyr Ile Val Lys Arg Asp Val Val Ala Gly Glu
785                 790                 795                 800

Cys Asp Lys Leu Gln Glu Asn Glu Asn Gly Glu Ile Cys Ile Gly Lys
                805                 810                 815

Arg Leu Val Lys Arg Pro Leu Phe Tyr Asn Leu Asp Ser Glu Asn Tyr
            820                 825                 830

Asp Lys Met Ile Ile Glu Lys Glu Asp Glu Pro Ile Tyr Ser Thr Gln
        835                 840                 845

Cys Gly Ile Ser Ile Leu Ser Ala Ser Arg Tyr Arg Leu Tyr Lys Leu
    850                 855                 860

Cys Lys Gln Phe Glu Asn Ile Asp Ile Ile Tyr Ser Asp Thr Asp Ser
865                 870                 875                 880

Ile Phe Val Lys Gln Lys Ser Val Asp Trp Glu Leu Phe Lys Ser Lys
                885                 890                 895

Cys Gly Ser Glu Leu Gly Gln Leu Asp Ser Thr Ile Asp Asp Thr Lys
            900                 905                 910
```

```
Asn Ala Ile Ile Ser Lys Met Tyr Ile Gly Gly Ala Lys Met Tyr Ala
        915                 920                 925

Phe Glu Tyr Leu Asn Asn Lys Asn Lys Leu Ile Thr Lys Leu His Cys
    930                 935                 940

Lys Gly Val Pro Asn Tyr Met Leu Ser Leu Asn Gln Phe Lys Tyr Leu
945                 950                 955                 960

Met Glu Ser Pro Asp Asn Thr Ile Ala Tyr Lys Phe Glu Ile Ile Arg
                965                 970                 975

Arg Lys Leu Val Asn Val Ile Thr Lys Asp Leu Ile Lys Asp Ile Lys
            980                 985                 990

Gln Thr
```

<210> SEQ ID NO 22
<211> LENGTH: 2985
<212> TYPE: DNA
<213> ORGANISM: Kluyveromyces lactis

<400> SEQUENCE: 22

```
atgaacgatg aattagcctt tttgaactcc caaatagatg attatagtga cgacattgaa      60

tttttgagaa ccgaagtctt tagaatcaat agatattcta aatcaatcta ttctttaatg     120

aagaattctt caaaggaagc tattaaagaa actattgagt ttaataagta tggtcaagaa     180

attcattcta agattaaaga aaaggaaatt tcattaattg aagcaattaa attgatggaa     240

aagaaatata aatatttgag atcattgaat aagactaaag ataaatctaa gaaaaagaaa     300

attcatacaa aagatattga aactttgaaa acaatctata aaacaaaagc tgattttgat     360

attagaaatt ttaaaaatgc tgaaactttt acttatgaaa attactcttt gttaattcca     420

tcagaaaagg aattgattga tttgatccca gaaatcgaag aagattactc ttactacttc     480

tacgtttcat taactatcac aggtccaact atctttggtg gtgttacaag aaaagttcca     540

atcatcgata cttatggtga cattaataag gatttctaca ataagattaa agaaaacatc     600

acaaaagttt tggatagagt tccattctac gaagaaaagg aatcagaaat tatttgtaag     660

aaagttttga tcactttgac agttaataag tgggaatcta tcgataagtg gtacaagaac     720

gttaagtcta agtctaaaaa gtttaaagat tttactttgt ttttagcttc tgatacttct     780

aaaaattgtg ttcaacaatg tgttgaatat ttgggtggta aatggaacac taactactct     840

ttggaaaaga tgatcccaca acaaaagatt gttacataca tcccattgtt gatggatatc     900

caatacgttc aatctatgga agatttgatc tcagatttcg atgaaccaaa cactgattgt     960

aagaacatcg ctagattgtt aaagtggaat ggtcacatgg gtgtgatcac aaagatcgac    1020

aaggatgtta agattaatag aatacaaaga aagagaatca tcgatgttga aaataaggaa    1080

gttaaagaag ttttctttga tattgaatct ttttcagatg aaactaaaca tcaaatccca    1140

tatttgattt gttggtctta cttgggtgaa ttatattaca gaacaggtaa aaattgtatc    1200

aaagaatttg ttgaagaaat tttatcttac aacgttgata tcatcttgta tgcttggtac    1260

ggttcaggta aggattacca acatgttttg ccatacatga agtctaaatg tattaaggat    1320

aagtacatta ttaagaataa tatgattact tacggtgaat tatactacga aaacgcaatc    1380

atatatttga aagatccata cttgtttatt ttaacatctt tggataaagc atctaaggct    1440

tttaatgtta ttaataaggg tgaatttcca cattctatca tccattcatg ggaagatttg    1500

aataagattt tgccaaactg ggttaagatc caaaagagaa tgattgaata taaagatgat    1560

aataagttga acatctatta caagaacatc gaaattttcg aaaatgatag aaattataat    1620
```

```
actatcttag aaaatgctat tgaatactgt aaagttgatg ttttggcaat ggaaaaggtt   1680

tggatcaagt ttaagaaatt gttggaaaag aatttgaaca ttactgtttc agttaagact   1740

tttacattat ctcaattgtc aatgaagatc atggaatcta aattgccaaa gtacgttaaa   1800

ttgtacgttc caacattgga agaatattca aagatcagaa atgctatcta tggtggtaga   1860

gttatttcta aaaatggtat ctatgaagaa aacatcgttt acgctgatgt tgtttcttta   1920

tacccatcag caatgaaatt gttgaagcat tcttatggta aaccaaaatt ggttgattac   1980

atcgatttcg aaaagcatgg tatctaccgt gttactttgt tgaataagca tgatcaagaa   2040

cctaaaaatt acttaaactt tgttccaaga agaattaata gaaaattgac ttgggaatgg   2100

ttcaagatac atgaaggttg gtatcataca tacgatttga tcatcgctaa gtctgaaggt   2160

ttcgatatct attgccatga aggtttcgaa tacccagaaa aggattacat tttcaatgat   2220

ttcattgata cattatactc tatgaaagaa actcatacag catgttcatg tgaagaacaa   2280

ccatgtccaa tcagaatggt tgctaagatc gcattgaatg gtggtggtta tggtaaattt   2340

gttcaaaaac caatcgataa ggaaatatat atcgttaaga gagatgttgt tgctggtgaa   2400

tgtgataaat tacaagaaaa cgaaaatggt gaaatttgta ttggtaaaag attggttaaa   2460

agaccattat tttataattt ggattcagaa aactacgata aaatgattat tgaaaaagaa   2520

gatgaaccaa tctattctac tcaatgtggt atctcaatct tgtctgcatc aagatataga   2580

ttatacaaat tgtgtaagca attcgaaaac atcgatatca tctattctga tacagattca   2640

atttttgtta aacaaaaatc agttgattgg gaattgttta aatctaagtg tggttcagaa   2700

ttaggtcaat tggattctac tatcgatgat actaagaacg ctatcatctc aaagatgtac   2760

attggtggtg ctaagatgta tgcttttgaa tacttaaaca ataagaataa gttgatcact   2820

aaattgcatt gtaaaggtgt tccaaactac atgttgtctt taaaccaatt caaatatttg   2880

atggaatcac cagataacac aattgcatat aaatttgaaa ttattagaag aaaattggta   2940

aatgtcataa ctaaggactt gatcaaagat atcaagcaga cttga                   2985
```

```
<210> SEQ ID NO 23
<211> LENGTH: 994
<212> TYPE: PRT
<213> ORGANISM: Kluyveromyces lactis

<400> SEQUENCE: 23

Met Asn Asp Glu Leu Ala Phe Leu Asn Ser Gln Ile Asp Asp Tyr Ser
1               5                   10                  15

Asp Asp Ile Glu Phe Leu Arg Thr Glu Val Phe Arg Ile Asn Arg Tyr
            20                  25                  30

Ser Lys Ser Ile Tyr Ser Leu Met Lys Asn Ser Ser Lys Glu Ala Ile
        35                  40                  45

Lys Glu Thr Ile Glu Phe Asn Lys Tyr Gly Gln Glu Ile His Ser Lys
    50                  55                  60

Ile Lys Glu Lys Glu Ile Ser Leu Ile Glu Ala Ile Lys Leu Met Glu
65                  70                  75                  80

Lys Lys Tyr Lys Tyr Leu Arg Ser Leu Asn Lys Thr Lys Asp Lys Ser
                85                  90                  95

Lys Lys Lys Lys Ile His Thr Lys Asp Ile Glu Thr Leu Lys Thr Ile
            100                 105                 110

Tyr Lys Thr Lys Ala Asp Phe Asp Ile Arg Asn Phe Lys Asn Ala Glu
        115                 120                 125
```

```
Thr Phe Thr Tyr Glu Asn Tyr Ser Leu Leu Ile Pro Ser Glu Lys Glu
    130                 135                 140

Leu Ile Asp Leu Ile Pro Glu Ile Glu Glu Asp Tyr Ser Tyr Tyr Phe
145                 150                 155                 160

Tyr Val Ser Leu Thr Ile Thr Gly Pro Thr Ile Phe Gly Gly Val Thr
                165                 170                 175

Arg Lys Val Pro Ile Ile Asp Thr Tyr Gly Asp Ile Asn Lys Asp Phe
            180                 185                 190

Tyr Asn Lys Ile Lys Glu Asn Ile Thr Lys Val Leu Asp Arg Val Pro
        195                 200                 205

Phe Tyr Glu Glu Lys Glu Ser Glu Ile Ile Cys Lys Lys Val Leu Ile
    210                 215                 220

Thr Leu Thr Val Asn Lys Trp Glu Ser Ile Asp Lys Trp Tyr Lys Asn
225                 230                 235                 240

Val Lys Ser Lys Ser Lys Lys Phe Lys Asp Phe Thr Leu Phe Leu Ala
                245                 250                 255

Ser Asp Thr Ser Lys Asn Cys Val Gln Gln Cys Val Glu Tyr Leu Gly
            260                 265                 270

Gly Lys Trp Asn Thr Asn Tyr Ser Leu Glu Lys Met Ile Pro Gln Gln
        275                 280                 285

Lys Ile Val Thr Tyr Ile Pro Leu Leu Met Asp Ile Gln Tyr Val Gln
    290                 295                 300

Ser Met Glu Asp Leu Ile Ser Asp Phe Asp Glu Pro Asn Thr Asp Cys
305                 310                 315                 320

Lys Asn Ile Ala Arg Leu Leu Lys Trp Asn Gly His Met Gly Val Ile
                325                 330                 335

Thr Lys Ile Asp Lys Asp Val Lys Ile Asn Arg Ile Gln Arg Lys Arg
            340                 345                 350

Ile Ile Asp Val Glu Asn Lys Glu Val Lys Glu Val Phe Phe Asp Ile
        355                 360                 365

Glu Ser Phe Ser Asp Glu Thr Lys His Gln Ile Pro Tyr Leu Ile Cys
    370                 375                 380

Trp Ser Tyr Leu Gly Glu Leu Tyr Tyr Arg Thr Gly Lys Asn Cys Ile
385                 390                 395                 400

Lys Glu Phe Val Glu Glu Ile Leu Ser Tyr Asn Val Asp Ile Ile Leu
                405                 410                 415

Tyr Ala Trp Tyr Gly Ser Gly Lys Asp Tyr Gln His Val Leu Pro Tyr
            420                 425                 430

Met Lys Ser Lys Cys Ile Lys Asp Lys Tyr Ile Ile Lys Asn Asn Met
        435                 440                 445

Ile Thr Tyr Gly Glu Leu Tyr Tyr Glu Asn Ala Ile Ile Tyr Leu Lys
    450                 455                 460

Asp Pro Tyr Leu Phe Ile Leu Thr Ser Leu Asp Lys Ala Ser Lys Ala
465                 470                 475                 480

Phe Asn Val Ile Asn Lys Gly Glu Phe Pro His Ser Ile Ile His Ser
                485                 490                 495

Trp Glu Asp Leu Asn Lys Ile Leu Pro Asn Trp Val Lys Ile Gln Lys
            500                 505                 510

Arg Met Ile Glu Tyr Lys Asp Asp Asn Lys Leu Asn Ile Tyr Tyr Lys
        515                 520                 525

Asn Ile Glu Ile Phe Glu Asn Asp Arg Asn Tyr Asn Thr Ile Leu Glu
    530                 535                 540
```

```
Asn Ala Ile Glu Tyr Cys Lys Val Asp Val Leu Ala Met Glu Lys Val
545                 550                 555                 560

Trp Ile Lys Phe Lys Lys Leu Leu Glu Lys Asn Leu Asn Ile Thr Val
                565                 570                 575

Ser Val Lys Thr Phe Thr Leu Ser Gln Leu Ser Met Lys Ile Met Glu
            580                 585                 590

Ser Lys Leu Pro Lys Tyr Val Lys Leu Tyr Val Pro Thr Leu Glu Glu
        595                 600                 605

Tyr Ser Lys Ile Arg Asn Ala Ile Tyr Gly Gly Arg Val Ile Ser Lys
    610                 615                 620

Asn Gly Ile Tyr Glu Glu Asn Ile Val Tyr Ala Asp Val Val Ser Leu
625                 630                 635                 640

Tyr Pro Ser Ala Met Lys Leu Leu Lys His Ser Tyr Gly Lys Pro Lys
                645                 650                 655

Leu Val Asp Tyr Ile Asp Phe Glu Lys His Gly Ile Tyr Arg Val Thr
            660                 665                 670

Leu Leu Asn Lys His Asp Gln Glu Pro Lys Asn Tyr Leu Asn Phe Val
        675                 680                 685

Pro Arg Arg Ile Asn Arg Lys Leu Thr Trp Glu Trp Phe Lys Ile His
    690                 695                 700

Glu Gly Trp Tyr His Thr Tyr Asp Leu Ile Ile Ala Lys Ser Glu Gly
705                 710                 715                 720

Phe Asp Ile Tyr Cys His Glu Gly Phe Glu Tyr Pro Glu Lys Asp Tyr
                725                 730                 735

Ile Phe Asn Asp Phe Ile Asp Thr Leu Tyr Ser Met Lys Glu Thr His
            740                 745                 750

Thr Ala Cys Ser Cys Glu Glu Gln Pro Cys Pro Ile Arg Met Val Ala
        755                 760                 765

Lys Ile Ala Leu Asn Gly Gly Gly Tyr Gly Lys Phe Val Gln Lys Pro
    770                 775                 780

Ile Asp Lys Glu Ile Tyr Ile Val Lys Arg Asp Val Val Ala Gly Glu
785                 790                 795                 800

Cys Asp Lys Leu Gln Glu Asn Glu Asn Gly Glu Ile Cys Ile Gly Lys
                805                 810                 815

Arg Leu Val Lys Arg Pro Leu Phe Tyr Asn Leu Asp Ser Glu Asn Tyr
            820                 825                 830

Asp Lys Met Ile Ile Glu Lys Glu Asp Glu Pro Ile Tyr Ser Thr Gln
        835                 840                 845

Cys Gly Ile Ser Ile Leu Ser Ala Ser Arg Tyr Arg Leu Tyr Lys Leu
    850                 855                 860

Cys Lys Gln Phe Glu Asn Ile Asp Ile Ile Tyr Ser Asp Thr Asp Ser
865                 870                 875                 880

Ile Phe Val Lys Gln Lys Ser Val Asp Trp Glu Leu Phe Lys Ser Lys
                885                 890                 895

Cys Gly Ser Glu Leu Gly Gln Leu Asp Ser Thr Ile Asp Asp Thr Lys
            900                 905                 910

Asn Ala Ile Ile Ser Lys Met Tyr Ile Gly Gly Ala Lys Met Tyr Ala
        915                 920                 925

Phe Glu Tyr Leu Asn Asn Lys Asn Lys Leu Ile Thr Lys Leu His Cys
    930                 935                 940

Lys Gly Val Pro Asn Tyr Met Leu Ser Leu Asn Gln Phe Lys Tyr Leu
945                 950                 955                 960
```

Met Glu Ser Pro Asp Asn Thr Ile Ala Tyr Lys Phe Glu Ile Ile Arg
965 970 975

Arg Lys Leu Val Asn Val Ile Thr Lys Asp Leu Ile Lys Asp Ile Lys
980 985 990

Gln Thr

<210> SEQ ID NO 24
<211> LENGTH: 2985
<212> TYPE: DNA
<213> ORGANISM: Kluyveromyces lactis

<400> SEQUENCE: 24
atgaacgatg aattagcctt tttgaactcc caaatagatg attatagtga cgacattgaa 60
tttttgagaa ccgaagtctt tagaatcaat agatattcta aatcaatcta ttctttaatg 120
aagaattctt caaaggaagc tattaaagaa actattgagt ttaataagta tggtcaagaa 180
attcattcta agattaaaga aaaggaaatt tcattaattg aagcaattaa attgatggaa 240
aagaaatata aatatttgag atcattgaat aagactaaag ataaatctaa gaaaaagaaa 300
attcatacaa aagatattga aactttgaaa acaatctata aaacaaaagc tgattttgat 360
attagaaatt ttaaaaatgc tgaaactttt acttatgaaa attactcttt gttaattcca 420
tcagaaaagg aattgattga tttgatccca gaaatcgaag aagattactc ttactacttc 480
tacgtttcat taactatcac aggtccaact atctttggtg gtgttacaag aaaagttcca 540
atcatcgata cttatggtga cattaataag gatttctaca ataagattaa agaaaacatc 600
acaaaagttt tggatagagt tccattctac gaagaaaagg aatcagaaat tatttgtaag 660
aaagttttga tcactttgac agttaataag tgggaatcta tcgataagtg gtacaagaac 720
gttaagtcta agtctaaaaa gtttaaagat tttactttgt ttttagcttc tgatacttct 780
aaaaattgtg ttcaacaatg tgttgaatat ttgggtggta aatggaacac taactactct 840
ttggaaaaga tgatcccaca acaaaagatt gttacataca tcccattgtt gatggatatc 900
caatacgttc aatctatgga agatttgatc tcagatttcg atgaaccaaa cactgattgt 960
aagaacatcg ctagattgtt aaagtggaat ggtcacatgg gtgtgatcac aaagatcgac 1020
aaggatgtta agattaatag aatacaaaga aagagaatca tcgatgttga aaataaggaa 1080
gttaaagaag ttttctttga tattgaacgg ttttcagatg aaactaaaca tcaaatccca 1140
tatttgattt gttggtctta cttgggtgaa ttatattaca gaacaggtaa aaattgtatc 1200
aaagaatttg ttgaagaaat tttatcttac aacgttgata tcatcttgta tgcttggtac 1260
ggttcaggtt atgattacca acatgttttg ccatacatga agtctaaatg tattaaggat 1320
aagtacatta ttaagaataa tatgattact tacggtgaat tatactacga aaacgcaatc 1380
atatatttga aagatccata cttgtttatt ttaacatctt tggataaagc atctaaggct 1440
tttaatgtta ttaataaggg tgaatttcca cattctatca tccattcatg ggaagatttg 1500
aataagattt tgccaaactg ggttaagatc caaaagagaa tgattgaata taaagatgat 1560
aataagttga acatctatta caagaacatc gaaattttcg aaaatgatag aaattataat 1620
actatcttag aaaatgctat tgaatactgt aaagttgatg ttttggcaat ggaaaaggtt 1680
tggatcaagt ttaagaaatt gttggaaaag aatttgaaca ttactgtttc agttaagact 1740
tttacattat ctcaattgtc aatgaagatc atggaatcta aattgccaaa gtacgttaaa 1800
ttgtacgttc caacattgga agaatattca aagatcagaa atgctatcta tggtggtaga 1860
gttatttcta aaaatggtat ctatgaagaa aacatcgttt acgctgatgt tgtttcttta 1920
tacccatcag caatgaaatt gttgaagcat tcttatggta aaccaaaatt ggttgattac 1980
atcgatttcg aaaagcatgg tatctaccgt gttactttgt tgaataagca tgatcaagaa 2040
cctaaaaatt acttaaactt tgttccaaga agaattaata gaaaattgac ttgggaatgg 2100
ttcaagatac atgaaggttg gtatcataca tacgatttga tcatcgctaa gtctgaaggt 2160
ttcgatatct attgccatga aggtttcgaa tacccagaaa aggattacat tttcaatgat 2220
ttcattgata cattatactc tatgaaagaa actcatacag catgttcatg tgaagaacaa 2280
ccatgtccaa tcagaatggt tgctaagatc gcattgaatg gtggtggtta tggtaaattt 2340
gttcaaaaac caatcgataa ggaaatatat atcgttaaga gagatgttgt tgctggtgaa 2400
tgtgataaat tacaagaaaa cgaaaatggt gaaatttgta ttggtaaaag attggttaaa 2460
agaccattat tttataattt ggattcagaa aactacgata aaatgattat tgaaaaagaa 2520
gatgaaccaa tctattctac tcaatgtggt atctcaatct tgtctgcatc aagatataga 2580
ttatacaaat tgtgtaagca attcgaaaac atcgatatca tctattctga tacagattca 2640
atttttgtta aacaaaaatc agttgattgg gaattgttta aatctaagtg tggttcagaa 2700
ttaggtcaat tggattctac tatcgatgat actaagaacg ctatcatctc aaagatgtac 2760
attggtggtg ctaagatgta tgcttttgaa tacttaaaca ataagaataa gttgatcact 2820
aaattgcatt gtaaaggtgt tccaaactac atgttgtctt taaaccaatt caaatatttg 2880
atggaatcac cagataacac aattgcatat aaatttgaaa ttattagaag aaaattggta 2940
aatgtcataa ctaaggactt gatcaaagat atcaagcaga cttga 2985

<210> SEQ ID NO 25
<211> LENGTH: 994
<212> TYPE: PRT
<213> ORGANISM: Kluyveromyces lactis

<400> SEQUENCE: 25

Met Asn Asp Glu Leu Ala Phe Leu Asn Ser Gln Ile Asp Asp Tyr Ser
1               5                   10                  15

Asp Asp Ile Glu Phe Leu Arg Thr Glu Val Phe Arg Ile Asn Arg Tyr
            20                  25                  30

Ser Lys Ser Ile Tyr Ser Leu Met Lys Asn Ser Ser Lys Glu Ala Ile
        35                  40                  45

Lys Glu Thr Ile Glu Phe Asn Lys Tyr Gly Gln Glu Ile His Ser Lys
    50                  55                  60

Ile Lys Glu Lys Glu Ile Ser Leu Ile Glu Ala Ile Lys Leu Met Glu
65                  70                  75                  80

Lys Lys Tyr Lys Tyr Leu Arg Ser Leu Asn Lys Thr Lys Asp Lys Ser
                85                  90                  95

Lys Lys Lys Lys Ile His Thr Lys Asp Ile Glu Thr Leu Lys Thr Ile
            100                 105                 110

Tyr Lys Thr Lys Ala Asp Phe Asp Ile Arg Asn Phe Lys Asn Ala Glu
        115                 120                 125

Thr Phe Thr Tyr Glu Asn Tyr Ser Leu Leu Ile Pro Ser Glu Lys Glu
    130                 135                 140

Leu Ile Asp Leu Ile Pro Glu Ile Glu Glu Asp Tyr Ser Tyr Tyr Phe
145                 150                 155                 160

Tyr Val Ser Leu Thr Ile Thr Gly Pro Thr Ile Phe Gly Gly Val Thr
                165                 170                 175

```
Arg Lys Val Pro Ile Ile Asp Thr Tyr Gly Asp Ile Asn Lys Asp Phe
            180                 185                 190

Tyr Asn Lys Ile Lys Glu Asn Ile Thr Lys Val Leu Asp Arg Val Pro
        195                 200                 205

Phe Tyr Glu Glu Lys Glu Ser Glu Ile Ile Cys Lys Lys Val Leu Ile
    210                 215                 220

Thr Leu Thr Val Asn Lys Trp Glu Ser Ile Asp Lys Trp Tyr Lys Asn
225                 230                 235                 240

Val Lys Ser Lys Ser Lys Lys Phe Lys Asp Phe Thr Leu Phe Leu Ala
                245                 250                 255

Ser Asp Thr Ser Lys Asn Cys Val Gln Gln Cys Val Glu Tyr Leu Gly
            260                 265                 270

Gly Lys Trp Asn Thr Asn Tyr Ser Leu Glu Lys Met Ile Pro Gln Gln
        275                 280                 285

Lys Ile Val Thr Tyr Ile Pro Leu Leu Met Asp Ile Gln Tyr Val Gln
    290                 295                 300

Ser Met Glu Asp Leu Ile Ser Asp Phe Asp Glu Pro Asn Thr Asp Cys
305                 310                 315                 320

Lys Asn Ile Ala Arg Leu Leu Lys Trp Asn Gly His Met Gly Val Ile
                325                 330                 335

Thr Lys Ile Asp Lys Asp Val Lys Ile Asn Arg Ile Gln Arg Lys Arg
            340                 345                 350

Ile Ile Asp Val Glu Asn Lys Glu Val Lys Glu Val Phe Phe Asp Ile
        355                 360                 365

Glu Arg Phe Ser Asp Glu Thr Lys His Gln Ile Pro Tyr Leu Ile Cys
    370                 375                 380

Trp Ser Tyr Leu Gly Glu Leu Tyr Tyr Arg Thr Gly Lys Asn Cys Ile
385                 390                 395                 400

Lys Glu Phe Val Glu Glu Ile Leu Ser Tyr Asn Val Asp Ile Ile Leu
                405                 410                 415

Tyr Ala Trp Tyr Gly Ser Gly Tyr Asp Tyr Gln His Val Leu Pro Tyr
            420                 425                 430

Met Lys Ser Lys Cys Ile Lys Asp Lys Tyr Ile Ile Lys Asn Asn Met
        435                 440                 445

Ile Thr Tyr Gly Glu Leu Tyr Tyr Glu Asn Ala Ile Ile Tyr Leu Lys
    450                 455                 460

Asp Pro Tyr Leu Phe Ile Leu Thr Ser Leu Asp Lys Ala Ser Lys Ala
465                 470                 475                 480

Phe Asn Val Ile Asn Lys Gly Glu Phe Pro His Ser Ile Ile His Ser
                485                 490                 495

Trp Glu Asp Leu Asn Lys Ile Leu Pro Asn Trp Val Lys Ile Gln Lys
            500                 505                 510

Arg Met Ile Glu Tyr Lys Asp Asp Asn Lys Leu Asn Ile Tyr Tyr Lys
        515                 520                 525

Asn Ile Glu Ile Phe Glu Asn Asp Arg Asn Tyr Asn Thr Ile Leu Glu
    530                 535                 540

Asn Ala Ile Glu Tyr Cys Lys Val Asp Val Leu Ala Met Glu Lys Val
545                 550                 555                 560

Trp Ile Lys Phe Lys Lys Leu Leu Glu Lys Asn Leu Asn Ile Thr Val
                565                 570                 575

Ser Val Lys Thr Phe Thr Leu Ser Gln Leu Ser Met Lys Ile Met Glu
            580                 585                 590
```

```
Ser Lys Leu Pro Lys Tyr Val Lys Leu Tyr Val Pro Thr Leu Glu Glu
        595                 600                 605

Tyr Ser Lys Ile Arg Asn Ala Ile Tyr Gly Gly Arg Val Ile Ser Lys
    610                 615                 620

Asn Gly Ile Tyr Glu Glu Asn Ile Val Tyr Ala Asp Val Val Ser Leu
625                 630                 635                 640

Tyr Pro Ser Ala Met Lys Leu Leu Lys His Ser Tyr Gly Lys Pro Lys
                645                 650                 655

Leu Val Asp Tyr Ile Asp Phe Glu Lys His Gly Ile Tyr Arg Val Thr
            660                 665                 670

Leu Leu Asn Lys His Asp Gln Glu Pro Lys Asn Tyr Leu Asn Phe Val
        675                 680                 685

Pro Arg Arg Ile Asn Arg Lys Leu Thr Trp Glu Trp Phe Lys Ile His
    690                 695                 700

Glu Gly Trp Tyr His Thr Tyr Asp Leu Ile Ile Ala Lys Ser Glu Gly
705                 710                 715                 720

Phe Asp Ile Tyr Cys His Glu Gly Phe Glu Tyr Pro Glu Lys Asp Tyr
                725                 730                 735

Ile Phe Asn Asp Phe Ile Asp Thr Leu Tyr Ser Met Lys Glu Thr His
            740                 745                 750

Thr Ala Cys Ser Cys Glu Glu Gln Pro Cys Pro Ile Arg Met Val Ala
        755                 760                 765

Lys Ile Ala Leu Asn Gly Gly Gly Tyr Gly Lys Phe Val Gln Lys Pro
    770                 775                 780

Ile Asp Lys Glu Ile Tyr Ile Val Lys Arg Asp Val Val Ala Gly Glu
785                 790                 795                 800

Cys Asp Lys Leu Gln Glu Asn Glu Asn Gly Glu Ile Cys Ile Gly Lys
                805                 810                 815

Arg Leu Val Lys Arg Pro Leu Phe Tyr Asn Leu Asp Ser Glu Asn Tyr
            820                 825                 830

Asp Lys Met Ile Ile Glu Lys Glu Asp Glu Pro Ile Tyr Ser Thr Gln
        835                 840                 845

Cys Gly Ile Ser Ile Leu Ser Ala Ser Arg Tyr Arg Leu Tyr Lys Leu
    850                 855                 860

Cys Lys Gln Phe Glu Asn Ile Asp Ile Ile Tyr Ser Asp Thr Asp Ser
865                 870                 875                 880

Ile Phe Val Lys Gln Lys Ser Val Asp Trp Glu Leu Phe Lys Ser Lys
                885                 890                 895

Cys Gly Ser Glu Leu Gly Gln Leu Asp Ser Thr Ile Asp Asp Thr Lys
            900                 905                 910

Asn Ala Ile Ile Ser Lys Met Tyr Ile Gly Gly Ala Lys Met Tyr Ala
        915                 920                 925

Phe Glu Tyr Leu Asn Asn Lys Asn Lys Leu Ile Thr Lys Leu His Cys
    930                 935                 940

Lys Gly Val Pro Asn Tyr Met Leu Ser Leu Asn Gln Phe Lys Tyr Leu
945                 950                 955                 960

Met Glu Ser Pro Asp Asn Thr Ile Ala Tyr Lys Phe Glu Ile Ile Arg
                965                 970                 975

Arg Lys Leu Val Asn Val Ile Thr Lys Asp Leu Ile Lys Asp Ile Lys
            980                 985                 990

Gln Thr
```

<210> SEQ ID NO 26
<211> LENGTH: 2985
<212> TYPE: DNA
<213> ORGANISM: Kluyveromyces lactis

<400> SEQUENCE: 26
atgaacgatg aattagcctt tttgaactcc caaatagatg attatagtga cgacattgaa 60
tttttgagaa ccgaagtctt tagaatcaat agatattcta aatcaatcta ttctttaatg 120
aagaattctt caaaggaagc tattaaagaa actattgagt ttaataagta tggtcaagaa 180
attcattcta agattaaaga aaaggaaatt tcattaattg aagcaattaa attgatggaa 240
aagaaatata aatatttgag atcattgaat aagactaaag ataaatctaa gaaaaagaaa 300
attcatacaa aagatattga aactttgaaa acaatctata aaacaaaagc tgattttgat 360
attagaaatt ttaaaaatgc tgaaactttt acttatgaaa attactcttt gttaattcca 420
tcagaaaagg aattgattga tttgatccca gaaatcgaag aagattactc ttactacttc 480
tacgtttcat taactatcac aggtccaact atctttggtg gtgttacaag aaaagttcca 540
atcatcgata cttatggtga cattaataag gatttctaca ataagattaa agaaaacatc 600
acaaaagttt tggatagagt tccattctac gaagaaaagg aatcagaaat tatttgtaag 660
aaagttttga tcactttgac agttaataag tgggaatcta tcgataagtg gtacaagaac 720
gttaagtcta agtctaaaaa gtttaaagat tttactttgt ttttagcttc tgatacttct 780
aaaaattgtg ttcaacaatg tgttgaatat ttgggtggta aatggaacac taactactct 840
ttggaaaaga tgatcccaca acaaaagatt gttacataca tcccattgtt gatggatatc 900
caatacgttc aatctatgga agatttgatc tcagatttcg atgaaccaaa cactgattgt 960
aagaacatcg ctagattgtt aaagtggaat ggtcacatgg gtgtgatcac aaagatcgac 1020
aaggatgtta agattaatag aatacaaaga aagagaatca tcgatgttga aaataaggaa 1080
gttaaagaag ttttctttga tattgaatct ttttcagatg aaactaaaca tcaaatccca 1140
tatttgattt gttggtctta cttgggtgaa ttatattaca gaacaggtaa aaattgtatc 1200
aaagaatttg ttgaagaaat tttatcttac aacgttgata tcatcttgta tgcttggtac 1260
ggttcaggtg ggattaccaa acatgttttg ccatacatga agtctaaatg tattaaggat 1320
aagtacatta ttaagaataa tatgattact tacggtgaat tatactacga aaacgcaatc 1380
atatatttga aagatccata cttgtttatt ttaacatctt tggataaagc atctaaggct 1440
tttaatgtta ttaataaggg tgaatttcca cattctatca tccattcatg ggaagatttg 1500
aataagattt tgccaaactg ggttaagatc caaaagagaa tgattgaata taaagatgat 1560
aataagttga acatctatta caagaacatc gaaattttcg aaaatgatag aaattataat 1620
actatcttag aaaatgctat tgaatactgt aaagttgatg ttttggcaat ggaaaaggtt 1680
tggatcaagt ttaagaaatt gttggaaaag aatttgaaca ttactgtttc agttaagact 1740
tttacattat ctcaattgtc aatgaagatc atggaatcta aattgccaaa gtacgttaaa 1800
ttgtacgttc caacattgga agaatattca aagatcagaa atgctatcta tggtggtaga 1860
gttatttcta aaaatggtat ctatgaagaa aacatcgttt acgctgatgt tgtttcttta 1920
tacccatcag caatgaaatt gttgaagcat tcttatggta aaccaaaatt ggttgattac 1980
atcgatttcg aaaagcatgg tatctaccgt gttactttgt tgaataagca tgatcaagaa 2040
cctaaaaatt acttaaactt tgttccaaga agaattaata gaaaattgac ttgggaatgg 2100
ttcaagatac atgaaggttg gtatcataca tacgatttga tcatcgctaa gtctgaaggt 2160

```
ttcgatatct attgccatga aggtttcgaa tacccagaaa aggattacat tttcaatgat   2220

ttcattgata cattatactc tatgaaagaa actcatacag catgttcatg tgaagaacaa   2280

ccatgtccaa tcagaatggt tgctaagatc gcattgaatg gtggtggtta tggtaaattt   2340

gttcaaaaac caatcgataa ggaaatatat atcgttaaga gagatgttgt tgctggtgaa   2400

tgtgataaat tacaagaaaa cgaaaatggt gaaatttgta ttggtaaaag attggttaaa   2460

agaccattat tttataattt ggattcagaa aactacgata aaatgattat tgaaaaagaa   2520

gatgaaccaa tctattctac tcaatgtggt atctcaatct tgtctgcatc aagatataga   2580

ttatacaaat tgtgtaagca attcgaaaac atcgatatca tctattctga tacagattca   2640

atttttgtta aacaaaaatc agttgattgg gaattgttta aatctaagtg tggttcagaa   2700

ttaggtcaat tggattctac tatcgatgat actaagaacg ctatcatctc aaagatgtac   2760

attggtggtg ctaagatgta tgcttttgaa tacttaaaca ataagaataa gttgatcact   2820

aaattgcatt gtaaaggtgt tccaaactac atgttgtctt taaaccaatt caaatatttg   2880

atggaatcac cagataacac aattgcatat aaatttgaaa ttattagaag aaaattggta   2940

aatgtcataa ctaaggactt gatcaaagat atcaagcaga cttga                  2985
```

<210> SEQ ID NO 27
<211> LENGTH: 994
<212> TYPE: PRT
<213> ORGANISM: Kluyveromyces lactis

<400> SEQUENCE: 27

```
Met Asn Asp Glu Leu Ala Phe Leu Asn Ser Gln Ile Asp Asp Tyr Ser
1               5                   10                  15

Asp Asp Ile Glu Phe Leu Arg Thr Glu Val Phe Arg Ile Asn Arg Tyr
            20                  25                  30

Ser Lys Ser Ile Tyr Ser Leu Met Lys Asn Ser Ser Lys Glu Ala Ile
        35                  40                  45

Lys Glu Thr Ile Glu Phe Asn Lys Tyr Gly Gln Glu Ile His Ser Lys
    50                  55                  60

Ile Lys Glu Lys Glu Ile Ser Leu Ile Glu Ala Ile Lys Leu Met Glu
65                  70                  75                  80

Lys Lys Tyr Lys Tyr Leu Arg Ser Leu Asn Lys Thr Lys Asp Lys Ser
                85                  90                  95

Lys Lys Lys Lys Ile His Thr Lys Asp Ile Glu Thr Leu Lys Thr Ile
            100                 105                 110

Tyr Lys Thr Lys Ala Asp Phe Asp Ile Arg Asn Phe Lys Asn Ala Glu
        115                 120                 125

Thr Phe Thr Tyr Glu Asn Tyr Ser Leu Leu Ile Pro Ser Glu Lys Glu
    130                 135                 140

Leu Ile Asp Leu Ile Pro Glu Ile Glu Glu Asp Tyr Ser Tyr Tyr Phe
145                 150                 155                 160

Tyr Val Ser Leu Thr Ile Thr Gly Pro Thr Ile Phe Gly Gly Val Thr
                165                 170                 175

Arg Lys Val Pro Ile Ile Asp Thr Tyr Gly Asp Ile Asn Lys Asp Phe
            180                 185                 190

Tyr Asn Lys Ile Lys Glu Asn Ile Thr Lys Val Leu Asp Arg Val Pro
        195                 200                 205

Phe Tyr Glu Glu Lys Glu Ser Glu Ile Ile Cys Lys Lys Val Leu Ile
    210                 215                 220
```

```
Thr Leu Thr Val Asn Lys Trp Glu Ser Ile Asp Lys Trp Tyr Lys Asn
225                 230                 235                 240

Val Lys Ser Lys Ser Lys Lys Phe Lys Asp Phe Thr Leu Phe Leu Ala
                245                 250                 255

Ser Asp Thr Ser Lys Asn Cys Val Gln Gln Cys Val Glu Tyr Leu Gly
            260                 265                 270

Gly Lys Trp Asn Thr Asn Tyr Ser Leu Glu Lys Met Ile Pro Gln Gln
        275                 280                 285

Lys Ile Val Thr Tyr Ile Pro Leu Leu Met Asp Ile Gln Tyr Val Gln
    290                 295                 300

Ser Met Glu Asp Leu Ile Ser Asp Phe Asp Glu Pro Asn Thr Asp Cys
305                 310                 315                 320

Lys Asn Ile Ala Arg Leu Leu Lys Trp Asn Gly His Met Gly Val Ile
                325                 330                 335

Thr Lys Ile Asp Lys Asp Val Lys Ile Asn Arg Ile Gln Arg Lys Arg
            340                 345                 350

Ile Ile Asp Val Glu Asn Lys Glu Val Lys Glu Val Phe Phe Asp Ile
        355                 360                 365

Glu Ser Phe Ser Asp Glu Thr Lys His Gln Ile Pro Tyr Leu Ile Cys
    370                 375                 380

Trp Ser Tyr Leu Gly Glu Leu Tyr Tyr Arg Thr Gly Lys Asn Cys Ile
385                 390                 395                 400

Lys Glu Phe Val Glu Glu Ile Leu Ser Tyr Asn Val Asp Ile Ile Leu
                405                 410                 415

Tyr Ala Trp Tyr Gly Ser Gly Gly Asp Tyr Gln His Val Leu Pro Tyr
            420                 425                 430

Met Lys Ser Lys Cys Ile Lys Asp Lys Tyr Ile Ile Lys Asn Asn Met
        435                 440                 445

Ile Thr Tyr Gly Glu Leu Tyr Tyr Glu Asn Ala Ile Ile Tyr Leu Lys
    450                 455                 460

Asp Pro Tyr Leu Phe Ile Leu Thr Ser Leu Asp Lys Ala Ser Lys Ala
465                 470                 475                 480

Phe Asn Val Ile Asn Lys Gly Glu Phe Pro His Ser Ile Ile His Ser
                485                 490                 495

Trp Glu Asp Leu Asn Lys Ile Leu Pro Asn Trp Val Lys Ile Gln Lys
            500                 505                 510

Arg Met Ile Glu Tyr Lys Asp Asp Asn Lys Leu Asn Ile Tyr Tyr Lys
        515                 520                 525

Asn Ile Glu Ile Phe Glu Asn Asp Arg Asn Tyr Asn Thr Ile Leu Glu
    530                 535                 540

Asn Ala Ile Glu Tyr Cys Lys Val Asp Val Leu Ala Met Glu Lys Val
545                 550                 555                 560

Trp Ile Lys Phe Lys Lys Leu Leu Glu Lys Asn Leu Asn Ile Thr Val
                565                 570                 575

Ser Val Lys Thr Phe Thr Leu Ser Gln Leu Ser Met Lys Ile Met Glu
            580                 585                 590

Ser Lys Leu Pro Lys Tyr Val Lys Leu Tyr Val Pro Thr Leu Glu Glu
        595                 600                 605

Tyr Ser Lys Ile Arg Asn Ala Ile Tyr Gly Gly Arg Val Ile Ser Lys
    610                 615                 620

Asn Gly Ile Tyr Glu Glu Asn Ile Val Tyr Ala Asp Val Val Ser Leu
625                 630                 635                 640
```

Tyr Pro Ser Ala Met Lys Leu Leu Lys His Ser Tyr Gly Lys Pro Lys
645 650 655

Leu Val Asp Tyr Ile Asp Phe Glu Lys His Gly Ile Tyr Arg Val Thr
660 665 670

Leu Leu Asn Lys His Asp Gln Glu Pro Lys Asn Tyr Leu Asn Phe Val
675 680 685

Pro Arg Arg Ile Asn Arg Lys Leu Thr Trp Glu Trp Phe Lys Ile His
690 695 700

Glu Gly Trp Tyr His Thr Tyr Asp Leu Ile Ile Ala Lys Ser Glu Gly
705 710 715 720

Phe Asp Ile Tyr Cys His Glu Gly Phe Glu Tyr Pro Glu Lys Asp Tyr
725 730 735

Ile Phe Asn Asp Phe Ile Asp Thr Leu Tyr Ser Met Lys Glu Thr His
740 745 750

Thr Ala Cys Ser Cys Glu Glu Gln Pro Cys Pro Ile Arg Met Val Ala
755 760 765

Lys Ile Ala Leu Asn Gly Gly Gly Tyr Gly Lys Phe Val Gln Lys Pro
770 775 780

Ile Asp Lys Glu Ile Tyr Ile Val Lys Arg Asp Val Val Ala Gly Glu
785 790 795 800

Cys Asp Lys Leu Gln Glu Asn Glu Asn Gly Glu Ile Cys Ile Gly Lys
805 810 815

Arg Leu Val Lys Arg Pro Leu Phe Tyr Asn Leu Asp Ser Glu Asn Tyr
820 825 830

Asp Lys Met Ile Ile Glu Lys Glu Asp Glu Pro Ile Tyr Ser Thr Gln
835 840 845

Cys Gly Ile Ser Ile Leu Ser Ala Ser Arg Tyr Arg Leu Tyr Lys Leu
850 855 860

Cys Lys Gln Phe Glu Asn Ile Asp Ile Ile Tyr Ser Asp Thr Asp Ser
865 870 875 880

Ile Phe Val Lys Gln Lys Ser Val Asp Trp Glu Leu Phe Lys Ser Lys
885 890 895

Cys Gly Ser Glu Leu Gly Gln Leu Asp Ser Thr Ile Asp Asp Thr Lys
900 905 910

Asn Ala Ile Ile Ser Lys Met Tyr Ile Gly Gly Ala Lys Met Tyr Ala
915 920 925

Phe Glu Tyr Leu Asn Asn Lys Asn Lys Leu Ile Thr Lys Leu His Cys
930 935 940

Lys Gly Val Pro Asn Tyr Met Leu Ser Leu Asn Gln Phe Lys Tyr Leu
945 950 955 960

Met Glu Ser Pro Asp Asn Thr Ile Ala Tyr Lys Phe Glu Ile Ile Arg
965 970 975

Arg Lys Leu Val Asn Val Ile Thr Lys Asp Leu Ile Lys Asp Ile Lys
980 985 990

Gln Thr

<210> SEQ ID NO 28
<211> LENGTH: 2985
<212> TYPE: DNA
<213> ORGANISM: Kluyveromyces lactis

<400> SEQUENCE: 28
atgaacgatg aattagcctt tttgaactcc caaatagatg attatagtga cgacattgaa 60
tttttgagaa ccgaagtctt tagaatcaat agatattcta aatcaatcta ttctttaatg 120

```
aagaattctt caaaggaagc tattaaagaa actattgagt ttaataagta tggtcaagaa    180
attcattcta agattaaaga aaaggaaatt tcattaattg aagcaattaa attgatggaa    240
aagaaatata aatatttgag atcattgaat aagactaaag ataaatctaa gaaaaagaaa    300
attcatacaa aagatattga aactttgaaa acaatctata aaacaaaagc tgattttgat    360
attagaaatt ttaaaaatgc tgaaactttt acttatgaaa attactcttt gttaattcca    420
tcagaaaagg aattgattga tttgatccca gaaatcgaag aagattactc ttactacttc    480
tacgtttcat taactatcac aggtccaact atctttggtg gtgttacaag aaaagttcca    540
atcatcgata cttatggtga cattaataag gatttctaca ataagattaa agaaaacatc    600
acaaaagttt tggatagagt tccattctac gaagaaaagg aatcagaaat tatttgtaag    660
aaagttttga tcactttgac agttaataag tgggaatcta tcgataagtg gtacaagaac    720
gttaagtcta agtctaaaaa gtttaaagat tttactttgt ttttagcttc tgatacttct    780
aaaaattgtg ttcaacaatg tgttgaatat ttgggtggta aatggaacac taactactct    840
ttggaaaaga tgatcccaca acaaaagatt gttacataca tcccattgtt gatggatatc    900
caatacgttc aatctatgga agatttgatc tcagatttcg atgaaccaaa cactgattgt    960
aagaacatcg ctagattgtt aaagtggaat ggtcacatgg gtgtgatcac aaagatcgac   1020
aaggatgtta agattaatag aatacaaaga aagagaatca tcgatgttga aaataaggaa   1080
gttaaagaag ttttctttga tattgaagag ttttcagatg aaactaaaca tcaaatccca   1140
tatttgattt gttggtctta cttgggtgaa ttatattaca gaacaggtaa aaattgtatc   1200
aaagaatttg ttgaagaaat tttatcttac aacgttgata tcatcttgta tgcttggtac   1260
ggttcaggtt atgattacca acatgttttg ccatacatga agtctaaatg tattaaggat   1320
aagtacatta ttaagaataa tatgattact tacggtgaat tatactacga aaacgcaatc   1380
atatatttga aagatccata cttgtttatt ttaacatctt tggataaagc atctaaggct   1440
tttaatgtta ttaataaggg tgaatttcca cattctatca tccattcatg ggaagatttg   1500
aataagattt tgccaaactg ggttaagatc caaaagagaa tgattgaata taaagatgat   1560
aataagttga acatctatta caagaacatc gaaattttcg aaaatgatag aaattataat   1620
actatcttag aaaatgctat tgaatactgt aaagttgatg ttttggcaat ggaaaaggtt   1680
tggatcaagt ttaagaaatt gttggaaaag aatttgaaca ttactgtttc agttaagact   1740
tttacattat ctcaattgtc aatgaagatc atggaatcta aattgccaaa gtacgttaaa   1800
ttgtacgttc caacattgga agaatattca aagatcagaa atgctatcta tggtggtaga   1860
gttatttcta aaaatggtat ctatgaagaa aacatcgttt acgctgatgt tgtttcttta   1920
tacccatcag caatgaaatt gttgaagcat tcttatggta aaccaaaatt ggttgattac   1980
atcgatttcg aaaagcatgg tatctaccgt gttactttgt tgaataagca tgatcaagaa   2040
cctaaaaatt acttaaactt tgttccaaga agaattaata gaaaattgac ttgggaatgg   2100
ttcaagatac atgaaggttg gtatcataca tacgatttga tcatcgctaa gtctgaaggt   2160
ttcgatatct attgccatga aggtttcgaa tacccagaaa aggattacat tttcaatgat   2220
ttcattgata cattatactc tatgaaagaa actcatacag catgttcatg tgaagaacaa   2280
ccatgtccaa tcagaatggt tgctaagatc gcattgaatg gtggtggtta tggtaaattt   2340
gttcaaaaac caatcgataa ggaaatatat atcgttaaga gagatgttgt tgctggtgaa   2400
tgtgataaat tacaagaaaa cgaaaatggt gaaatttgta ttggtaaaag attggttaaa   2460
```

```
agaccattat tttataattt ggattcagaa aactacgata aaatgattat tgaaaaagaa   2520

gatgaaccaa tctattctac tcaatgtggt atctcaatct tgtctgcatc aagatataga   2580

ttatacaaat tgtgtaagca attcgaaaac atcgatatca tctattctga tacagattca   2640

atttttgtta aacaaaaatc agttgattgg gaattgttta aatctaagtg tggttcagaa   2700

ttaggtcaat tggattctac tatcgatgat actaagaacg ctatcatctc aaagatgtac   2760

attggtggtg ctaagatgta tgcttttgaa tacttaaaca ataagaataa gttgatcact   2820

aaattgcatt gtaaaggtgt tccaaactac atgttgtctt taaaccaatt caaatatttg   2880

atggaatcac cagataacac aattgcatat aaatttgaaa ttattagaag aaaattggta   2940

aatgtcataa ctaaggactt gatcaaagat atcaagcaga cttga                   2985
```

```
<210> SEQ ID NO 29
<211> LENGTH: 994
<212> TYPE: PRT
<213> ORGANISM: Kluyveromyces lactis

<400> SEQUENCE: 29

Met Asn Asp Glu Leu Ala Phe Leu Asn Ser Gln Ile Asp Asp Tyr Ser
1               5                   10                  15

Asp Asp Ile Glu Phe Leu Arg Thr Glu Val Phe Arg Ile Asn Arg Tyr
            20                  25                  30

Ser Lys Ser Ile Tyr Ser Leu Met Lys Asn Ser Ser Lys Glu Ala Ile
        35                  40                  45

Lys Glu Thr Ile Glu Phe Asn Lys Tyr Gly Gln Glu Ile His Ser Lys
    50                  55                  60

Ile Lys Glu Lys Glu Ile Ser Leu Ile Glu Ala Ile Lys Leu Met Glu
65                  70                  75                  80

Lys Lys Tyr Lys Tyr Leu Arg Ser Leu Asn Lys Thr Lys Asp Lys Ser
                85                  90                  95

Lys Lys Lys Lys Ile His Thr Lys Asp Ile Glu Thr Leu Lys Thr Ile
            100                 105                 110

Tyr Lys Thr Lys Ala Asp Phe Asp Ile Arg Asn Phe Lys Asn Ala Glu
        115                 120                 125

Thr Phe Thr Tyr Glu Asn Tyr Ser Leu Leu Ile Pro Ser Glu Lys Glu
    130                 135                 140

Leu Ile Asp Leu Ile Pro Glu Ile Glu Glu Asp Tyr Ser Tyr Tyr Phe
145                 150                 155                 160

Tyr Val Ser Leu Thr Ile Thr Gly Pro Thr Ile Phe Gly Gly Val Thr
                165                 170                 175

Arg Lys Val Pro Ile Ile Asp Thr Tyr Gly Asp Ile Asn Lys Asp Phe
            180                 185                 190

Tyr Asn Lys Ile Lys Glu Asn Ile Thr Lys Val Leu Asp Arg Val Pro
        195                 200                 205

Phe Tyr Glu Glu Lys Glu Ser Glu Ile Ile Cys Lys Lys Val Leu Ile
    210                 215                 220

Thr Leu Thr Val Asn Lys Trp Glu Ser Ile Asp Lys Trp Tyr Lys Asn
225                 230                 235                 240

Val Lys Ser Lys Ser Lys Lys Phe Lys Asp Phe Thr Leu Phe Leu Ala
                245                 250                 255

Ser Asp Thr Ser Lys Asn Cys Val Gln Gln Cys Val Glu Tyr Leu Gly
            260                 265                 270

Gly Lys Trp Asn Thr Asn Tyr Ser Leu Glu Lys Met Ile Pro Gln Gln
        275                 280                 285
```

```
Lys Ile Val Thr Tyr Ile Pro Leu Leu Met Asp Ile Gln Tyr Val Gln
    290                 295                 300

Ser Met Glu Asp Leu Ile Ser Asp Phe Asp Glu Pro Asn Thr Asp Cys
305                 310                 315                 320

Lys Asn Ile Ala Arg Leu Leu Lys Trp Asn Gly His Met Gly Val Ile
                325                 330                 335

Thr Lys Ile Asp Lys Asp Val Lys Ile Asn Arg Ile Gln Arg Lys Arg
            340                 345                 350

Ile Ile Asp Val Glu Asn Lys Glu Val Lys Glu Val Phe Phe Asp Ile
        355                 360                 365

Glu Glu Phe Ser Asp Glu Thr Lys His Gln Ile Pro Tyr Leu Ile Cys
    370                 375                 380

Trp Ser Tyr Leu Gly Glu Leu Tyr Tyr Arg Thr Gly Lys Asn Cys Ile
385                 390                 395                 400

Lys Glu Phe Val Glu Glu Ile Leu Ser Tyr Asn Val Asp Ile Ile Leu
                405                 410                 415

Tyr Ala Trp Tyr Gly Ser Gly Tyr Asp Tyr Gln His Val Leu Pro Tyr
            420                 425                 430

Met Lys Ser Lys Cys Ile Lys Asp Lys Tyr Ile Ile Lys Asn Asn Met
        435                 440                 445

Ile Thr Tyr Gly Glu Leu Tyr Tyr Glu Asn Ala Ile Ile Tyr Leu Lys
    450                 455                 460

Asp Pro Tyr Leu Phe Ile Leu Thr Ser Leu Asp Lys Ala Ser Lys Ala
465                 470                 475                 480

Phe Asn Val Ile Asn Lys Gly Glu Phe Pro His Ser Ile Ile His Ser
                485                 490                 495

Trp Glu Asp Leu Asn Lys Ile Leu Pro Asn Trp Val Lys Ile Gln Lys
            500                 505                 510

Arg Met Ile Glu Tyr Lys Asp Asp Asn Lys Leu Asn Ile Tyr Tyr Lys
        515                 520                 525

Asn Ile Glu Ile Phe Glu Asn Asp Arg Asn Tyr Asn Thr Ile Leu Glu
    530                 535                 540

Asn Ala Ile Glu Tyr Cys Lys Val Asp Val Leu Ala Met Glu Lys Val
545                 550                 555                 560

Trp Ile Lys Phe Lys Lys Leu Leu Glu Lys Asn Leu Asn Ile Thr Val
                565                 570                 575

Ser Val Lys Thr Phe Thr Leu Ser Gln Leu Ser Met Lys Ile Met Glu
            580                 585                 590

Ser Lys Leu Pro Lys Tyr Val Lys Leu Tyr Val Pro Thr Leu Glu Glu
        595                 600                 605

Tyr Ser Lys Ile Arg Asn Ala Ile Tyr Gly Gly Arg Val Ile Ser Lys
    610                 615                 620

Asn Gly Ile Tyr Glu Glu Asn Ile Val Tyr Ala Asp Val Val Ser Leu
625                 630                 635                 640

Tyr Pro Ser Ala Met Lys Leu Leu Lys His Ser Tyr Gly Lys Pro Lys
                645                 650                 655

Leu Val Asp Tyr Ile Asp Phe Glu Lys His Gly Ile Tyr Arg Val Thr
            660                 665                 670

Leu Leu Asn Lys His Asp Gln Glu Pro Lys Asn Tyr Leu Asn Phe Val
        675                 680                 685

Pro Arg Arg Ile Asn Arg Lys Leu Thr Trp Glu Trp Phe Lys Ile His
    690                 695                 700
```

```
Glu Gly Trp Tyr His Thr Tyr Asp Leu Ile Ile Ala Lys Ser Glu Gly
705                 710                 715                 720

Phe Asp Ile Tyr Cys His Glu Gly Phe Glu Tyr Pro Glu Lys Asp Tyr
                725                 730                 735

Ile Phe Asn Asp Phe Ile Asp Thr Leu Tyr Ser Met Lys Glu Thr His
            740                 745                 750

Thr Ala Cys Ser Cys Glu Glu Gln Pro Cys Pro Ile Arg Met Val Ala
        755                 760                 765

Lys Ile Ala Leu Asn Gly Gly Gly Tyr Gly Lys Phe Val Gln Lys Pro
    770                 775                 780

Ile Asp Lys Glu Ile Tyr Ile Val Lys Arg Asp Val Val Ala Gly Glu
785                 790                 795                 800

Cys Asp Lys Leu Gln Glu Asn Glu Asn Gly Glu Ile Cys Ile Gly Lys
                805                 810                 815

Arg Leu Val Lys Arg Pro Leu Phe Tyr Asn Leu Asp Ser Glu Asn Tyr
            820                 825                 830

Asp Lys Met Ile Ile Glu Lys Glu Asp Glu Pro Ile Tyr Ser Thr Gln
        835                 840                 845

Cys Gly Ile Ser Ile Leu Ser Ala Ser Arg Tyr Arg Leu Tyr Lys Leu
    850                 855                 860

Cys Lys Gln Phe Glu Asn Ile Asp Ile Ile Tyr Ser Asp Thr Asp Ser
865                 870                 875                 880

Ile Phe Val Lys Gln Lys Ser Val Asp Trp Glu Leu Phe Lys Ser Lys
                885                 890                 895

Cys Gly Ser Glu Leu Gly Gln Leu Asp Ser Thr Ile Asp Asp Thr Lys
            900                 905                 910

Asn Ala Ile Ile Ser Lys Met Tyr Ile Gly Gly Ala Lys Met Tyr Ala
        915                 920                 925

Phe Glu Tyr Leu Asn Asn Lys Asn Lys Leu Ile Thr Lys Leu His Cys
    930                 935                 940

Lys Gly Val Pro Asn Tyr Met Leu Ser Leu Asn Gln Phe Lys Tyr Leu
945                 950                 955                 960

Met Glu Ser Pro Asp Asn Thr Ile Ala Tyr Lys Phe Glu Ile Ile Arg
                965                 970                 975

Arg Lys Leu Val Asn Val Ile Thr Lys Asp Leu Ile Lys Asp Ile Lys
            980                 985                 990

Gln Thr
```

<210> SEQ ID NO 30
<211> LENGTH: 2985
<212> TYPE: DNA
<213> ORGANISM: Kluyveromyces lactis

<400> SEQUENCE: 30

```
atgaacgatg aattagcctt tttgaactcc caaatagatg attatagtga cgacattgaa      60

tttttgagaa ccgaagtctt tagaatcaat agatattcta aatcaatcta ttctttaatg     120

aagaattctt caaaggaagc tattaaagaa actattgagt ttaataagta tggtcaagaa     180

attcattcta agattaaaga aaaggaaatt tcattaattg aagcaattaa attgatggaa     240

aagaaatata aatatttgag atcattgaat aagactaaag ataaatctaa gaaaaagaaa     300

attcatacaa aagatattga aactttgaaa acaatctata aaacaaaagc tgattttgat     360

attagaaatt ttaaaaatgc tgaaactttt acttatgaaa attactcttt gttaattcca     420

tcagaaaagg aattgattga tttgatccca gaaatcgaag aagattactc ttactacttc     480
```

```
tacgtttcat taactatcac aggtccaact atctttggtg gtgttacaag aaaagttcca    540
atcatcgata cttatggtga cattaataag gatttctaca ataagattaa agaaaacatc    600
acaaaagttt tggatagagt tccattctac gaagaaaagg aatcagaaat tatttgtaag    660
aaagttttga tcactttgac agttaataag tgggaatcta tcgataagtg gtacaagaac    720
gttaagtcta agtctaaaaa gtttaaagat tttactttgt ttttagcttc tgatacttct    780
aaaaattgtg ttcaacaatg tgttgaatat ttgggtggta aatggaacac taactactct    840
ttggaaaaga tgatcccaca acaaaagatt gttacataca tcccattgtt gatggatatc    900
caatacgttc aatctatgga agatttgatc tcagatttcg atgaaccaaa cactgattgt    960
aagaacatcg ctagattgtt aaagtggaat ggtcacatgg gtgtgatcac aaagatcgac   1020
aaggatgtta agattaatag aatacaaaga aagagaatca tcgatgttga aaataaggaa   1080
gttaaagaag ttttctttga tattgaaaag ttttcagatg aaactaaaca tcaaatccca   1140
tatttgattt gttggtctta cttgggtgaa ttatattaca gaacaggtaa aaattgtatc   1200
aaagaatttg ttgaagaaat tttatcttac aacgttgata tcatcttgta tgcttggtac   1260
ggttcaggtt atgattacca acatgttttg ccatacatga agtctaaatg tattaaggat   1320
aagtacatta ttaagaataa tatgattact tacggtgaat tatactacga aaacgcaatc   1380
atatatttga aagatccata cttgtttatt ttaacatctt tggataaagc atctaaggct   1440
tttaatgtta ttaataaggg tgaatttcca cattctatca tccattcatg ggaagatttg   1500
aataagattt tgccaaactg ggttaagatc caaaagagaa tgattgaata taaagatgat   1560
aataagttga acatctatta caagaacatc gaaattttcg aaaatgatag aaattataat   1620
actatcttag aaaatgctat tgaatactgt aaagttgatg ttttggcaat ggaaaaggtt   1680
tggatcaagt ttaagaaatt gttggaaaag aatttgaaca ttactgtttc agttaagact   1740
tttacattat ctcaattgtc aatgaagatc atggaatcta aattgccaaa gtacgttaaa   1800
ttgtacgttc caacattgga agaatattca aagatcagaa atgctatcta tggtggtaga   1860
gttatttcta aaaatggtat ctatgaagaa aacatcgttt acgctgatgt tgtttcttta   1920
tacccatcag caatgaaatt gttgaagcat tcttatggta aaccaaaatt ggttgattac   1980
atcgatttcg aaaagcatgg tatctaccgt gttactttgt tgaataagca tgatcaagaa   2040
cctaaaaatt acttaaactt tgttccaaga agaattaata gaaaattgac ttgggaatgg   2100
ttcaagatac atgaaggttg gtatcataca tacgatttga tcatcgctaa gtctgaaggt   2160
ttcgatatct attgccatga aggtttcgaa tacccagaaa aggattacat tttcaatgat   2220
ttcattgata cattatactc tatgaaagaa actcatacag catgttcatg tgaagaacaa   2280
ccatgtccaa tcagaatggt tgctaagatc gcattgaatg gtggtggtta tggtaaattt   2340
gttcaaaaac caatcgataa ggaaatatat atcgttaaga gagatgttgt tgctggtgaa   2400
tgtgataaat tacaagaaaa cgaaaatggt gaaatttgta ttggtaaaag attggttaaa   2460
agaccattat tttataattt ggattcagaa aactacgata aaatgattat tgaaaaagaa   2520
gatgaaccaa tctattctac tcaatgtggt atctcaatct tgtctgcatc aagatataga   2580
ttatacaaat tgtgtaagca attcgaaaac atcgatatca tctattctga tacagattca   2640
atttttgtta aacaaaaatc agttgattgg gaattgttta aatctaagtg tggttcagaa   2700
ttaggtcaat tggattctac tatcgatgat actaagaacg ctatcatctc aaagatgtac   2760
attggtggtg ctaagatgta tgcttttgaa tacttaaaca ataagaataa gttgatcact   2820
```

```
aaattgcatt gtaaaggtgt tccaaactac atgttgtctt taaaccaatt caaatatttg   2880

atggaatcac cagataacac aattgcatat aaatttgaaa ttattagaag aaaattggta   2940

aatgtcataa ctaaggactt gatcaaagat atcaagcaga cttga                    2985


<210> SEQ ID NO 31
<211> LENGTH: 994
<212> TYPE: PRT
<213> ORGANISM: Kluyveromyces lactis

<400> SEQUENCE: 31

Met Asn Asp Glu Leu Ala Phe Leu Asn Ser Gln Ile Asp Asp Tyr Ser
1               5                   10                  15

Asp Asp Ile Glu Phe Leu Arg Thr Glu Val Phe Arg Ile Asn Arg Tyr
            20                  25                  30

Ser Lys Ser Ile Tyr Ser Leu Met Lys Asn Ser Ser Lys Glu Ala Ile
        35                  40                  45

Lys Glu Thr Ile Glu Phe Asn Lys Tyr Gly Gln Glu Ile His Ser Lys
    50                  55                  60

Ile Lys Glu Lys Glu Ile Ser Leu Ile Glu Ala Ile Lys Leu Met Glu
65                  70                  75                  80

Lys Lys Tyr Lys Tyr Leu Arg Ser Leu Asn Lys Thr Lys Asp Lys Ser
                85                  90                  95

Lys Lys Lys Lys Ile His Thr Lys Asp Ile Glu Thr Leu Lys Thr Ile
            100                 105                 110

Tyr Lys Thr Lys Ala Asp Phe Asp Ile Arg Asn Phe Lys Asn Ala Glu
        115                 120                 125

Thr Phe Thr Tyr Glu Asn Tyr Ser Leu Leu Ile Pro Ser Glu Lys Glu
    130                 135                 140

Leu Ile Asp Leu Ile Pro Glu Ile Glu Glu Asp Tyr Ser Tyr Tyr Phe
145                 150                 155                 160

Tyr Val Ser Leu Thr Ile Thr Gly Pro Thr Ile Phe Gly Gly Val Thr
                165                 170                 175

Arg Lys Val Pro Ile Ile Asp Thr Tyr Gly Asp Ile Asn Lys Asp Phe
            180                 185                 190

Tyr Asn Lys Ile Lys Glu Asn Ile Thr Lys Val Leu Asp Arg Val Pro
        195                 200                 205

Phe Tyr Glu Glu Lys Glu Ser Glu Ile Ile Cys Lys Lys Val Leu Ile
    210                 215                 220

Thr Leu Thr Val Asn Lys Trp Glu Ser Ile Asp Lys Trp Tyr Lys Asn
225                 230                 235                 240

Val Lys Ser Lys Ser Lys Lys Phe Lys Asp Phe Thr Leu Phe Leu Ala
                245                 250                 255

Ser Asp Thr Ser Lys Asn Cys Val Gln Gln Cys Val Glu Tyr Leu Gly
            260                 265                 270

Gly Lys Trp Asn Thr Asn Tyr Ser Leu Glu Lys Met Ile Pro Gln Gln
        275                 280                 285

Lys Ile Val Thr Tyr Ile Pro Leu Leu Met Asp Ile Gln Tyr Val Gln
    290                 295                 300

Ser Met Glu Asp Leu Ile Ser Asp Phe Asp Glu Pro Asn Thr Asp Cys
305                 310                 315                 320

Lys Asn Ile Ala Arg Leu Leu Lys Trp Asn Gly His Met Gly Val Ile
                325                 330                 335

Thr Lys Ile Asp Lys Asp Val Lys Ile Asn Arg Ile Gln Arg Lys Arg
            340                 345                 350
```

```
Ile Ile Asp Val Glu Asn Lys Glu Val Lys Glu Val Phe Phe Asp Ile
        355                 360                 365

Glu Lys Phe Ser Asp Glu Thr Lys His Gln Ile Pro Tyr Leu Ile Cys
    370                 375                 380

Trp Ser Tyr Leu Gly Glu Leu Tyr Tyr Arg Thr Gly Lys Asn Cys Ile
385                 390                 395                 400

Lys Glu Phe Val Glu Glu Ile Leu Ser Tyr Asn Val Asp Ile Ile Leu
                405                 410                 415

Tyr Ala Trp Tyr Gly Ser Gly Tyr Asp Tyr Gln His Val Leu Pro Tyr
            420                 425                 430

Met Lys Ser Lys Cys Ile Lys Asp Lys Tyr Ile Ile Lys Asn Asn Met
        435                 440                 445

Ile Thr Tyr Gly Glu Leu Tyr Tyr Glu Asn Ala Ile Ile Tyr Leu Lys
    450                 455                 460

Asp Pro Tyr Leu Phe Ile Leu Thr Ser Leu Asp Lys Ala Ser Lys Ala
465                 470                 475                 480

Phe Asn Val Ile Asn Lys Gly Glu Phe Pro His Ser Ile Ile His Ser
                485                 490                 495

Trp Glu Asp Leu Asn Lys Ile Leu Pro Asn Trp Val Lys Ile Gln Lys
            500                 505                 510

Arg Met Ile Glu Tyr Lys Asp Asp Asn Lys Leu Asn Ile Tyr Tyr Lys
        515                 520                 525

Asn Ile Glu Ile Phe Glu Asn Asp Arg Asn Tyr Asn Thr Ile Leu Glu
    530                 535                 540

Asn Ala Ile Glu Tyr Cys Lys Val Asp Val Leu Ala Met Glu Lys Val
545                 550                 555                 560

Trp Ile Lys Phe Lys Lys Leu Leu Glu Lys Asn Leu Asn Ile Thr Val
                565                 570                 575

Ser Val Lys Thr Phe Thr Leu Ser Gln Leu Ser Met Lys Ile Met Glu
            580                 585                 590

Ser Lys Leu Pro Lys Tyr Val Lys Leu Tyr Val Pro Thr Leu Glu Glu
        595                 600                 605

Tyr Ser Lys Ile Arg Asn Ala Ile Tyr Gly Gly Arg Val Ile Ser Lys
    610                 615                 620

Asn Gly Ile Tyr Glu Glu Asn Ile Val Tyr Ala Asp Val Val Ser Leu
625                 630                 635                 640

Tyr Pro Ser Ala Met Lys Leu Leu Lys His Ser Tyr Gly Lys Pro Lys
                645                 650                 655

Leu Val Asp Tyr Ile Asp Phe Glu Lys His Gly Ile Tyr Arg Val Thr
            660                 665                 670

Leu Leu Asn Lys His Asp Gln Glu Pro Lys Asn Tyr Leu Asn Phe Val
        675                 680                 685

Pro Arg Arg Ile Asn Arg Lys Leu Thr Trp Glu Trp Phe Lys Ile His
    690                 695                 700

Glu Gly Trp Tyr His Thr Tyr Asp Leu Ile Ile Ala Lys Ser Glu Gly
705                 710                 715                 720

Phe Asp Ile Tyr Cys His Glu Gly Phe Glu Tyr Pro Glu Lys Asp Tyr
                725                 730                 735

Ile Phe Asn Asp Phe Ile Asp Thr Leu Tyr Ser Met Lys Glu Thr His
            740                 745                 750

Thr Ala Cys Ser Cys Glu Glu Gln Pro Cys Pro Ile Arg Met Val Ala
        755                 760                 765
```

-continued

```
Lys Ile Ala Leu Asn Gly Gly Gly Tyr Gly Lys Phe Val Gln Lys Pro
    770                 775                 780

Ile Asp Lys Glu Ile Tyr Ile Val Lys Arg Asp Val Val Ala Gly Glu
785                 790                 795                 800

Cys Asp Lys Leu Gln Glu Asn Glu Asn Gly Glu Ile Cys Ile Gly Lys
                805                 810                 815

Arg Leu Val Lys Arg Pro Leu Phe Tyr Asn Leu Asp Ser Glu Asn Tyr
            820                 825                 830

Asp Lys Met Ile Ile Glu Lys Glu Asp Glu Pro Ile Tyr Ser Thr Gln
        835                 840                 845

Cys Gly Ile Ser Ile Leu Ser Ala Ser Arg Tyr Arg Leu Tyr Lys Leu
    850                 855                 860

Cys Lys Gln Phe Glu Asn Ile Asp Ile Ile Tyr Ser Asp Thr Asp Ser
865                 870                 875                 880

Ile Phe Val Lys Gln Lys Ser Val Asp Trp Glu Leu Phe Lys Ser Lys
                885                 890                 895

Cys Gly Ser Glu Leu Gly Gln Leu Asp Ser Thr Ile Asp Asp Thr Lys
            900                 905                 910

Asn Ala Ile Ile Ser Lys Met Tyr Ile Gly Gly Ala Lys Met Tyr Ala
        915                 920                 925

Phe Glu Tyr Leu Asn Asn Lys Asn Lys Leu Ile Thr Lys Leu His Cys
    930                 935                 940

Lys Gly Val Pro Asn Tyr Met Leu Ser Leu Asn Gln Phe Lys Tyr Leu
945                 950                 955                 960

Met Glu Ser Pro Asp Asn Thr Ile Ala Tyr Lys Phe Glu Ile Ile Arg
                965                 970                 975

Arg Lys Leu Val Asn Val Ile Thr Lys Asp Leu Ile Lys Asp Ile Lys
            980                 985                 990

Gln Thr


<210> SEQ ID NO 32
<211> LENGTH: 2985
<212> TYPE: DNA
<213> ORGANISM: Kluyveromyces lactis

<400> SEQUENCE: 32

atgaacgatg aattagcctt tttgaactcc caaatagatg attatagtga cgacattgaa      60

tttttgagaa ccgaagtctt tagaatcaat agatattcta aatcaatcta ttctttaatg     120

aagaattctt caaaggaagc tattaaagaa actattgagt ttaataagta tggtcaagaa     180

attcattcta agattaaaga aaaggaaatt tcattaattg aagcaattaa attgatggaa     240

aagaaatata aatatttgag atcattgaat aagactaaag ataaatctaa gaaaaagaaa     300

attcatacaa aagatattga aactttgaaa acaatctata aaacaaaagc tgattttgat     360

attagaaatt ttaaaaatgc tgaaactttt acttatgaaa attactcttt gttaattcca     420

tcagaaaagg aattgattga tttgatccca gaaatcgaag aagattactc ttactacttc     480

tacgtttcat taactatcac aggtccaact atctttggtg gtgttacaag aaaagttcca     540

atcatcgata cttatggtga cattaataag gatttctaca ataagattaa agaaaacatc     600

acaaaagttt tggatagagt tccattctac gaagaaaagg aatcagaaat tatttgtaag     660

aaagttttga tcactttgac agttaataag tgggaatcta tcgataagtg gtacaagaac     720

gttaagtcta agtctaaaaa gtttaaagat tttactttgt ttttagcttc tgatacttct     780

aaaaattgtg ttcaacaatg tgttgaatat ttgggtggta aatggaacac taactactct     840
```

```
ttggaaaaga tgatcccaca acaaaagatt gttacataca tcccattgtt gatggatatc     900
caatacgttc aatctatgga agatttgatc tcagatttcg atgaaccaaa cactgattgt     960
aagaacatcg ctagattgtt aaagtggaat ggtcacatgg gtgtgatcac aaagatcgac    1020
aaggatgtta agattaatag aatacaaaga aagagaatca tcgatgttga aaataaggaa    1080
gttaaagaag ttttctttga tattgaatct ttttcagatg aaactaaaca tcaaatccca    1140
tatttgattt gttggtctta cttgggtgaa ttatattaca gaacaggtaa aaattgtatc    1200
aaagaatttg ttgaagaaat tttatcttac aacgttgata tcatcttgta tgcttggtac    1260
ggttcaggtc gggattacca acatgttttg ccatacatga agtctaaatg tattaaggat    1320
aagtacatta ttaagaataa tatgattact tacggtgaat tatactacga aaacgcaatc    1380
atatatttga aagatccata cttgtttatt ttaacatctt tggataaagc atctaaggct    1440
tttaatgtta ttaataaggg tgaatttcca cattctatca tccattcatg ggaagatttg    1500
aataagattt tgccaaactg ggttaagatc caaaagagaa tgattgaata taaagatgat    1560
aataagttga acatctatta caagaacatc gaaattttcg aaaatgatag aaattataat    1620
actatcttag aaaatgctat tgaatactgt aaagttgatg ttttggcaat ggaaaaggtt    1680
tggatcaagt ttaagaaatt gttggaaaag aatttgaaca ttactgtttc agttaagact    1740
tttacattat ctcaattgtc aatgaagatc atggaatcta aattgccaaa gtacgttaaa    1800
ttgtacgttc caacattgga agaatattca aagatcagaa atgctatcta tggtggtaga    1860
gttatttcta aaaatggtat ctatgaagaa aacatcgttt acgctgatgt tgtttcttta    1920
tacccatcag caatgaaatt gttgaagcat tcttatggta aaccaaaatt ggttgattac    1980
atcgatttcg aaaagcatgg tatctaccgt gttactttgt tgaataagca tgatcaagaa    2040
cctaaaaatt acttaaactt tgttccaaga agaattaata gaaaattgac ttgggaatgg    2100
ttcaagatac atgaaggttg gtatcataca tacgatttga tcatcgctaa gtctgaaggt    2160
ttcgatatct attgccatga aggtttcgaa tacccagaaa aggattacat tttcaatgat    2220
ttcattgata cattatactc tatgaaagaa actcatacag catgttcatg tgaagaacaa    2280
ccatgtccaa tcagaatggt tgctaagatc gcattgaatg gtggtggtta tggtaaattt    2340
gttcaaaaac caatcgataa ggaaatatat atcgttaaga gagatgttgt tgctggtgaa    2400
tgtgataaat tacaagaaaa cgaaaatggt gaaatttgta ttggtaaaag attggttaaa    2460
agaccattat tttataattt ggattcagaa aactacgata aaatgattat tgaaaaagaa    2520
gatgaaccaa tctattctac tcaatgtggt atctcaatct tgtctgcatc aagatataga    2580
ttatacaaat tgtgtaagca attcgaaaac atcgatatca tctattctga tacagattca    2640
atttttgtta aacaaaaatc agttgattgg gaattgttta aatctaagtg tggttcagaa    2700
ttaggtcaat tggattctac tatcgatgat actaagaacg ctatcatctc aaagatgtac    2760
attggtggtg ctaagatgta tgcttttgaa tacttaaaca ataagaataa gttgatcact    2820
aaattgcatt gtaaaggtgt tccaaactac atgttgtctt taaaccaatt caaatatttg    2880
atggaatcac cagataacac aattgcatat aaatttgaaa ttattagaag aaaattggta    2940
aatgtcataa ctaaggactt gatcaaagat atcaagcaga cttga                   2985
```

<210> SEQ ID NO 33
<211> LENGTH: 994
<212> TYPE: PRT
<213> ORGANISM: Kluyveromyces lactis

<400> SEQUENCE: 33

```
Met Asn Asp Glu Leu Ala Phe Leu Asn Ser Gln Ile Asp Asp Tyr Ser
1               5                   10                  15

Asp Asp Ile Glu Phe Leu Arg Thr Glu Val Phe Arg Ile Asn Arg Tyr
            20                  25                  30

Ser Lys Ser Ile Tyr Ser Leu Met Lys Asn Ser Ser Lys Glu Ala Ile
        35                  40                  45

Lys Glu Thr Ile Glu Phe Asn Lys Tyr Gly Gln Glu Ile His Ser Lys
    50                  55                  60

Ile Lys Glu Lys Glu Ile Ser Leu Ile Glu Ala Ile Lys Leu Met Glu
65                  70                  75                  80

Lys Lys Tyr Lys Tyr Leu Arg Ser Leu Asn Lys Thr Lys Asp Lys Ser
                85                  90                  95

Lys Lys Lys Lys Ile His Thr Lys Asp Ile Glu Thr Leu Lys Thr Ile
            100                 105                 110

Tyr Lys Thr Lys Ala Asp Phe Asp Ile Arg Asn Phe Lys Asn Ala Glu
        115                 120                 125

Thr Phe Thr Tyr Glu Asn Tyr Ser Leu Leu Ile Pro Ser Glu Lys Glu
    130                 135                 140

Leu Ile Asp Leu Ile Pro Glu Ile Glu Glu Asp Tyr Ser Tyr Tyr Phe
145                 150                 155                 160

Tyr Val Ser Leu Thr Ile Thr Gly Pro Thr Ile Phe Gly Gly Val Thr
                165                 170                 175

Arg Lys Val Pro Ile Ile Asp Thr Tyr Gly Asp Ile Asn Lys Asp Phe
            180                 185                 190

Tyr Asn Lys Ile Lys Glu Asn Ile Thr Lys Val Leu Asp Arg Val Pro
        195                 200                 205

Phe Tyr Glu Glu Lys Glu Ser Glu Ile Ile Cys Lys Lys Val Leu Ile
    210                 215                 220

Thr Leu Thr Val Asn Lys Trp Glu Ser Ile Asp Lys Trp Tyr Lys Asn
225                 230                 235                 240

Val Lys Ser Lys Ser Lys Lys Phe Lys Asp Phe Thr Leu Phe Leu Ala
                245                 250                 255

Ser Asp Thr Ser Lys Asn Cys Val Gln Gln Cys Val Glu Tyr Leu Gly
            260                 265                 270

Gly Lys Trp Asn Thr Asn Tyr Ser Leu Glu Lys Met Ile Pro Gln Gln
        275                 280                 285

Lys Ile Val Thr Tyr Ile Pro Leu Leu Met Asp Ile Gln Tyr Val Gln
    290                 295                 300

Ser Met Glu Asp Leu Ile Ser Asp Phe Asp Glu Pro Asn Thr Asp Cys
305                 310                 315                 320

Lys Asn Ile Ala Arg Leu Leu Lys Trp Asn Gly His Met Gly Val Ile
                325                 330                 335

Thr Lys Ile Asp Lys Asp Val Lys Ile Asn Arg Ile Gln Arg Lys Arg
            340                 345                 350

Ile Ile Asp Val Glu Asn Lys Glu Val Lys Glu Val Phe Phe Asp Ile
        355                 360                 365

Glu Ser Phe Ser Asp Glu Thr Lys His Gln Ile Pro Tyr Leu Ile Cys
    370                 375                 380

Trp Ser Tyr Leu Gly Glu Leu Tyr Tyr Arg Thr Gly Lys Asn Cys Ile
385                 390                 395                 400

Lys Glu Phe Val Glu Glu Ile Leu Ser Tyr Asn Val Asp Ile Ile Leu
                405                 410                 415
```

```
Tyr Ala Trp Tyr Gly Ser Gly Arg Asp Tyr Gln His Val Leu Pro Tyr
            420                 425                 430

Met Lys Ser Lys Cys Ile Lys Asp Lys Tyr Ile Ile Lys Asn Asn Met
        435                 440                 445

Ile Thr Tyr Gly Glu Leu Tyr Tyr Glu Asn Ala Ile Ile Tyr Leu Lys
    450                 455                 460

Asp Pro Tyr Leu Phe Ile Leu Thr Ser Leu Asp Lys Ala Ser Lys Ala
465                 470                 475                 480

Phe Asn Val Ile Asn Lys Gly Glu Phe Pro His Ser Ile Ile His Ser
                485                 490                 495

Trp Glu Asp Leu Asn Lys Ile Leu Pro Asn Trp Val Lys Ile Gln Lys
            500                 505                 510

Arg Met Ile Glu Tyr Lys Asp Asp Asn Lys Leu Asn Ile Tyr Tyr Lys
        515                 520                 525

Asn Ile Glu Ile Phe Glu Asn Asp Arg Asn Tyr Asn Thr Ile Leu Glu
    530                 535                 540

Asn Ala Ile Glu Tyr Cys Lys Val Asp Val Leu Ala Met Glu Lys Val
545                 550                 555                 560

Trp Ile Lys Phe Lys Lys Leu Leu Glu Lys Asn Leu Asn Ile Thr Val
                565                 570                 575

Ser Val Lys Thr Phe Thr Leu Ser Gln Leu Ser Met Lys Ile Met Glu
            580                 585                 590

Ser Lys Leu Pro Lys Tyr Val Lys Leu Tyr Val Pro Thr Leu Glu Glu
        595                 600                 605

Tyr Ser Lys Ile Arg Asn Ala Ile Tyr Gly Gly Arg Val Ile Ser Lys
    610                 615                 620

Asn Gly Ile Tyr Glu Glu Asn Ile Val Tyr Ala Asp Val Val Ser Leu
625                 630                 635                 640

Tyr Pro Ser Ala Met Lys Leu Leu Lys His Ser Tyr Gly Lys Pro Lys
                645                 650                 655

Leu Val Asp Tyr Ile Asp Phe Glu Lys His Gly Ile Tyr Arg Val Thr
            660                 665                 670

Leu Leu Asn Lys His Asp Gln Glu Pro Lys Asn Tyr Leu Asn Phe Val
        675                 680                 685

Pro Arg Arg Ile Asn Arg Lys Leu Thr Trp Glu Trp Phe Lys Ile His
    690                 695                 700

Glu Gly Trp Tyr His Thr Tyr Asp Leu Ile Ile Ala Lys Ser Glu Gly
705                 710                 715                 720

Phe Asp Ile Tyr Cys His Glu Gly Phe Glu Tyr Pro Glu Lys Asp Tyr
                725                 730                 735

Ile Phe Asn Asp Phe Ile Asp Thr Leu Tyr Ser Met Lys Glu Thr His
            740                 745                 750

Thr Ala Cys Ser Cys Glu Glu Gln Pro Cys Pro Ile Arg Met Val Ala
        755                 760                 765

Lys Ile Ala Leu Asn Gly Gly Gly Tyr Gly Lys Phe Val Gln Lys Pro
    770                 775                 780

Ile Asp Lys Glu Ile Tyr Ile Val Lys Arg Asp Val Val Ala Gly Glu
785                 790                 795                 800

Cys Asp Lys Leu Gln Glu Asn Glu Asn Gly Glu Ile Cys Ile Gly Lys
                805                 810                 815

Arg Leu Val Lys Arg Pro Leu Phe Tyr Asn Leu Asp Ser Glu Asn Tyr
            820                 825                 830
```

```
Asp Lys Met Ile Ile Glu Lys Glu Asp Glu Pro Ile Tyr Ser Thr Gln
        835                 840                 845

Cys Gly Ile Ser Ile Leu Ser Ala Ser Arg Tyr Arg Leu Tyr Lys Leu
    850                 855                 860

Cys Lys Gln Phe Glu Asn Ile Asp Ile Ile Tyr Ser Asp Thr Asp Ser
865                 870                 875                 880

Ile Phe Val Lys Gln Lys Ser Val Asp Trp Glu Leu Phe Lys Ser Lys
                885                 890                 895

Cys Gly Ser Glu Leu Gly Gln Leu Asp Ser Thr Ile Asp Asp Thr Lys
            900                 905                 910

Asn Ala Ile Ile Ser Lys Met Tyr Ile Gly Gly Ala Lys Met Tyr Ala
        915                 920                 925

Phe Glu Tyr Leu Asn Asn Lys Asn Lys Leu Ile Thr Lys Leu His Cys
    930                 935                 940

Lys Gly Val Pro Asn Tyr Met Leu Ser Leu Asn Gln Phe Lys Tyr Leu
945                 950                 955                 960

Met Glu Ser Pro Asp Asn Thr Ile Ala Tyr Lys Phe Glu Ile Ile Arg
                965                 970                 975

Arg Lys Leu Val Asn Val Ile Thr Lys Asp Leu Ile Lys Asp Ile Lys
            980                 985                 990

Gln Thr
```

<210> SEQ ID NO 34
<211> LENGTH: 2985
<212> TYPE: DNA
<213> ORGANISM: Kluyveromyces lactis

<400> SEQUENCE: 34

```
atgaacgatg aattagcctt tttgaactcc caaatagatg attatagtga cgacattgaa      60

tttttgagaa ccgaagtctt tagaatcaat agatattcta aatcaatcta ttctttaatg     120

aagaattctt caaaggaagc tattaaagaa actattgagt ttaataagta tggtcaagaa     180

attcattcta agattaaaga aaaggaaatt tcattaattg aagcaattaa attgatggaa     240

aagaaatata aatatttgag atcattgaat aagactaaag ataaatctaa gaaaaagaaa     300

attcatacaa aagatattga aactttgaaa acaatctata aaacaaaagc tgattttgat     360

attagaaatt ttaaaaatgc tgaaactttt acttatgaaa attactcttt gttaattcca     420

tcagaaaagg aattgattga tttgatccca gaaatcgaag aagattactc ttactacttc     480

tacgtttcat taactatcac aggtccaact atctttggtg gtgttacaag aaaagttcca     540

atcatcgata cttatggtga cattaataag gatttctaca ataagattaa agaaaacatc     600

acaaaagttt tggatagagt tccattctac gaagaaaagg aatcagaaat tatttgtaag     660

aaagttttga tcactttgac agttaataag tgggaatcta tcgataagtg gtacaagaac     720

gttaagtcta agtctaaaaa gtttaaagat tttactttgt ttttagcttc tgatacttct     780

aaaaattgtg ttcaacaatg tgttgaatat ttgggtggta aatggaacac taactactct     840

ttggaaaaga tgatcccaca acaaaagatt gttacataca tcccattgtt gatggatatc     900

caatacgttc aatctatgga agatttgatc tcagatttcg atgaaccaaa cactgattgt     960

aagaacatcg ctagattgtt aaagtggaat ggtcacatgg gtgtgatcac aaagatcgac    1020

aaggatgtta agattaatag aatacaaaga aagagaatca tcgatgttga aaataaggaa    1080

gttaaagaag ttttctttga tattgaattg ttttcagatg aaactaaaca tcaaatccca    1140

tatttgattt gttggtctta cttgggtgaa ttatattaca gaacaggtaa aaattgtatc    1200
```

aaagaatttg ttgaagaaat tttatcttac aacgttgata tcatcttgta tgcttggtac 1260
ggttcaggtt atgattacca acatgttttg ccatacatga agtctaaatg tattaaggat 1320
aagtacatta ttaagaataa tatgattact tacggtgaat tatactacga aaacgcaatc 1380
atatatttga aagatccata cttgtttatt ttaacatctt tggataaagc atctaaggct 1440
tttaatgtta ttaataaggg tgaatttcca cattctatca tccattcatg ggaagatttg 1500
aataagattt tgccaaactg ggttaagatc caaaagagaa tgattgaata taaagatgat 1560
aataagttga acatctatta caagaacatc gaaattttcg aaaatgatag aaattataat 1620
actatcttag aaaatgctat tgaatactgt aaagttgatg ttttggcaat ggaaaaggtt 1680
tggatcaagt ttaagaaatt gttggaaaag aatttgaaca ttactgtttc agttaagact 1740
tttacattat ctcaattgtc aatgaagatc atggaatcta aattgccaaa gtacgttaaa 1800
ttgtacgttc caacattgga agaatattca aagatcagaa atgctatcta tggtggtaga 1860
gttatttcta aaaatggtat ctatgaagaa aacatcgttt acgctgatgt tgtttcttta 1920
tacccatcag caatgaaatt gttgaagcat tcttatggta aaccaaaatt ggttgattac 1980
atcgatttcg aaaagcatgg tatctaccgt gttactttgt tgaataagca tgatcaagaa 2040
cctaaaaatt acttaaactt tgttccaaga agaattaata gaaaattgac ttgggaatgg 2100
ttcaagatac atgaaggttg gtatcataca tacgatttga tcatcgctaa gtctgaaggt 2160
ttcgatatct attgccatga aggtttcgaa tacccagaaa aggattacat tttcaatgat 2220
ttcattgata cattatactc tatgaaagaa actcatacag catgttcatg tgaagaacaa 2280
ccatgtccaa tcagaatggt tgctaagatc gcattgaatg gtggtggtta tggtaaattt 2340
gttcaaaaac caatcgataa ggaaatatat atcgttaaga gagatgttgt tgctggtgaa 2400
tgtgataaat tacaagaaaa cgaaaatggt gaaatttgta ttggtaaaag attggttaaa 2460
agaccattat tttataattt ggattcagaa aactacgata aaatgattat tgaaaaagaa 2520
gatgaaccaa tctattctac tcaatgtggt atctcaatct tgtctgcatc aagatataga 2580
ttatacaaat tgtgtaagca attcgaaaac atcgatatca tctattctga tacagattca 2640
atttttgtta aacaaaaatc agttgattgg gaattgttta aatctaagtg tggttcagaa 2700
ttaggtcaat tggattctac tatcgatgat actaagaacg ctatcatctc aaagatgtac 2760
attggtggtg ctaagatgta tgcttttgaa tacttaaaca ataagaataa gttgatcact 2820
aaattgcatt gtaaaggtgt tccaaactac atgttgtctt taaaccaatt caaatatttg 2880
atggaatcac cagataacac aattgcatat aaatttgaaa ttattagaag aaaattggta 2940
aatgtcataa ctaaggactt gatcaaagat atcaagcaga cttga 2985

<210> SEQ ID NO 35
<211> LENGTH: 994
<212> TYPE: PRT
<213> ORGANISM: Kluyveromyces lactis

<400> SEQUENCE: 35

Met Asn Asp Glu Leu Ala Phe Leu Asn Ser Gln Ile Asp Asp Tyr Ser
1 5 10 15

Asp Asp Ile Glu Phe Leu Arg Thr Glu Val Phe Arg Ile Asn Arg Tyr
20 25 30

Ser Lys Ser Ile Tyr Ser Leu Met Lys Asn Ser Ser Lys Glu Ala Ile
35 40 45

```
Lys Glu Thr Ile Glu Phe Asn Lys Tyr Gly Gln Glu Ile His Ser Lys
    50                  55                  60

Ile Lys Glu Lys Glu Ile Ser Leu Ile Glu Ala Ile Lys Leu Met Glu
65                  70                  75                  80

Lys Lys Tyr Lys Tyr Leu Arg Ser Leu Asn Lys Thr Lys Asp Lys Ser
                85                  90                  95

Lys Lys Lys Lys Ile His Thr Lys Asp Ile Glu Thr Leu Lys Thr Ile
            100                 105                 110

Tyr Lys Thr Lys Ala Asp Phe Asp Ile Arg Asn Phe Lys Asn Ala Glu
        115                 120                 125

Thr Phe Thr Tyr Glu Asn Tyr Ser Leu Leu Ile Pro Ser Glu Lys Glu
    130                 135                 140

Leu Ile Asp Leu Ile Pro Glu Ile Glu Glu Asp Tyr Ser Tyr Tyr Phe
145                 150                 155                 160

Tyr Val Ser Leu Thr Ile Thr Gly Pro Thr Ile Phe Gly Gly Val Thr
                165                 170                 175

Arg Lys Val Pro Ile Ile Asp Thr Tyr Gly Asp Ile Asn Lys Asp Phe
            180                 185                 190

Tyr Asn Lys Ile Lys Glu Asn Ile Thr Lys Val Leu Asp Arg Val Pro
        195                 200                 205

Phe Tyr Glu Glu Lys Glu Ser Glu Ile Ile Cys Lys Lys Val Leu Ile
    210                 215                 220

Thr Leu Thr Val Asn Lys Trp Glu Ser Ile Asp Lys Trp Tyr Lys Asn
225                 230                 235                 240

Val Lys Ser Lys Ser Lys Lys Phe Lys Asp Phe Thr Leu Phe Leu Ala
                245                 250                 255

Ser Asp Thr Ser Lys Asn Cys Val Gln Gln Cys Val Glu Tyr Leu Gly
            260                 265                 270

Gly Lys Trp Asn Thr Asn Tyr Ser Leu Glu Lys Met Ile Pro Gln Gln
        275                 280                 285

Lys Ile Val Thr Tyr Ile Pro Leu Leu Met Asp Ile Gln Tyr Val Gln
    290                 295                 300

Ser Met Glu Asp Leu Ile Ser Asp Phe Asp Glu Pro Asn Thr Asp Cys
305                 310                 315                 320

Lys Asn Ile Ala Arg Leu Leu Lys Trp Asn Gly His Met Gly Val Ile
                325                 330                 335

Thr Lys Ile Asp Lys Asp Val Lys Ile Asn Arg Ile Gln Arg Lys Arg
            340                 345                 350

Ile Ile Asp Val Glu Asn Lys Glu Val Lys Glu Val Phe Phe Asp Ile
        355                 360                 365

Glu Leu Phe Ser Asp Glu Thr Lys His Gln Ile Pro Tyr Leu Ile Cys
    370                 375                 380

Trp Ser Tyr Leu Gly Glu Leu Tyr Tyr Arg Thr Gly Lys Asn Cys Ile
385                 390                 395                 400

Lys Glu Phe Val Glu Glu Ile Leu Ser Tyr Asn Val Asp Ile Ile Leu
                405                 410                 415

Tyr Ala Trp Tyr Gly Ser Gly Tyr Asp Tyr Gln His Val Leu Pro Tyr
            420                 425                 430

Met Lys Ser Lys Cys Ile Lys Asp Lys Tyr Ile Ile Lys Asn Asn Met
        435                 440                 445

Ile Thr Tyr Gly Glu Leu Tyr Tyr Glu Asn Ala Ile Ile Tyr Leu Lys
    450                 455                 460
```

```
Asp Pro Tyr Leu Phe Ile Leu Thr Ser Leu Asp Lys Ala Ser Lys Ala
465                 470                 475                 480

Phe Asn Val Ile Asn Lys Gly Glu Phe Pro His Ser Ile Ile His Ser
                485                 490                 495

Trp Glu Asp Leu Asn Lys Ile Leu Pro Asn Trp Val Lys Ile Gln Lys
            500                 505                 510

Arg Met Ile Glu Tyr Lys Asp Asp Asn Lys Leu Asn Ile Tyr Tyr Lys
        515                 520                 525

Asn Ile Glu Ile Phe Glu Asn Asp Arg Asn Tyr Asn Thr Ile Leu Glu
    530                 535                 540

Asn Ala Ile Glu Tyr Cys Lys Val Asp Val Leu Ala Met Glu Lys Val
545                 550                 555                 560

Trp Ile Lys Phe Lys Lys Leu Leu Glu Lys Asn Leu Asn Ile Thr Val
                565                 570                 575

Ser Val Lys Thr Phe Thr Leu Ser Gln Leu Ser Met Lys Ile Met Glu
            580                 585                 590

Ser Lys Leu Pro Lys Tyr Val Lys Leu Tyr Val Pro Thr Leu Glu Glu
        595                 600                 605

Tyr Ser Lys Ile Arg Asn Ala Ile Tyr Gly Gly Arg Val Ile Ser Lys
    610                 615                 620

Asn Gly Ile Tyr Glu Glu Asn Ile Val Tyr Ala Asp Val Val Ser Leu
625                 630                 635                 640

Tyr Pro Ser Ala Met Lys Leu Leu Lys His Ser Tyr Gly Lys Pro Lys
                645                 650                 655

Leu Val Asp Tyr Ile Asp Phe Glu Lys His Gly Ile Tyr Arg Val Thr
            660                 665                 670

Leu Leu Asn Lys His Asp Gln Glu Pro Lys Asn Tyr Leu Asn Phe Val
        675                 680                 685

Pro Arg Arg Ile Asn Arg Lys Leu Thr Trp Glu Trp Phe Lys Ile His
    690                 695                 700

Glu Gly Trp Tyr His Thr Tyr Asp Leu Ile Ile Ala Lys Ser Glu Gly
705                 710                 715                 720

Phe Asp Ile Tyr Cys His Glu Gly Phe Glu Tyr Pro Glu Lys Asp Tyr
                725                 730                 735

Ile Phe Asn Asp Phe Ile Asp Thr Leu Tyr Ser Met Lys Glu Thr His
            740                 745                 750

Thr Ala Cys Ser Cys Glu Glu Gln Pro Cys Pro Ile Arg Met Val Ala
        755                 760                 765

Lys Ile Ala Leu Asn Gly Gly Gly Tyr Gly Lys Phe Val Gln Lys Pro
    770                 775                 780

Ile Asp Lys Glu Ile Tyr Ile Val Lys Arg Asp Val Val Ala Gly Glu
785                 790                 795                 800

Cys Asp Lys Leu Gln Glu Asn Glu Asn Gly Glu Ile Cys Ile Gly Lys
                805                 810                 815

Arg Leu Val Lys Arg Pro Leu Phe Tyr Asn Leu Asp Ser Glu Asn Tyr
            820                 825                 830

Asp Lys Met Ile Ile Glu Lys Glu Asp Glu Pro Ile Tyr Ser Thr Gln
        835                 840                 845

Cys Gly Ile Ser Ile Leu Ser Ala Ser Arg Tyr Arg Leu Tyr Lys Leu
    850                 855                 860

Cys Lys Gln Phe Glu Asn Ile Asp Ile Ile Tyr Ser Asp Thr Asp Ser
865                 870                 875                 880
```

```
Ile Phe Val Lys Gln Lys Ser Val Asp Trp Glu Leu Phe Lys Ser Lys
                885                 890                 895

Cys Gly Ser Glu Leu Gly Gln Leu Asp Ser Thr Ile Asp Asp Thr Lys
            900                 905                 910

Asn Ala Ile Ile Ser Lys Met Tyr Ile Gly Gly Ala Lys Met Tyr Ala
        915                 920                 925

Phe Glu Tyr Leu Asn Asn Lys Asn Lys Leu Ile Thr Lys Leu His Cys
    930                 935                 940

Lys Gly Val Pro Asn Tyr Met Leu Ser Leu Asn Gln Phe Lys Tyr Leu
945                 950                 955                 960

Met Glu Ser Pro Asp Asn Thr Ile Ala Tyr Lys Phe Glu Ile Ile Arg
                965                 970                 975

Arg Lys Leu Val Asn Val Ile Thr Lys Asp Leu Ile Lys Asp Ile Lys
            980                 985                 990

Gln Thr
```

<210> SEQ ID NO 36
<211> LENGTH: 2985
<212> TYPE: DNA
<213> ORGANISM: Kluyveromyces lactis

<400> SEQUENCE: 36

```
atgaacgatg aattagcctt tttgaactcc caaatagatg attatagtga cgacattgaa      60
tttttgagaa ccgaagtctt tagaatcaat agatattcta aatcaatcta ttctttaatg     120
aagaattctt caaaggaagc tattaaagaa actattgagt ttaataagta tggtcaagaa     180
attcattcta agattaaaga aaaggaaatt tcattaattg aagcaattaa attgatggaa     240
aagaaatata aatatttgag atcattgaat aagactaaag ataaatctaa gaaaaagaaa     300
attcatacaa aagatattga aactttgaaa acaatctata aaacaaaagc tgattttgat     360
attagaaatt ttaaaaatgc tgaaactttt acttatgaaa attactcttt gttaattcca     420
tcagaaaagg aattgattga tttgatccca gaaatcgaag aagattactc ttactacttc     480
tacgtttcat taactatcac aggtccaact atctttggtg gtgttacaag aaaagttcca     540
atcatcgata cttatggtga cattaataag gatttctaca ataagattaa agaaaacatc     600
acaaaagttt tggatagagt tccattctac gaagaaaagg aatcagaaat tatttgtaag     660
aaagttttga tcactttgac agttaataag tgggaatcta tcgataagtg gtacaagaac     720
gttaagtcta agtctaaaaa gtttaaagat tttactttgt ttttagcttc tgatacttct     780
aaaaattgtg ttcaacaatg tgttgaatat ttgggtggta aatggaacac taactactct     840
ttggaaaaga tgatcccaca acaaaagatt gttacataca tcccattgtt gatggatatc     900
caatacgttc aatctatgga agatttgatc tcagatttcg atgaaccaaa cactgattgt     960
aagaacatcg ctagattgtt aaagtggaat ggtcacatgg gtgtgatcac aaagatcgac    1020
aaggatgtta agattaatag aatacaaaga aagagaatca tcgatgttga aaataaggaa    1080
gttaaagaag ttttctttga tattgaatct ttttcagatg aaactaaaca tcaaatccca    1140
tatttgattt gttggtctta cttgggtgaa ttatattaca gaacaggtaa aaattgtatc    1200
aaagaatttg ttgaagaaat tttatcttac aacgttgata tcatcttgta tgcttggtac    1260
ggttcaggtt atgattacca acatgttttg ccatacatga agtctaaatg tattaaggat    1320
aagtacatta ttaagaataa tatgattact tacggtgaat tatactacga aaacgcaatc    1380
atatatttga aagatccata cttgtttatt ttaacatctg atgataaagc atctaaggct    1440
```

tttaatgtta ttaataaggg tgaatttcca cattctatca tccattcatg ggaagatttg 1500
aataagattt tgccaaactg ggttaagatc caaaagagaa tgattgaata taaagatgat 1560
aataagttga acatctatta caagaacatc gaaattttcg aaaatgatag aaattataat 1620
actatcttag aaaatgctat tgaatactgt aaagttgatg ttttggcaat ggaaaaggtt 1680
tggatcaagt ttaagaaatt gttggaaaag aatttgaaca ttactgtttc agttaagact 1740
tttacattat ctcaattgtc aatgaagatc atggaatcta aattgccaaa gtacgttaaa 1800
ttgtacgttc caacattgga agaatattca aagatcagaa atgctatcta tggtggtaga 1860
gttatttcta aaaatggtat ctatgaagaa aacatcgttt acgctgatgt tgtttcttta 1920
tacccatcag caatgaaatt gttgaagcat tcttatggta aaccaaaatt ggttgattac 1980
atcgatttcg aaaagcatgg tatctaccgt gttactttgt tgaataagca tgatcaagaa 2040
cctaaaaatt acttaaactt tgttccaaga agaattaata gaaaattgac ttgggaatgg 2100
ttcaagatac atgaaggttg gtatcataca tacgatttga tcatcgctaa gtctgaaggt 2160
ttcgatatct attgccatga aggtttcgaa tacccagaaa aggattacat tttcaatgat 2220
ttcattgata cattatactc tatgaaagaa actcatacag catgttcatg tgaagaacaa 2280
ccatgtccaa tcagaatggt tgctaagatc gcattgaatg gtggtggtta tggtaaattt 2340
gttcaaaaac caatcgataa ggaaatatat atcgttaaga gagatgttgt tgctggtgaa 2400
tgtgataaat tacaagaaaa cgaaaatggt gaaatttgta ttggtaaaag attggttaaa 2460
agaccattat tttataattt ggattcagaa aactacgata aaatgattat tgaaaaagaa 2520
gatgaaccaa tctattctac tcaatgtggt atctcaatct tgtctgcatc aagatataga 2580
ttatacaaat tgtgtaagca attcgaaaac atcgatatca tctattctga tacagattca 2640
atttttgtta aacaaaaatc agttgattgg gaattgttta aatctaagtg tggttcagaa 2700
ttaggtcaat tggattctac tatcgatgat actaagaacg ctatcatctc aaagatgtac 2760
attggtggtg ctaagatgta tgcttttgaa tacttaaaca ataagaataa gttgatcact 2820
aaattgcatt gtaaaggtgt tccaaactac atgttgtctt taaaccaatt caaatatttg 2880
atggaatcac cagataacac aattgcatat aaatttgaaa ttattagaag aaaattggta 2940
aatgtcataa ctaaggactt gatcaaagat atcaagcaga cttga 2985

<210> SEQ ID NO 37
<211> LENGTH: 994
<212> TYPE: PRT
<213> ORGANISM: Kluyveromyces lactis

<400> SEQUENCE: 37

Met Asn Asp Glu Leu Ala Phe Leu Asn Ser Gln Ile Asp Asp Tyr Ser
1 5 10 15

Asp Asp Ile Glu Phe Leu Arg Thr Glu Val Phe Arg Ile Asn Arg Tyr
20 25 30

Ser Lys Ser Ile Tyr Ser Leu Met Lys Asn Ser Ser Lys Glu Ala Ile
35 40 45

Lys Glu Thr Ile Glu Phe Asn Lys Tyr Gly Gln Glu Ile His Ser Lys
50 55 60

Ile Lys Glu Lys Glu Ile Ser Leu Ile Glu Ala Ile Lys Leu Met Glu
65 70 75 80

Lys Lys Tyr Lys Tyr Leu Arg Ser Leu Asn Lys Thr Lys Asp Lys Ser
85 90 95

-continued

```
Lys Lys Lys Lys Ile His Thr Lys Asp Ile Glu Thr Leu Lys Thr Ile
            100                 105                 110

Tyr Lys Thr Lys Ala Asp Phe Asp Ile Arg Asn Phe Lys Asn Ala Glu
        115                 120                 125

Thr Phe Thr Tyr Glu Asn Tyr Ser Leu Leu Ile Pro Ser Glu Lys Glu
    130                 135                 140

Leu Ile Asp Leu Ile Pro Glu Ile Glu Glu Asp Tyr Ser Tyr Tyr Phe
145                 150                 155                 160

Tyr Val Ser Leu Thr Ile Thr Gly Pro Thr Ile Phe Gly Gly Val Thr
                165                 170                 175

Arg Lys Val Pro Ile Ile Asp Thr Tyr Gly Asp Ile Asn Lys Asp Phe
            180                 185                 190

Tyr Asn Lys Ile Lys Glu Asn Ile Thr Lys Val Leu Asp Arg Val Pro
        195                 200                 205

Phe Tyr Glu Glu Lys Glu Ser Glu Ile Ile Cys Lys Lys Val Leu Ile
    210                 215                 220

Thr Leu Thr Val Asn Lys Trp Glu Ser Ile Asp Lys Trp Tyr Lys Asn
225                 230                 235                 240

Val Lys Ser Lys Ser Lys Lys Phe Lys Asp Phe Thr Leu Phe Leu Ala
                245                 250                 255

Ser Asp Thr Ser Lys Asn Cys Val Gln Gln Cys Val Glu Tyr Leu Gly
            260                 265                 270

Gly Lys Trp Asn Thr Asn Tyr Ser Leu Glu Lys Met Ile Pro Gln Gln
        275                 280                 285

Lys Ile Val Thr Tyr Ile Pro Leu Leu Met Asp Ile Gln Tyr Val Gln
    290                 295                 300

Ser Met Glu Asp Leu Ile Ser Asp Phe Asp Glu Pro Asn Thr Asp Cys
305                 310                 315                 320

Lys Asn Ile Ala Arg Leu Leu Lys Trp Asn Gly His Met Gly Val Ile
                325                 330                 335

Thr Lys Ile Asp Lys Asp Val Lys Ile Asn Arg Ile Gln Arg Lys Arg
            340                 345                 350

Ile Ile Asp Val Glu Asn Lys Glu Val Lys Glu Val Phe Phe Asp Ile
        355                 360                 365

Glu Ser Phe Ser Asp Glu Thr Lys His Gln Ile Pro Tyr Leu Ile Cys
    370                 375                 380

Trp Ser Tyr Leu Gly Glu Leu Tyr Tyr Arg Thr Gly Lys Asn Cys Ile
385                 390                 395                 400

Lys Glu Phe Val Glu Glu Ile Leu Ser Tyr Asn Val Asp Ile Ile Leu
                405                 410                 415

Tyr Ala Trp Tyr Gly Ser Gly Tyr Asp Tyr Gln His Val Leu Pro Tyr
            420                 425                 430

Met Lys Ser Lys Cys Ile Lys Asp Lys Tyr Ile Ile Lys Asn Asn Met
        435                 440                 445

Ile Thr Tyr Gly Glu Leu Tyr Tyr Glu Asn Ala Ile Ile Tyr Leu Lys
    450                 455                 460

Asp Pro Tyr Leu Phe Ile Leu Thr Ser Asp Asp Lys Ala Ser Lys Ala
465                 470                 475                 480

Phe Asn Val Ile Asn Lys Gly Glu Phe Pro His Ser Ile Ile His Ser
                485                 490                 495

Trp Glu Asp Leu Asn Lys Ile Leu Pro Asn Trp Val Lys Ile Gln Lys
            500                 505                 510
```

```
Arg Met Ile Glu Tyr Lys Asp Asp Asn Lys Leu Asn Ile Tyr Tyr Lys
        515                 520                 525

Asn Ile Glu Ile Phe Glu Asn Asp Arg Asn Tyr Asn Thr Ile Leu Glu
    530                 535                 540

Asn Ala Ile Glu Tyr Cys Lys Val Asp Val Leu Ala Met Glu Lys Val
545                 550                 555                 560

Trp Ile Lys Phe Lys Lys Leu Leu Glu Lys Asn Leu Asn Ile Thr Val
                565                 570                 575

Ser Val Lys Thr Phe Thr Leu Ser Gln Leu Ser Met Lys Ile Met Glu
            580                 585                 590

Ser Lys Leu Pro Lys Tyr Val Lys Leu Tyr Val Pro Thr Leu Glu Glu
        595                 600                 605

Tyr Ser Lys Ile Arg Asn Ala Ile Tyr Gly Gly Arg Val Ile Ser Lys
    610                 615                 620

Asn Gly Ile Tyr Glu Glu Asn Ile Val Tyr Ala Asp Val Val Ser Leu
625                 630                 635                 640

Tyr Pro Ser Ala Met Lys Leu Leu Lys His Ser Tyr Gly Lys Pro Lys
                645                 650                 655

Leu Val Asp Tyr Ile Asp Phe Glu Lys His Gly Ile Tyr Arg Val Thr
            660                 665                 670

Leu Leu Asn Lys His Asp Gln Glu Pro Lys Asn Tyr Leu Asn Phe Val
        675                 680                 685

Pro Arg Arg Ile Asn Arg Lys Leu Thr Trp Glu Trp Phe Lys Ile His
    690                 695                 700

Glu Gly Trp Tyr His Thr Tyr Asp Leu Ile Ile Ala Lys Ser Glu Gly
705                 710                 715                 720

Phe Asp Ile Tyr Cys His Glu Gly Phe Glu Tyr Pro Glu Lys Asp Tyr
                725                 730                 735

Ile Phe Asn Asp Phe Ile Asp Thr Leu Tyr Ser Met Lys Glu Thr His
            740                 745                 750

Thr Ala Cys Ser Cys Glu Glu Gln Pro Cys Pro Ile Arg Met Val Ala
        755                 760                 765

Lys Ile Ala Leu Asn Gly Gly Gly Tyr Gly Lys Phe Val Gln Lys Pro
    770                 775                 780

Ile Asp Lys Glu Ile Tyr Ile Val Lys Arg Asp Val Val Ala Gly Glu
785                 790                 795                 800

Cys Asp Lys Leu Gln Glu Asn Glu Asn Gly Glu Ile Cys Ile Gly Lys
                805                 810                 815

Arg Leu Val Lys Arg Pro Leu Phe Tyr Asn Leu Asp Ser Glu Asn Tyr
            820                 825                 830

Asp Lys Met Ile Ile Glu Lys Glu Asp Glu Pro Ile Tyr Ser Thr Gln
        835                 840                 845

Cys Gly Ile Ser Ile Leu Ser Ala Ser Arg Tyr Arg Leu Tyr Lys Leu
    850                 855                 860

Cys Lys Gln Phe Glu Asn Ile Asp Ile Ile Tyr Ser Asp Thr Asp Ser
865                 870                 875                 880

Ile Phe Val Lys Gln Lys Ser Val Asp Trp Glu Leu Phe Lys Ser Lys
                885                 890                 895

Cys Gly Ser Glu Leu Gly Gln Leu Asp Ser Thr Ile Asp Asp Thr Lys
            900                 905                 910

Asn Ala Ile Ile Ser Lys Met Tyr Ile Gly Gly Ala Lys Met Tyr Ala
        915                 920                 925
```

Phe Glu Tyr Leu Asn Asn Lys Asn Lys Leu Ile Thr Lys Leu His Cys
930 935 940

Lys Gly Val Pro Asn Tyr Met Leu Ser Leu Asn Gln Phe Lys Tyr Leu
945 950 955 960

Met Glu Ser Pro Asp Asn Thr Ile Ala Tyr Lys Phe Glu Ile Ile Arg
965 970 975

Arg Lys Leu Val Asn Val Ile Thr Lys Asp Leu Ile Lys Asp Ile Lys
980 985 990

Gln Thr

<210> SEQ ID NO 38
<211> LENGTH: 2985
<212> TYPE: DNA
<213> ORGANISM: Kluyveromyces lactis

<400> SEQUENCE: 38
atgaacgatg aattagcctt tttgaactcc caaatagatg attatagtga cgacattgaa 60
tttttgagaa ccgaagtctt tagaatcaat agatattcta aatcaatcta ttctttaatg 120
aagaattctt caaaggaagc tattaaagaa actattgagt ttaataagta tggtcaagaa 180
attcattcta agattaaaga aaaggaaatt tcattaattg aagcaattaa attgatggaa 240
aagaaatata aatatttgag atcattgaat aagactaaag ataaatctaa gaaaaagaaa 300
attcatacaa aagatattga aactttgaaa acaatctata aaacaaaagc tgattttgat 360
attagaaatt ttaaaaatgc tgaaactttt acttatgaaa attactcttt gttaattcca 420
tcagaaaagg aattgattga tttgatccca gaaatcgaag aagattactc ttactacttc 480
tacgtttcat taactatcac aggtccaact atctttggtg gtgttacaag aaaagttcca 540
atcatcgata cttatggtga cattaataag gatttctaca ataagattaa agaaaacatc 600
acaaaagttt tggatagagt tccattctac gaagaaaagg aatcagaaat tatttgtaag 660
aaagttttga tcactttgac agttaataag tgggaatcta tcgataagtg gtacaagaac 720
gttaagtcta agtctaaaaa gtttaaagat tttactttgt ttttagcttc tgatacttct 780
aaaaattgtg ttcaacaatg tgttgaatat ttgggtggta aatggaacac taactactct 840
ttggaaaaga tgatcccaca acaaaagatt gttacataca tcccattgtt gatggatatc 900
caatacgttc aatctatgga agatttgatc tcagatttcg atgaaccaaa cactgattgt 960
aagaacatcg ctagattgtt aaagtggaat ggtcacatgg gtgtgatcac aaagatcgac 1020
aaggatgtta agattaatag aatacaaaga aagagaatca tcgatgttga aaataaggaa 1080
gttaaagaag ttttctttga tattgaatct ttttcagatg aaactaaaca tcaaatccca 1140
tatttgattt gttggtctta cttgggtgaa ttatattaca gaacaggtaa aaattgtatc 1200
aaagaatttg ttgaagaaat tttatcttac aacgttgata tcatcttgta tgcttggtac 1260
ggttcaggtt atgattacca acatgttttg ccatacatga agtctaaatg tattaaggat 1320
aagtacatta ttaagaataa tatgattact tacggtgaat tatactacga aaacgcaatc 1380
atatatttga aagatccata cttgtttatt ttaacatctt tggataaagc atctaaggct 1440
tttaatgtta ttaataaggg tgaatttcca cattctatca tccattcatg ggaagatttg 1500
aataagattt tgccaaactg ggttaagatc caaaagagaa tgattgaata taaagatgat 1560
aataagttga acatctatta caagaacatc gaaattttcg aaaatgatag aaattataat 1620
actatcttag aaaatgctat tgaatactgt aaagttgatg ttttggcaat ggaaaaggtt 1680
tggatcaagt ttaagaaatt gttggaaaag aatttgaaca ttactgtttc agttaagact 1740

```
tttacattat ctcaattgtc aatgaagatc atggaatcta aattgccaaa gtacgttaaa   1800

ttgtacgttc caacattgga agaatattca aagatcagaa atgctatcta tggtggtaga   1860

gttatttcta aaaatggtat ctatgaagaa aacatcgttt acgctgatgt tgtttcttta   1920

tacccatcag caatgaaatt gttgaagcat tcttatggta aaccaaaatt ggttgattac   1980

atcgatttcg aaaagcatgg tatctaccgt gttactttgt tgaataagca tgatcaagaa   2040

cctaaaaatt acttaaactt tgttccaaga agaattaata gaaaattgac ttgggaatgg   2100

ttcaagatac atgaaggttg gtatcataca tacgatttga tcatcgctaa gtctgaaggt   2160

ttcgatatct attgccatga aggtttcgaa tacccagaaa aggattacat tttcaatgat   2220

ttcattgata cattatactc tatgaaagaa actcatacag catgttcatg tgaagaacaa   2280

ccatgtccaa tcagaatggt tgctaagatc gcattgaatg gtggtggtta tggtaaattt   2340

gttcaaaaac caatcgataa ggaaatatat atcgttaaga gagatgttgt tgctggtgaa   2400

tgtgataaat tacaagaaaa cgaaaatggt gaaatttgta ttggtaaaag attggttaaa   2460

agaccattat tttataattt ggattcagaa aactacgata aaatgattat tgaaaaagaa   2520

gatgaaccaa tctattctac tcaatgtggt atctcaatct tgtctgcatc aagatataga   2580

ttatacaaat tgtgtaagca attcgaaaac atcgatatca tctattctga tacagattca   2640

attgcggtta aacaaaaatc agttgattgg gaattgttta aatctaagtg tggttcagaa   2700

ttaggtcaat tggattctac tatcgatgat actaagaacg ctatcatctc aaagatgtac   2760

attggtggtg ctaagatgta tgcttttgaa tacttaaaca ataagaataa gttgatcact   2820

aaattgcatt gtaaaggtgt tccaaactac atgttgtctt taaaccaatt caaatatttg   2880

atggaatcac cagataacac aattgcatat aaatttgaaa ttattagaag aaaattggta   2940

aatgtcataa ctaaggactt gatcaaagat atcaagcaga cttga                   2985
```

<210> SEQ ID NO 39
<211> LENGTH: 994
<212> TYPE: PRT
<213> ORGANISM: Kluyveromyces lactis

<400> SEQUENCE: 39

```
Met Asn Asp Glu Leu Ala Phe Leu Asn Ser Gln Ile Asp Asp Tyr Ser
1               5                   10                  15

Asp Asp Ile Glu Phe Leu Arg Thr Glu Val Phe Arg Ile Asn Arg Tyr
            20                  25                  30

Ser Lys Ser Ile Tyr Ser Leu Met Lys Asn Ser Ser Lys Glu Ala Ile
        35                  40                  45

Lys Glu Thr Ile Glu Phe Asn Lys Tyr Gly Gln Glu Ile His Ser Lys
    50                  55                  60

Ile Lys Glu Lys Glu Ile Ser Leu Ile Glu Ala Ile Lys Leu Met Glu
65                  70                  75                  80

Lys Lys Tyr Lys Tyr Leu Arg Ser Leu Asn Lys Thr Lys Asp Lys Ser
                85                  90                  95

Lys Lys Lys Lys Ile His Thr Lys Asp Ile Glu Thr Leu Lys Thr Ile
            100                 105                 110

Tyr Lys Thr Lys Ala Asp Phe Asp Ile Arg Asn Phe Lys Asn Ala Glu
        115                 120                 125

Thr Phe Thr Tyr Glu Asn Tyr Ser Leu Leu Ile Pro Ser Glu Lys Glu
    130                 135                 140
```

```
Leu Ile Asp Leu Ile Pro Glu Ile Glu Glu Asp Tyr Ser Tyr Tyr Phe
145                 150                 155                 160

Tyr Val Ser Leu Thr Ile Thr Gly Pro Thr Ile Phe Gly Gly Val Thr
                165                 170                 175

Arg Lys Val Pro Ile Ile Asp Thr Tyr Gly Asp Ile Asn Lys Asp Phe
            180                 185                 190

Tyr Asn Lys Ile Lys Glu Asn Ile Thr Lys Val Leu Asp Arg Val Pro
        195                 200                 205

Phe Tyr Glu Glu Lys Glu Ser Glu Ile Ile Cys Lys Lys Val Leu Ile
    210                 215                 220

Thr Leu Thr Val Asn Lys Trp Glu Ser Ile Asp Lys Trp Tyr Lys Asn
225                 230                 235                 240

Val Lys Ser Lys Ser Lys Lys Phe Lys Asp Phe Thr Leu Phe Leu Ala
                245                 250                 255

Ser Asp Thr Ser Lys Asn Cys Val Gln Gln Cys Val Glu Tyr Leu Gly
            260                 265                 270

Gly Lys Trp Asn Thr Asn Tyr Ser Leu Glu Lys Met Ile Pro Gln Gln
        275                 280                 285

Lys Ile Val Thr Tyr Ile Pro Leu Leu Met Asp Ile Gln Tyr Val Gln
    290                 295                 300

Ser Met Glu Asp Leu Ile Ser Asp Phe Asp Glu Pro Asn Thr Asp Cys
305                 310                 315                 320

Lys Asn Ile Ala Arg Leu Leu Lys Trp Asn Gly His Met Gly Val Ile
                325                 330                 335

Thr Lys Ile Asp Lys Asp Val Lys Ile Asn Arg Ile Gln Arg Lys Arg
            340                 345                 350

Ile Ile Asp Val Glu Asn Lys Glu Val Lys Glu Val Phe Phe Asp Ile
        355                 360                 365

Glu Ser Phe Ser Asp Glu Thr Lys His Gln Ile Pro Tyr Leu Ile Cys
    370                 375                 380

Trp Ser Tyr Leu Gly Glu Leu Tyr Tyr Arg Thr Gly Lys Asn Cys Ile
385                 390                 395                 400

Lys Glu Phe Val Glu Glu Ile Leu Ser Tyr Asn Val Asp Ile Ile Leu
                405                 410                 415

Tyr Ala Trp Tyr Gly Ser Gly Tyr Asp Tyr Gln His Val Leu Pro Tyr
            420                 425                 430

Met Lys Ser Lys Cys Ile Lys Asp Lys Tyr Ile Ile Lys Asn Asn Met
        435                 440                 445

Ile Thr Tyr Gly Glu Leu Tyr Tyr Glu Asn Ala Ile Ile Tyr Leu Lys
    450                 455                 460

Asp Pro Tyr Leu Phe Ile Leu Thr Ser Leu Asp Lys Ala Ser Lys Ala
465                 470                 475                 480

Phe Asn Val Ile Asn Lys Gly Glu Phe Pro His Ser Ile Ile His Ser
                485                 490                 495

Trp Glu Asp Leu Asn Lys Ile Leu Pro Asn Trp Val Lys Ile Gln Lys
            500                 505                 510

Arg Met Ile Glu Tyr Lys Asp Asp Asn Lys Leu Asn Ile Tyr Tyr Lys
        515                 520                 525

Asn Ile Glu Ile Phe Glu Asn Asp Arg Asn Tyr Asn Thr Ile Leu Glu
    530                 535                 540

Asn Ala Ile Glu Tyr Cys Lys Val Asp Val Leu Ala Met Glu Lys Val
545                 550                 555                 560
```

```
Trp Ile Lys Phe Lys Lys Leu Leu Glu Lys Asn Leu Asn Ile Thr Val
                565                 570                 575

Ser Val Lys Thr Phe Thr Leu Ser Gln Leu Ser Met Lys Ile Met Glu
            580                 585                 590

Ser Lys Leu Pro Lys Tyr Val Lys Leu Tyr Val Pro Thr Leu Glu Glu
        595                 600                 605

Tyr Ser Lys Ile Arg Asn Ala Ile Tyr Gly Gly Arg Val Ile Ser Lys
    610                 615                 620

Asn Gly Ile Tyr Glu Glu Asn Ile Val Tyr Ala Asp Val Val Ser Leu
625                 630                 635                 640

Tyr Pro Ser Ala Met Lys Leu Leu Lys His Ser Tyr Gly Lys Pro Lys
                645                 650                 655

Leu Val Asp Tyr Ile Asp Phe Glu Lys His Gly Ile Tyr Arg Val Thr
            660                 665                 670

Leu Leu Asn Lys His Asp Gln Glu Pro Lys Asn Tyr Leu Asn Phe Val
        675                 680                 685

Pro Arg Arg Ile Asn Arg Lys Leu Thr Trp Glu Trp Phe Lys Ile His
    690                 695                 700

Glu Gly Trp Tyr His Thr Tyr Asp Leu Ile Ile Ala Lys Ser Glu Gly
705                 710                 715                 720

Phe Asp Ile Tyr Cys His Glu Gly Phe Glu Tyr Pro Glu Lys Asp Tyr
                725                 730                 735

Ile Phe Asn Asp Phe Ile Asp Thr Leu Tyr Ser Met Lys Glu Thr His
            740                 745                 750

Thr Ala Cys Ser Cys Glu Glu Gln Pro Cys Pro Ile Arg Met Val Ala
        755                 760                 765

Lys Ile Ala Leu Asn Gly Gly Gly Tyr Gly Lys Phe Val Gln Lys Pro
    770                 775                 780

Ile Asp Lys Glu Ile Tyr Ile Val Lys Arg Asp Val Val Ala Gly Glu
785                 790                 795                 800

Cys Asp Lys Leu Gln Glu Asn Glu Asn Gly Glu Ile Cys Ile Gly Lys
                805                 810                 815

Arg Leu Val Lys Arg Pro Leu Phe Tyr Asn Leu Asp Ser Glu Asn Tyr
            820                 825                 830

Asp Lys Met Ile Ile Glu Lys Glu Asp Glu Pro Ile Tyr Ser Thr Gln
        835                 840                 845

Cys Gly Ile Ser Ile Leu Ser Ala Ser Arg Tyr Arg Leu Tyr Lys Leu
    850                 855                 860

Cys Lys Gln Phe Glu Asn Ile Asp Ile Ile Tyr Ser Asp Thr Asp Ser
865                 870                 875                 880

Ile Ala Val Lys Gln Lys Ser Val Asp Trp Glu Leu Phe Lys Ser Lys
                885                 890                 895

Cys Gly Ser Glu Leu Gly Gln Leu Asp Ser Thr Ile Asp Asp Thr Lys
            900                 905                 910

Asn Ala Ile Ile Ser Lys Met Tyr Ile Gly Gly Ala Lys Met Tyr Ala
        915                 920                 925

Phe Glu Tyr Leu Asn Asn Lys Asn Lys Leu Ile Thr Lys Leu His Cys
    930                 935                 940

Lys Gly Val Pro Asn Tyr Met Leu Ser Leu Asn Gln Phe Lys Tyr Leu
945                 950                 955                 960

Met Glu Ser Pro Asp Asn Thr Ile Ala Tyr Lys Phe Glu Ile Ile Arg
                965                 970                 975
```

Arg Lys Leu Val Asn Val Ile Thr Lys Asp Leu Ile Lys Asp Ile Lys
980 985 990

Gln Thr

<210> SEQ ID NO 40
<211> LENGTH: 2985
<212> TYPE: DNA
<213> ORGANISM: Kluyveromyces lactis

<400> SEQUENCE: 40
atgaacgatg aattagcctt tttgaactcc caaatagatg attatagtga cgacattgaa 60
tttttgagaa ccgaagtctt tagaatcaat agatattcta aatcaatcta ttctttaatg 120
aagaattctt caaaggaagc tattaaagaa actattgagt ttaataagta tggtcaagaa 180
attcattcta agattaaaga aaaggaaatt tcattaattg aagcaattaa attgatggaa 240
aagaaatata aatatttgag atcattgaat aagactaaag ataaatctaa gaaaaagaaa 300
attcatacaa aagatattga aactttgaaa acaatctata aaacaaaagc tgattttgat 360
attagaaatt ttaaaaatgc tgaaactttt acttatgaaa attactcttt gttaattcca 420
tcagaaaagg aattgattga tttgatccca gaaatcgaag aagattactc ttactacttc 480
tacgtttcat taactatcac aggtccaact atctttggtg gtgttacaag aaaagttcca 540
atcatcgata cttatggtga cattaataag gatttctaca ataagattaa agaaaacatc 600
acaaaagttt tggatagagt tccattctac gaagaaaagg aatcagaaat tatttgtaag 660
aaagttttga tcactttgac agttaataag tgggaatcta tcgataagtg gtacaagaac 720
gttaagtcta agtctaaaaa gtttaaagat tttactttgt ttttagcttc tgatacttct 780
aaaaattgtg ttcaacaatg tgttgaatat ttgggtggta aatggaacac taactactct 840
ttggaaaaga tgatcccaca acaaaagatt gttacataca tcccattgtt gatggatatc 900
caatacgttc aatctatgga agatttgatc tcagatttcg atgaaccaaa cactgattgt 960
aagaacatcg ctagattgtt aaagtggaat ggtcacatgg gtgtgatcac aaagatcgac 1020
aaggatgtta agattaatag aatacaaaga aagagaatca tcgatgttga aaataaggaa 1080
gttaaagaag ttttctttga tattgaatct ttttcagatg aaactaaaca tcaaatccca 1140
tatttgattt gttggtctta cttgggtgaa ttatattaca gaacaggtaa aaattgtatc 1200
aaagaatttg ttgaagaaat tttatcttac aacgttgata tcatcttgta tgcttggtac 1260
ggttcaggtt atgattacca acatgttttg ccatacatga agtctaaatg tattaaggat 1320
aagtacatta ttaagaataa tatgattact tacggtgaat tatactacga aaacgcaatc 1380
atatatttga aagatccata cttgtttatt ttaacatctt tggataaagc atctaaggct 1440
tttaatgtta ttaataaggg tgaatttcca cattctatca tccattcatg ggaagatttg 1500
aataagattt tgccaaactg ggttaagatc caaaagagaa tgattgaata taaagatgat 1560
aataagttga acatctatta caagaacatc gaaattttcg aaaatgatag aaattataat 1620
actatcttag aaaatgctat tgaatactgt aaagttgatg ttttggcaat ggaaaaggtt 1680
tggatcaagt ttaagaaatt gttggaaaag aatttgaaca ttactgtttc agttaagact 1740
tttacattat ctcaattgtc aatgaagatc atggaatcta aattgccaaa gtacgttaaa 1800
ttgtacgttc caacattgga agaatattca aagatcagaa atgctatcta tggtggtaga 1860
gttatttcta aaaatggtat ctatgaagaa aacatcgttt acgctgatgt tgtttcttta 1920
tacccatcag caatgaaatt gttgaagcat tcttatggta aaccaaaatt ggttgattac 1980
atcgatttcg aaaagcatgg tatctaccgt gttactttgt tgaataagca tgatcaagaa 2040
cctaaaaatt acttaaactt tgttccaaga agaattaata gaaaattgac ttgggaatgg 2100
ttcaagatac atgaaggttg gtatcataca tacgatttga tcatcgctaa gtctgaaggt 2160
ttcgatatct attgccatga aggtttcgaa tacccagaaa aggattacat tttcaatgat 2220
ttcattgata cattatactc tatgaaagaa actcatacag catgttcatg tgaagaacaa 2280
ccatgtccaa tcagaatggt tgctaagatc gcattgaatg gtggtggtta tggtaaattt 2340
gttcaaaaac caatcgataa ggaaatatat atcgttaaga gagatgttgt tgctggtgaa 2400
tgtgataaat tacaagaaaa cgaaaatggt gaaatttgta ttggtaaaag attggttaaa 2460
agaccattat tttataattt ggattcagaa aactacgata aaatgattat tgaaaaagaa 2520
gatgaaccaa tctattctac tcaatgtggt atctcaatct tgtctgcatc aagatataga 2580
ttatacaaat tgtgtaagca attcgaaaac atcgatatca tctattctga tacagattca 2640
attgtggtta aacaaaaatc agttgattgg gaattgttta aatctaagtg tggttcagaa 2700
ttaggtcaat tggattctac tatcgatgat actaagaacg ctatcatctc aaagatgtac 2760
attggtggtg ctaagatgta tgcttttgaa tacttaaaca ataagaataa gttgatcact 2820
aaattgcatt gtaaaggtgt tccaaactac atgttgtctt taaaccaatt caaatatttg 2880
atggaatcac cagataacac aattgcatat aaatttgaaa ttattagaag aaaattggta 2940
aatgtcataa ctaaggactt gatcaaagat atcaagcaga cttga 2985

<210> SEQ ID NO 41
<211> LENGTH: 994
<212> TYPE: PRT
<213> ORGANISM: Kluyveromyces lactis

<400> SEQUENCE: 41

Met Asn Asp Glu Leu Ala Phe Leu Asn Ser Gln Ile Asp Asp Tyr Ser
1 5 10 15

Asp Asp Ile Glu Phe Leu Arg Thr Glu Val Phe Arg Ile Asn Arg Tyr
20 25 30

Ser Lys Ser Ile Tyr Ser Leu Met Lys Asn Ser Ser Lys Glu Ala Ile
35 40 45

Lys Glu Thr Ile Glu Phe Asn Lys Tyr Gly Gln Glu Ile His Ser Lys
50 55 60

Ile Lys Glu Lys Glu Ile Ser Leu Ile Glu Ala Ile Lys Leu Met Glu
65 70 75 80

Lys Lys Tyr Lys Tyr Leu Arg Ser Leu Asn Lys Thr Lys Asp Lys Ser
85 90 95

Lys Lys Lys Lys Ile His Thr Lys Asp Ile Glu Thr Leu Lys Thr Ile
100 105 110

Tyr Lys Thr Lys Ala Asp Phe Asp Ile Arg Asn Phe Lys Asn Ala Glu
115 120 125

Thr Phe Thr Tyr Glu Asn Tyr Ser Leu Leu Ile Pro Ser Glu Lys Glu
130 135 140

Leu Ile Asp Leu Ile Pro Glu Ile Glu Glu Asp Tyr Ser Tyr Tyr Phe
145 150 155 160

Tyr Val Ser Leu Thr Ile Thr Gly Pro Thr Ile Phe Gly Gly Val Thr
165 170 175

Arg Lys Val Pro Ile Ile Asp Thr Tyr Gly Asp Ile Asn Lys Asp Phe
180 185 190

-continued

```
Tyr Asn Lys Ile Lys Glu Asn Ile Thr Lys Val Leu Asp Arg Val Pro
        195                 200                 205

Phe Tyr Glu Glu Lys Glu Ser Glu Ile Ile Cys Lys Lys Val Leu Ile
    210                 215                 220

Thr Leu Thr Val Asn Lys Trp Glu Ser Ile Asp Lys Trp Tyr Lys Asn
225                 230                 235                 240

Val Lys Ser Lys Ser Lys Lys Phe Lys Asp Phe Thr Leu Phe Leu Ala
                245                 250                 255

Ser Asp Thr Ser Lys Asn Cys Val Gln Gln Cys Val Glu Tyr Leu Gly
            260                 265                 270

Gly Lys Trp Asn Thr Asn Tyr Ser Leu Glu Lys Met Ile Pro Gln Gln
        275                 280                 285

Lys Ile Val Thr Tyr Ile Pro Leu Leu Met Asp Ile Gln Tyr Val Gln
    290                 295                 300

Ser Met Glu Asp Leu Ile Ser Asp Phe Asp Glu Pro Asn Thr Asp Cys
305                 310                 315                 320

Lys Asn Ile Ala Arg Leu Leu Lys Trp Asn Gly His Met Gly Val Ile
                325                 330                 335

Thr Lys Ile Asp Lys Asp Val Lys Ile Asn Arg Ile Gln Arg Lys Arg
            340                 345                 350

Ile Ile Asp Val Glu Asn Lys Glu Val Lys Glu Val Phe Phe Asp Ile
        355                 360                 365

Glu Ser Phe Ser Asp Glu Thr Lys His Gln Ile Pro Tyr Leu Ile Cys
    370                 375                 380

Trp Ser Tyr Leu Gly Glu Leu Tyr Tyr Arg Thr Gly Lys Asn Cys Ile
385                 390                 395                 400

Lys Glu Phe Val Glu Glu Ile Leu Ser Tyr Asn Val Asp Ile Ile Leu
                405                 410                 415

Tyr Ala Trp Tyr Gly Ser Gly Tyr Asp Tyr Gln His Val Leu Pro Tyr
            420                 425                 430

Met Lys Ser Lys Cys Ile Lys Asp Lys Tyr Ile Ile Lys Asn Asn Met
        435                 440                 445

Ile Thr Tyr Gly Glu Leu Tyr Tyr Glu Asn Ala Ile Ile Tyr Leu Lys
    450                 455                 460

Asp Pro Tyr Leu Phe Ile Leu Thr Ser Leu Asp Lys Ala Ser Lys Ala
465                 470                 475                 480

Phe Asn Val Ile Asn Lys Gly Glu Phe Pro His Ser Ile Ile His Ser
                485                 490                 495

Trp Glu Asp Leu Asn Lys Ile Leu Pro Asn Trp Val Lys Ile Gln Lys
            500                 505                 510

Arg Met Ile Glu Tyr Lys Asp Asp Asn Lys Leu Asn Ile Tyr Tyr Lys
        515                 520                 525

Asn Ile Glu Ile Phe Glu Asn Asp Arg Asn Tyr Asn Thr Ile Leu Glu
    530                 535                 540

Asn Ala Ile Glu Tyr Cys Lys Val Asp Val Leu Ala Met Glu Lys Val
545                 550                 555                 560

Trp Ile Lys Phe Lys Lys Leu Leu Glu Lys Asn Leu Asn Ile Thr Val
                565                 570                 575

Ser Val Lys Thr Phe Thr Leu Ser Gln Leu Ser Met Lys Ile Met Glu
            580                 585                 590

Ser Lys Leu Pro Lys Tyr Val Lys Leu Tyr Val Pro Thr Leu Glu Glu
        595                 600                 605
```

```
Tyr Ser Lys Ile Arg Asn Ala Ile Tyr Gly Gly Arg Val Ile Ser Lys
    610                 615                 620

Asn Gly Ile Tyr Glu Glu Asn Ile Val Tyr Ala Asp Val Val Ser Leu
625                 630                 635                 640

Tyr Pro Ser Ala Met Lys Leu Leu Lys His Ser Tyr Gly Lys Pro Lys
                645                 650                 655

Leu Val Asp Tyr Ile Asp Phe Glu Lys His Gly Ile Tyr Arg Val Thr
            660                 665                 670

Leu Leu Asn Lys His Asp Gln Glu Pro Lys Asn Tyr Leu Asn Phe Val
        675                 680                 685

Pro Arg Arg Ile Asn Arg Lys Leu Thr Trp Glu Trp Phe Lys Ile His
    690                 695                 700

Glu Gly Trp Tyr His Thr Tyr Asp Leu Ile Ile Ala Lys Ser Glu Gly
705                 710                 715                 720

Phe Asp Ile Tyr Cys His Glu Gly Phe Glu Tyr Pro Glu Lys Asp Tyr
                725                 730                 735

Ile Phe Asn Asp Phe Ile Asp Thr Leu Tyr Ser Met Lys Glu Thr His
            740                 745                 750

Thr Ala Cys Ser Cys Glu Glu Gln Pro Cys Pro Ile Arg Met Val Ala
        755                 760                 765

Lys Ile Ala Leu Asn Gly Gly Gly Tyr Gly Lys Phe Val Gln Lys Pro
    770                 775                 780

Ile Asp Lys Glu Ile Tyr Ile Val Lys Arg Asp Val Val Ala Gly Glu
785                 790                 795                 800

Cys Asp Lys Leu Gln Glu Asn Glu Asn Gly Glu Ile Cys Ile Gly Lys
                805                 810                 815

Arg Leu Val Lys Arg Pro Leu Phe Tyr Asn Leu Asp Ser Glu Asn Tyr
            820                 825                 830

Asp Lys Met Ile Ile Glu Lys Glu Asp Glu Pro Ile Tyr Ser Thr Gln
        835                 840                 845

Cys Gly Ile Ser Ile Leu Ser Ala Ser Arg Tyr Arg Leu Tyr Lys Leu
    850                 855                 860

Cys Lys Gln Phe Glu Asn Ile Asp Ile Ile Tyr Ser Asp Thr Asp Ser
865                 870                 875                 880

Ile Val Val Lys Gln Lys Ser Val Asp Trp Glu Leu Phe Lys Ser Lys
                885                 890                 895

Cys Gly Ser Glu Leu Gly Gln Leu Asp Ser Thr Ile Asp Asp Thr Lys
            900                 905                 910

Asn Ala Ile Ile Ser Lys Met Tyr Ile Gly Gly Ala Lys Met Tyr Ala
        915                 920                 925

Phe Glu Tyr Leu Asn Asn Lys Asn Lys Leu Ile Thr Lys Leu His Cys
    930                 935                 940

Lys Gly Val Pro Asn Tyr Met Leu Ser Leu Asn Gln Phe Lys Tyr Leu
945                 950                 955                 960

Met Glu Ser Pro Asp Asn Thr Ile Ala Tyr Lys Phe Glu Ile Ile Arg
                965                 970                 975

Arg Lys Leu Val Asn Val Ile Thr Lys Asp Leu Ile Lys Asp Ile Lys
            980                 985                 990

Gln Thr
```

<210> SEQ ID NO 42
<211> LENGTH: 2985
<212> TYPE: DNA

<213> ORGANISM: Kluyveromyces lactis

<400> SEQUENCE: 42
atgaacgatg aattagcctt tttgaactcc caaatagatg attatagtga cgacattgaa 60
tttttgagaa ccgaagtctt tagaatcaat agatattcta aatcaatcta ttctttaatg 120
aagaattctt caaaggaagc tattaaagaa actattgagt ttaataagta tggtcaagaa 180
attcattcta agattaaaga aaaggaaatt tcattaattg aagcaattaa attgatggaa 240
aagaaatata aatatttgag atcattgaat aagactaaag ataaatctaa gaaaaagaaa 300
attcatacaa aagatattga aactttgaaa acaatctata aaacaaaagc tgattttgat 360
attagaaatt ttaaaaatgc tgaaactttt acttatgaaa attactcttt gttaattcca 420
tcagaaaagg aattgattga tttgatccca gaaatcgaag aagattactc ttactacttc 480
tacgtttcat taactatcac aggtccaact atctttggtg gtgttacaag aaaagttcca 540
atcatcgata cttatggtga cattaataag gatttctaca ataagattaa agaaaacatc 600
acaaaagttt tggatagagt tccattctac gaagaaaagg aatcagaaat tatttgtaag 660
aaagttttga tcactttgac agttaataag tgggaatcta tcgataagtg gtacaagaac 720
gttaagtcta agtctaaaaa gtttaaagat tttactttgt ttttagcttc tgatacttct 780
aaaaattgtg ttcaacaatg tgttgaatat ttgggtggta aatggaacac taactactct 840
ttggaaaaga tgatcccaca acaaaagatt gttacataca tcccattgtt gatggatatc 900
caatacgttc aatctatgga agatttgatc tcagatttcg atgaaccaaa cactgattgt 960
aagaacatcg ctagattgtt aaagtggaat ggtcacatgg gtgtgatcac aaagatcgac 1020
aaggatgtta agattaatag aatacaaaga aagagaatca tcgatgttga aaataaggaa 1080
gttaaagaag ttttctttga tattgaatct ttttcagatg aaactaaaca tcaaatccca 1140
tatttgattt gttggtctta cttgggtgaa ttatattaca gaacaggtaa aaattgtatc 1200
aaagaatttg ttgaagaaat tttatcttac aacgttgata tcatcttgta tgcttggtac 1260
ggttcaggtt atgattacca acatgttttg ccatacatga agtctaaatg tattaaggat 1320
aagtacatta ttaagaataa tatgattact tacggtgaat tatactacga aaacgcaatc 1380
atatatttga aagatccata cttgtttatt ttaacatctg cggataaagc atctaaggct 1440
tttaatgtta ttaataaggg tgaatttcca cattctatca tccattcatg ggaagatttg 1500
aataagattt tgccaaactg ggttaagatc caaaagagaa tgattgaata taaagatgat 1560
aataagttga acatctatta caagaacatc gaaattttcg aaaatgatag aaattataat 1620
actatcttag aaaatgctat tgaatactgt aaagttgatg ttttggcaat ggaaaaggtt 1680
tggatcaagt ttaagaaatt gttggaaaag aatttgaaca ttactgtttc agttaagact 1740
tttacattat ctcaattgtc aatgaagatc atggaatcta aattgccaaa gtacgttaaa 1800
ttgtacgttc caacattgga agaatattca aagatcagaa atgctatcta tggtggtaga 1860
gttatttcta aaaatggtat ctatgaagaa aacatcgttt acgctgatgt tgtttcttta 1920
tacccatcag caatgaaatt gttgaagcat tcttatggta aaccaaaatt ggttgattac 1980
atcgatttcg aaaagcatgg tatctaccgt gttactttgt tgaataagca tgatcaagaa 2040
cctaaaaatt acttaaactt tgttccaaga agaattaata gaaaattgac ttgggaatgg 2100
ttcaagatac atgaaggttg gtatcataca tacgatttga tcatcgctaa gtctgaaggt 2160
ttcgatatct attgccatga aggtttcgaa tacccagaaa aggattacat tttcaatgat 2220
ttcattgata cattatactc tatgaaagaa actcatacag catgttcatg tgaagaacaa 2280

```
ccatgtccaa tcagaatggt tgctaagatc gcattgaatg gtggtggtta tggtaaattt   2340

gttcaaaaac caatcgataa ggaaatatat atcgttaaga gagatgttgt tgctggtgaa   2400

tgtgataaat tacaagaaaa cgaaaatggt gaaatttgta ttggtaaaag attggttaaa   2460

agaccattat tttataattt ggattcagaa aactacgata aaatgattat tgaaaaagaa   2520

gatgaaccaa tctattctac tcaatgtggt atctcaatct tgtctgcatc aagatataga   2580

ttatacaaat tgtgtaagca attcgaaaac atcgatatca tctattctga tacagattca   2640

atttttgtta aacaaaaatc agttgattgg gaattgttta aatctaagtg tggttcagaa   2700

ttaggtcaat tggattctac tatcgatgat actaagaacg ctatcatctc aaagatgtac   2760

attggtggtg ctaagatgta tgcttttgaa tacttaaaca ataagaataa gttgatcact   2820

aaattgcatt gtaaaggtgt tccaaactac atgttgtctt taaaccaatt caaatatttg   2880

atggaatcac cagataacac aattgcatat aaatttgaaa ttattagaag aaaattggta   2940

aatgtcataa ctaaggactt gatcaaagat atcaagcaga cttga                  2985
```

<210> SEQ ID NO 43
<211> LENGTH: 994
<212> TYPE: PRT
<213> ORGANISM: Kluyveromyces lactis

<400> SEQUENCE: 43

```
Met Asn Asp Glu Leu Ala Phe Leu Asn Ser Gln Ile Asp Asp Tyr Ser
1               5                   10                  15

Asp Asp Ile Glu Phe Leu Arg Thr Glu Val Phe Arg Ile Asn Arg Tyr
            20                  25                  30

Ser Lys Ser Ile Tyr Ser Leu Met Lys Asn Ser Ser Lys Glu Ala Ile
        35                  40                  45

Lys Glu Thr Ile Glu Phe Asn Lys Tyr Gly Gln Glu Ile His Ser Lys
    50                  55                  60

Ile Lys Glu Lys Glu Ile Ser Leu Ile Glu Ala Ile Lys Leu Met Glu
65                  70                  75                  80

Lys Lys Tyr Lys Tyr Leu Arg Ser Leu Asn Lys Thr Lys Asp Lys Ser
                85                  90                  95

Lys Lys Lys Lys Ile His Thr Lys Asp Ile Glu Thr Leu Lys Thr Ile
            100                 105                 110

Tyr Lys Thr Lys Ala Asp Phe Asp Ile Arg Asn Phe Lys Asn Ala Glu
        115                 120                 125

Thr Phe Thr Tyr Glu Asn Tyr Ser Leu Leu Ile Pro Ser Glu Lys Glu
    130                 135                 140

Leu Ile Asp Leu Ile Pro Glu Ile Glu Glu Asp Tyr Ser Tyr Tyr Phe
145                 150                 155                 160

Tyr Val Ser Leu Thr Ile Thr Gly Pro Thr Ile Phe Gly Gly Val Thr
                165                 170                 175

Arg Lys Val Pro Ile Ile Asp Thr Tyr Gly Asp Ile Asn Lys Asp Phe
            180                 185                 190

Tyr Asn Lys Ile Lys Glu Asn Ile Thr Lys Val Leu Asp Arg Val Pro
        195                 200                 205

Phe Tyr Glu Glu Lys Glu Ser Glu Ile Ile Cys Lys Lys Val Leu Ile
    210                 215                 220

Thr Leu Thr Val Asn Lys Trp Glu Ser Ile Asp Lys Trp Tyr Lys Asn
225                 230                 235                 240
```

```
Val Lys Ser Lys Ser Lys Lys Phe Lys Asp Phe Thr Leu Phe Leu Ala
                245                 250                 255

Ser Asp Thr Ser Lys Asn Cys Val Gln Gln Cys Val Glu Tyr Leu Gly
            260                 265                 270

Gly Lys Trp Asn Thr Asn Tyr Ser Leu Glu Lys Met Ile Pro Gln Gln
        275                 280                 285

Lys Ile Val Thr Tyr Ile Pro Leu Leu Met Asp Ile Gln Tyr Val Gln
    290                 295                 300

Ser Met Glu Asp Leu Ile Ser Asp Phe Asp Glu Pro Asn Thr Asp Cys
305                 310                 315                 320

Lys Asn Ile Ala Arg Leu Leu Lys Trp Asn Gly His Met Gly Val Ile
                325                 330                 335

Thr Lys Ile Asp Lys Asp Val Lys Ile Asn Arg Ile Gln Arg Lys Arg
            340                 345                 350

Ile Ile Asp Val Glu Asn Lys Glu Val Lys Glu Val Phe Phe Asp Ile
        355                 360                 365

Glu Ser Phe Ser Asp Glu Thr Lys His Gln Ile Pro Tyr Leu Ile Cys
    370                 375                 380

Trp Ser Tyr Leu Gly Glu Leu Tyr Tyr Arg Thr Gly Lys Asn Cys Ile
385                 390                 395                 400

Lys Glu Phe Val Glu Glu Ile Leu Ser Tyr Asn Val Asp Ile Ile Leu
                405                 410                 415

Tyr Ala Trp Tyr Gly Ser Gly Tyr Asp Tyr Gln His Val Leu Pro Tyr
            420                 425                 430

Met Lys Ser Lys Cys Ile Lys Asp Lys Tyr Ile Ile Lys Asn Asn Met
        435                 440                 445

Ile Thr Tyr Gly Glu Leu Tyr Tyr Glu Asn Ala Ile Ile Tyr Leu Lys
    450                 455                 460

Asp Pro Tyr Leu Phe Ile Leu Thr Ser Ala Asp Lys Ala Ser Lys Ala
465                 470                 475                 480

Phe Asn Val Ile Asn Lys Gly Glu Phe Pro His Ser Ile Ile His Ser
                485                 490                 495

Trp Glu Asp Leu Asn Lys Ile Leu Pro Asn Trp Val Lys Ile Gln Lys
            500                 505                 510

Arg Met Ile Glu Tyr Lys Asp Asp Asn Lys Leu Asn Ile Tyr Tyr Lys
        515                 520                 525

Asn Ile Glu Ile Phe Glu Asn Asp Arg Asn Tyr Asn Thr Ile Leu Glu
    530                 535                 540

Asn Ala Ile Glu Tyr Cys Lys Val Asp Val Leu Ala Met Glu Lys Val
545                 550                 555                 560

Trp Ile Lys Phe Lys Lys Leu Leu Glu Lys Asn Leu Asn Ile Thr Val
                565                 570                 575

Ser Val Lys Thr Phe Thr Leu Ser Gln Leu Ser Met Lys Ile Met Glu
            580                 585                 590

Ser Lys Leu Pro Lys Tyr Val Lys Leu Tyr Val Pro Thr Leu Glu Glu
        595                 600                 605

Tyr Ser Lys Ile Arg Asn Ala Ile Tyr Gly Gly Arg Val Ile Ser Lys
    610                 615                 620

Asn Gly Ile Tyr Glu Glu Asn Ile Val Tyr Ala Asp Val Val Ser Leu
625                 630                 635                 640

Tyr Pro Ser Ala Met Lys Leu Leu Lys His Ser Tyr Gly Lys Pro Lys
                645                 650                 655
```

Leu Val Asp Tyr Ile Asp Phe Glu Lys His Gly Ile Tyr Arg Val Thr
660 665 670

Leu Leu Asn Lys His Asp Gln Glu Pro Lys Asn Tyr Leu Asn Phe Val
675 680 685

Pro Arg Arg Ile Asn Arg Lys Leu Thr Trp Glu Trp Phe Lys Ile His
690 695 700

Glu Gly Trp Tyr His Thr Tyr Asp Leu Ile Ile Ala Lys Ser Glu Gly
705 710 715 720

Phe Asp Ile Tyr Cys His Glu Gly Phe Glu Tyr Pro Glu Lys Asp Tyr
725 730 735

Ile Phe Asn Asp Phe Ile Asp Thr Leu Tyr Ser Met Lys Glu Thr His
740 745 750

Thr Ala Cys Ser Cys Glu Glu Gln Pro Cys Pro Ile Arg Met Val Ala
755 760 765

Lys Ile Ala Leu Asn Gly Gly Gly Tyr Gly Lys Phe Val Gln Lys Pro
770 775 780

Ile Asp Lys Glu Ile Tyr Ile Val Lys Arg Asp Val Val Ala Gly Glu
785 790 795 800

Cys Asp Lys Leu Gln Glu Asn Glu Asn Gly Glu Ile Cys Ile Gly Lys
805 810 815

Arg Leu Val Lys Arg Pro Leu Phe Tyr Asn Leu Asp Ser Glu Asn Tyr
820 825 830

Asp Lys Met Ile Ile Glu Lys Glu Asp Glu Pro Ile Tyr Ser Thr Gln
835 840 845

Cys Gly Ile Ser Ile Leu Ser Ala Ser Arg Tyr Arg Leu Tyr Lys Leu
850 855 860

Cys Lys Gln Phe Glu Asn Ile Asp Ile Ile Tyr Ser Asp Thr Asp Ser
865 870 875 880

Ile Phe Val Lys Gln Lys Ser Val Asp Trp Glu Leu Phe Lys Ser Lys
885 890 895

Cys Gly Ser Glu Leu Gly Gln Leu Asp Ser Thr Ile Asp Asp Thr Lys
900 905 910

Asn Ala Ile Ile Ser Lys Met Tyr Ile Gly Gly Ala Lys Met Tyr Ala
915 920 925

Phe Glu Tyr Leu Asn Asn Lys Asn Lys Leu Ile Thr Lys Leu His Cys
930 935 940

Lys Gly Val Pro Asn Tyr Met Leu Ser Leu Asn Gln Phe Lys Tyr Leu
945 950 955 960

Met Glu Ser Pro Asp Asn Thr Ile Ala Tyr Lys Phe Glu Ile Ile Arg
965 970 975

Arg Lys Leu Val Asn Val Ile Thr Lys Asp Leu Ile Lys Asp Ile Lys
980 985 990

Gln Thr

<210> SEQ ID NO 44
<211> LENGTH: 2985
<212> TYPE: DNA
<213> ORGANISM: Kluyveromyces lactis

<400> SEQUENCE: 44
atgaacgatg aattagcctt tttgaactcc caaatagatg attatagtga cgacattgaa 60
tttttgagaa ccgaagtctt tagaatcaat agatattcta aatcaatcta ttctttaatg 120
aagaattctt caaaggaagc tattaaagaa actattgagt ttaataagta tggtcaagaa 180

-continued

```
attcattcta agattaaaga aaaggaaatt tcattaattg aagcaattaa attgatggaa    240
aagaaatata aatatttgag atcattgaat aagactaaag ataaatctaa gaaaaagaaa    300
attcatacaa aagatattga aactttgaaa acaatctata aaacaaaagc tgattttgat    360
attagaaatt ttaaaaatgc tgaaactttt acttatgaaa attactcttt gttaattcca    420
tcagaaaagg aattgattga tttgatccca gaaatcgaag aagattactc ttactacttc    480
tacgtttcat taactatcac aggtccaact atctttggtg gtgttacaag aaaagttcca    540
atcatcgata cttatggtga cattaataag gatttctaca ataagattaa agaaaacatc    600
acaaaagttt tggatagagt tccattctac gaagaaaagg aatcagaaat tatttgtaag    660
aaagttttga tcactttgac agttaataag tgggaatcta tcgataagtg gtacaagaac    720
gttaagtcta agtctaaaaa gtttaaagat tttactttgt ttttagcttc tgatacttct    780
aaaaattgtg ttcaacaatg tgttgaatat ttgggtggta aatggaacac taactactct    840
ttggaaaaga tgatcccaca acaaaagatt gttacataca tcccattgtt gatggatatc    900
caatacgttc aatctatgga agatttgatc tcagatttcg atgaaccaaa cactgattgt    960
aagaacatcg ctagattgtt aaagtggaat ggtcacatgg gtgtgatcac aaagatcgac   1020
aaggatgtta agattaatag aatacaaaga aagagaatca tcgatgttga aaataaggaa   1080
gttaaagaag ttttctttga tattgaatct ttttcagatg aaactaaaca tcaaatccca   1140
tatttgattt gttggtctta cttgggtgaa ttatattaca gaacaggtaa aaattgtatc   1200
aaagaatttg ttgaagaaat tttatcttac aacgttgata tcatcttgta tgcttggtac   1260
ggttcaggtt atgattacca acatgttttg ccatacatga agtctaaatg tattaaggat   1320
aagtacatta ttaagaataa tatgattact tacggtgaat tatactacga aaacgcaatc   1380
atatatttga aagatccata cttgtttatt ttaacatctt tggataaagc atctaaggct   1440
tttaatgtta ttaataaggg tgaatttcca cattctatca tccattcatg ggaagatttg   1500
aataagattt tgccaaactg ggttaagatc caaaagagaa tgattgaata taaagatgat   1560
aataagttga acatctatta caagaacatc gaaattttcg aaaatgatag aaattataat   1620
actatcttag aaaatgctat tgaatactgt aaagttgatg ttttggcaat ggaaaaggtt   1680
tggatcaagt ttaagaaatt gttggaaaag aatttgaaca ttactgtttc agttaagact   1740
tttacattat ctcaattgtc aatgaagatc atggaatcta aattgccaaa gtacgttaaa   1800
ttgtacgttc caacattgga agaatattca aagatcagaa atgctatcta tggtggtaga   1860
gttatttcta aaaatggtat ctatgaagaa aacatcgttt acgctgatgt tgtttcttta   1920
tacccatcag caatgaaatt gttgaagcat tcttatggta aaccaaaatt ggttgattac   1980
atcgatttcg aaaagcatgg tatctaccgt gttactttgt tgaataagca tgatcaagaa   2040
cctaaaaatt acttaaactt tgttccaaga agaattaata gaaaattgac ttgggaatgg   2100
ttcaagatac atgaaggttg gtatcataca tacgatttga tcatcgctaa gtctgaaggt   2160
ttcgatatct attgccatga aggtttcgaa tacccagaaa aggattacat tttcaatgat   2220
ttcattgata cattatactc tatgaaagaa actcatacag catgttcatg tgaagaacaa   2280
ccatgtccaa tcagaatggt tgctaagatc gcattgaatg gtggtggtta tggtaaattt   2340
gttcaaaaac caatcgataa ggaaatatat atcgttaaga gagatgttgt tgctggtgaa   2400
tgtgataaat tacaagaaaa cgaaaatggt gaaatttgta ttggtaaaag attggttaaa   2460
agaccattat tttataattt ggattcagaa aactacgata aaatgattat tgaaaaagaa   2520
gatgaaccaa tctattctac tcaatgtggt atctcaatct tgtctgcatc aagatataga   2580
```

```
ttatacaaat tgtgtaagca attcgaaaac atcgatatca tctattctga tacagattca   2640

attcgggtta aacaaaaatc agttgattgg gaattgttta aatctaagtg tggttcagaa   2700

ttaggtcaat tggattctac tatcgatgat actaagaacg ctatcatctc aaagatgtac   2760

attggtggtg ctaagatgta tgcttttgaa tacttaaaca ataagaataa gttgatcact   2820

aaattgcatt gtaaaggtgt tccaaactac atgttgtctt taaaccaatt caaatatttg   2880

atggaatcac cagataacac aattgcatat aaatttgaaa ttattagaag aaaattggta   2940

aatgtcataa ctaaggactt gatcaaagat atcaagcaga cttga                  2985
```

<210> SEQ ID NO 45
<211> LENGTH: 994
<212> TYPE: PRT
<213> ORGANISM: Kluyveromyces lactis

<400> SEQUENCE: 45

```
Met Asn Asp Glu Leu Ala Phe Leu Asn Ser Gln Ile Asp Asp Tyr Ser
1               5                   10                  15

Asp Asp Ile Glu Phe Leu Arg Thr Glu Val Phe Arg Ile Asn Arg Tyr
            20                  25                  30

Ser Lys Ser Ile Tyr Ser Leu Met Lys Asn Ser Ser Lys Glu Ala Ile
        35                  40                  45

Lys Glu Thr Ile Glu Phe Asn Lys Tyr Gly Gln Glu Ile His Ser Lys
    50                  55                  60

Ile Lys Glu Lys Glu Ile Ser Leu Ile Glu Ala Ile Lys Leu Met Glu
65                  70                  75                  80

Lys Lys Tyr Lys Tyr Leu Arg Ser Leu Asn Lys Thr Lys Asp Lys Ser
                85                  90                  95

Lys Lys Lys Lys Ile His Thr Lys Asp Ile Glu Thr Leu Lys Thr Ile
            100                 105                 110

Tyr Lys Thr Lys Ala Asp Phe Asp Ile Arg Asn Phe Lys Asn Ala Glu
        115                 120                 125

Thr Phe Thr Tyr Glu Asn Tyr Ser Leu Leu Ile Pro Ser Glu Lys Glu
    130                 135                 140

Leu Ile Asp Leu Ile Pro Glu Ile Glu Glu Asp Tyr Ser Tyr Tyr Phe
145                 150                 155                 160

Tyr Val Ser Leu Thr Ile Thr Gly Pro Thr Ile Phe Gly Gly Val Thr
                165                 170                 175

Arg Lys Val Pro Ile Ile Asp Thr Tyr Gly Asp Ile Asn Lys Asp Phe
            180                 185                 190

Tyr Asn Lys Ile Lys Glu Asn Ile Thr Lys Val Leu Asp Arg Val Pro
        195                 200                 205

Phe Tyr Glu Glu Lys Glu Ser Glu Ile Ile Cys Lys Lys Val Leu Ile
    210                 215                 220

Thr Leu Thr Val Asn Lys Trp Glu Ser Ile Asp Lys Trp Tyr Lys Asn
225                 230                 235                 240

Val Lys Ser Lys Ser Lys Lys Phe Lys Asp Phe Thr Leu Phe Leu Ala
                245                 250                 255

Ser Asp Thr Ser Lys Asn Cys Val Gln Gln Cys Val Glu Tyr Leu Gly
            260                 265                 270

Gly Lys Trp Asn Thr Asn Tyr Ser Leu Glu Lys Met Ile Pro Gln Gln
        275                 280                 285

Lys Ile Val Thr Tyr Ile Pro Leu Leu Met Asp Ile Gln Tyr Val Gln
    290                 295                 300
```

Ser Met Glu Asp Leu Ile Ser Asp Phe Asp Glu Pro Asn Thr Asp Cys
305 310 315 320

Lys Asn Ile Ala Arg Leu Leu Lys Trp Asn Gly His Met Gly Val Ile
325 330 335

Thr Lys Ile Asp Lys Asp Val Lys Ile Asn Arg Ile Gln Arg Lys Arg
340 345 350

Ile Ile Asp Val Glu Asn Lys Glu Val Lys Glu Val Phe Phe Asp Ile
355 360 365

Glu Ser Phe Ser Asp Glu Thr Lys His Gln Ile Pro Tyr Leu Ile Cys
370 375 380

Trp Ser Tyr Leu Gly Glu Leu Tyr Tyr Arg Thr Gly Lys Asn Cys Ile
385 390 395 400

Lys Glu Phe Val Glu Glu Ile Leu Ser Tyr Asn Val Asp Ile Ile Leu
405 410 415

Tyr Ala Trp Tyr Gly Ser Gly Tyr Asp Tyr Gln His Val Leu Pro Tyr
420 425 430

Met Lys Ser Lys Cys Ile Lys Asp Lys Tyr Ile Ile Lys Asn Asn Met
435 440 445

Ile Thr Tyr Gly Glu Leu Tyr Tyr Glu Asn Ala Ile Ile Tyr Leu Lys
450 455 460

Asp Pro Tyr Leu Phe Ile Leu Thr Ser Leu Asp Lys Ala Ser Lys Ala
465 470 475 480

Phe Asn Val Ile Asn Lys Gly Glu Phe Pro His Ser Ile Ile His Ser
485 490 495

Trp Glu Asp Leu Asn Lys Ile Leu Pro Asn Trp Val Lys Ile Gln Lys
500 505 510

Arg Met Ile Glu Tyr Lys Asp Asp Asn Lys Leu Asn Ile Tyr Tyr Lys
515 520 525

Asn Ile Glu Ile Phe Glu Asn Asp Arg Asn Tyr Asn Thr Ile Leu Glu
530 535 540

Asn Ala Ile Glu Tyr Cys Lys Val Asp Val Leu Ala Met Glu Lys Val
545 550 555 560

Trp Ile Lys Phe Lys Lys Leu Leu Glu Lys Asn Leu Asn Ile Thr Val
565 570 575

Ser Val Lys Thr Phe Thr Leu Ser Gln Leu Ser Met Lys Ile Met Glu
580 585 590

Ser Lys Leu Pro Lys Tyr Val Lys Leu Tyr Val Pro Thr Leu Glu Glu
595 600 605

Tyr Ser Lys Ile Arg Asn Ala Ile Tyr Gly Gly Arg Val Ile Ser Lys
610 615 620

Asn Gly Ile Tyr Glu Glu Asn Ile Val Tyr Ala Asp Val Val Ser Leu
625 630 635 640

Tyr Pro Ser Ala Met Lys Leu Leu Lys His Ser Tyr Gly Lys Pro Lys
645 650 655

Leu Val Asp Tyr Ile Asp Phe Glu Lys His Gly Ile Tyr Arg Val Thr
660 665 670

Leu Leu Asn Lys His Asp Gln Glu Pro Lys Asn Tyr Leu Asn Phe Val
675 680 685

Pro Arg Arg Ile Asn Arg Lys Leu Thr Trp Glu Trp Phe Lys Ile His
690 695 700

Glu Gly Trp Tyr His Thr Tyr Asp Leu Ile Ile Ala Lys Ser Glu Gly
705 710 715 720

```
Phe Asp Ile Tyr Cys His Glu Gly Phe Glu Tyr Pro Glu Lys Asp Tyr
                725                 730                 735

Ile Phe Asn Asp Phe Ile Asp Thr Leu Tyr Ser Met Lys Glu Thr His
            740                 745                 750

Thr Ala Cys Ser Cys Glu Glu Gln Pro Cys Pro Ile Arg Met Val Ala
        755                 760                 765

Lys Ile Ala Leu Asn Gly Gly Gly Tyr Gly Lys Phe Val Gln Lys Pro
    770                 775                 780

Ile Asp Lys Glu Ile Tyr Ile Val Lys Arg Asp Val Val Ala Gly Glu
785                 790                 795                 800

Cys Asp Lys Leu Gln Glu Asn Glu Asn Gly Glu Ile Cys Ile Gly Lys
                805                 810                 815

Arg Leu Val Lys Arg Pro Leu Phe Tyr Asn Leu Asp Ser Glu Asn Tyr
            820                 825                 830

Asp Lys Met Ile Ile Glu Lys Glu Asp Glu Pro Ile Tyr Ser Thr Gln
        835                 840                 845

Cys Gly Ile Ser Ile Leu Ser Ala Ser Arg Tyr Arg Leu Tyr Lys Leu
    850                 855                 860

Cys Lys Gln Phe Glu Asn Ile Asp Ile Ile Tyr Ser Asp Thr Asp Ser
865                 870                 875                 880

Ile Arg Val Lys Gln Lys Ser Val Asp Trp Glu Leu Phe Lys Ser Lys
                885                 890                 895

Cys Gly Ser Glu Leu Gly Gln Leu Asp Ser Thr Ile Asp Asp Thr Lys
            900                 905                 910

Asn Ala Ile Ile Ser Lys Met Tyr Ile Gly Gly Ala Lys Met Tyr Ala
        915                 920                 925

Phe Glu Tyr Leu Asn Asn Lys Asn Lys Leu Ile Thr Lys Leu His Cys
    930                 935                 940

Lys Gly Val Pro Asn Tyr Met Leu Ser Leu Asn Gln Phe Lys Tyr Leu
945                 950                 955                 960

Met Glu Ser Pro Asp Asn Thr Ile Ala Tyr Lys Phe Glu Ile Ile Arg
                965                 970                 975

Arg Lys Leu Val Asn Val Ile Thr Lys Asp Leu Ile Lys Asp Ile Lys
            980                 985                 990

Gln Thr


<210> SEQ ID NO 46
<211> LENGTH: 2985
<212> TYPE: DNA
<213> ORGANISM: Kluyveromyces lactis

<400> SEQUENCE: 46

atgaacgatg aattagcctt tttgaactcc caaatagatg attatagtga cgacattgaa      60

tttttgagaa ccgaagtctt tagaatcaat agatattcta aatcaatcta ttctttaatg     120

aagaattctt caaaggaagc tattaaagaa actattgagt ttaataagta tggtcaagaa     180

attcattcta agattaaaga aaaggaaatt tcattaattg aagcaattaa attgatggaa     240

aagaaatata aatatttgag atcattgaat aagactaaag ataaatctaa gaaaaagaaa     300

attcatacaa aagatattga aactttgaaa acaatctata aaacaaaagc tgattttgat     360

attagaaatt ttaaaaatgc tgaaactttt acttatgaaa attactcttt gttaattcca     420

tcagaaaagg aattgattga tttgatccca gaaatcgaag aagattactc ttactacttc     480

tacgtttcat taactatcac aggtccaact atctttggtg gtgttacaag aaaagttcca     540
```

```
atcatcgata cttatggtga cattaataag gatttctaca ataagattaa agaaaacatc     600
acaaaagttt tggatagagt tccattctac gaagaaaagg aatcagaaat tatttgtaag     660
aaagttttga tcactttgac agttaataag tgggaatcta tcgataagtg gtacaagaac     720
gttaagtcta agtctaaaaa gtttaaagat tttactttgt ttttagcttc tgatacttct     780
aaaaattgtg ttcaacaatg tgttgaatat ttgggtggta aatggaacac taactactct     840
ttggaaaaga tgatcccaca acaaaagatt gttacataca tcccattgtt gatggatatc     900
caatacgttc aatctatgga agatttgatc tcagatttcg atgaaccaaa cactgattgt     960
aagaacatcg ctagattgtt aaagtggaat ggtcacatgg gtgtgatcac aaagatcgac    1020
aaggatgtta agattaatag aatacaaaga aagagaatca tcgatgttga aaataaggaa    1080
gttaaagaag ttttctttga tattgaatct ttttcagatg aaactaaaca tcaaatccca    1140
tatttgattt gttggtctta cttgggtgaa ttatattaca gaacaggtaa aaattgtatc    1200
aaagaatttg ttgaagaaat tttatcttac aacgttgata tcatcttgta tgcttggtac    1260
ggttcaggtt atgattacca acatgttttg ccatacatga agtctaaatg tattaaggat    1320
aagtacatta ttaagaataa tatgattact tacggtgaat tatactacga aaacgcaatc    1380
atatatttga aagatccata cttgtttatt ttaacatctg ttgataaagc atctaaggct    1440
tttaatgtta ttaataaggg tgaatttcca cattctatca tccattcatg ggaagatttg    1500
aataagattt tgccaaactg ggttaagatc caaaagagaa tgattgaata taaagatgat    1560
aataagttga acatctatta caagaacatc gaaattttcg aaaatgatag aaattataat    1620
actatcttag aaaatgctat tgaatactgt aaagttgatg ttttggcaat ggaaaaggtt    1680
tggatcaagt ttaagaaatt gttggaaaag aatttgaaca ttactgtttc agttaagact    1740
tttacattat ctcaattgtc aatgaagatc atggaatcta aattgccaaa gtacgttaaa    1800
ttgtacgttc caacattgga agaatattca aagatcagaa atgctatcta tggtggtaga    1860
gttatttcta aaaatggtat ctatgaagaa aacatcgttt acgctgatgt tgtttcttta    1920
tacccatcag caatgaaatt gttgaagcat tcttatggta aaccaaaatt ggttgattac    1980
atcgatttcg aaaagcatgg tatctaccgt gttactttgt tgaataagca tgatcaagaa    2040
cctaaaaatt acttaaactt tgttccaaga agaattaata gaaaattgac ttgggaatgg    2100
ttcaagatac atgaaggttg gtatcataca tacgatttga tcatcgctaa gtctgaaggt    2160
ttcgatatct attgccatga aggtttcgaa tacccagaaa aggattacat tttcaatgat    2220
ttcattgata cattatactc tatgaaagaa actcatacag catgttcatg tgaagaacaa    2280
ccatgtccaa tcagaatggt tgctaagatc gcattgaatg gtggtggtta tggtaaattt    2340
gttcaaaaac caatcgataa ggaaatatat atcgttaaga gagatgttgt tgctggtgaa    2400
tgtgataaat tacaagaaaa cgaaaatggt gaaatttgta ttggtaaaag attggttaaa    2460
agaccattat tttataattt ggattcagaa aactacgata aaatgattat tgaaaaagaa    2520
gatgaaccaa tctattctac tcaatgtggt atctcaatct tgtctgcatc aagatataga    2580
ttatacaaat tgtgtaagca attcgaaaac atcgatatca tctattctga tacagattca    2640
atttttgtta aacaaaaatc agttgattgg gaattgttta aatctaagtg tggttcagaa    2700
ttaggtcaat tggattctac tatcgatgat actaagaacg ctatcatctc aaagatgtac    2760
attggtggtg ctaagatgta tgcttttgaa tacttaaaca ataagaataa gttgatcact    2820
```

aaattgcatt gtaaaggtgt tccaaactac atgttgtctt taaaccaatt caaatatttg 2880
atggaatcac cagataacac aattgcatat aaatttgaaa ttattagaag aaaattggta 2940
aatgtcataa ctaaggactt gatcaaagat atcaagcaga cttga 2985

<210> SEQ ID NO 47
<211> LENGTH: 994
<212> TYPE: PRT
<213> ORGANISM: Kluyveromyces lactis

<400> SEQUENCE: 47

Met Asn Asp Glu Leu Ala Phe Leu Asn Ser Gln Ile Asp Asp Tyr Ser
1 5 10 15

Asp Asp Ile Glu Phe Leu Arg Thr Glu Val Phe Arg Ile Asn Arg Tyr
20 25 30

Ser Lys Ser Ile Tyr Ser Leu Met Lys Asn Ser Ser Lys Glu Ala Ile
35 40 45

Lys Glu Thr Ile Glu Phe Asn Lys Tyr Gly Gln Glu Ile His Ser Lys
50 55 60

Ile Lys Glu Lys Glu Ile Ser Leu Ile Glu Ala Ile Lys Leu Met Glu
65 70 75 80

Lys Lys Tyr Lys Tyr Leu Arg Ser Leu Asn Lys Thr Lys Asp Lys Ser
85 90 95

Lys Lys Lys Lys Ile His Thr Lys Asp Ile Glu Thr Leu Lys Thr Ile
100 105 110

Tyr Lys Thr Lys Ala Asp Phe Asp Ile Arg Asn Phe Lys Asn Ala Glu
115 120 125

Thr Phe Thr Tyr Glu Asn Tyr Ser Leu Leu Ile Pro Ser Glu Lys Glu
130 135 140

Leu Ile Asp Leu Ile Pro Glu Ile Glu Glu Asp Tyr Ser Tyr Tyr Phe
145 150 155 160

Tyr Val Ser Leu Thr Ile Thr Gly Pro Thr Ile Phe Gly Gly Val Thr
165 170 175

Arg Lys Val Pro Ile Ile Asp Thr Tyr Gly Asp Ile Asn Lys Asp Phe
180 185 190

Tyr Asn Lys Ile Lys Glu Asn Ile Thr Lys Val Leu Asp Arg Val Pro
195 200 205

Phe Tyr Glu Glu Lys Glu Ser Glu Ile Ile Cys Lys Lys Val Leu Ile
210 215 220

Thr Leu Thr Val Asn Lys Trp Glu Ser Ile Asp Lys Trp Tyr Lys Asn
225 230 235 240

Val Lys Ser Lys Ser Lys Lys Phe Lys Asp Phe Thr Leu Phe Leu Ala
245 250 255

Ser Asp Thr Ser Lys Asn Cys Val Gln Gln Cys Val Glu Tyr Leu Gly
260 265 270

Gly Lys Trp Asn Thr Asn Tyr Ser Leu Glu Lys Met Ile Pro Gln Gln
275 280 285

Lys Ile Val Thr Tyr Ile Pro Leu Leu Met Asp Ile Gln Tyr Val Gln
290 295 300

Ser Met Glu Asp Leu Ile Ser Asp Phe Asp Glu Pro Asn Thr Asp Cys
305 310 315 320

Lys Asn Ile Ala Arg Leu Leu Lys Trp Asn Gly His Met Gly Val Ile
325 330 335

```
Thr Lys Ile Asp Lys Asp Val Lys Ile Asn Arg Ile Gln Arg Lys Arg
                340                 345                 350

Ile Ile Asp Val Glu Asn Lys Glu Val Lys Glu Val Phe Phe Asp Ile
        355                 360                 365

Glu Ser Phe Ser Asp Glu Thr Lys His Gln Ile Pro Tyr Leu Ile Cys
    370                 375                 380

Trp Ser Tyr Leu Gly Glu Leu Tyr Tyr Arg Thr Gly Lys Asn Cys Ile
385                 390                 395                 400

Lys Glu Phe Val Glu Glu Ile Leu Ser Tyr Asn Val Asp Ile Ile Leu
                405                 410                 415

Tyr Ala Trp Tyr Gly Ser Gly Tyr Asp Tyr Gln His Val Leu Pro Tyr
            420                 425                 430

Met Lys Ser Lys Cys Ile Lys Asp Lys Tyr Ile Ile Lys Asn Asn Met
        435                 440                 445

Ile Thr Tyr Gly Glu Leu Tyr Tyr Glu Asn Ala Ile Ile Tyr Leu Lys
    450                 455                 460

Asp Pro Tyr Leu Phe Ile Leu Thr Ser Val Asp Lys Ala Ser Lys Ala
465                 470                 475                 480

Phe Asn Val Ile Asn Lys Gly Glu Phe Pro His Ser Ile Ile His Ser
                485                 490                 495

Trp Glu Asp Leu Asn Lys Ile Leu Pro Asn Trp Val Lys Ile Gln Lys
            500                 505                 510

Arg Met Ile Glu Tyr Lys Asp Asp Asn Lys Leu Asn Ile Tyr Tyr Lys
        515                 520                 525

Asn Ile Glu Ile Phe Glu Asn Asp Arg Asn Tyr Asn Thr Ile Leu Glu
    530                 535                 540

Asn Ala Ile Glu Tyr Cys Lys Val Asp Val Leu Ala Met Glu Lys Val
545                 550                 555                 560

Trp Ile Lys Phe Lys Lys Leu Leu Glu Lys Asn Leu Asn Ile Thr Val
                565                 570                 575

Ser Val Lys Thr Phe Thr Leu Ser Gln Leu Ser Met Lys Ile Met Glu
            580                 585                 590

Ser Lys Leu Pro Lys Tyr Val Lys Leu Tyr Val Pro Thr Leu Glu Glu
        595                 600                 605

Tyr Ser Lys Ile Arg Asn Ala Ile Tyr Gly Gly Arg Val Ile Ser Lys
    610                 615                 620

Asn Gly Ile Tyr Glu Glu Asn Ile Val Tyr Ala Asp Val Val Ser Leu
625                 630                 635                 640

Tyr Pro Ser Ala Met Lys Leu Leu Lys His Ser Tyr Gly Lys Pro Lys
                645                 650                 655

Leu Val Asp Tyr Ile Asp Phe Glu Lys His Gly Ile Tyr Arg Val Thr
            660                 665                 670

Leu Leu Asn Lys His Asp Gln Glu Pro Lys Asn Tyr Leu Asn Phe Val
        675                 680                 685

Pro Arg Arg Ile Asn Arg Lys Leu Thr Trp Glu Trp Phe Lys Ile His
    690                 695                 700

Glu Gly Trp Tyr His Thr Tyr Asp Leu Ile Ile Ala Lys Ser Glu Gly
705                 710                 715                 720

Phe Asp Ile Tyr Cys His Glu Gly Phe Glu Tyr Pro Glu Lys Asp Tyr
                725                 730                 735

Ile Phe Asn Asp Phe Ile Asp Thr Leu Tyr Ser Met Lys Glu Thr His
            740                 745                 750
```

```
Thr Ala Cys Ser Cys Glu Glu Gln Pro Cys Pro Ile Arg Met Val Ala
        755                 760                 765

Lys Ile Ala Leu Asn Gly Gly Gly Tyr Gly Lys Phe Val Gln Lys Pro
    770                 775                 780

Ile Asp Lys Glu Ile Tyr Ile Val Lys Arg Asp Val Val Ala Gly Glu
785                 790                 795                 800

Cys Asp Lys Leu Gln Glu Asn Glu Asn Gly Glu Ile Cys Ile Gly Lys
                805                 810                 815

Arg Leu Val Lys Arg Pro Leu Phe Tyr Asn Leu Asp Ser Glu Asn Tyr
            820                 825                 830

Asp Lys Met Ile Ile Glu Lys Glu Asp Glu Pro Ile Tyr Ser Thr Gln
        835                 840                 845

Cys Gly Ile Ser Ile Leu Ser Ala Ser Arg Tyr Arg Leu Tyr Lys Leu
    850                 855                 860

Cys Lys Gln Phe Glu Asn Ile Asp Ile Ile Tyr Ser Asp Thr Asp Ser
865                 870                 875                 880

Ile Phe Val Lys Gln Lys Ser Val Asp Trp Glu Leu Phe Lys Ser Lys
                885                 890                 895

Cys Gly Ser Glu Leu Gly Gln Leu Asp Ser Thr Ile Asp Asp Thr Lys
            900                 905                 910

Asn Ala Ile Ile Ser Lys Met Tyr Ile Gly Gly Ala Lys Met Tyr Ala
        915                 920                 925

Phe Glu Tyr Leu Asn Asn Lys Asn Lys Leu Ile Thr Lys Leu His Cys
    930                 935                 940

Lys Gly Val Pro Asn Tyr Met Leu Ser Leu Asn Gln Phe Lys Tyr Leu
945                 950                 955                 960

Met Glu Ser Pro Asp Asn Thr Ile Ala Tyr Lys Phe Glu Ile Ile Arg
                965                 970                 975

Arg Lys Leu Val Asn Val Ile Thr Lys Asp Leu Ile Lys Asp Ile Lys
            980                 985                 990

Gln Thr
```

<210> SEQ ID NO 48
<211> LENGTH: 7617
<212> TYPE: DNA
<213> ORGANISM: Kluyveromyces lactis

<400> SEQUENCE: 48

```
gagctcgtgt tgttatccga tacaaccgga tatttttctt ttaatgagtc taaaccgtga      60

tagcttcagg ttaatacaat caaaaaaagc tcaaatattc ttttaatgcc gcgttcacag     120

attccaattg aatacaacta ggtagttcat tatatgaagc ctttgctact atttttcact     180

atagtctgcc ttcaccttaa tgcagacatc cacatatttt aatcacttta aaataaaaag     240

gaagatatat tagaagctat gatccaatct gtaagccaga ttaaaattca cgaactcttc     300

tttcatttga attgaatgct ttgagttggg gtagattatc gcaaattact catcacattt     360

attgactacg aacttgctga tgtccttttt ttatttatat ttttcttcag tgaagcgatt     420

tttttttac acagaccaag acggaaaaaa gtagctaagg aagaaaacaa aatcatgaaa     480

aaaatgtgaa gtgatcatgc acatcgcatc aacttaaaca ttggcttaga gatatataga     540

gttagagttt acggcaacct ttaagcacca ataccttttg gcatagtcta aagacctggt     600

tcttaatttt aaacaaattt aactaaagat ttccctatca aagaagtaac gagttgacag     660

attttctcaa aataaatcga tactgcattt ctaggcatat ccagcgagat ctatgaacga     720
```

```
tgaattagcc tttttgaact cccaaataga tgattatagt gacgacattg aatttttgag    780
aaccgaagtc tttagaatca atagatattc taaatcaatc tattctttaa tgaagaattc    840
ttcaaaggaa gctattaaag aaactattga gtttaataag tatggtcaag aaattcattc    900
taagattaaa gaaaaggaaa tttcattaat tgaagcaatt aaattgatgg aaaagaaata    960
taaatatttg agatcattga ataagactaa agataaatct aagaaaaaga aaattcatac   1020
aaaagatatt gaaactttga aaacaatcta taaaacaaaa gctgattttg atattagaaa   1080
ttttaaaaat gctgaaactt ttacttatga aaattactct ttgttaattc catcagaaaa   1140
ggaattgatt gatttgatcc cagaaatcga agaagattac tcttactact tctacgtttc   1200
attaactatc acaggtccaa ctatctttgg tggtgttaca agaaaagttc caatcatcga   1260
tacttatggt gacattaata aggatttcta caataagatt aaagaaaaca tcacaaaagt   1320
tttggataga gttccattct acgaagaaaa ggaatcagaa attatttgta agaaagtttt   1380
gatcactttg acagttaata agtgggaatc tatcgataag tggtacaaga acgttaagtc   1440
taagtctaaa aagtttaaag attttacttt gtttttagct tctgatactt ctaaaaattg   1500
tgttcaacaa tgtgttgaat atttgggtgg taaatggaac actaactact ctttggaaaa   1560
gatgatccca caacaaaaga ttgttacata catcccattg ttgatggata tccaatacgt   1620
tcaatctatg gaagatttga tctcagattt cgatgaacca aacactgatt gtaagaacat   1680
cgctagattg ttaaagtgga atggtcacat gggtgtgatc acaaagatcg acaaggatgt   1740
taagattaat agaatacaaa gaaagagaat catcgatgtt gaaaataagg aagttaaaga   1800
agttttcttt gatattgaat ctttttcaga tgaaactaaa catcaaatcc catatttgat   1860
ttgttggtct tacttgggtg aattatatta cagaacaggt aaaaattgta tcaaagaatt   1920
tgttgaagaa attttatctt acaacgttga tatcatcttg tatgcttggt acggttcagg   1980
ttatgattac caacatgttt tgccatacat gaagtctaaa tgtattaagg ataagtacat   2040
tattaagaat aatatgatta cttacggtga attatactac gaaaacgcaa tcatatattt   2100
gaaagatcca tacttgttta ttttaacatc tttggataaa gcatctaagg cttttaatgt   2160
tattaataag ggtgaatttc cacattctat catccattca tgggaagatt tgaataagat   2220
tttgccaaac tgggttaaga tccaaaagag aatgattgaa tataaagatg ataataagtt   2280
gaacatctat tacaagaaca tcgaaatttt cgaaaatgat agaaattata atactatctt   2340
agaaaatgct attgaatact gtaaagttga tgttttggca atggaaaagg tttggatcaa   2400
gtttaagaaa ttgttggaaa agaatttgaa cattactgtt tcagttaaga cttttacatt   2460
atctcaattg tcaatgaaga tcatggaatc taaattgcca aagtacgtta aattgtacgt   2520
tccaacattg gaagaatatt caaagatcag aaatgctatc tatggtggta gagttatttc   2580
taaaaatggt atctatgaag aaaacatcgt ttacgctgat gttgtttctt tataccaatc   2640
agcaatgaaa ttgttgaagc attcttatgg taaaccaaaa ttggttgatt acatcgattt   2700
cgaaaagcat ggtatctacc gtgttacttt gttgaataag catgatcaag aacctaaaaa   2760
ttacttaaac tttgttccaa gaagaattaa tagaaaattg acttgggaat ggttcaagat   2820
acatgaaggt tggtatcata catacgattt gatcatcgct aagtctgaag gtttcgatat   2880
ctattgccat gaaggtttcg aatacccaga aaaggattac attttcaatg atttcattga   2940
tacattatac tctatgaaag aaactcatac agcatgttca tgtgaagaac aaccatgtcc   3000
aatcagaatg gttgctaaga tcgcattgaa tggtggtggt tatggtaaat ttgttcaaaa   3060
accaatcgat aaggaaatat atatcgttaa gagagatgtt gttgctggtg aatgtgataa   3120
```

attacaagaa aacgaaaatg gtgaaatttg tattggtaaa agattggtta aaagaccatt 3180
attttataat ttggattcag aaaactacga taaaatgatt attgaaaaag aagatgaacc 3240
aatctattct actcaatgtg gtatctcaat cttgtctgca tcaagatata gattatacaa 3300
attgtgtaag caattcgaaa acatcgatat catctattct gatacagatt caatttttgt 3360
taaacaaaaa tcagttgatt gggaattgtt taaatctaag tgtggttcag aattaggtca 3420
attggattct actatcgatg atactaagaa cgctatcatc tcaaagatgt acattggtgg 3480
tgctaagatg tatgcttttg aatacttaaa caataagaat aagttgatca ctaaattgca 3540
ttgtaaaggt gttccaaact acatgttgtc tttaaaccaa ttcaaatatt tgatggaatc 3600
accagataac acaattgcat ataaatttga aattattaga agaaaattgg taaatgtcat 3660
aactaaggac ttgatcaaag atatcaagca gacttgactc gaggcgaatt tcttatgatt 3720
tatgattttt attattaaat aagttataaa aaaaataagt gtatacaaat tttaaagtga 3780
ctcttaggtt ttaaaacgaa aattcttatt cttgagtaac tctttcctgt aggtcaggtt 3840
gctttctcag gtatagcatg aggtcgctca ctagtccatg gacgcgtggt accggccgcg 3900
ttgctggcgt ttttccatag gctcggcccc cctgacgagc atcacaaaaa tcgacgctca 3960
agtcagaggt ggcgaaaccc gacaggacta taaagatacc aggcgttccc ccctggaagc 4020
tccctcgtgc gctctcctgt tccgaccctg ccgcttaccg gatacctgtc cgcctttctc 4080
ccttcgggaa gcgtggcgct ttctcaatgc tcacgctgta ggtatctcag ttcggtgtag 4140
gtcgttcgct ccaagctggg ctgtgtgcac gaaccccccg ttcagcccga ccgctgcgcc 4200
ttatccggta actatcgtct tgagtccaac ccggtaagac acgacttatc gccactggca 4260
gcagccactg gtaacaggat tagcagagcg aggtatgtag gcggtgctac agagttcttg 4320
aagtggtggc ctaactacgg ctacactaga aggacagtat ttggtatctg cgctctgctg 4380
aagccagtta ccttcggaaa aagagttggt agctcttgat ccggcaaaca aaccaccgct 4440
ggtagcggtg gtttttttgt ttgcaagcag cagattacgc gcagaaaaaa aggatctcaa 4500
gaagatcctt tgatcttttc tacggggtct gacgctcagt ggaacgaaaa ctcacgttaa 4560
gggattttgg tcatgactga tccttcaact cagcaaaagt tcgatttatt caacaaagcc 4620
acgttgtgtc tcaaaatctc tgatgttaca ttgcacaaga taaaaatata tcatcatgaa 4680
caataaaact gtctgcttac ataaacagta atacaagggg tgttatgagc catattcaac 4740
gggaaacgtc ttgctccagg ccgcgattaa attccaacat ggatgctgat ttatatgggt 4800
ataaatgggc tcgcgataat gtcgggcaat caggtgcgac aatctatcga ttgtatggga 4860
agcccgatgc gccagagttg tttctgaaac atggcaaagg tagcgttgcc aatgatgtta 4920
cagatgagat ggtcagacta aactggctga cggaatttat gcctcttccg accatcaagc 4980
attttatccg tactcctgat gatgcatggt tactcaccac tgcgatcccc gggaaaacag 5040
cattccaggt attagaagaa tatcctgatt caggtgaaaa tattgttgat gcgctggcag 5100
tgttcctgcg ccggttgcat tcgattcctg tttgtaattg tccttttaac agcgatcgcg 5160
tatttcgtct cgctcaggcg caatcacgaa tgaataacgg tttggttgat gcgagtgatt 5220
ttgatgacga gcgtaatggc tggcctgttg aacaagtctg gaaagaaatg cataagcttt 5280
tgccattctc accggattca gtcgtcactc atggtgattt ctcacttgat aaccttattt 5340
ttgacgaggg gaaattaata ggttgtattg atgttggacg agtcggaatc gcagaccgat 5400
accaggatct tgccatccta tggaactgcc tcggtgagtt ttctccttca ttacagaaac 5460

```
ggctttttca aaaatatggt attgataatc ctgatatgaa taaattgcag tttcatttga   5520
tgctcgatga gtttttctaa tcagaattgg ttaattggtt gtaacacggt ccttttcatc   5580
acgtgctata aaaataatta taatttaaat tttttaatat aaatatataa attaaaaata   5640
gaaagtaaaa aaagaaatta aagaaaaaat agtttttgtt ttccgaagat gtaaaagact   5700
ctagggggat cgccaacaaa tactaccttt tatcttgctc ttcctgctct caggtattaa   5760
tgccgaattg tttcatcttg tctgtgtaga agaccacaca cgaaaatcct gtgattttac   5820
attttactta tcgttaatcg aatgtatatc tatttaatct gcttttcttg tctaataaat   5880
atatatgtaa agtacgcttt ttgttgaaat tttttaaacc tttgtttatt tttttttctt   5940
cattccgtaa ctcttctacc ttctttattt actttctaaa atccaaatac aaaacataaa   6000
aataaataaa cacagagtaa attcccaaat tattccatca ttaaaagata cgaggcgcgt   6060
gtaagttaca ggcaagcgat ccgtcctaag aaaccattat tatcatgaca ttaacctata   6120
aaaataggcg tatcacgagg ccctttcgtc tcgcgcgttt cggtgatgac ggtgaaaacc   6180
tctgacacat gcagctcccg gagacggtca cagcttgtct gtaagcggat gccgggagca   6240
gacaagcccg tcagggcgcg tcagcgggtg ttggcgggtg tcggggctgg cttaactatg   6300
cggcatcaga gcagattgta ctgagagtgc accacgcttt tcaattcaat tcatcatttt   6360
tttttattc ttttttttga ttttttaaga gcttggtgag cgctaggagt cactgccagg   6420
tatcgtttga acacggcatt agtcagggaa gtcataacac agtcctttcc cgcaattttc   6480
tttttctatt actcttggcc tcctctagta cactctatat ttttttatgc ctcggtaatg   6540
attttcattt tttttttcc acctagcgga tgactctttt tttttcttag cgattggcat   6600
tatcacataa tgaattatac attatataaa gtaatgtgat ttcttcgaag aatatactaa   6660
aaaatgagca ggcaagataa acgaaggcaa agatgacaga gcagaaagcc ctagtaaagc   6720
gtattacaaa tgaaaccaag attcagattg cgatctcttt aaagggtggt cccctagcga   6780
tagagcactc gatcttccca gaaaaagagg cagaagcagt agcagaacag gccacacaat   6840
cgcaagtgat taacgtccac acaggtatag ggtttctgga ccatatgata catgctctgg   6900
ccaagcattc cggctggtcg ctaatcgttg agtgcattgg tgacttacac atagacgacc   6960
atcacaccac tgaagactgc gggattgctc tcggtcaagc ttttaaagag gccctagggg   7020
ccgtgcgtgg agtaaaaagg tttggatcag gatttgcgcc tttggatgag gcactttcca   7080
gagcggtggt tgatctttcg aacaggccgt acgcagttgt cgaacttggt ttgcaaaggg   7140
agaaagtagg tgatctctct tgcgagatga tcccgcattt tcttgaaagc tttgcagagg   7200
ctagcagaat taccctccac gttgattgtc tgcgaggcaa gaatgatcat caccgtagtg   7260
agagtgcgtt caaggctctt gcggttgcca taagagaagc cacctcgccc aatggtacca   7320
acgatgttcc ctccaccaaa ggtgttctta tgtagtgaca ccgattattt aaagctgctg   7380
catacgatat atatacatgt gtatatatgt atacctatga atgtcagtaa gtatgtatac   7440
gaacagtatg atactgaaga tgacaaggta atgcatcatt ctatacgtgt cattctgaac   7500
gaggcgcgct ttcctttttt ctttttgctt tttctttttt tttctcttga actcgagaaa   7560
aaaaatatgc ggtgtgaaat accgcacaga tgcgtaagga gaaaataccg catcagg      7617
```

<210> SEQ ID NO 49
<211> LENGTH: 7596
<212> TYPE: DNA
<213> ORGANISM: Kluyveromyces lactis

<400> SEQUENCE: 49
gagctcgtgt tgttatccga tacaaccgga tatttttctt ttaatgagtc taaaccgtga 60
tagcttcagg ttaatacaat caaaaaaagc tcaaatattc ttttaatgcc gcgttcacag 120
attccaattg aatacaacta ggtagttcat tatatgaagc ctttgctact atttttcact 180
atagtctgcc ttcaccttaa tgcagacatc cacatatttt aatcacttta aaataaaaag 240
gaagatatat tagaagctat gatccaatct gtaagccaga ttaaaattca cgaactcttc 300
tttcatttga attgaatgct ttgagttggg gtagattatc gcaaattact catcacattt 360
attgactacg aacttgctga tgtccttttt ttatttatat ttttcttcag tgaagcgatt 420
tttttttac acagaccaag acggaaaaaa gtagctaagg aagaaaacaa aatcatgaaa 480
aaaatgtgaa gtgatcatgc acatcgcatc aacttaaaca ttggcttaga gatatataga 540
gttagagttt acggcaacct ttaagcacca ataccttttg gcatagtcta aagacctggt 600
tcttaatttt aaacaaattt aactaaagat ttccctatca aagaagtaac gagttgacag 660
attttctcaa aataaatcga tactgcattt ctaggcatat ccagcgagat ctatggacta 720
caaagacaaa gcattaaacg acttgagaaa cgtatacgca gacttcgact ccttgccatt 780
ggacttcaga caaatcttaa ttaaggatag agctacattg ttgcaaaagg aagacgttga 840
aaagaaaatt ttggaaagac aagaagatgc caaaaagtac gctgaatact tgaagcaatc 900
agaaatccca gaaagaatct ccttacctaa catcaagaga cataagggtg tatcaatctc 960
ctttgaagaa acatctgaag atatggtctt ggaaccaaga ccttttatct tcgacggttt 1020
gaacatcaga tgtttcagaa gagaaaccat attcagtttg aaaaataaga ttttgaacat 1080
ggttaaggaa tcttcatcct ttaaaaacgt ttcaagacaa agtgtatctt ttatgtactt 1140
caaaattttt aataagggta aagttattgc aagtacaaag tctgttaaca tctatgaaga 1200
taagatcgac gaaagattgg aagatttgtg taacaacttc gatgacgtat tgaaaaagat 1260
tatagacgtc acctatggtt acgaatcctt attcgttagt gaaacttact cttacgtaat 1320
attctatgct aaatcaatct actttccaca acctagatgc gttaacaact ggggtaacaa 1380
catcccaaac atcttgacat tcgattcctt taagcttttc accgcaaaca aaaacaacgt 1440
tagttgtatc aagcaatgtt caagattttt gtggcaaaaa gatttcaaca ctttagaaga 1500
aatgatagaa tacaagaacg gtaatatttg tatcgtcaca ccacaattgc atatcaacga 1560
tgttagagac atcaagtcat tcaacgatat cagattgtac tcagaatccc ctattaaaac 1620
attttccgtt attgataaca ctatcacata tttgttttac ttcaaggaac atttgggtgt 1680
tatttttaac atcactaagt caagacatga tagaagagta acaaaatttt caccattgtc 1740
caagttcagt gacgtcaaaa atatcactgt ttgtttcgat atcgaaagtt acttcgaccc 1800
agaaaaggaa tctaaccaag ttaacatccc tttcatttgt tgcgcttcaa tcatctataa 1860
taaggttatt ggtaacatcg tcgattttga aggtagagac tgtgtcgcac aaatgatcga 1920
atacgttgta gatatttgcg gtgaattgaa cataagttct gttgaattga tcgcccataa 1980
cggtggtggt tatgatttcc actacatctt gtcatccatg tataatccag ctgcaattaa 2040
aaacatattg atcagaaaca actcttttat ttcttttaat ttcgcacatg atggtgtcaa 2100
gttctctgtt aaggacagtt actcattttt gttgtgtagt ttggccaacg cttctaaagc 2160
atttttaaac gaagaaactt ttaagaaaac tgatttccct catcacgact tgaaaactgc 2220
cgatgactta tataaggtct acaaggaatg gagttctgtt aacacagaaa ttaaccatgt 2280
cgttgaaaag gaaaagttgt tgatcacctc tgaacacatc gttaacttca ccaagaacga 2340
taagagtaag actttgatcg aatggtctaa ggattactgt agaaacgacg tattggtctt 2400
gtctaaggtt tggttggagt ttaaaaacgc tgtagaagat atttttaact gcgaattggt 2460
agaccaaacc atgactttgg ctggtttgtc atacaagttg ttccaagcaa acatgccatt 2520
cgatgtcgaa ttgagacatc ctaataagga agactacttc aacatgagag aagcattgat 2580
tggtggtaga tgtatctctg ttaacggtat ctacaaggat gttttgtgct tagacgtaaa 2640
atcattatat ccagcttcta tggctttcta tgatcaacct tacggttctt ttaagagagt 2700
ttcatccaga ccaaaagatg aattgggtat ctattacgtt agagtaaccc caaacagaaa 2760
caacaagtca aactttttcc ctatcagatc ccataataag atcacttaca acaacttcga 2820
agaatcaact tatattgctt ggtacacaaa cgttgatatc gacattggtt tgtcagaagg 2880
tcacaacatc gaatacatcc ctttcgattc ctatggtaac attggttact catggtccaa 2940
aaagggtaaa atttttgaaa agtacatcaa ggatgttttg tacaaattga agataaaata 3000
tgaaaagcaa aataacaagg taaaaagaaa tgtcatcaaa aagatcatga actcattgtg 3060
gggtaaattc gcccaaaagt gggttaactt cgaatacttc atcaagtcag aagatgacat 3120
tgatttcgaa tccgaagaag catataaaat ttgggataca gacttcatgt tgatcaaaaa 3180
gattaaggaa tctacctaca gttctaagcc aatacaaaac ggtgttttta ctttaagttg 3240
ggccagatat cacatgaagt ctatttggga tgcaggtgcc aaagaaggtg ctgaatgtat 3300
ctattcagat acagactcca tattcgttca taaggaacac ttcaaaaaga atgcaaagtt 3360
tatgttgaac ggtttgaaag taccaatcat cggttctgaa gtcggtcaat ctgaattaga 3420
atgtgaattt gataaattgt tgtgcgccgg taaaaagcaa tacatgggtt tctacactta 3480
cttccaagat ggtaaacctt gcatcaagga aaagaaaaga ttcaaaggta taccaagtaa 3540
ctacatcata cctgaattgt atgctcactt gttatctggt gcagataagg aagccaaaat 3600
tcaattttta aaattcagaa gagaatgggg ttccgtcaag ggttacatag aaaataagac 3660
tgtcaaagcc acctaactcg aggcgaattt cttatgattt atgattttta ttattaaata 3720
agttataaaa aaaataagtg tatacaaatt ttaaagtgac tcttaggttt taaaacgaaa 3780
attcttattc ttgagtaact ctttcctgta ggtcaggttg ctttctcagg tatagcatga 3840
ggtcgctcac tagtccatgg acgcgtggta ccggccgcgt tgctggcgtt tttccatagg 3900
ctcggccccc ctgacgagca tcacaaaaat cgacgctcaa gtcagaggtg gcgaaacccg 3960
acaggactat aaagatacca ggcgttcccc cctggaagct ccctcgtgcg ctctcctgtt 4020
ccgaccctgc cgcttaccgg atacctgtcc gcctttctcc cttcgggaag cgtggcgctt 4080
tctcaatgct cacgctgtag gtatctcagt tcggtgtagg tcgttcgctc caagctgggc 4140
tgtgtgcacg aaccccccgt tcagcccgac cgctgcgcct tatccggtaa ctatcgtctt 4200
gagtccaacc cggtaagaca cgacttatcg ccactggcag cagccactgg taacaggatt 4260
agcagagcga ggtatgtagg cggtgctaca gagttcttga agtggtggcc taactacggc 4320
tacactagaa ggacagtatt tggtatctgc gctctgctga agccagttac cttcggaaaa 4380
agagttggta gctcttgatc cggcaaacaa accaccgctg gtagcggtgg tttttttgtt 4440
tgcaagcagc agattacgcg cagaaaaaaa ggatctcaag aagatccttt gatcttttct 4500
acggggtctg acgctcagtg gaacgaaaac tcacgttaag ggattttggt catgactgat 4560
ccttcaactc agcaaaagtt cgatttattc aacaaagcca cgttgtgtct caaaatctct 4620
gatgttacat tgcacaagat aaaaatatat catcatgaac aataaaactg tctgcttaca 4680

```
taaacagtaa tacaaggggt gttatgagcc atattcaacg ggaaacgtct tgctccaggc   4740
cgcgattaaa ttccaacatg gatgctgatt tatatgggta taaatgggct cgcgataatg   4800
tcgggcaatc aggtgcgaca atctatcgat tgtatgggaa gcccgatgcg ccagagttgt   4860
ttctgaaaca tggcaaaggt agcgttgcca atgatgttac agatgagatg gtcagactaa   4920
actggctgac ggaatttatg cctcttccga ccatcaagca ttttatccgt actcctgatg   4980
atgcatggtt actcaccact gcgatccccg ggaaaacagc attccaggta ttagaagaat   5040
atcctgattc aggtgaaaat attgttgatg cgctggcagt gttcctgcgc cggttgcatt   5100
cgattcctgt ttgtaattgt ccttttaaca gcgatcgcgt atttcgtctc gctcaggcgc   5160
aatcacgaat gaataacggt ttggttgatg cgagtgattt tgatgacgag cgtaatggct   5220
ggcctgttga acaagtctgg aaagaaatgc ataagctttt gccattctca ccggattcag   5280
tcgtcactca tggtgatttc tcacttgata accttatttt tgacgagggg aaattaatag   5340
gttgtattga tgttggacga gtcggaatcg cagaccgata ccaggatctt gccatcctat   5400
ggaactgcct cggtgagttt tctccttcat tacagaaacg gctttttcaa aaatatggta   5460
ttgataatcc tgatatgaat aaattgcagt ttcatttgat gctcgatgag tttttctaat   5520
cagaattggt taattggttg taacacggtc cttttcatca cgtgctataa aaataattat   5580
aatttaaatt ttttaatata aatatataaa ttaaaaatag aaagtaaaaa aagaaattaa   5640
agaaaaaata gtttttgttt tccgaagatg taaaagactc taggggggatc gccaacaaat  5700
actacctttt atcttgctct tcctgctctc aggtattaat gccgaattgt ttcatcttgt   5760
ctgtgtagaa gaccacacac gaaaatcctg tgattttaca ttttacttat cgttaatcga   5820
atgtatatct atttaatctg cttttcttgt ctaataaata tatatgtaaa gtacgctttt   5880
tgttgaaatt ttttaaacct ttgtttattt tttttcttc attccgtaac tcttctacct    5940
tctttattta ctttctaaaa tccaaataca aaacataaaa ataaataaac acagagtaaa   6000
ttcccaaatt attccatcat taaaagatac gaggcgcgtg taagttacag gcaagcgatc   6060
cgtcctaaga aaccattatt atcatgacat taacctataa aaataggcgt atcacgaggc   6120
cctttcgtct cgcgcgtttc ggtgatgacg gtgaaaacct ctgacacatg cagctcccgg   6180
agacggtcac agcttgtctg taagcggatg ccgggagcag acaagcccgt cagggcgcgt   6240
cagcgggtgt tggcgggtgt cggggctggc ttaactatgc ggcatcagag cagattgtac   6300
tgagagtgca ccacgctttt caattcaatt catcattttt tttttattct tttttttgat   6360
tttttaagag cttggtgagc gctaggagtc actgccaggt atcgtttgaa cacggcatta   6420
gtcagggaag tcataacaca gtcctttccc gcaattttct tttctatta ctcttggcct    6480
cctctagtac actctatatt tttttatgcc tcggtaatga ttttcatttt tttttttcca   6540
cctagcggat gactcttttt ttttcttagc gattggcatt atcacataat gaattataca   6600
ttatataaag taatgtgatt tcttcgaaga atatactaaa aaatgagcag gcaagataaa   6660
cgaaggcaaa gatgacagag cagaaagccc tagtaaagcg tattacaaat gaaaccaaga   6720
ttcagattgc gatctcttta aagggtggtc ccctagcgat agagcactcg atcttcccag   6780
aaaaagaggc agaagcagta gcagaacagg ccacacaatc gcaagtgatt aacgtccaca   6840
caggtatagg gtttctggac catatgatac atgctctggc caagcattcc ggctggtcgc   6900
taatcgttga gtgcattggt gacttacaca tagacgacca tcacaccact gaagactgcg   6960
ggattgctct cggtcaagct tttaaagagg ccctaggggc cgtgcgtgga gtaaaaaggt   7020
```

ttggatcagg atttgcgcct ttggatgagg cactttccag agcggtggtt gatctttcga 7080
acaggccgta cgcagttgtc gaacttggtt tgcaaaggga gaaagtaggt gatctctctt 7140
gcgagatgat cccgcatttt cttgaaagct ttgcagaggc tagcagaatt accctccacg 7200
ttgattgtct gcgaggcaag aatgatcatc accgtagtga gagtgcgttc aaggctcttg 7260
cggttgccat aagagaagcc acctcgccca atggtaccaa cgatgttccc tccaccaaag 7320
gtgttcttat gtagtgacac cgattattta aagctgctgc atacgatata tatacatgtg 7380
tatatatgta tacctatgaa tgtcagtaag tatgtatacg aacagtatga tactgaagat 7440
gacaaggtaa tgcatcattc tatacgtgtc attctgaacg aggcgcgctt tcctttttc 7500 tttttgcttt ttcttttttt ttctcttgaa ctcgagaaaa aaaatatgcg gtgtgaaata 7560
ccgcacagat gcgtaaggag aaaataccgc atcagg 7596

<210> SEQ ID NO 50
<211> LENGTH: 7596
<212> TYPE: DNA
<213> ORGANISM: Kluyveromyces lactis

<400> SEQUENCE: 50
gagctcgtgt tgttatccga tacaaccgga tatttttctt ttaatgagtc taaaccgtga 60
tagcttcagg ttaatacaat caaaaaaagc tcaaatattc ttttaatgcc gcgttcacag 120
attccaattg aatacaacta ggtagttcat tatatgaagc ctttgctact atttttcact 180
atagtctgcc ttcaccttaa tgcagacatc cacatatttt aatcacttta aaataaaaag 240
gaagatatat tagaagctat gatccaatct gtaagccaga ttaaaattca cgaactcttc 300
tttcatttga attgaatgct ttgagttggg gtagattatc gcaaattact catcacattt 360
attgactacg aacttgctga tgtccttttt ttatttatat ttttcttcag tgaagcgatt 420 tttttttac acagaccaag acggaaaaaa gtagctaagg aagaaaacaa aatcatgaaa 480
aaaatgtgaa gtgatcatgc acatcgcatc aacttaaaca ttggcttaga gatatataga 540
gttagagttt acggcaacct ttaagcacca ataccttttg gcatagtcta aagacctggt 600
tcttaatttt aaacaaattt aactaaagat ttccctatca aagaagtaac gagttgacag 660
attttctcaa aataaatcga tactgcattt ctaggcatat ccagcgagat ctatggacta 720
caaagacaaa gcattaaacg acttgagaaa cgtatacgca gacttcgact ccttgccatt 780
ggacttcaga caaatcttaa ttaaggatag agctacattg ttgcaaaagg aagacgttga 840
aaagaaaatt ttggaaagac aagaagatgc caaaaagtac gctgaatact tgaagcaatc 900
agaaatccca gaaagaatct ccttacctaa catcaagaga cataagggtg tatcaatctc 960
ctttgaagaa acatctgaag atatggtctt ggaaccaaga ccttttatct tcgacggttt 1020
gaacatcaga tgtttcagaa gagaaaccat attcagtttg aaaaataaga ttttgaacat 1080
ggttaaggaa tcttcatcct ttaaaaacgt ttcaagacaa agtgtatctt ttatgtactt 1140
caaaattttt aataagggta aagttattgc aagtacaaag tctgttaaca tctatgaaga 1200
taagatcgac gaaagattgg aagatttgtg taacaacttc gatgacgtat tgaaaaagat 1260
tatagacgtc acctatggtt acgaatcctt attcgttagt gaaacttact cttacgtaat 1320
attctatgct aaatcaatct actttccaca acctagatgc gttaacaact ggggtaacaa 1380
catcccaaac atcttgacat tcgattcctt taagcttttc accgcaaaca aaaacaacgt 1440
tagttgtatc aagcaatgtt caagattttt gtggcaaaaa gatttcaaca ctttagaaga 1500
aatgatagaa tacaagaacg gtaatatttg tatcgtcaca ccacaattgc atatcaacga 1560

```
tgttagagac atcaagtcat tcaacgatat cagattgtac tcagaatccc ctattaaaac   1620
attttccgtt attgataaca ctatcacata tttgttttac ttcaaggaac atttgggtgt   1680
tatttttaac atcactaagt caagacatga tagaagagta acaaaatttt caccattgtc   1740
caagttcagt gacgtcaaaa atatcactgt ttgtttcgat atcgaaagtt acttcgaccc   1800
agaaaaggaa tctaaccaag ttaacatccc tttcatttgt tgcgcttcaa tcatctataa   1860
taaggttatt ggtaacatcg tcgattttga aggtagagac tgtgtcgcac aaatgatcga   1920
atacgttgta gatatttgcg gtgaattgaa cataagttct gttgaattga tcgcccataa   1980
cggtggtggt tatgatttcc actacatctt gtcatccatg tataatccag ctgcaattaa   2040
aaacatattg atcagaaaca actcttttat ttcttttaat ttcgcacatg atggtgtcaa   2100
gttctctgtt aaggacagtt actcattttt gttgtgtagt gttgccaacg cttctaaagc   2160
atttttaaac gaagaaactt ttaagaaaac tgatttccct catcacgact tgaaaactgc   2220
cgatgactta tataaggtct acaaggaatg gagttctgtt aacacagaaa ttaaccatgt   2280
cgttgaaaag gaaaagttgt tgatcacctc tgaacacatc gttaacttca ccaagaacga   2340
taagagtaag actttgatcg aatggtctaa ggattactgt agaaacgacg tattggtctt   2400
gtctaaggtt tggttggagt ttaaaaacgc tgtagaagat atttttaact gcgaattggt   2460
agaccaaacc atgactttgg ctggtttgtc atacaagttg ttccaagcaa acatgccatt   2520
cgatgtcgaa ttgagacatc ctaataagga agactacttc aacatgagag aagcattgat   2580
tggtggtaga tgtatctctg ttaacggtat ctacaaggat gttttgtgct atgacgtaaa   2640
atcattatat ccagcttcta tggctttcta tgatcaacct tacggttctt ttaagagagt   2700
ttcatccaga ccaaaagatg aattgggtat ctattacgtt agagtaaccc caaacagaaa   2760
caacaagtca aactttttcc ctatcagatc ccataataag atcacttaca acaacttcga   2820
agaatcaact tatattgctt ggtacacaaa cgttgatatc gacattggtt tgtcagaagg   2880
tcacaacatc gaatacatcc ctttcgattc ctatggtaac attggttact catggtccaa   2940
aaagggtaaa atttttgaaa agtacatcaa ggatgttttg tacaaattga agataaaata   3000
tgaaaagcaa aataacaagg taaaaagaaa tgtcatcaaa aagatcatga actcattgtg   3060
gggtaaattc gcccaaaagt gggttaactt cgaatacttc atcaagtcag aagatgacat   3120
tgatttcgaa tccgaagaag catataaaat taacgataca gacttcatgt tgatcaaaaa   3180
gattaaggaa tctacctaca gttctaagcc aatacaaaac ggtgttttta ctttaagttg   3240
ggccagatat cacatgaagt ctatttggga tgcaggtgcc aaagaaggtg ctgaatgtat   3300
ctattcagat acagactcca tattcgttca taaggaacac ttcaaaaaga atgcaaagtt   3360
tatgttgaac ggtttgaaag taccaatcat cggttctgaa gtcggtcaat tggaattaga   3420
atgtgaattt gataaattgt tgtgcgccgg taaaaagcaa tacatgggtt tctacactta   3480
cttccaagat ggtaaacctt gcatcaagga aaagaaaaga ttcaaaggta taccaagtaa   3540
ctacatcata cctgaattgt atgctcactt gttatctggt gcagataagg aagccaaaat   3600
tcaattttta aaattcagaa gagaatgggg ttccgtcaag ggttacatag aaaataagac   3660
tgtcaaagcc acctaactcg aggcgaattt cttatgattt atgattttta ttattaaata   3720
agttataaaa aaaataagtg tatacaaatt ttaaagtgac tcttaggttt taaaacgaaa   3780
attcttattc ttgagtaact ctttcctgta ggtcaggttg ctttctcagg tatagcatga   3840
ggtcgctcac tagtccatgg acgcgtggta ccggccgcgt tgctggcgtt tttccatagg   3900
```

```
ctcggccccc ctgacgagca tcacaaaaat cgacgctcaa gtcagaggtg gcgaaacccg   3960
acaggactat aaagatacca ggcgtttccc cctggaagct ccctcgtgcg ctctcctgtt   4020
ccgaccctgc cgcttaccgg atacctgtcc gcctttctcc cttcgggaag cgtggcgctt   4080
tctcaatgct cacgctgtag gtatctcagt tcggtgtagg tcgttcgctc caagctgggc   4140
tgtgtgcacg aaccccccgt tcagcccgac cgctgcgcct tatccggtaa ctatcgtctt   4200
gagtccaacc cggtaagaca cgacttatcg ccactggcag cagccactgg taacaggatt   4260
agcagagcga ggtatgtagg cggtgctaca gagttcttga agtggtggcc taactacggc   4320
tacactagaa ggacagtatt tggtatctgc gctctgctga agccagttac cttcggaaaa   4380
agagttggta gctcttgatc cggcaaacaa accaccgctg gtagcggtgg tttttttgtt   4440
tgcaagcagc agattacgcg cagaaaaaaa ggatctcaag aagatccttt gatcttttct   4500
acggggtctg acgctcagtg gaacgaaaac tcacgttaag ggattttggt catgactgat   4560
ccttcaactc agcaaaagtt cgatttattc aacaaagcca cgttgtgtct caaaatctct   4620
gatgttacat tgcacaagat aaaaatatat catcatgaac aataaaactg tctgcttaca   4680
taaacagtaa tacaaggggt gttatgagcc atattcaacg ggaaacgtct tgctccaggc   4740
cgcgattaaa ttccaacatg gatgctgatt tatatgggta taaatgggct cgcgataatg   4800
tcgggcaatc aggtgcgaca atctatcgat tgtatgggaa gcccgatgcg ccagagttgt   4860
ttctgaaaca tggcaaaggt agcgttgcca atgatgttac agatgagatg gtcagactaa   4920
actggctgac ggaatttatg cctcttccga ccatcaagca ttttatccgt actcctgatg   4980
atgcatggtt actcaccact gcgatccccg ggaaaacagc attccaggta ttagaagaat   5040
atcctgattc aggtgaaaat attgttgatg cgctggcagt gttcctgcgc cggttgcatt   5100
cgattcctgt ttgtaattgt ccttttaaca gcgatcgcgt atttcgtctc gctcaggcgc   5160
aatcacgaat gaataacggt ttggttgatg cgagtgattt tgatgacgag cgtaatggct   5220
ggcctgttga acaagtctgg aaagaaatgc ataagctttt gccattctca ccggattcag   5280
tcgtcactca tggtgatttc tcacttgata accttatttt tgacgagggg aaattaatag   5340
gttgtattga tgttggacga gtcggaatcg cagaccgata ccaggatctt gccatcctat   5400
ggaactgcct cggtgagttt tctccttcat tacagaaacg gctttttcaa aaatatggta   5460
ttgataatcc tgatatgaat aaattgcagt ttcatttgat gctcgatgag tttttctaat   5520
cagaattggt taattggttg taacacggtc cttttcatca cgtgctataa aaataattat   5580
aatttaaatt ttttaatata aatatataaa ttaaaaatag aaagtaaaaa aagaaattaa   5640
agaaaaaata gtttttgttt tccgaagatg taaaagactc tagggggatc gccaacaaat   5700
actacctttt atcttgctct tcctgctctc aggtattaat gccgaattgt ttcatcttgt   5760
ctgtgtagaa gaccacacac gaaaatcctg tgattttaca ttttacttat cgttaatcga   5820
atgtatatct atttaatctg cttttcttgt ctaataaata tatatgtaaa gtacgctttt   5880
tgttgaaatt ttttaaacct ttgtttattt ttttttcttc attccgtaac tcttctacct   5940
tctttattta ctttctaaaa tccaaataca aaacataaaa ataaataaac acagagtaaa   6000
ttcccaaatt attccatcat taaaagatac gaggcgcgtg taagttacag gcaagcgatc   6060
cgtcctaaga aaccattatt atcatgacat taacctataa aaataggcgt atcacgaggc   6120
cctttcgtct cgcgcgtttc ggtgatgacg gtgaaaacct ctgacacatg cagctcccgg   6180
agacggtcac agcttgtctg taagcggatg ccgggagcag acaagcccgt cagggcgcgt   6240
cagcgggtgt tggcgggtgt cggggctggc ttaactatgc ggcatcagag cagattgtac   6300
```

```
tgagagtgca ccacgctttt caattcaatt catcattttt tttttattct ttttttttgat   6360

tttttaagag cttggtgagc gctaggagtc actgccaggt atcgtttgaa cacggcatta   6420

gtcagggaag tcataacaca gtcctttccc gcaatttttct ttttctatta ctcttggcct   6480

cctctagtac actctatatt tttttatgcc tcggtaatga ttttcatttt tttttttcca   6540

cctagcggat gactcttttt ttttcttagc gattggcatt atcacataat gaattataca   6600

ttatataaag taatgtgatt tcttcgaaga atatactaaa aaatgagcag gcaagataaa   6660

cgaaggcaaa gatgacagag cagaaagccc tagtaaagcg tattacaaat gaaaccaaga   6720

ttcagattgc gatctcttta aagggtggtc ccctagcgat agagcactcg atcttcccag   6780

aaaaagaggc agaagcagta gcagaacagg ccacacaatc gcaagtgatt aacgtccaca   6840

caggtatagg gtttctggac catatgatac atgctctggc caagcattcc ggctggtcgc   6900

taatcgttga gtgcattggt gacttacaca tagacgacca tcacaccact gaagactgcg   6960

ggattgctct cggtcaagct tttaaaagagg ccctaggggc cgtgcgtgga gtaaaaaggt   7020

ttggatcagg atttgcgcct ttggatgagg cactttccag agcggtggtt gatctttcga   7080

acaggccgta cgcagttgtc gaacttggtt tgcaaaggga gaaagtaggt gatctctctt   7140

gcgagatgat cccgcatttt cttgaaagct ttgcagaggc tagcagaatt accctccacg   7200

ttgattgtct gcgaggcaag aatgatcatc accgtagtga gagtgcgttc aaggctcttg   7260

cggttgccat aagagaagcc acctcgccca atggtaccaa cgatgttccc tccaccaaag   7320

gtgttcttat gtagtgacac cgattattta aagctgctgc atacgatata tatacatgtg   7380

tatatatgta tacctatgaa tgtcagtaag tatgtatacg aacagtatga tactgaagat   7440

gacaaggtaa tgcatcattc tatacgtgtc attctgaacg aggcgcgctt tcctttttttc   7500

tttttgcttt ttcttttttt ttctcttgaa ctcgagaaaa aaaatatgcg gtgtgaaata   7560

ccgcacagat gcgtaaggag aaaataccgc atcagg                              7596
```

<210> SEQ ID NO 51
<211> LENGTH: 7617
<212> TYPE: DNA
<213> ORGANISM: Kluyveromyces lactis

<400> SEQUENCE: 51

```
gagctcgtgt tgttatccga tacaaccgga tatttttctt ttaatgagtc taaaccgtga     60

tagcttcagg ttaatacaat caaaaaaagc tcaaatattc ttttaatgcc gcgttcacag    120

attccaattg aatacaacta ggtagttcat tatatgaagc ctttgctact atttttcact    180

atagtctgcc ttcaccttaa tgcagacatc cacatatttt aatcacttta aaataaaaag    240

gaagatatat tagaagctat gatccaatct gtaagccaga ttaaaattca cgaactcttc    300

tttcatttga attgaatgct ttgagttggg gtagattatc gcaaattact catcacattt    360

attgactacg aacttgctga tgtccttttt ttatttatat ttttcttcag tgaagcgatt    420

tttttttttac acagaccaag acggaaaaaa gtagctaagg aagaaaaacaa aatcatgaaa    480

aaaatgtgaa gtgatcatgc acatcgcatc aacttaaaca ttggcttaga gatatataga    540

gttagagttt acggcaacct ttaagcacca ataccttttg gcatagtcta aagacctggt    600

tcttaatttt aaacaaattt aactaaagat ttccctatca aagaagtaac gagttgacag    660

attttctcaa aataaatcga tactgcattt ctaggcatat ccagcgagat ctatgaacga    720

tgaattagcc tttttgaact cccaaataga tgattatagt gacgacattg aatttttgag    780
```

-continued

```
aaccgaagtc tttagaatca atagatattc taaatcaatc tattctttaa tgaagaattc    840
ttcaaaggaa gctattaaag aaactattga gtttaataag tatggtcaag aaattcattc    900
taagattaaa gaaaaggaaa tttcattaat tgaagcaatt aaattgatgg aaaagaaata    960
taaatatttg agatcattga ataagactaa agataaatct aagaaaaaga aaattcatac   1020
aaaagatatt gaaactttga aaacaatcta taaaacaaaa gctgattttg atattagaaa   1080
ttttaaaaat gctgaaactt ttacttatga aaattactct ttgttaattc catcagaaaa   1140
ggaattgatt gatttgatcc cagaaatcga agaagattac tcttactact tctacgtttc   1200
attaactatc acaggtccaa ctatctttgg tggtgttaca agaaaagttc caatcatcga   1260
tacttatggt gacattaata aggatttcta caataagatt aaagaaaaca tcacaaaagt   1320
tttggataga gttccattct acgaagaaaa ggaatcagaa attatttgta agaaagtttt   1380
gatcactttg acagttaata agtgggaatc tatcgataag tggtacaaga acgttaagtc   1440
taagtctaaa aagtttaaag attttacttt gtttttagct tctgatactt ctaaaaattg   1500
tgttcaacaa tgtgttgaat atttgggtgg taaatggaac actaactact ctttggaaaa   1560
gatgatccca caacaaaaga ttgttacata catcccattg ttgatggata tccaatacgt   1620
tcaatctatg gaagatttga tctcagattt cgatgaacca aacactgatt gtaagaacat   1680
cgctagattg ttaaagtgga atggtcacat gggtgtgatc acaaagatcg acaaggatgt   1740
taagattaat agaatacaaa gaaagagaat catcgatgtt gaaaataagg aagttaaaga   1800
agttttcttt gatattgaat ctttttcaga tgaaactaaa catcaaatcc catatttgat   1860
ttgttggtct tacttgggtg aattatatta cagaacaggt aaaaattgta tcaaagaatt   1920
tgttgaagaa attttatctt acaacgttga tatcatcttg tatgcttggt acggttcagg   1980
tcaggattac caacatgttt tgccatacat gaagtctaaa tgtattaagg ataagtacat   2040
tattaagaat aatatgatta cttacggtga attatactac gaaaacgcaa tcatatattt   2100
gaaagatcca tacttgttta ttttaacatc tttggataaa gcatctaagg cttttaatgt   2160
tattaataag ggtgaatttc cacattctat catccattca tgggaagatt tgaataagat   2220
tttgccaaac tgggttaaga tccaaaagag aatgattgaa tataaagatg ataataagtt   2280
gaacatctat tacaagaaca tcgaaatttt cgaaaatgat agaaattata atactatctt   2340
agaaaatgct attgaatact gtaaagttga tgttttggca atggaaaagg tttggatcaa   2400
gtttaagaaa ttgttggaaa agaatttgaa cattactgtt tcagttaaga cttttacatt   2460
atctcaattg tcaatgaaga tcatggaatc taaattgcca aagtacgtta aattgtacgt   2520
tccaacattg gaagaatatt caaagatcag aaatgctatc tatggtggta gagttatttc   2580
taaaaatggt atctatgaag aaaacatcgt ttacgctgat gttgtttctt tatacccatc   2640
agcaatgaaa ttgttgaagc attcttatgg taaaccaaaa ttggttgatt acatcgattt   2700
cgaaaagcat ggtatctacc gtgttacttt gttgaataag catgatcaag aacctaaaaa   2760
ttacttaaac tttgttccaa gaagaattaa tagaaaattg acttgggaat ggttcaagat   2820
acatgaaggt tggtatcata catacgattt gatcatcgct aagtctgaag gtttcgatat   2880
ctattgccat gaaggtttcg aatacccaga aaaggattac attttcaatg atttcattga   2940
tacattatac tctatgaaag aaactcatac agcatgttca tgtgaagaac aaccatgtcc   3000
aatcagaatg gttgctaaga tcgcattgaa tggtggtggt tatggtaaat ttgttcaaaa   3060
accaatcgat aaggaaatat atatcgttaa gagagatgtt gttgctggtg aatgtgataa   3120
attacaagaa aacgaaaatg gtgaaatttg tattggtaaa agattggtta aaagaccatt   3180
```

```
attttataat ttggattcag aaaactacga taaaatgatt attgaaaaag aagatgaacc   3240
aatctattct actcaatgtg gtatctcaat cttgtctgca tcaagatata gattatacaa   3300
attgtgtaag caattcgaaa acatcgatat catctattct gatacagatt caatttttgt   3360
taaacaaaaa tcagttgatt gggaattgtt taaatctaag tgtggttcag aattaggtca   3420
attggattct actatcgatg atactaagaa cgctatcatc tcaaagatgt acattggtgg   3480
tgctaagatg tatgcttttg aatacttaaa caataagaat aagttgatca ctaaattgca   3540
ttgtaaaggt gttccaaact acatgttgtc tttaaaccaa ttcaaatatt tgatggaatc   3600
accagataac acaattgcat ataaatttga aattattaga agaaaattgg taaatgtcat   3660
aactaaggac ttgatcaaag atatcaagca gacttgactc gaggcgaatt tcttatgatt   3720
tatgattttt attattaaat aagttataaa aaaaataagt gtatacaaat tttaaagtga   3780
ctcttaggtt ttaaaacgaa aattcttatt cttgagtaac tctttcctgt aggtcaggtt   3840
gctttctcag gtatagcatg aggtcgctca ctagtccatg gacgcgtggt accggccgcg   3900
ttgctggcgt ttttccatag gctcggcccc cctgacgagc atcacaaaaa tcgacgctca   3960
agtcagaggt ggcgaaaccc gacaggacta taaagatacc aggcgttccc cctggaagc    4020
tccctcgtgc gctctcctgt tccgaccctg ccgcttaccg gatacctgtc cgcctttctc   4080
ccttcgggaa gcgtggcgct ttctcaatgc tcacgctgta ggtatctcag ttcggtgtag   4140
gtcgttcgct ccaagctggg ctgtgtgcac gaaccccccg ttcagcccga ccgctgcgcc   4200
ttatccggta actatcgtct tgagtccaac ccggtaagac acgacttatc gccactggca   4260
gcagccactg gtaacaggat tagcagagcg aggtatgtag gcggtgctac agagttcttg   4320
aagtggtggc ctaactacgg ctacactaga aggacagtat ttggtatctg cgctctgctg   4380
aagccagtta ccttcggaaa aagagttggt agctcttgat ccggcaaaca aaccaccgct   4440
ggtagcggtg gtttttttgt ttgcaagcag cagattacgc gcagaaaaaa aggatctcaa   4500
gaagatcctt tgatcttttc tacggggtct gacgctcagt ggaacgaaaa ctcacgttaa   4560
gggattttgg tcatgactga tccttcaact cagcaaaagt tcgatttatt caacaaagcc   4620
acgttgtgtc tcaaaatctc tgatgttaca ttgcacaaga taaaaatata tcatcatgaa   4680
caataaaact gtctgcttac ataaacagta atacaagggg tgttatgagc catattcaac   4740
gggaaacgtc ttgctccagg ccgcgattaa attccaacat ggatgctgat ttatatgggt   4800
ataaatgggc tcgcgataat gtcgggcaat caggtgcgac aatctatcga ttgtatggga   4860
agcccgatgc gccagagttg tttctgaaac atggcaaagg tagcgttgcc aatgatgtta   4920
cagatgagat ggtcagacta aactggctga cggaatttat gcctcttccg accatcaagc   4980
attttatccg tactcctgat gatgcatggt tactcaccac tgcgatcccc gggaaaacag   5040
cattccaggt attagaagaa tatcctgatt caggtgaaaa tattgttgat gcgctggcag   5100
tgttcctgcg ccggttgcat tcgattcctg tttgtaattg tccttttaac agcgatcgcg   5160
tatttcgtct cgctcaggcg caatcacgaa tgaataacgg tttggttgat gcgagtgatt   5220
ttgatgacga gcgtaatggc tggcctgttg aacaagtctg gaaagaaatg cataagcttt   5280
tgccattctc accggattca gtcgtcactc atggtgattt ctcacttgat aaccttattt   5340
ttgacgaggg gaaattaata ggttgtattg atgttggacg agtcggaatc gcagaccgat   5400
accaggatct tgccatccta tggaactgcc tcggtgagtt ttctccttca ttacagaaac   5460
ggctttttca aaaatatggt attgataatc ctgatatgaa taaattgcag tttcatttga   5520
```

```
tgctcgatga gtttttctaa tcagaattgg ttaattggtt gtaacacggt ccttttcatc   5580
acgtgctata aaaataatta taatttaaat tttttaatat aaatatataa attaaaaata   5640
gaaagtaaaa aaagaaatta aagaaaaaat agtttttgtt ttccgaagat gtaaaagact   5700
ctagggggat cgccaacaaa tactaccttt tatcttgctc ttcctgctct caggtattaa   5760
tgccgaattg tttcatcttg tctgtgtaga agaccacaca cgaaaatcct gtgattttac   5820
attttactta tcgttaatcg aatgtatatc tatttaatct gcttttcttg tctaataaat   5880
atatatgtaa agtacgcttt ttgttgaaat tttttaaacc tttgtttatt tttttttctt   5940
cattccgtaa ctcttctacc ttctttattt actttctaaa atccaaatac aaaacataaa   6000
aataaataaa cacagagtaa attcccaaat tattccatca ttaaaagata cgaggcgcgt   6060
gtaagttaca ggcaagcgat ccgtcctaag aaaccattat tatcatgaca ttaacctata   6120
aaaataggcg tatcacgagg ccctttcgtc tcgcgcgttt cggtgatgac ggtgaaaacc   6180
tctgacacat gcagctcccg gagacggtca cagcttgtct gtaagcggat gccgggagca   6240
gacaagcccg tcagggcgcg tcagcgggtg ttggcgggtg tcggggctgg cttaactatg   6300
cggcatcaga gcagattgta ctgagagtgc accacgcttt tcaattcaat tcatcatttt   6360
tttttattc ttttttttga tttttaaga gcttggtgag cgctaggagt cactgccagg   6420
tatcgtttga acacggcatt agtcagggaa gtcataacac agtcctttcc cgcaattttc   6480
tttttctatt actcttggcc tcctctagta cactctatat ttttttatgc ctcggtaatg   6540
attttcattt tttttttcc acctagcgga tgactctttt tttttcttag cgattggcat   6600
tatcacataa tgaattatac attatataaa gtaatgtgat ttcttcgaag aatatactaa   6660
aaaatgagca ggcaagataa acgaaggcaa agatgacaga gcagaaagcc ctagtaaagc   6720
gtattacaaa tgaaaccaag attcagattg cgatctcttt aaagggtggt cccctagcga   6780
tagagcactc gatcttccca gaaaaagagg cagaagcagt agcagaacag gccacacaat   6840
cgcaagtgat taacgtccac acaggtatag ggtttctgga ccatatgata catgctctgg   6900
ccaagcattc cggctggtcg ctaatcgttg agtgcattgg tgacttacac atagacgacc   6960
atcacaccac tgaagactgc gggattgctc tcggtcaagc ttttaaagag gccctagggg   7020
ccgtgcgtgg agtaaaaagg tttggatcag gatttgcgcc tttggatgag gcactttcca   7080
gagcggtggt tgatctttcg aacaggccgt acgcagttgt cgaacttggt ttgcaaaggg   7140
agaaagtagg tgatctctct tgcgagatga tcccgcattt tcttgaaagc tttgcagagg   7200
ctagcagaat taccctccac gttgattgtc tgcgaggcaa gaatgatcat caccgtagtg   7260
agagtgcgtt caaggctctt gcggttgcca taagagaagc cacctcgccc aatggtacca   7320
acgatgttcc ctccaccaaa ggtgttctta tgtagtgaca ccgattattt aaagctgctg   7380
catacgatat atatacatgt gtatatatgt atacctatga atgtcagtaa gtatgtatac   7440
gaacagtatg atactgaaga tgacaaggta atgcatcatt ctatacgtgt cattctgaac   7500
gaggcgcgct ttcctttttt ctttttgctt tttctttttt tttctcttga actcgagaaa   7560
aaaaatatgc ggtgtgaaat accgcacaga tgcgtaagga gaaaataccg catcagg      7617
```

<210> SEQ ID NO 52
<211> LENGTH: 7617
<212> TYPE: DNA
<213> ORGANISM: Kluyveromyces lactis

<400> SEQUENCE: 52
gagctcgtgt tgttatccga tacaaccgga tatttttctt ttaatgagtc taaaccgtga 60
tagcttcagg ttaatacaat caaaaaaagc tcaaatattc ttttaatgcc gcgttcacag 120
attccaattg aatacaacta ggtagttcat tatatgaagc ctttgctact atttttcact 180
atagtctgcc ttcaccttaa tgcagacatc cacatatttt aatcacttta aaataaaaag 240
gaagatatat tagaagctat gatccaatct gtaagccaga ttaaaattca cgaactcttc 300
tttcatttga attgaatgct ttgagttggg gtagattatc gcaaattact catcacattt 360
attgactacg aacttgctga tgtccttttt ttatttatat ttttcttcag tgaagcgatt 420
ttttttttac acagaccaag acggaaaaaa gtagctaagg aagaaaacaa aatcatgaaa 480
aaaatgtgaa gtgatcatgc acatcgcatc aacttaaaca ttggcttaga gatatataga 540
gttagagttt acggcaacct ttaagcacca ataccttttg gcatagtcta aagacctggt 600
tcttaatttt aaacaaattt aactaaagat ttccctatca aagaagtaac gagttgacag 660
attttctcaa aataaatcga tactgcattt ctaggcatat ccagcgagat ctatgaacga 720
tgaattagcc tttttgaact cccaaataga tgattatagt gacgacattg aatttttgag 780
aaccgaagtc tttagaatca atagatattc taaatcaatc tattctttaa tgaagaattc 840
ttcaaaggaa gctattaaag aaactattga gtttaataag tatggtcaag aaattcattc 900
taagattaaa gaaaaggaaa tttcattaat tgaagcaatt aaattgatgg aaaagaaata 960
taaatatttg agatcattga ataagactaa agataaatct aagaaaaaga aaattcatac 1020
aaaagatatt gaaactttga aaacaatcta taaaacaaaa gctgattttg atattagaaa 1080
ttttaaaaat gctgaaactt ttacttatga aaattactct ttgttaattc catcagaaaa 1140
ggaattgatt gatttgatcc cagaaatcga agaagattac tcttactact tctacgtttc 1200
attaactatc acaggtccaa ctatctttgg tggtgttaca agaaaagttc caatcatcga 1260
tacttatggt gacattaata aggatttcta caataagatt aaagaaaaca tcacaaaagt 1320
tttggataga gttccattct acgaagaaaa ggaatcagaa attatttgta agaaagtttt 1380
gatcactttg acagttaata agtgggaatc tatcgataag tggtacaaga acgttaagtc 1440
taagtctaaa aagtttaaag attttacttt gtttttagct tctgatactt ctaaaaattg 1500
tgttcaacaa tgtgttgaat atttgggtgg taaatggaac actaactact ctttggaaaa 1560
gatgatccca caacaaaaga ttgttacata catcccattg ttgatggata tccaatacgt 1620
tcaatctatg gaagatttga tctcagattt cgatgaacca aacactgatt gtaagaacat 1680
cgctagattg ttaaagtgga atggtcacat gggtgtgatc acaaagatcg acaaggatgt 1740
taagattaat agaatacaaa gaaagagaat catcgatgtt gaaaataagg aagttaaaga 1800
agttttcttt gatattgaac agttttcaga tgaaactaaa catcaaatcc catatttgat 1860
ttgttggtct tacttgggtg aattatatta cagaacaggt aaaaattgta tcaaagaatt 1920
tgttgaagaa attttatctt acaacgttga tatcatcttg tatgcttggt acggttcagg 1980
ttatgattac caacatgttt tgccatacat gaagtctaaa tgtattaagg ataagtacat 2040
tattaagaat aatatgatta cttacggtga attatactac gaaaacgcaa tcatatattt 2100
gaaagatcca tacttgttta ttttaacatc tttggataaa gcatctaagg cttttaatgt 2160
tattaataag ggtgaatttc cacattctat catccattca tgggaagatt tgaataagat 2220
tttgccaaac tgggttaaga tccaaaagag aatgattgaa tataaagatg ataataagtt 2280
gaacatctat tacaagaaca tcgaaatttt cgaaaatgat agaaattata atactatctt 2340
agaaaatgct attgaatact gtaaagttga tgttttggca atggaaaagg tttggatcaa 2400
gtttaagaaa ttgttggaaa agaatttgaa cattactgtt tcagttaaga cttttacatt 2460
atctcaattg tcaatgaaga tcatggaatc taaattgcca aagtacgtta aattgtacgt 2520
tccaacattg gaagaatatt caaagatcag aaatgctatc tatggtggta gagttatttc 2580
taaaaatggt atctatgaag aaaacatcgt ttacgctgat gttgtttctt tatacccatc 2640
agcaatgaaa ttgttgaagc attcttatgg taaaccaaaa ttggttgatt acatcgattt 2700
cgaaaagcat ggtatctacc gtgttacttt gttgaataag catgatcaag aacctaaaaa 2760
ttacttaaac tttgttccaa gaagaattaa tagaaaattg acttgggaat ggttcaagat 2820
acatgaaggt tggtatcata catacgattt gatcatcgct aagtctgaag gtttcgatat 2880
ctattgccat gaaggtttcg aataccagaa aaaggattac attttcaatg atttcattga 2940
tacattatac tctatgaaag aaactcatac agcatgttca tgtgaagaac aaccatgtcc 3000
aatcagaatg gttgctaaga tcgcattgaa tggtggtggt tatggtaaat ttgttcaaaa 3060
accaatcgat aaggaaatat atatcgttaa gagagatgtt gttgctggtg aatgtgataa 3120
attacaagaa aacgaaaatg gtgaaatttg tattggtaaa agattggtta aaagaccatt 3180
attttataat ttggattcag aaaactacga taaaatgatt attgaaaaag aagatgaacc 3240
aatctattct actcaatgtg gtatctcaat cttgtctgca tcaagatata gattatacaa 3300
attgtgtaag caattcgaaa acatcgatat catctattct gatacagatt caatttttgt 3360
taaacaaaaa tcagttgatt gggaattgtt taaatctaag tgtggttcag aattaggtca 3420
attggattct actatcgatg atactaagaa cgctatcatc tcaaagatgt acattggtgg 3480
tgctaagatg tatgcttttg aatacttaaa caataagaat aagttgatca ctaaattgca 3540
ttgtaaaggt gttccaaact acatgttgtc tttaaaccaa ttcaaatatt tgatggaatc 3600
accagataac acaattgcat ataaatttga aattattaga agaaaattgg taaatgtcat 3660
aactaaggac ttgatcaaag atatcaagca gacttgactc gaggcgaatt tcttatgatt 3720
tatgattttt attattaaat aagttataaa aaaaataagt gtatacaaat tttaaagtga 3780
ctcttaggtt ttaaaacgaa aattcttatt cttgagtaac tctttcctgt aggtcaggtt 3840
gctttctcag gtatagcatg aggtcgctca ctagtccatg gacgcgtggt accggccgcg 3900
ttgctggcgt ttttccatag gctcggcccc cctgacgagc atcacaaaaa tcgacgctca 3960
agtcagaggt ggcgaaaccc gacaggacta taaagatacc aggcgttccc cctggaagc 4020
tccctcgtgc gctctcctgt tccgaccctg ccgcttaccg gatacctgtc cgcctttctc 4080
ccttcgggaa gcgtggcgct ttctcaatgc tcacgctgta ggtatctcag ttcggtgtag 4140
gtcgttcgct ccaagctggg ctgtgtgcac gaaccccccg ttcagcccga ccgctgcgcc 4200
ttatccggta actatcgtct tgagtccaac ccggtaagac acgacttatc gccactggca 4260
gcagccactg gtaacaggat tagcagagcg aggtatgtag gcggtgctac agagttcttg 4320
aagtggtggc ctaactacgg ctacactaga aggacagtat ttggtatctg cgctctgctg 4380
aagccagtta ccttcggaaa aagagttggt agctcttgat ccggcaaaca aaccaccgct 4440
ggtagcggtg gtttttttgt ttgcaagcag cagattacgc gcagaaaaaa aggatctcaa 4500
gaagatcctt tgatcttttc tacggggtct gacgctcagt ggaacgaaaa ctcacgttaa 4560
gggattttgg tcatgactga tccttcaact cagcaaaagt tcgatttatt caacaaagcc 4620
acgttgtgtc tcaaaatctc tgatgttaca ttgcacaaga taaaaatata tcatcatgaa 4680
caataaaact gtctgcttac ataaacagta atacaagggg tgttatgagc catattcaac 4740
gggaaacgtc ttgctccagg ccgcgattaa attccaacat ggatgctgat ttatatgggt 4800
ataaatgggc tcgcgataat gtcgggcaat caggtgcgac aatctatcga ttgtatggga 4860
agcccgatgc gccagagttg tttctgaaac atggcaaagg tagcgttgcc aatgatgtta 4920
cagatgagat ggtcagacta aactggctga cggaatttat gcctcttccg accatcaagc 4980
attttatccg tactcctgat gatgcatggt tactcaccac tgcgatcccc gggaaaacag 5040
cattccaggt attagaagaa tatcctgatt caggtgaaaa tattgttgat gcgctggcag 5100
tgttcctgcg ccggttgcat tcgattcctg tttgtaattg tccttttaac agcgatcgcg 5160
tatttcgtct cgctcaggcg caatcacgaa tgaataacgg tttggttgat gcgagtgatt 5220
ttgatgacga gcgtaatggc tggcctgttg aacaagtctg gaaagaaatg cataagcttt 5280
tgccattctc accggattca gtcgtcactc atggtgattt ctcacttgat aaccttattt 5340
ttgacgaggg gaaattaata ggttgtattg atgttggacg agtcggaatc gcagaccgat 5400
accaggatct tgccatccta tggaactgcc tcggtgagtt ttctccttca ttacagaaac 5460
ggctttttca aaaatatggt attgataatc ctgatatgaa taaattgcag tttcatttga 5520
tgctcgatga gtttttctaa tcagaattgg ttaattggtt gtaacacggt cctttttcatc 5580
acgtgctata aaaataatta taatttaaat tttttaatat aaatatataa attaaaaata 5640
gaaagtaaaa aaagaaatta aagaaaaaat agtttttgtt ttccgaagat gtaaaagact 5700
ctagggggat cgccaacaaa tactaccttt tatcttgctc ttcctgctct caggtattaa 5760
tgccgaattg tttcatcttg tctgtgtaga agaccacaca cgaaaatcct gtgattttac 5820
attttactta tcgttaatcg aatgtatatc tatttaatct gcttttcttg tctaataaat 5880
atatatgtaa agtacgcttt ttgttgaaat tttttaaacc tttgtttatt tttttttctt 5940
cattccgtaa ctcttctacc ttctttattt actttctaaa atccaaatac aaaacataaa 6000
aataaataaa cacagagtaa attcccaaat tattccatca ttaaaagata cgaggcgcgt 6060
gtaagttaca ggcaagcgat ccgtcctaag aaaccattat tatcatgaca ttaacctata 6120
aaaataggcg tatcacgagg ccctttcgtc tcgcgcgttt cggtgatgac ggtgaaaacc 6180
tctgacacat gcagctcccg gagacggtca cagcttgtct gtaagcggat gccgggagca 6240
gacaagcccg tcagggcgcg tcagcgggtg ttggcgggtg tcggggctgg cttaactatg 6300
cggcatcaga gcagattgta ctgagagtgc accacgcttt tcaattcaat tcatcatttt 6360
tttttattc tttttttga tttttaaga gcttggtgag cgctaggagt cactgccagg 6420
tatcgtttga acacggcatt agtcagggaa gtcataacac agtcctttcc cgcaattttc 6480
tttttctatt actcttggcc tcctctagta cactctatat ttttttatgc ctcggtaatg 6540
attttcattt tttttttcc acctagcgga tgactctttt tttttcttag cgattggcat 6600
tatcacataa tgaattatac attatataaa gtaatgtgat ttcttcgaag aatatactaa 6660
aaaatgagca ggcaagataa acgaaggcaa agatgacaga gcagaaagcc ctagtaaagc 6720
gtattacaaa tgaaaccaag attcagattg cgatctcttt aaagggtggt cccctagcga 6780
tagagcactc gatcttccca gaaaaagagg cagaagcagt agcagaacag gccacacaat 6840
cgcaagtgat taacgtccac acaggtatag ggtttctgga ccatatgata catgctctgg 6900
ccaagcattc cggctggtcg ctaatcgttg agtgcattgg tgacttacac atagacgacc 6960
atcacaccac tgaagactgc gggattgctc tcggtcaagc ttttaaagag gccctagggg 7020

```
ccgtgcgtgg agtaaaaagg tttggatcag gatttgcgcc tttggatgag gcactttcca   7080

gagcggtggt tgatctttcg aacaggccgt acgcagttgt cgaacttggt ttgcaaaggg   7140

agaaagtagg tgatctctct tgcgagatga tcccgcattt tcttgaaagc tttgcagagg   7200

ctagcagaat taccctccac gttgattgtc tgcgaggcaa gaatgatcat caccgtagtg   7260

agagtgcgtt caaggctctt gcggttgcca taagagaagc cacctcgccc aatggtacca   7320

acgatgttcc ctccaccaaa ggtgttctta tgtagtgaca ccgattattt aaagctgctg   7380

catacgatat atatacatgt gtatatatgt atacctatga atgtcagtaa gtatgtatac   7440

gaacagtatg atactgaaga tgacaaggta atgcatcatt ctatacgtgt cattctgaac   7500

gaggcgcgct ttcctttttt ctttttgctt tttctttttt tttctcttga actcgagaaa   7560

aaaaatatgc ggtgtgaaat accgcacaga tgcgtaagga gaaaataccg catcagg      7617


<210> SEQ ID NO 53
<211> LENGTH: 572
<212> TYPE: PRT
<213> ORGANISM: Bacillus Phage Phi29

<400> SEQUENCE: 53

Met Pro Arg Lys Met Tyr Ser Cys Asp Phe Glu Thr Thr Thr Lys Val
1               5                   10                  15

Glu Asp Cys Arg Val Trp Ala Tyr Gly Tyr Met Asn Ile Glu Asp His
            20                  25                  30

Ser Glu Tyr Lys Ile Gly Asn Ser Leu Asp Glu Phe Met Ala Trp Val
        35                  40                  45

Leu Lys Val Gln Ala Asp Leu Tyr Phe His Asn Leu Lys Phe Asp Gly
    50                  55                  60

Ala Phe Ile Ile Asn Trp Leu Glu Arg Asn Gly Phe Lys Trp Ser Ala
65                  70                  75                  80

Asp Gly Leu Pro Asn Thr Tyr Asn Thr Ile Ile Ser Arg Met Gly Gln
                85                  90                  95

Trp Tyr Met Ile Asp Ile Cys Leu Gly Tyr Lys Gly Lys Arg Lys Ile
            100                 105                 110

His Thr Val Ile Tyr Asp Ser Leu Lys Lys Leu Pro Phe Pro Val Lys
        115                 120                 125

Lys Ile Ala Lys Asp Phe Lys Leu Thr Val Leu Lys Gly Asp Ile Asp
    130                 135                 140

Tyr His Lys Glu Arg Pro Val Gly Tyr Lys Ile Thr Pro Glu Glu Tyr
145                 150                 155                 160

Ala Tyr Ile Lys Asn Asp Ile Gln Ile Ile Ala Glu Ala Leu Leu Ile
                165                 170                 175

Gln Phe Lys Gln Gly Leu Asp Arg Met Thr Ala Gly Ser Asp Ser Leu
            180                 185                 190

Lys Gly Phe Lys Asp Ile Ile Thr Thr Lys Lys Phe Lys Lys Val Phe
        195                 200                 205

Pro Thr Leu Ser Leu Gly Leu Asp Lys Glu Val Arg Tyr Ala Tyr Arg
    210                 215                 220

Gly Gly Phe Thr Trp Leu Asn Asp Arg Phe Lys Glu Lys Glu Ile Gly
225                 230                 235                 240

Glu Gly Met Val Phe Asp Val Asn Ser Leu Tyr Pro Ala Gln Met Tyr
                245                 250                 255

Ser Arg Leu Leu Pro Tyr Gly Glu Pro Ile Val Phe Glu Gly Lys Tyr
            260                 265                 270
```

```
Val Trp Asp Glu Asp Tyr Pro Leu His Ile Gln His Ile Arg Cys Glu
        275                 280                 285

Phe Glu Leu Lys Glu Gly Tyr Ile Pro Thr Ile Gln Ile Lys Arg Ser
    290                 295                 300

Arg Phe Tyr Lys Gly Asn Glu Tyr Leu Lys Ser Ser Gly Gly Glu Ile
305                 310                 315                 320

Ala Asp Leu Trp Leu Ser Asn Val Asp Leu Glu Leu Met Lys Glu His
                325                 330                 335

Tyr Asp Leu Tyr Asn Val Glu Tyr Ile Ser Gly Leu Lys Phe Lys Ala
            340                 345                 350

Thr Thr Gly Leu Phe Lys Asp Phe Ile Asp Lys Trp Thr Tyr Ile Lys
        355                 360                 365

Thr Thr Ser Glu Gly Ala Ile Lys Gln Leu Ala Lys Leu Met Leu Asn
    370                 375                 380

Ser Leu Tyr Gly Lys Phe Ala Ser Asn Pro Asp Val Thr Gly Lys Val
385                 390                 395                 400

Pro Tyr Leu Lys Glu Asn Gly Ala Leu Gly Phe Arg Leu Gly Glu Glu
                405                 410                 415

Glu Thr Lys Asp Pro Val Tyr Thr Pro Met Gly Val Phe Ile Thr Ala
            420                 425                 430

Trp Ala Arg Tyr Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Ile
    450                 455                 460

Pro Asp Val Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Met Lys Glu Val Asp Gly Lys Leu Val Glu
            500                 505                 510

Gly Ser Pro Asp Asp Tyr Thr Asp Ile Lys Phe Ser Val Lys Cys Ala
        515                 520                 525

Gly Met Thr Asp Lys Ile Lys Lys Glu Val Thr Phe Glu Asn Phe Lys
    530                 535                 540

Val Gly Phe Ser Arg Lys Met Lys Pro Lys Pro Val Gln Val Pro Gly
545                 550                 555                 560

Gly Val Val Leu Val Asp Asp Thr Phe Thr Ile Lys
                565                 570
```

<210> SEQ ID NO 54
<211> LENGTH: 578
<212> TYPE: PRT
<213> ORGANISM: Bacillus Phage GA1

<400> SEQUENCE: 54

```
Met Ala Arg Ser Val Tyr Val Cys Asp Phe Glu Thr Thr Thr Asp Pro
1               5                   10                  15

Glu Asp Cys Arg Leu Trp Ala Trp Gly Trp Met Asp Ile Tyr Asn Thr
            20                  25                  30

Asp Lys Trp Ser Tyr Gly Glu Asp Ile Asp Ser Phe Met Glu Trp Ala
        35                  40                  45

Leu Asn Ser Asn Ser Asp Ile Tyr Phe His Asn Leu Lys Phe Asp Gly
    50                  55                  60

Ser Phe Ile Leu Pro Trp Trp Leu Arg Asn Gly Tyr Val His Thr Glu
65                  70                  75                  80
```

Glu Asp Arg Thr Asn Thr Pro Lys Glu Phe Thr Thr Thr Ile Ser Gly
85 90 95

Met Gly Gln Trp Tyr Ala Val Asp Val Cys Ile Asn Thr Arg Gly Lys
100 105 110

Asn Lys Asn His Val Val Phe Tyr Asp Ser Leu Lys Lys Leu Pro Phe
115 120 125

Lys Val Glu Gln Ile Ala Lys Gly Phe Gly Leu Pro Val Leu Lys Gly
130 135 140

Asp Ile Asp Tyr Lys Lys Tyr Arg Pro Val Gly Tyr Val Met Asp Asp
145 150 155 160

Asn Glu Ile Glu Tyr Leu Lys His Asp Leu Leu Ile Val Ala Leu Ala
165 170 175

Leu Arg Ser Met Phe Asp Asn Asp Phe Thr Ser Met Thr Val Gly Ser
180 185 190

Asp Ala Leu Asn Thr Tyr Lys Glu Met Leu Gly Val Lys Gln Trp Glu
195 200 205

Lys Tyr Phe Pro Val Leu Ser Leu Lys Val Asn Ser Glu Ile Arg Lys
210 215 220

Ala Tyr Lys Gly Gly Phe Thr Trp Val Asn Pro Lys Tyr Gln Gly Glu
225 230 235 240

Thr Val Tyr Gly Gly Met Val Phe Asp Val Asn Ser Met Tyr Pro Ala
245 250 255

Met Met Lys Asn Lys Leu Leu Pro Tyr Gly Glu Pro Val Met Phe Lys
260 265 270

Gly Glu Tyr Lys Lys Asn Val Glu Tyr Pro Leu Tyr Ile Gln Gln Val
275 280 285

Arg Cys Phe Phe Glu Leu Lys Lys Asp Lys Ile Pro Cys Ile Gln Ile
290 295 300

Lys Gly Asn Ala Arg Phe Gly Gln Asn Glu Tyr Leu Ser Thr Ser Gly
305 310 315 320

Asp Glu Tyr Val Asp Leu Tyr Val Thr Asn Val Asp Trp Glu Leu Ile
325 330 335

Lys Lys His Tyr Asp Ile Phe Glu Glu Glu Phe Ile Gly Gly Phe Met
340 345 350

Phe Lys Gly Phe Ile Gly Phe Phe Asp Glu Tyr Ile Asp Arg Phe Met
355 360 365

Glu Ile Lys Asn Ser Pro Asp Ser Ser Ala Glu Gln Ser Leu Gln Ala
370 375 380

Lys Leu Met Leu Asn Ser Leu Tyr Gly Lys Phe Ala Thr Asn Pro Asp
385 390 395 400

Ile Thr Gly Lys Val Pro Tyr Leu Asp Glu Asn Gly Val Leu Lys Phe
405 410 415

Arg Lys Gly Glu Leu Lys Glu Arg Asp Pro Val Tyr Thr Pro Met Gly
420 425 430

Cys Phe Ile Thr Ala Tyr Ala Arg Glu Asn Ile Leu Ser Asn Ala Gln
435 440 445

Lys Leu Tyr Pro Arg Phe Ile Tyr Ala Asp Thr Asp Ser Ile His Val
450 455 460

Glu Gly Leu Gly Glu Val Asp Ala Ile Lys Asp Val Ile Asp Pro Lys
465 470 475 480

Lys Leu Gly Tyr Trp Asp His Glu Ala Thr Phe Gln Arg Ala Arg Tyr
485 490 495

Val Arg Gln Lys Thr Tyr Phe Ile Glu Thr Thr Trp Lys Glu Asn Asp
500 505 510

Lys Gly Lys Leu Val Val Cys Glu Pro Gln Asp Ala Thr Lys Val Lys
515 520 525

Pro Lys Ile Ala Cys Ala Gly Met Ser Asp Ala Ile Lys Glu Arg Ile
530 535 540

Arg Phe Asn Glu Phe Lys Ile Gly Tyr Ser Thr His Gly Ser Leu Lys
545 550 555 560

Pro Lys Asn Val Leu Gly Gly Val Val Leu Met Asp Tyr Pro Phe Ala
565 570 575

Ile Lys

<210> SEQ ID NO 55
<211> LENGTH: 553
<212> TYPE: PRT
<213> ORGANISM: Enterobacteria Phage PRD1

<400> SEQUENCE: 55

Met Pro Arg Arg Ser Arg Lys Lys Val Glu Tyr Lys Ile Ala Ala Phe
1 5 10 15

Asp Phe Glu Thr Asp Pro Phe Lys His Asp Arg Ile Pro Lys Pro Phe
20 25 30

Ser Trp Gly Phe Tyr Asn Gly Glu Ile Tyr Lys Asp Tyr Trp Gly Asp
35 40 45

Asp Cys Ile Glu Gln Phe Ile Tyr Trp Leu Asp Thr Ile Glu Glu Pro
50 55 60

His Val Ile Tyr Ala His Asn Gly Gly Lys Phe Asp Phe Leu Phe Leu
65 70 75 80

Met Lys Tyr Phe Arg Gly Lys Leu Lys Ile Val Asn Gly Arg Ile Leu
85 90 95

Glu Val Glu His Gly Ile His Lys Phe Arg Asp Ser Tyr Ala Ile Leu
100 105 110

Pro Val Pro Leu Ala Ala Ser Asp Glu Lys Ile Glu Ile Asp Tyr Gly
115 120 125

Lys Met Glu Arg Glu Thr Arg Glu Gln His Lys Ala Glu Ile Leu Glu
130 135 140

Tyr Leu Lys Gly Asp Cys Val Thr Leu His Lys Met Val Ser Leu Phe
145 150 155 160

Ile Ala Glu Phe Gly Met Arg Leu Thr Ile Gly Gly Thr Ala Met Asn
165 170 175

Glu Leu Lys Gln Phe His Pro Tyr Asp Pro Val Arg Lys Gly Phe Asp
180 185 190

Glu Ala Met Arg Pro Phe Tyr Phe Gly Gly Arg Cys Gln Ala Phe Glu
195 200 205

Lys Gly Ile Ile Glu Asp Asp Ile Lys Val Tyr Asp Val Asn Ser Met
210 215 220

Tyr Pro His Ala Met Arg Asn Phe Arg His Pro Phe Ser Asp Glu Phe
225 230 235 240

Tyr Glu Ala Asn Glu Ile Thr Glu Glu Thr Tyr Phe Ile Glu Trp Glu
245 250 255

Gly Glu Asn Asn Gly Ala Val Pro Val Arg Thr Lys Thr Gly Leu Asp
260 265 270

Phe Asn Gln Arg Ser Gly Ile Phe His Thr Ser Ile His Glu Trp Arg
275 280 285

Ala Gly Ile Asp Thr Gly Thr Ile Lys Pro Asn Arg Ile Ile Arg Thr
290 295 300

Ile Asn Phe Thr Glu Thr Thr Thr Phe Gly Ala Phe Ile Asp His Phe
305 310 315 320

Phe Ser Lys Arg Asp Ala Ala Lys Lys Ala Gly Asp Leu Phe His Asn
325 330 335

Ile Phe Tyr Lys Leu Ile Leu Asn Ser Ser Tyr Gly Lys Phe Ala Gln
340 345 350

Asn Pro Glu Asn Tyr Lys Glu Trp Cys Ile Thr Glu Gly Gly Ile Tyr
355 360 365

Leu Glu Gly Tyr Asp Gly Glu Gly Cys Glu Val Gln Glu His Leu Asp
370 375 380

Tyr Ile Leu Trp Gly Arg Pro Ala Glu Met Phe Asn Tyr Phe Asn Val
385 390 395 400

Ala Val Ala Ala Ser Ile Thr Gly Ala Ala Arg Ser Val Leu Leu Arg
405 410 415

Ala Leu Ala Gln Ala Glu Arg Pro Leu Tyr Cys Asp Thr Asp Ser Ile
420 425 430

Ile Cys Arg Asp Leu Lys Asn Val Pro Leu Asp Ala Tyr Gln Leu Gly
435 440 445

Ala Trp Asp Leu Glu Ala Thr Gly Asp Lys Ile Ala Ile Ala Gly Lys
450 455 460

Lys Leu Tyr Ala Leu Tyr Ala Gly Asp Asn Cys Val Lys Ile Ala Ser
465 470 475 480

Lys Gly Ala Ser Leu Val Pro Arg Asp Ile Gly Phe Leu Met Pro Pro
485 490 495

Asp Met Glu Pro Lys Ala Ala Lys Lys Val Ala Gln Gln Lys Ala Lys
500 505 510

Asn Ile Gly Gly Glu Lys Ile Leu Lys Val Ala Asn Gly Gly Val Tyr
515 520 525

Asp Phe Val Asn Asp Ala Pro Ser Phe Lys Leu Asn Gly Asn Val Gln
530 535 540

Phe Ile Lys Arg Thr Ile Lys Gly Thr
545 550

<210> SEQ ID NO 56
<211> LENGTH: 898
<212> TYPE: PRT
<213> ORGANISM: Escherichia Phage T4

<400> SEQUENCE: 56

Met Lys Glu Phe Tyr Ile Ser Ile Glu Thr Val Gly Asn Asn Ile Val
1 5 10 15

Glu Arg Tyr Ile Asp Glu Asn Gly Lys Glu Arg Thr Arg Glu Val Glu
20 25 30

Tyr Leu Pro Thr Met Phe Arg His Cys Lys Glu Glu Ser Lys Tyr Lys
35 40 45

Asp Ile Tyr Gly Lys Asn Cys Ala Pro Gln Lys Phe Pro Ser Met Lys
50 55 60

Asp Ala Arg Asp Trp Met Lys Arg Met Glu Asp Ile Gly Leu Glu Ala
65 70 75 80

Leu Gly Met Asn Asp Phe Lys Leu Ala Tyr Ile Ser Asp Thr Tyr Gly
85 90 95

Ser Glu Ile Val Tyr Asp Arg Lys Phe Val Arg Val Ala Asn Cys Asp
100 105 110

```
Ile Glu Val Thr Gly Asp Lys Phe Pro Asp Pro Met Lys Ala Glu Tyr
        115                 120                 125

Glu Ile Asp Ala Ile Thr His Tyr Asp Ser Ile Asp Asp Arg Phe Tyr
    130                 135                 140

Val Phe Asp Leu Leu Asn Ser Met Tyr Gly Ser Val Ser Lys Trp Asp
145                 150                 155                 160

Ala Lys Leu Ala Ala Lys Leu Asp Cys Glu Gly Gly Asp Glu Val Pro
                165                 170                 175

Gln Glu Ile Leu Asp Arg Val Ile Tyr Met Pro Phe Asp Asn Glu Arg
            180                 185                 190

Asp Met Leu Met Glu Tyr Ile Asn Leu Trp Glu Gln Lys Arg Pro Ala
        195                 200                 205

Ile Phe Thr Gly Trp Asn Ile Glu Gly Phe Asp Val Pro Tyr Ile Met
    210                 215                 220

Asn Arg Val Lys Met Ile Leu Gly Glu Arg Ser Met Lys Arg Phe Ser
225                 230                 235                 240

Pro Ile Gly Arg Val Lys Ser Lys Leu Ile Gln Asn Met Tyr Gly Ser
                245                 250                 255

Lys Glu Ile Tyr Ser Ile Asp Gly Val Ser Ile Leu Asp Tyr Leu Asp
            260                 265                 270

Leu Tyr Lys Lys Phe Ala Phe Thr Asn Leu Pro Ser Phe Ser Leu Glu
        275                 280                 285

Ser Val Ala Gln His Glu Thr Lys Lys Gly Lys Leu Pro Tyr Asp Gly
    290                 295                 300

Pro Ile Asn Lys Leu Arg Glu Thr Asn His Gln Arg Tyr Ile Ser Tyr
305                 310                 315                 320

Asn Ile Ile Asp Val Glu Ser Val Gln Ala Ile Asp Lys Ile Arg Gly
                325                 330                 335

Phe Ile Asp Leu Val Leu Ser Met Ser Tyr Tyr Ala Lys Met Pro Phe
            340                 345                 350

Ser Gly Val Met Ser Pro Ile Lys Thr Trp Asp Ala Ile Ile Phe Asn
        355                 360                 365

Ser Leu Lys Gly Glu His Lys Val Ile Pro Gln Gln Gly Ser His Val
    370                 375                 380

Lys Gln Ser Phe Pro Gly Ala Phe Val Phe Glu Pro Lys Pro Ile Ala
385                 390                 395                 400

Arg Arg Tyr Ile Met Ser Phe Asp Leu Thr Ser Leu Tyr Pro Ser Ile
                405                 410                 415

Ile Arg Gln Val Asn Ile Ser Pro Glu Thr Ile Arg Gly Gln Phe Lys
            420                 425                 430

Val His Pro Ile His Glu Tyr Ile Ala Gly Thr Ala Pro Lys Pro Ser
        435                 440                 445

Asp Glu Tyr Ser Cys Ser Pro Asn Gly Trp Met Tyr Asp Lys His Gln
    450                 455                 460

Glu Gly Ile Ile Pro Lys Glu Ile Ala Lys Val Phe Phe Gln Arg Lys
465                 470                 475                 480

Asp Trp Lys Lys Lys Met Phe Ala Glu Glu Met Asn Ala Glu Ala Ile
                485                 490                 495

Lys Lys Ile Ile Met Lys Gly Ala Gly Ser Cys Ser Thr Lys Pro Glu
            500                 505                 510

Val Glu Arg Tyr Val Lys Phe Ser Asp Asp Phe Leu Asn Glu Leu Ser
        515                 520                 525
```

```
Asn Tyr Thr Glu Ser Val Leu Asn Ser Leu Ile Glu Glu Cys Glu Lys
    530                 535                 540

Ala Ala Thr Leu Ala Asn Thr Asn Gln Leu Asn Arg Lys Ile Leu Ile
545                 550                 555                 560

Asn Ser Leu Tyr Gly Ala Leu Gly Asn Ile His Phe Arg Tyr Tyr Asp
                565                 570                 575

Leu Arg Asn Ala Thr Ala Ile Thr Ile Phe Gly Gln Val Gly Ile Gln
            580                 585                 590

Trp Ile Ala Arg Lys Ile Asn Glu Tyr Leu Asn Lys Val Cys Gly Thr
        595                 600                 605

Asn Asp Glu Asp Phe Ile Ala Ala Gly Asp Thr Asp Ser Val Tyr Val
    610                 615                 620

Cys Val Asp Lys Val Ile Glu Lys Val Gly Leu Asp Arg Phe Lys Glu
625                 630                 635                 640

Gln Asn Asp Leu Val Glu Phe Met Asn Gln Phe Gly Lys Lys Lys Met
                645                 650                 655

Glu Pro Met Ile Asp Val Ala Tyr Arg Glu Leu Cys Asp Tyr Met Asn
            660                 665                 670

Asn Arg Glu His Leu Met His Met Asp Arg Glu Ala Ile Ser Cys Pro
        675                 680                 685

Pro Leu Gly Ser Lys Gly Val Gly Gly Phe Trp Lys Ala Lys Lys Arg
    690                 695                 700

Tyr Ala Leu Asn Val Tyr Asp Met Glu Asp Lys Arg Phe Ala Glu Pro
705                 710                 715                 720

His Leu Lys Ile Met Gly Met Glu Thr Gln Gln Ser Ser Thr Pro Lys
                725                 730                 735

Ala Val Gln Glu Ala Leu Glu Glu Ser Ile Arg Arg Ile Leu Gln Glu
            740                 745                 750

Gly Glu Glu Ser Val Gln Glu Tyr Tyr Lys Asn Phe Glu Lys Glu Tyr
        755                 760                 765

Arg Gln Leu Asp Tyr Lys Val Ile Ala Glu Val Lys Thr Ala Asn Asp
    770                 775                 780

Ile Ala Lys Tyr Asp Asp Lys Gly Trp Pro Gly Phe Lys Cys Pro Phe
785                 790                 795                 800

His Ile Arg Gly Val Leu Thr Tyr Arg Arg Ala Val Ser Gly Leu Gly
                805                 810                 815

Val Ala Pro Ile Leu Asp Gly Asn Lys Val Met Val Leu Pro Leu Arg
            820                 825                 830

Glu Gly Asn Pro Phe Gly Asp Lys Cys Ile Ala Trp Pro Ser Gly Thr
        835                 840                 845

Glu Leu Pro Lys Glu Ile Arg Ser Asp Val Leu Ser Trp Ile Asp His
    850                 855                 860

Ser Thr Leu Phe Gln Lys Ser Phe Val Lys Pro Leu Ala Gly Met Cys
865                 870                 875                 880

Glu Ser Ala Gly Met Asp Tyr Glu Glu Lys Ala Ser Leu Asp Phe Leu
                885                 890                 895

Phe Gly
```

<210> SEQ ID NO 57
<211> LENGTH: 903
<212> TYPE: PRT
<213> ORGANISM: Escherichia Phage RB69

<400> SEQUENCE: 57

Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
            20                  25                  30

Tyr Lys Pro Ser Leu Phe Ala His Cys Pro Glu Ser Gln Ala Thr Lys
        35                  40                  45

Tyr Phe Asp Ile Tyr Gly Lys Pro Cys Thr Arg Lys Leu Phe Ala Asn
    50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
        115                 120                 125

Ala Lys His Pro Ile Asp Ala Ile Thr His Tyr Asp Ser Ile Asp Asp
    130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175

Glu Val Pro Ser Glu Ile Ile Asp Lys Ile Ile Tyr Met Pro Phe Asp
            180                 185                 190

Asn Glu Lys Glu Leu Leu Met Glu Tyr Leu Asn Phe Trp Gln Gln Lys
        195                 200                 205

Thr Pro Val Ile Leu Thr Gly Trp Asn Val Glu Ser Phe Asp Ile Pro
    210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                245                 250                 255

Tyr Gly Ser Arg Glu Ile Ile Thr Leu Phe Gly Ile Ser Val Leu Asp
            260                 265                 270

Tyr Ile Asp Leu Tyr Lys Lys Phe Ser Phe Thr Asn Gln Pro Ser Tyr
        275                 280                 285

Ser Leu Asp Tyr Ile Ser Glu Phe Glu Leu Asn Val Gly Lys Leu Lys
    290                 295                 300

Tyr Asp Gly Pro Ile Ser Lys Leu Arg Glu Ser Asn His Gln Arg Tyr
305                 310                 315                 320

Ile Ser Tyr Asn Ile Ile Asp Val Tyr Arg Val Leu Gln Ile Asp Ala
                325                 330                 335

Lys Arg Gln Phe Ile Asn Leu Ser Leu Asp Met Gly Tyr Tyr Ala Lys
            340                 345                 350

Ile Gln Ile Gln Ser Val Phe Ser Pro Ile Lys Thr Trp Asp Ala Ile
        355                 360                 365

Ile Phe Asn Ser Leu Lys Glu Gln Asn Lys Val Ile Pro Gln Gly Arg
    370                 375                 380

Ser His Pro Val Gln Pro Tyr Pro Gly Ala Phe Val Lys Glu Pro Ile
385                 390                 395                 400

```
Pro Asn Arg Tyr Lys Tyr Val Met Ser Phe Asp Leu Thr Ser Leu Tyr
                405                 410                 415

Pro Ser Ile Ile Arg Gln Val Asn Ile Ser Pro Glu Thr Ile Ala Gly
            420                 425                 430

Thr Phe Lys Val Ala Pro Leu His Asp Tyr Ile Asn Ala Val Ala Glu
        435                 440                 445

Arg Pro Ser Asp Val Tyr Ser Cys Ser Pro Asn Gly Met Met Tyr Tyr
    450                 455                 460

Lys Asp Arg Asp Gly Val Val Pro Thr Glu Ile Thr Lys Val Phe Asn
465                 470                 475                 480

Gln Arg Lys Glu His Lys Gly Tyr Met Leu Ala Ala Gln Arg Asn Gly
                485                 490                 495

Glu Ile Ile Lys Glu Ala Leu His Asn Pro Asn Leu Ser Val Asp Glu
            500                 505                 510

Pro Leu Asp Val Asp Tyr Arg Phe Asp Phe Ser Asp Glu Ile Lys Glu
        515                 520                 525

Lys Ile Lys Lys Leu Ser Ala Lys Ser Leu Asn Glu Met Leu Phe Arg
    530                 535                 540

Ala Gln Arg Thr Glu Val Ala Gly Met Thr Ala Gln Ile Asn Arg Lys
545                 550                 555                 560

Leu Leu Ile Asn Ser Leu Tyr Gly Ala Leu Gly Asn Val Trp Phe Arg
                565                 570                 575

Tyr Tyr Asp Leu Arg Asn Ala Thr Ala Ile Thr Thr Phe Gly Gln Met
            580                 585                 590

Ala Leu Gln Trp Ile Glu Arg Lys Val Asn Glu Tyr Leu Asn Glu Val
        595                 600                 605

Cys Gly Thr Glu Gly Glu Ala Phe Val Leu Tyr Gly Asp Thr Asp Ser
    610                 615                 620

Ile Tyr Val Ser Ala Asp Lys Ile Ile Asp Lys Val Gly Glu Ser Lys
625                 630                 635                 640

Phe Arg Asp Thr Asn His Trp Val Asp Phe Leu Asp Lys Phe Ala Arg
                645                 650                 655

Glu Arg Met Glu Pro Ala Ile Asp Arg Gly Phe Arg Glu Met Cys Glu
            660                 665                 670

Tyr Met Asn Asn Lys Gln His Leu Met Phe Met Asp Arg Glu Ala Ile
        675                 680                 685

Ala Gly Pro Pro Leu Gly Ser Lys Gly Ile Gly Gly Phe Trp Thr Gly
    690                 695                 700

Lys Lys Arg Tyr Ala Leu Asn Val Trp Asp Met Glu Gly Thr Arg Tyr
705                 710                 715                 720

Ala Glu Pro Lys Leu Lys Ile Met Gly Leu Glu Thr Gln Lys Ser Ser
                725                 730                 735

Thr Pro Lys Ala Val Gln Lys Ala Leu Lys Glu Cys Ile Arg Arg Met
            740                 745                 750

Leu Gln Glu Gly Glu Glu Ser Leu Gln Glu Tyr Phe Lys Glu Phe Glu
        755                 760                 765

Lys Glu Phe Arg Gln Leu Asn Tyr Ile Ser Ile Ala Ser Val Ser Ser
    770                 775                 780

Ala Asn Asn Ile Ala Lys Tyr Asp Val Gly Gly Phe Pro Gly Pro Lys
785                 790                 795                 800

Cys Pro Phe His Ile Arg Gly Ile Leu Thr Tyr Asn Arg Ala Ile Lys
                805                 810                 815
```

```
Gly Asn Ile Asp Ala Pro Gln Val Val Glu Gly Glu Lys Val Tyr Val
            820                 825                 830

Leu Pro Leu Arg Glu Gly Asn Pro Phe Gly Asp Lys Cys Ile Ala Trp
        835                 840                 845

Pro Ser Gly Thr Glu Ile Thr Asp Leu Ile Lys Asp Asp Val Leu His
    850                 855                 860

Trp Met Asp Tyr Thr Val Leu Leu Glu Lys Thr Phe Ile Lys Pro Leu
865                 870                 875                 880

Glu Gly Phe Thr Ser Ala Ala Lys Leu Asp Tyr Glu Lys Lys Ala Ser
                885                 890                 895

Leu Phe Asp Met Phe Asp Phe
            900
```

<210> SEQ ID NO 58
<211> LENGTH: 1095
<212> TYPE: DNA
<213> ORGANISM: Saccharomyces cerevisiae

<400> SEQUENCE: 58

```
atgtctgccc ctaagaagat cgtcgttttg ccaggtgacc acgttggtca agaaatcaca     60

gccgaagcca ttaaggttct taaagctatt tctgatgttc gttccaatgt caagttcgat    120

ttcgaaaatc atttaattgg tggtgctgct atcgatgcta caggtgttcc acttccagat    180

gaggcgctgg aagcctccaa gaaggctgat gccgttttgt taggtgctgt gggtggtcct    240

aaatggggta ccggtagtgt tagacctgaa caaggtttac taaaaatccg taaagaactt    300

caattgtacg ccaacttaag accatgtaac tttgcatccg actctctttt agacttatct    360

ccaatcaagc cacaatttgc taaaggtact gacttcgttg ttgtcagaga attagtggga    420

ggtatttact ttggtaagag aaaggaagac gatggtgatg gtgtcgcttg ggatagtgaa    480

caatacaccg ttccagaagt gcaaagaatc acaagaatgg ccgctttcat ggccctacaa    540

catgagccac cattgcctat ttggtccttg gataaagcta atgttttggc ctcttcaaga    600

ttatggagaa aaactgtgga ggaaaccatc aagaacgaat tccctacatt gaaggttcaa    660

catcaattga ttgattctgc cgccatgatc ctagttaaga acccaaccca cctaaatggt    720

attataatca ccagcaacat gtttggtgat atcatctccg atgaagcctc cgttatccca    780

ggttccttgg gtttgttgcc atctgcgtcc ttggcctctt tgccagacaa gaacaccgca    840

tttggtttgt acgaaccatg ccacggttct gctccagatt tgccaaagaa taaggtcaac    900

cctatcgcca ctatcttgtc tgctgcaatg atgttgaaat tgtcattgaa cttgcctgaa    960

gaaggtaagg ccattgaaga tgcagttaaa aaggttttgg atgcaggtat cagaactggt   1020

gatttaggtg gttccaacag taccaccgaa gtcggtgatg ctgtcgccga agaagttaag   1080

aaaatccttg cttaa                                                    1095
```

<210> SEQ ID NO 59
<211> LENGTH: 2661
<212> TYPE: DNA
<213> ORGANISM: Saccharomyces cerevisiae

<400> SEQUENCE: 59

```
atggaaggaa gatcagattt tgtggcgact tcacagtccg gaagtgaaat gagccatagt     60

gaaactagga atagaactgg gatgaatgct aggaaaagga aattcgcctg tgtggaatgt    120

cgtcagcaga agtcgaaatg tgatgctcac gaaagagcac cggagccatg cactaagtgt    180

gctaaaaaga atgtcccatg cattttaaaa cgagatttca gaagaactta taaaagagca    240
```

```
aggaacgaag ccattgaaaa aagattcaag gaactcacca gaactttgac aaatttaact    300
tcggatgaaa ttttgaagaa aattgaagag gaacaggaaa ttgttttgga taacagtaat    360
ttcacaaaag aaaaagtaaa acaactcagg aagagtgctt ttgagacgac agaaatagaa    420
ccgagatcat acaaaacact tcgaggagaa cctatttctt acagtaccaa cagaagacat    480
acggattctt ctcctttaac gctcttaagc tcgtcgacaa acttcgaccc tgttcactca    540
acaaacgtta tgacagatga tcaacttaag tgcttgccaa aaagcctggg cgacgtatat    600
ttgtcaagca gcgatattgc tgagctgttt caagaatttg cgacaaaata tcatcaattt    660
ttacccgtcg ttgacctttc gaaaggagca gagcgaattt atcacttatc tccttgctta    720
ttctgggtca tcctgctcat tggtttaagg cggaaatttg gggctacaga cttaatgact    780
cgattatcag tgctagtaaa gtcagtttta tcagaaatca caatatctcc aataattcga    840
tatactccat cagataagga cgaacccgtt ctaaatgtag catctgtata ttccgtgcaa    900
gcatttcttt tatacacgtt ctggcctccc ttaacctctt cattaagcgc cgacacttcg    960
tggaatacca taggaacagc gatgttccaa gcgcttcggg taggactaaa ttgtgcaggt   1020
ttttcaaaag agtatgcttc ggcaaattca gaattagtta acgagcaaat acgaacttgg   1080
atttgctgca atgttgtatc tcaaacagtt gcatcatcat ttggtttccc agcttatgtt   1140
tcatttgatt atttagtaat cagctctatt agagtaccaa attcaaaaag ccaagtagat   1200
atacccaatg aactaagaca aatggctcaa attgctagat ttgagaacca aatcgtaaac   1260
acaatgaact ccaccccggc gagtgttact gggatggtaa gtcaggaaga gaagcagccc   1320
ttgttacacg ttcttaatca acaactaagt caattggaga ttagtcttga agaaaataac   1380
ctagatgata tccgaaaatt tttattacta gtggccaagg ttcacttatt aacctattac   1440
ttcactgatg ttacctccca aagtgctgga aaatcaaatg gtaatattta tgagggatca   1500
tattccatta tggaactcga tacaagtttt gaaacgaaac gtggattggt gaaagtttat   1560
aatgccgccg taaactttct tatacatgcc aatagtatgt gggaacatga tcctaccatt   1620
attaagtact ttcctggttt gtttgtcttg aatatatggc aatctgcctg tattattagt   1680
aaactcatac attcatcact tcattcaatg ctagatgtta actcaggcaa aaaagcttat   1740
aacaacgcaa tttcattgac gtttaatgcc tcagttttaa aatatgatat ggcgtacaga   1800
tcatccggaa taatgcgaag catatggagt ttatttgcta atatgtatga tgcctggaaa   1860
aacgaccaaa aggaaggtgg aggtagacta aataatgatt tcaatttagg catcaccata   1920
aaatctagga tgtcagtaaa cgtttttttt gactgcttat atattctaaa agagaaatgt   1980
ggtatggcca aattggagag agagaccaag gtttctacag cttacaatgt tgatgaagag   2040
gaagaggaag atgaagatga ggagggagaa gaagaagaag aagaagaaga actaagtagt   2100
aaagttccag aaaatatgga tagccagcaa ctaaggacaa ggaaattcac caatgtaagg   2160
catccagaaa agaaagcaag aaaaataatt gaaacaattc cgctagaccc aaatccaata   2220
aatgcaggct ctaccagcag tggaagctca ttaacgaccc caaatagtca agtagcgaac   2280
actatatcat atagaggaat cctcaataaa atgtcaccta gggaacaact gaatcatgca   2340
aatttagatt ccagtgtttc tacagacatc aaggacactg aagctgtcaa tgaacctctg   2400
ccaataggga ggaatgctga acatccggca aatcaaccgc ctctttcaat aacacaaatg   2460
caagaaaaca cactacctgc gacacaagcc aactcttctc tattagaaac gtatcccatt   2520
gttcaatcaa accccgttac aactacaatc aaagaatcac ccaattccat catggcaggt   2580
```

tgggataact gggaatctga tatggtttgg agggatgttg atattttaat gaatgaattt 2640
gcgttcaatc ccaaggttta a 2661

<210> SEQ ID NO 60
<211> LENGTH: 20
<212> TYPE: DNA
<213> ORGANISM: artificial sequence
<220> FEATURE:
<223> OTHER INFORMATION: synthetic construct

<400> SEQUENCE: 60
gctaatgttt tggcctcttc 20

<210> SEQ ID NO 61
<211> LENGTH: 20
<212> TYPE: DNA
<213> ORGANISM: artificial sequence
<220> FEATURE:
<223> OTHER INFORMATION: synthetic construct

<400> SEQUENCE: 61
atttaggtgg gttgggttct 20

<210> SEQ ID NO 62
<211> LENGTH: 18
<212> TYPE: DNA
<213> ORGANISM: artificial sequence
<220> FEATURE:
<223> OTHER INFORMATION: synthetic construct

<400> SEQUENCE: 62
cagcaactaa ggacaagg 18

<210> SEQ ID NO 63
<211> LENGTH: 18
<212> TYPE: DNA
<213> ORGANISM: artificial sequence
<220> FEATURE:
<223> OTHER INFORMATION: synthetic construct

<400> SEQUENCE: 63
ggtcgttaat gagcttcc 18

<210> SEQ ID NO 64
<211> LENGTH: 6
<212> TYPE: PRT
<213> ORGANISM: artificial sequence
<220> FEATURE:
<223> OTHER INFORMATION: synthetic construct

<400> SEQUENCE: 64

Phe Asp Ile Glu Ser Tyr
1 5

<210> SEQ ID NO 65
<211> LENGTH: 6
<212> TYPE: PRT
<213> ORGANISM: artificial sequence
<220> FEATURE:
<223> OTHER INFORMATION: synthetic construct

<400> SEQUENCE: 65

Cys Asp Phe Glu Thr Thr
1 5

<210> SEQ ID NO 66
<211> LENGTH: 6
<212> TYPE: PRT
<213> ORGANISM: artificial sequence
<220> FEATURE:
<223> OTHER INFORMATION: synthetic construct

<400> SEQUENCE: 66

Phe Asp Phe Glu Thr Asp
1               5

<210> SEQ ID NO 67
<211> LENGTH: 6
<212> TYPE: PRT
<213> ORGANISM: artificial sequence
<220> FEATURE:
<223> OTHER INFORMATION: synthetic construct

<400> SEQUENCE: 67

Cys Asp Ile Glu Val Thr
1               5

<210> SEQ ID NO 68
<211> LENGTH: 6
<212> TYPE: PRT
<213> ORGANISM: artificial sequence
<220> FEATURE:
<223> OTHER INFORMATION: synthetic construct

<400> SEQUENCE: 68

Phe Asp Ile Glu Val Thr
1               5

<210> SEQ ID NO 69
<211> LENGTH: 12
<212> TYPE: PRT
<213> ORGANISM: artificial sequence
<220> FEATURE:
<223> OTHER INFORMATION: synthetic construct

<400> SEQUENCE: 69

Ile Ala His Asn Gly Gly Gly Tyr Asp Phe His Tyr
1               5                   10

<210> SEQ ID NO 70
<211> LENGTH: 11
<212> TYPE: PRT
<213> ORGANISM: artificial sequence
<220> FEATURE:
<223> OTHER INFORMATION: synthetic construct

<400> SEQUENCE: 70

Tyr Phe His Asn Leu Lys Phe Asp Gly Ala Phe
1               5                   10

<210> SEQ ID NO 71
<211> LENGTH: 11
<212> TYPE: PRT
<213> ORGANISM: artificial sequence
<220> FEATURE:
<223> OTHER INFORMATION: synthetic construct

<400> SEQUENCE: 71

Tyr Phe His Asn Leu Lys Phe Asp Gly Ser Phe
1               5                   10

<210> SEQ ID NO 72

<211> LENGTH: 12
<212> TYPE: PRT
<213> ORGANISM: artificial sequence
<220> FEATURE:
<223> OTHER INFORMATION: synthetic construct

<400> SEQUENCE: 72

Tyr Ala His Asn Gly Gly Lys Phe Asp Phe Leu Phe
1 5 10

<210> SEQ ID NO 73
<211> LENGTH: 12
<212> TYPE: PRT
<213> ORGANISM: artificial sequence
<220> FEATURE:
<223> OTHER INFORMATION: synthetic construct

<400> SEQUENCE: 73

Thr Gly Trp Asn Ile Glu Gly Phe Asp Val Pro Tyr
1 5 10

<210> SEQ ID NO 74
<211> LENGTH: 12
<212> TYPE: PRT
<213> ORGANISM: artificial sequence
<220> FEATURE:
<223> OTHER INFORMATION: synthetic construct

<400> SEQUENCE: 74

Thr Gly Trp Asn Val Glu Ser Phe Asp Ile Pro Tyr
1 5 10

<210> SEQ ID NO 75
<211> LENGTH: 19
<212> TYPE: PRT
<213> ORGANISM: artificial sequence
<220> FEATURE:
<223> OTHER INFORMATION: synthetic construct

<400> SEQUENCE: 75

Lys Lys Lys Lys Lys Lys Lys Lys Lys Lys Lys Lys Lys Leu Ala Asn
1 5 10 15

Ala Ser Lys

<210> SEQ ID NO 76
<211> LENGTH: 19
<212> TYPE: PRT
<213> ORGANISM: artificial sequence
<220> FEATURE:
<223> OTHER INFORMATION: synthetic construct

<400> SEQUENCE: 76

Arg Arg Arg Arg Arg Arg Arg Arg Arg Arg Arg Arg Arg Lys Gly Lys
1 5 10 15

Arg Lys Ile

<210> SEQ ID NO 77
<211> LENGTH: 19
<212> TYPE: PRT
<213> ORGANISM: artificial sequence
<220> FEATURE:
<223> OTHER INFORMATION: synthetic construct

<400> SEQUENCE: 77

Gly Gly Gly Gly Gly Gly Gly Gly Gly Gly Gly Gly Gly Arg Gly Lys
1               5                   10                  15

Asn Lys Asn

<210> SEQ ID NO 78
<211> LENGTH: 22
<212> TYPE: PRT
<213> ORGANISM: artificial sequence
<220> FEATURE:
<223> OTHER INFORMATION: synthetic construct

<400> SEQUENCE: 78

Lys Lys Lys Lys Lys Lys Lys Lys Lys Lys Lys Lys Lys Lys Lys Lys
1               5                   10                  15

Glu His Gly Ile His Lys
            20

<210> SEQ ID NO 79
<211> LENGTH: 21
<212> TYPE: PRT
<213> ORGANISM: artificial sequence
<220> FEATURE:
<223> OTHER INFORMATION: synthetic construct

<400> SEQUENCE: 79

Arg Arg Arg Arg Arg Arg Arg Arg Arg Arg Arg Arg Arg Arg Arg Tyr
1               5                   10                  15

Gly Ser Lys Glu Ile
            20

<210> SEQ ID NO 80
<211> LENGTH: 21
<212> TYPE: PRT
<213> ORGANISM: artificial sequence
<220> FEATURE:
<223> OTHER INFORMATION: synthetic construct

<400> SEQUENCE: 80

Arg Arg Arg Arg Arg Arg Arg Arg Arg Arg Arg Arg Arg Arg Arg Tyr
1               5                   10                  15

Gly Ser Arg Glu Ile
            20

<210> SEQ ID NO 81
<211> LENGTH: 6
<212> TYPE: PRT
<213> ORGANISM: artificial sequence
<220> FEATURE:
<223> OTHER INFORMATION: synthetic construct

<400> SEQUENCE: 81

Glu Thr Phe Lys Lys Thr
1               5

<210> SEQ ID NO 82
<211> LENGTH: 6
<212> TYPE: PRT
<213> ORGANISM: artificial sequence
<220> FEATURE:
<223> OTHER INFORMATION: synthetic construct

<400> SEQUENCE: 82

Asp Ser Leu Lys Lys Leu
1               5

<210> SEQ ID NO 83
<211> LENGTH: 6
<212> TYPE: PRT
<213> ORGANISM: artificial sequence
<220> FEATURE:
<223> OTHER INFORMATION: synthetic construct

<400> SEQUENCE: 83

Asp Ser Tyr Ala Ile Leu
1               5

<210> SEQ ID NO 84
<211> LENGTH: 6
<212> TYPE: PRT
<213> ORGANISM: artificial sequence
<220> FEATURE:
<223> OTHER INFORMATION: synthetic construct

<400> SEQUENCE: 84

Asp Leu Tyr Lys Lys Phe
1               5

<210> SEQ ID NO 85
<211> LENGTH: 6
<212> TYPE: PRT
<213> ORGANISM: artificial sequence
<220> FEATURE:
<223> OTHER INFORMATION: synthetic construct

<400> SEQUENCE: 85

Glu His Ile Val Asn Phe
1               5

<210> SEQ ID NO 86
<211> LENGTH: 6
<212> TYPE: PRT
<213> ORGANISM: artificial sequence
<220> FEATURE:
<223> OTHER INFORMATION: synthetic construct

<400> SEQUENCE: 86

Lys Gly Asp Ile Asp Tyr
1               5

<210> SEQ ID NO 87
<211> LENGTH: 6
<212> TYPE: PRT
<213> ORGANISM: artificial sequence
<220> FEATURE:
<223> OTHER INFORMATION: synthetic construct

<400> SEQUENCE: 87

Lys Ile Glu Ile Asp Tyr
1               5

<210> SEQ ID NO 88
<211> LENGTH: 8
<212> TYPE: PRT
<213> ORGANISM: artificial sequence
<220> FEATURE:
<223> OTHER INFORMATION: synthetic construct

<400> SEQUENCE: 88

Gln His Glu Thr Lys Lys Gly Lys
1 5

<210> SEQ ID NO 89
<211> LENGTH: 8
<212> TYPE: PRT
<213> ORGANISM: artificial sequence
<220> FEATURE:
<223> OTHER INFORMATION: synthetic construct

<400> SEQUENCE: 89

Glu Phe Glu Leu Asn Val Gly Lys
1 5

<210> SEQ ID NO 90
<211> LENGTH: 9
<212> TYPE: PRT
<213> ORGANISM: artificial sequence
<220> FEATURE:
<223> OTHER INFORMATION: synthetic construct

<400> SEQUENCE: 90

Tyr Cys Arg Asn Asp Val Leu Val Leu
1 5

<210> SEQ ID NO 91
<211> LENGTH: 9
<212> TYPE: PRT
<213> ORGANISM: artificial sequence
<220> FEATURE:
<223> OTHER INFORMATION: synthetic construct

<400> SEQUENCE: 91

Tyr Ile Lys Asn Asp Ile Gln Ile Ile
1 5

<210> SEQ ID NO 92
<211> LENGTH: 9
<212> TYPE: PRT
<213> ORGANISM: artificial sequence
<220> FEATURE:
<223> OTHER INFORMATION: synthetic construct

<400> SEQUENCE: 92

Tyr Leu Lys His Asp Leu Leu Ile Val
1 5

<210> SEQ ID NO 93
<211> LENGTH: 9
<212> TYPE: PRT
<213> ORGANISM: artificial sequence
<220> FEATURE:
<223> OTHER INFORMATION: synthetic construct

<400> SEQUENCE: 93

Tyr Leu Lys Gly Asp Cys Val Thr Leu
1 5

<210> SEQ ID NO 94
<211> LENGTH: 9
<212> TYPE: PRT
<213> ORGANISM: artificial sequence
<220> FEATURE:
<223> OTHER INFORMATION: synthetic construct

<400> SEQUENCE: 94

Tyr Ile Ser Tyr Asn Ile Ile Asp Val
1 5

<210> SEQ ID NO 95
<211> LENGTH: 11
<212> TYPE: PRT
<213> ORGANISM: artificial sequence
<220> FEATURE:
<223> OTHER INFORMATION: synthetic construct

<400> SEQUENCE: 95

Leu Asp Val Lys Ser Leu Tyr Pro Ala Ser Met
1 5 10

<210> SEQ ID NO 96
<211> LENGTH: 11
<212> TYPE: PRT
<213> ORGANISM: artificial sequence
<220> FEATURE:
<223> OTHER INFORMATION: synthetic construct

<400> SEQUENCE: 96

Phe Asp Val Asn Ser Leu Tyr Pro Ala Gln Met
1 5 10

<210> SEQ ID NO 97
<211> LENGTH: 11
<212> TYPE: PRT
<213> ORGANISM: artificial sequence
<220> FEATURE:
<223> OTHER INFORMATION: synthetic construct

<400> SEQUENCE: 97

Phe Asp Val Asn Ser Met Tyr Pro Ala Met Met
1 5 10

<210> SEQ ID NO 98
<211> LENGTH: 11
<212> TYPE: PRT
<213> ORGANISM: artificial sequence
<220> FEATURE:
<223> OTHER INFORMATION: synthetic construct

<400> SEQUENCE: 98

Tyr Asp Val Asn Ser Met Tyr Pro His Ala Met
1 5 10

<210> SEQ ID NO 99
<211> LENGTH: 11
<212> TYPE: PRT
<213> ORGANISM: artificial sequence
<220> FEATURE:
<223> OTHER INFORMATION: synthetic construct

<400> SEQUENCE: 99

Phe Asp Leu Thr Ser Leu Tyr Pro Ser Ile Ile
1 5 10

<210> SEQ ID NO 100
<211> LENGTH: 9
<212> TYPE: PRT
<213> ORGANISM: artificial sequence
<220> FEATURE:
<223> OTHER INFORMATION: synthetic construct

<400> SEQUENCE: 100

Tyr Ile Lys Asp Val Leu Tyr Lys Leu
1 5

<210> SEQ ID NO 101
<211> LENGTH: 7
<212> TYPE: PRT
<213> ORGANISM: artificial sequence
<220> FEATURE:
<223> OTHER INFORMATION: synthetic construct

<400> SEQUENCE: 101

Phe Ile Asp Lys Trp Thr Tyr
1 5

<210> SEQ ID NO 102
<211> LENGTH: 8
<212> TYPE: PRT
<213> ORGANISM: artificial sequence
<220> FEATURE:
<223> OTHER INFORMATION: synthetic construct

<400> SEQUENCE: 102

Tyr Ile Asp Arg Phe Met Glu Ile
1 5

<210> SEQ ID NO 103
<211> LENGTH: 8
<212> TYPE: PRT
<213> ORGANISM: artificial sequence
<220> FEATURE:
<223> OTHER INFORMATION: synthetic construct

<400> SEQUENCE: 103

Phe Ile Asp His Phe Phe Ser Lys
1 5

<210> SEQ ID NO 104
<211> LENGTH: 8
<212> TYPE: PRT
<213> ORGANISM: artificial sequence
<220> FEATURE:
<223> OTHER INFORMATION: synthetic construct

<400> SEQUENCE: 104

Phe Ser Asp Asp Phe Leu Asn Glu
1 5

<210> SEQ ID NO 105
<211> LENGTH: 8
<212> TYPE: PRT
<213> ORGANISM: artificial sequence
<220> FEATURE:
<223> OTHER INFORMATION: synthetic construct

<400> SEQUENCE: 105

Phe Ser Asp Glu Ile Lys Glu Ile
1 5

<210> SEQ ID NO 106
<211> LENGTH: 12
<212> TYPE: PRT
<213> ORGANISM: artificial sequence
<220> FEATURE:
<223> OTHER INFORMATION: synthetic construct

<400> SEQUENCE: 106

Lys Ile Ile Met Asn Ser Leu Trp Gly Lys Phe Ala
1 5 10

<210> SEQ ID NO 107
<211> LENGTH: 12
<212> TYPE: PRT
<213> ORGANISM: artificial sequence
<220> FEATURE:
<223> OTHER INFORMATION: synthetic construct

<400> SEQUENCE: 107

Lys Leu Met Leu Asn Ser Leu Tyr Gly Lys Phe Ala
1 5 10

<210> SEQ ID NO 108
<211> LENGTH: 12
<212> TYPE: PRT
<213> ORGANISM: artificial sequence
<220> FEATURE:
<223> OTHER INFORMATION: synthetic construct

<400> SEQUENCE: 108

Lys Leu Ile Leu Asn Ser Ser Tyr Gly Lys Phe Ala
1 5 10

<210> SEQ ID NO 109
<211> LENGTH: 12
<212> TYPE: PRT
<213> ORGANISM: artificial sequence
<220> FEATURE:
<223> OTHER INFORMATION: synthetic construct

<400> SEQUENCE: 109

Lys Ile Leu Ile Asn Ser Leu Tyr Gly Ala Leu Gly
1 5 10

<210> SEQ ID NO 110
<211> LENGTH: 12
<212> TYPE: PRT
<213> ORGANISM: artificial sequence
<220> FEATURE:
<223> OTHER INFORMATION: synthetic construct

<400> SEQUENCE: 110

Lys Leu Leu Ile Asn Ser Leu Tyr Gly Ala Leu Gly
1 5 10

<210> SEQ ID NO 111
<211> LENGTH: 7
<212> TYPE: PRT
<213> ORGANISM: artificial sequence
<220> FEATURE:
<223> OTHER INFORMATION: synthetic construct

<400> SEQUENCE: 111

Thr Leu Ser Trp Ala Arg Tyr
1 5

<210> SEQ ID NO 112
<211> LENGTH: 7
<212> TYPE: PRT
<213> ORGANISM: artificial sequence
<220> FEATURE:
<223> OTHER INFORMATION: synthetic construct

<400> SEQUENCE: 112

Ile Thr Ala Trp Ala Arg Tyr
1 5

<210> SEQ ID NO 113
<211> LENGTH: 7
<212> TYPE: PRT
<213> ORGANISM: artificial sequence
<220> FEATURE:
<223> OTHER INFORMATION: synthetic construct

<400> SEQUENCE: 113

Ile Thr Ala Tyr Ala Arg Glu
1 5

<210> SEQ ID NO 114
<211> LENGTH: 6
<212> TYPE: PRT
<213> ORGANISM: artificial sequence
<220> FEATURE:
<223> OTHER INFORMATION: synthetic construct

<400> SEQUENCE: 114

Ile Thr Gly Ala Ala Arg
1 5

<210> SEQ ID NO 115
<211> LENGTH: 7
<212> TYPE: PRT
<213> ORGANISM: artificial sequence
<220> FEATURE:
<223> OTHER INFORMATION: synthetic construct

<400> SEQUENCE: 115

Gly Ile Gln Trp Ile Ala Arg
1 5

<210> SEQ ID NO 116
<211> LENGTH: 7
<212> TYPE: PRT
<213> ORGANISM: artificial sequence
<220> FEATURE:
<223> OTHER INFORMATION: synthetic construct

<400> SEQUENCE: 116

Ala Leu Gln Trp Ile Glu Arg
1 5

<210> SEQ ID NO 117
<211> LENGTH: 7
<212> TYPE: PRT
<213> ORGANISM: artificial sequence
<220> FEATURE:
<223> OTHER INFORMATION: synthetic construct

<400> SEQUENCE: 117

Tyr Ser Asp Thr Asp Ser Ile
1 5

<210> SEQ ID NO 118
<211> LENGTH: 7
<212> TYPE: PRT
<213> ORGANISM: artificial sequence
<220> FEATURE:
<223> OTHER INFORMATION: synthetic construct

<400> SEQUENCE: 118

Tyr Cys Asp Thr Asp Ser Ile
1               5

<210> SEQ ID NO 119
<211> LENGTH: 7
<212> TYPE: PRT
<213> ORGANISM: artificial sequence
<220> FEATURE:
<223> OTHER INFORMATION: synthetic construct

<400> SEQUENCE: 119

Tyr Ala Asp Thr Asp Ser Ile
1               5

<210> SEQ ID NO 120
<211> LENGTH: 7
<212> TYPE: PRT
<213> ORGANISM: artificial sequence
<220> FEATURE:
<223> OTHER INFORMATION: synthetic construct

<400> SEQUENCE: 120

Ala Gly Asp Thr Asp Ser Val
1               5

<210> SEQ ID NO 121
<211> LENGTH: 7
<212> TYPE: PRT
<213> ORGANISM: artificial sequence
<220> FEATURE:
<223> OTHER INFORMATION: synthetic construct

<400> SEQUENCE: 121

Tyr Gly Asp Thr Asp Ser Ile
1               5

<210> SEQ ID NO 122
<211> LENGTH: 4
<212> TYPE: PRT
<213> ORGANISM: artificial sequence
<220> FEATURE:
<223> OTHER INFORMATION: synthetic construct

<400> SEQUENCE: 122

Lys Lys Gln Tyr
1

<210> SEQ ID NO 123
<211> LENGTH: 4
<212> TYPE: PRT
<213> ORGANISM: artificial sequence
<220> FEATURE:
<223> OTHER INFORMATION: synthetic construct

<400> SEQUENCE: 123

Gln Lys Thr Tyr
1

<210> SEQ ID NO 124
<211> LENGTH: 4
<212> TYPE: PRT
<213> ORGANISM: artificial sequence
<220> FEATURE:
<223> OTHER INFORMATION: synthetic construct

```
<400> SEQUENCE: 124

Lys Lys Leu Tyr
1


<210> SEQ ID NO 125
<211> LENGTH: 4
<212> TYPE: PRT
<213> ORGANISM: artificial sequence
<220> FEATURE:
<223> OTHER INFORMATION: synthetic construct

<400> SEQUENCE: 125

Lys Lys Arg Tyr
1
```